(12) United States Patent
Barrett et al.

(10) Patent No.: US 10,556,862 B2
(45) Date of Patent: Feb. 11, 2020

(54) DIFLUOROLACTAM COMPOUNDS AS EP$_4$ RECEPTOR-SELECTIVE AGONISTS FOR USE IN THE TREATMENT OF EP$_4$-MEDIATED DISEASES AND CONDITIONS

(71) Applicant: Cayman Chemical Company, Inc., Ann Arbor, MI (US)

(72) Inventors: Stephen Douglas Barrett, Hartland, MI (US); Fred Lawrence Ciske, Dexter, MI (US); Joseph Michael Colombo, Ann Arbor, MI (US); Gregory William Endres, Saline, MI (US); Bradlee David Germain, Ann Arbor, MI (US); Andriy Komilov, Ypsilanti, MI (US); James Bernard Kramer, Sylvania, OH (US); Adam Uzieblo, Farmington Hills, MI (US); Kirk M. Maxey, Ann Arbor, MI (US)

(73) Assignee: CAYMAN CHEMICAL COMPANY, INC., Ann Arbor, MI (US)

( * ) Notice: Subject to any disclaimer, the term of this patent is extended or adjusted under 35 U.S.C. 154(b) by 0 days.

(21) Appl. No.: 16/155,400

(22) Filed: Oct. 9, 2018

(65) Prior Publication Data
US 2019/0092722 A1 Mar. 28, 2019

Related U.S. Application Data

(60) Division of application No. 15/267,440, filed on Sep. 16, 2016, now abandoned, which is a continuation of application No. 14/872,967, filed on Oct. 1, 2015, now Pat. No. 9,487,478, which is a continuation of application No. 14/415,506, filed as application No. PCT/US2013/051263 on Jul. 19, 2013, now Pat. No. 9,180,116.

(60) Provisional application No. 61/673,514, filed on Jul. 19, 2012, provisional application No. 61/793,929, filed on Mar. 15, 2013.

(51) Int. Cl.
| | | |
|---|---|---|
| A61K 31/4015 | (2006.01) |
| A61K 31/4025 | (2006.01) |
| C07D 207/26 | (2006.01) |
| C07D 409/06 | (2006.01) |
| C07D 207/273 | (2006.01) |
| A61L 24/00 | (2006.01) |
| A61L 24/02 | (2006.01) |
| A61L 27/12 | (2006.01) |
| A61L 27/36 | (2006.01) |
| A61L 27/54 | (2006.01) |
| A61L 27/58 | (2006.01) |

(52) U.S. Cl.
CPC ...... *C07D 207/273* (2013.01); *A61K 31/4015* (2013.01); *A61K 31/4025* (2013.01); *A61L 24/0015* (2013.01); *A61L 24/0042* (2013.01); *A61L 24/02* (2013.01); *A61L 27/12* (2013.01); *A61L 27/365* (2013.01); *A61L 27/3608* (2013.01); *A61L 27/54* (2013.01); *A61L 27/58* (2013.01); *C07D 207/26* (2013.01); *C07D 409/06* (2013.01); *A61L 2300/412* (2013.01); *A61L 2300/604* (2013.01); *A61L 2430/02* (2013.01)

(58) Field of Classification Search
CPC ............ A61K 31/4015; A61K 31/4025; C07D 207/26; C07D 409/06
See application file for complete search history.

(56) References Cited

U.S. PATENT DOCUMENTS

| | | | |
|---|---|---|---|
| 3,975,399 A | 8/1976 | DeFranco et al. |
| 4,073,934 A | 2/1978 | Skuballa et al. |
| 4,177,346 A | 12/1979 | Nelson |
| 4,235,930 A | 11/1980 | Skuballa et al. |

(Continued)

FOREIGN PATENT DOCUMENTS

| | | |
|---|---|---|
| CA | 1085859 | 9/1980 |
| EP | 0046082 B1 | 6/1985 |

(Continued)

OTHER PUBLICATIONS

Qian et al. (STN Abstract Accession No. 2009:205982) Published 2009.*
Billot, X. et al. "Discovery of a Potent and Selective Agonist of the Prostaglandin EP$_4$ Receptor," *Biorganic & Medicinal Chemistry Letters*, 2003, 13, 1129-1132.
Cameron, K.O. et al. "Discovery of Highly Selective EP4 Receptor Agonists That Stimulate New Bone Formation and Restore Bone Mass in Ovariectomized Rats," *Biorganic & Medicinal Chemistry Letters*, 2006, 16, 1799-1802.
Database PubChem Compound [Online] NCBI; Nov. 30, 2012, XP002725496, Database accession No. CID 66622708, compound CID 66622708.

(Continued)

Primary Examiner — Robert H Havlin
(74) Attorney, Agent, or Firm — Barnes & Thornburg

(57) ABSTRACT

Disclosed herein are compounds of formula (I)

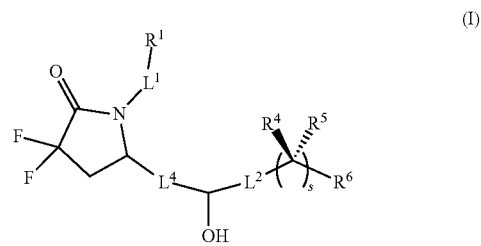

(I)

and therapeutic methods of treatment with compounds of formula (I), wherein $L^1$, $L^2$, $L^4$, $R^1$, $R^4$, $R^5$, $R^6$, and s are as defined in the specification. Compounds of formula (I) are EP4 agonists useful in the treatment of glaucoma, neuropathic pain, and related disorders.

4 Claims, 1 Drawing Sheet

(56) References Cited

U.S. PATENT DOCUMENTS

| | | | |
|---|---|---|---|
| 4,456,613 | A | 6/1984 | Wang |
| 5,288,878 | A | 2/1994 | Harre et al. |
| 6,849,657 | B2 | 2/2005 | Elworthy et al. |
| 6,900,336 | B2 * | 5/2005 | Elworthy ............. C07D 207/26 548/543 |
| 7,276,531 | B2 * | 10/2007 | Araldi ................ C07D 207/267 514/422 |
| 7,419,999 | B2 | 9/2008 | Araldi et al. |
| 2005/0239872 | A1 | 10/2005 | Billot et al. |
| 2006/0167081 | A1 | 7/2006 | Billot et al. |
| 2016/0060253 | A1 | 3/2016 | Barrett et al. |

FOREIGN PATENT DOCUMENTS

| | | |
|---|---|---|
| GB | 1553595 A1 | 10/1979 |
| GB | 1583163 A1 | 1/1981 |
| WO | WO 2002/042268 A2 | 5/2002 |
| WO | WO 2003/007941 A1 | 1/2003 |
| WO | WO 2003/008377 A1 | 1/2003 |
| WO | WO 2003/047513 A2 | 6/2003 |
| WO | WO 2003/077910 A1 | 9/2003 |
| WO | WO 2003/103604 A2 | 12/2003 |
| WO | WO 2004/037786 A2 | 5/2004 |
| WO | WO 2009/023193 A1 | 2/2009 |
| WO | WO 2009/055289 A2 | 4/2009 |
| WO | WO 2011/003058 A1 | 1/2011 |
| WO | WO 2012/063207 A1 | 5/2012 |
| WO | WO 2014/015246 A1 | 1/2014 |
| WO | WO 2014/015247 A1 | 1/2014 |

OTHER PUBLICATIONS

Elworthy, T.R. et al. "Lactams as $EP_4$ Prostanoid Receptor Agonists. 3. Discovery of N-Ethylbenzoic Acid 2-Pyrrolidinones as Subtype Selective Agents," *J. Med. Chem.*, 2004, 20, 6124-6127.

Elworthy, T.R. et al. "Lactams as $EP_4$ Prostanoid Receptor Subtype Selective Agonists. Part 1: 2-Pyrrolidinones-Stereochemical and Lower Side-Chain Optimization," *Biorganic & Medicinal Chemistry Letters*, 2004, 14, 1655-1659.

Fustero, S. et al. "A New Tandem Cross Metathesis-Intramolecular Aza-Michael Reaction for the Synthesis of α,α-Difluorinated Lactams," *Synthesis*, 2012, 44, 1863-1873.

International Search Report and Written Opinion for corresponding International Application No. PCT/US2014/028933, dated Mar. 30, 2015 (17 pages).

Kambe, T. et al., "Discovery of novel prostaglandin analogs as potent and selective EP2/EP4 dual agonists," *Bioorganic & Medicinal Chemistry* 20 (2012) 2235-2251.

Kambe, T. et al. "Synthesis and Evaluation of γ-lactam Analogs of $PGE_2$ as EP4 and EP2/EP4 Agonists," *Bioorganic & Medicinal Chemistry*, 2012, 20, 3502-3522.

Kirk, K.L. et al., "Fluorination in Medicinal Chemistry: Methods, Strategies, and Recent Developments," *Organic Process Research & Development*, 2008, 12, 305-321.

Konas, D.W. et al., "Synthesis of $_L$-4,4-Difluoroglutamic Acid via Electrophilic Difluorination of a Lactam," *Organic Letters*, 1999, 1(13), 2105-2107.

Li, B-H. et al. "Rational and Practical Synthesis of α,α-difluoro-γ-lactams," *J. Fluorine Chemistry*, 2012, 133, 163-166.

Ma, J-A. et al., "Asymmetric Fluorination, Trifluoromethylation, and Perfluoroalkylation Reactions," *Chem. Rev.* 2004, 104, 6119-6146.

Martinez-Montero, S., et al., "Synthesis, evaluation of anti-HIV-1 and anti-HCV activity of novel 2',3'-dideoxy-2',2'-difluoro-4'-azanucleosides," *Bioorganic & Medicinal Chemistry* 20 (2012) 6885-6893.

Nair S.K. et al. "Novel Synthesis of CP-734432, an EP4 Agonist, Using Sharpless Asymmetric Dihydroxylation," *Tetrahedron Letters*, 2010, 51, 1451-1454.

Sankar, G. et al., "Electrophilic NF Fluorinating Agents," *Chem. Rev.* 1996, 1737-1755.

Skuballa, W. et al., "Synthesis of a New Chemically and Metabolically Stable Prostacyclin Analogue with High and Long-Lasting Oral Activity," *Journal of Medicinal Chemistry*, 1986, 29(3), 313-315.

Smith, R.L. et al. "Prostaglandin Isosteres. 1. (8-Aza-, 8,10-Diaza-, and 8-Aza-11-thia)-9-oxoprostanoic Acids and Their Derivatives," *J. Med. Chem.*, 1977, 20, 1292-1299.

Wang, C-L.J. et al. "Azaprostanoids I. Synthesis of (RAC)-8-Aza-11-Deoxy-15-Deoxy-16-Hydroxy-16-Methylprostaglandins," *Tetrahedron Letters*, 1982, 10, 1067-1070.

Xiao, Y. et al. "Synthesis and Evaluation of a γ-lactam as a Highly Selective $EP_2$ and $EP_4$ Receptor Agonist," *Biorganic & Medicinal Chemistry Letters*, 2008, 18, 821-824.

Ye, Z. et al., "Asymmetric Synthesis of Fluorine-containing Compounds Using Organocatalysts," *Chimia*, 2011, 65(12), 902-908.

* cited by examiner

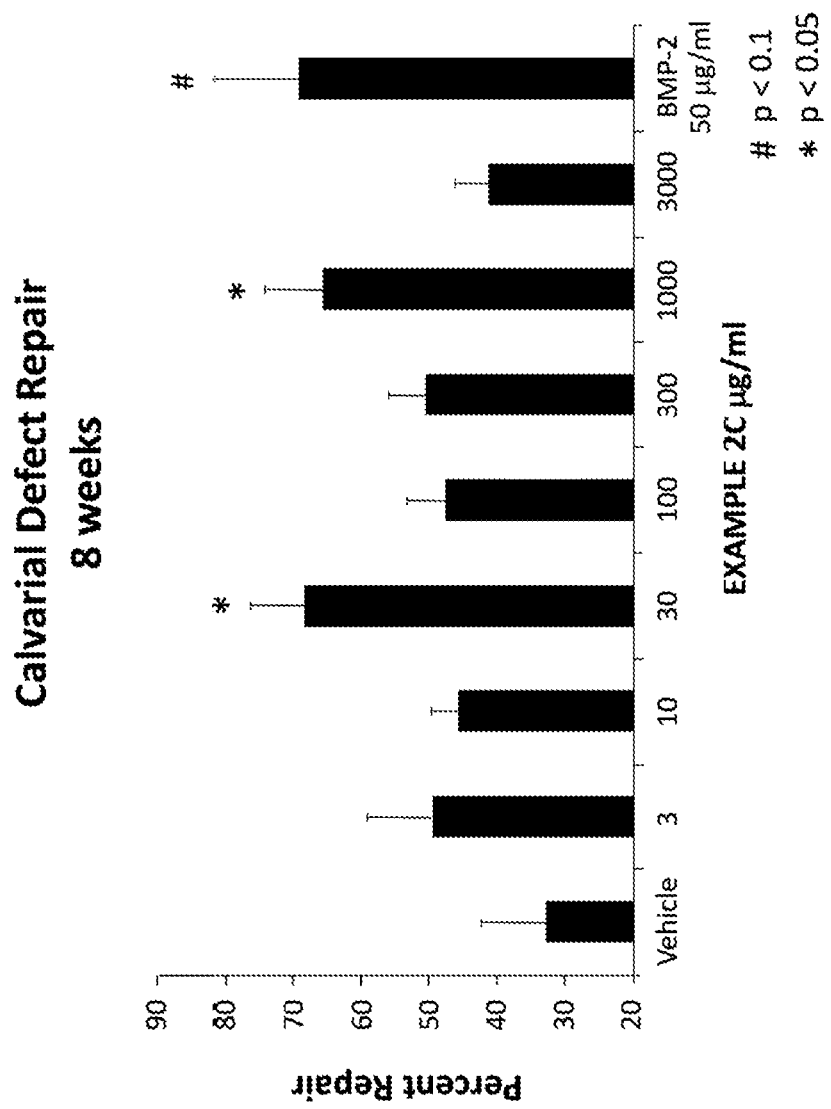

DIFLUOROLACTAM COMPOUNDS AS $EP_4$ RECEPTOR-SELECTIVE AGONISTS FOR USE IN THE TREATMENT OF $EP_4$-MEDIATED DISEASES AND CONDITIONS

RELATED APPLICATIONS

This application is a divisional of U.S. application Ser. No. 15/267,440, filed Sep. 16, 2016, which is a continuation of U.S. application Ser. No. 14/872,967, filed Oct. 1, 2015, which is a continuation of U.S. application Ser. No. 14/415,506, filed Feb. 24, 2015, which is the U.S. National Phase under 35 U.S.C. § 371 of International Patent Application No. PCT/US2013/051263, filed Jul. 19, 2013, which claims priority to and the benefit of U.S. Provisional Application Ser. No. 61/793,929, filed Mar. 15, 2013, and U.S. Provisional Application Ser. No. 61/673,514, filed Jul. 19, 2012. The entire contents of these patent applications are hereby incorporated herein by reference.

FIELD OF THE INVENTION

The subject matter disclosed and claimed herein centers on novel $EP_4$ receptor-selective 3,3-difluoropyrrolidin-2-one (γ-lactam) derivatives and their uses as therapies for $EP_4$ receptor-mediated diseases and conditions.

BACKGROUND OF THE INVENTION

All references, including patents and patent applications, are hereby incorporated by reference in their entireties.

Arachidonic acid (abbreviated as AA herein) is a ubiquitous polyunsaturated fatty acid (PUFA) that is found esterified to phospholipids at the secondary alcohol of glycerol in all mammalian cellular membranes. Enzymatic hydrolysis of esterified AA by calcium ($Ca^{2+}$)-induced cytosolic phospholipase 2 (cPLA2) releases free AA, which may be further catalytically converted by the cyclooxygenase (COX) into the intermediate prostaglandin H2 followed by subsequent enzymatic isomerization into the naturally occurring prostaglandins (PGs) and thromboxanes. The five primary prostanoids include prostaglandin $F_{2\alpha}$ ($PGF_{2\alpha}$), prostaglandin $D_2$ ($PGD_2$), prostaglandin $I_2$ ($PGI_2$), thromboxane $A_2$ ($TxA_2$), and prostaglandin E2 (PGE2), (Jahn, U. et al., *Angew. Chem. Int. Ed.* 2008, 47, 5894-5955; Wymann, M. P. et al., *Nat. Rev. Mol. Cell. Biol.* 2008, 9, 162-176; Samuelsson, B. et al., *Ann. Rev. Biochem.* 1978, 47, 997-1029). These five prostaglandins are lipid mediators that interact with nine specific members of a distinct prostanoid subfamily of G-protein-coupled receptors (GPCRs), designated FP, $DP_{1-2}$, IP, TP, and $EP_{1-4}$, respectively (Breyer, R. M. et al., *Annu. Rev. Pharmacol. Toxicol.* 2001, 41, 661-690). Prostaglandin and PG receptor pharmacology, signaling, and physiology have been studied and well documented (Hata, A. N. et al., *Pharmacol. Ther.* 2004, 103(2), 147-166; ElAttar, T. M. A., *J. Oral Pathol. Med.* 1978, 7(5), 239-252; Poyser, N. L., *Clinics in Endocrinology and Metabolism* 1973, 2(3), 393-410). Prostaglandins are short-lived local signaling molecules that are not stored in cells or tissues but are produced as needed by specific cells of virtually all body tissues. Their target cells reside in the immediate vicinity of their secretion sites. Well-known PG functions include regulation of cell stimulation, growth, and differentiation, immune response and inflammation, allergy, asthma, pain, vasomotor action, neuromodulation, intraocular pressure, and platelet aggregation, as well as mediation of fever, managing of renal blood flow, and induction of labor (Negishi, M. et al., *Prog. Lipid Res.* 1993, 32(4), 417-434).

As is the case for most prostaglandins, the biosynthesis of $PGE_2$ commences with liberation of free AA from its esterified form in the cell membrane. One key enzyme involved in $PGE_2$ biosynthesis is prostaglandin H synthase (PGHS). PGHS possesses both a COX and a peroxidase function. The COX activity promotes conversion of free AA to the unstable endoperoxide prostaglandin $G_2$ ($PGG_2$) via double oxygen insertion. One inserted oxygen molecule is subsequently reduced by the peroxidase activity of PGHS to provide the versatile biosynthetic cascade intermediate $PGH_2$. The glutathione-dependent enzyme prostaglandin E synthase (PGES) promotes isomerization of $PGH_2$ to $PGE_2$ via peroxide ring opening of $PGH_2$ to provide the highly functionalized hydroxypentanone scaffold of $PGE_2$.

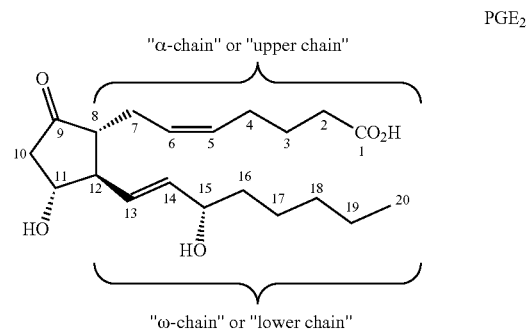

The physiology of $PGE_2$ and the pharmacology of its four known complementary receptor subtypes designated $EP_1$, $EP_2$, $EP_3$, and $EP_4$ are among the most widely studied and published fields of PG research (Sugimoto, Y. et al., *J. Biol. Chem.* 2007, 282(16), 11613-11617; Suzuki, J. et al., *Prostaglandins* 2010, 127-133; Regan, J. et al., *Life Sciences* 2003, 74(2-3), 143-153; Bouayad, A. et al., *Current Ther. Res.* 2002, 63(10), 669-681; Breyer, M. et al., *Kidney Int, Suppl.* 1998, 67, S88-S94; Breyer, M. et al., *Amer. J. Physiol.* 2000, 279(1, Part 2), F12-F23; Negishi, M. et al., *Recent Res. Dev. Endocrinol.* 2000, 1(1), 133-143; Ma, W. et al., *Prog. Inflamm. Res.* 2006, 39-93; Mutoh, M. et al., *Current Pharmaceutical Design* 2006, 12(19), 2375-2382; Hebert, R. et al., *Current Topics in Pharmacology* 2002, 6, 129-137; Coleman, R. et al., *Pharm. Rev.* 1994, 46(2), 205-229). PGE2 binds to each of the four EP receptors with high affinity (Anderson, L. et al., *Journal of Reproduction and Fertility*, 1999, 116, 133-141). The prostaglandin $PGE_1$ (saturated α-chain analog of $PGE_2$), the major eicosanoid synthesized biologically from dihomo-γ-linolenic acid (DGLA) in response to various stimuli, also binds efficiently to all four EP receptor subtypes.

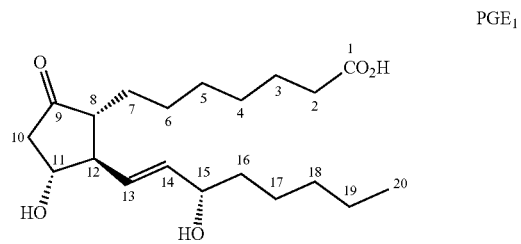 [SMILES: CCCCC[C@H](O)/C=C/[C@H]1[C@H](O)CC(=O)[C@@H]1CCCCCCC(=O)O]

The EP$_4$ receptor is expressed in a wide variety of tissues including those of the skeletal, muscular, central and peripheral nervous, immune, respiratory, cardiovascular, digestive, excretory, and reproductive tissues and is known to be involved in such processes and conditions as bone growth and remodeling, osteoporosis, relaxation of smooth muscle, neuroprotection, ocular inflammation, immune response, and cancer. Modulation of the EP$_4$ receptor may also be involved in the neonatal development of the circulatory system (Fan, F. et al., *Clinical and Experimental Pharmacology and Physiology*, 2010, 37, 574-580; Bouayad, A. et al., *Current Ther. Res.* 2002, 63(10), 669-681; Bouayad, A. et al., *Am. J. Physiol. Heart Circ. Physiol.* 2001, 280, H2342-H2349). Activation of the EP$_4$ receptor by PGE$_2$ increases intracellular cAMP levels, leading to downstream effects associated with antiapoptotic activity and cytoprotection (Fujino, H. and Regan, J., *Trends in Pharmacological Sciences*, 2003, 24(7), 335-340; Hoshino, T. et al., *J. Biol. Chem.*, 2003, 278(15), 12752-12758; Takahashi, S. et al., *Biochem. Pharmacol.*, 1999, 58(12), 1997-2002; Quiroga, J. et al., *Pharmacol. Ther.*, 1993, 58(1), 67-91).

EP$_4$ receptor agonists are reported to be useful in lowering intraocular pressure and to have application in treating glaucoma. Prasanna, G. et al., *Exp. Eye Res.*, 2009, 89 (5), 608-17; Luu, K. et al., *J. Pharmacol. Exp. Ther.* 2009, 331(2), 627-635; Saeki, T. et al, *Invest. Ophthalmol. Vis. Sci.*, 2009, 50 (5) 2201-2208.

EP$_4$ receptor agonists are also reported to induce bone remodeling and to have use in the treatment of osteoporosis. Iwaniec, U. et al., *Osteoporosis International*, 2007, 18 (3), 351-362; Aguirre, J. et al., *J. Bone and Min. Res.*, 2007, 22(6), 877-888; Yoshida, K. et al., *Proc. Natl. Acad. Sci. USA*, 2002, 99 (7), 4580-4585. Hayashi, K. et al., *J. Bone Joint Surg. Br.*, 2005, 87-B (8), 1150-6.

SUMMARY OF THE INVENTION

In one aspect, the present invention provides compounds of formula (I)

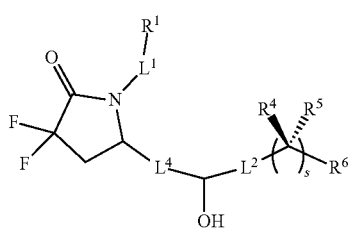

or a pharmaceutically acceptable salt thereof, wherein:

$L^1$ is a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;

b) —$(CH_2)_t$-G-$(CH_2)_p$—; wherein t is 0, 1, or 2, p is 0, 1, 2, or 3, and t+p=0, 1, 2, 3, or 4; or c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{13}$)=C($R^{13}$)-$G^2$-, wherein n is 1, 2, 3, 4, or 5, p is 0, 1, 2, or 3, and n+p=1, 2, 3, 4, 5, or 6;

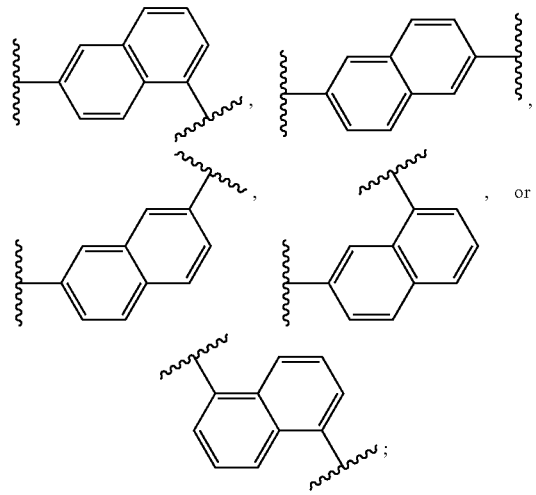

$G^1$ is O, C(O), S, S(O), S(O)$_2$, or $NR^8$; wherein $R^8$ is H, $C_1$-$C_4$ alkyl, or $C_1$-$C_4$alkylcarbonyl;

$G^2$ is wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^1$ is COOR$^{10}$, CONR$^{10}$R$^{11}$, CH$_2$OR$^{10}$, SO$_3$R$^{10}$, SO$_2$NR$^{10}$R$^{11}$, PO(OR$^{10}$)$_2$, or tetrazol-5-yl;

$R^{10}$ is H, $C_1$-$C_4$ alkyl, or aryl;

$R^{11}$ is H, $C_1$-$C_4$ alkyl, COR$^{12}$, OR$^{10}$, or SO$_2$R$^{12}$;

$R^{12}$ is $C_1$-$C_4$ alkyl;

$R^{13}$, at each occurrence, is independently H or $C_1$-$C_4$alkyl;

$L^4$ is —C($R^2$)$_2$—C($R^3$)$_2$—, —C($R^2$)=C($R^3$)—, —C≡C—, or wherein $R^2$ and $R^3$ are each H, CH$_3$, fluoro, or chloro;

$L^2$ is —CH$_2$— or a bond;

$R^4$ and $R^5$ are each independently H, F, CF$_3$, or $C_1$-$C_4$ alkyl; or $R^4$ and $R^5$ together with the carbon to which they are attached form a $C_3$-$C_5$ cycloalkyl,

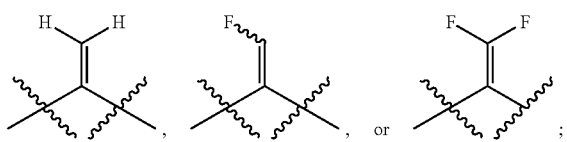

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy; and wherein the $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, and $C_3$-$C_{10}$haloalkynyl are optionally substituted with a substituent selected from the group consisting of $COOR^{10'}$, $CONR^{10'}R^{11'}$, $CH_2OR^{10'}$, $SO_3R^{10'}$, $SO_2NR^{10'}R^{11'}$, $PO(OR^{10'})_2$, and tetrazol-5-yl;

$R^{10'}$ is H, $C_1$-$C_4$ alkyl, or aryl;

$R^{11'}$ is H, $C_1$-$C_4$ alkyl, $COR^{12'}$, $OR^{10'}$, or $SO_2R^{12'}$;

$R^{12'}$ is $C_1$-$C_4$ alkyl;

$L^3$ is $C_1$-$C_6$alkylene, $C_2$-$C_6$alkenylene, $C_2$-$C_6$alkynylene, —$(CH_2)_m$-$G^3$-$(CH_2)_q$—, —$(CH_2)_m$-$G^4$-$(CH_2)_q$—, or -$G^5$-C≡C—; wherein the $C_1$-$C_5$alkylene, $C_2$-$C_6$alkenylene, and $C_2$-$C_6$alkynylene are optionally substituted with 1, 2, 3, or 4 fluoro substituents; and wherein m and q are each independently 0, 1, 2, or 3 and m+q=0, 1, 2, 3, or 4;

$G^3$ is O, C(O), S, S(O), S(O)$_2$, or $NR^9$; wherein $R^9$ is H, $C_1$-$C_4$ alkyl, or $C_1$-$C_4$alkylcarbonyl;

$G^4$ is

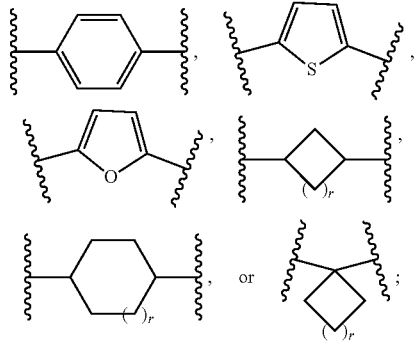

wherein $G^4$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$G^5$ is

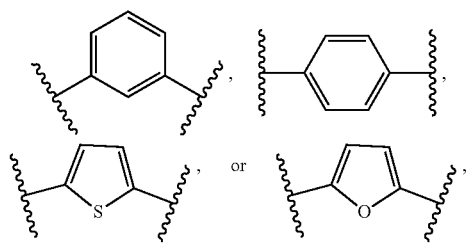

wherein $G^5$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy;

r is 0 or 1; and s is 0 or 1.

In another aspect, the present invention provides compounds of formula (Ia)

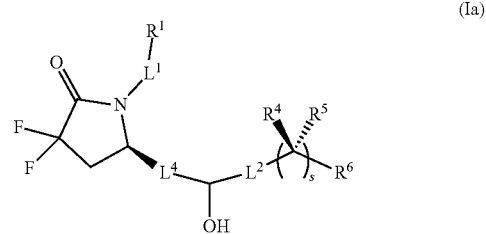

(Ia)

or a pharmaceutically acceptable salt thereof, wherein $R^1$, $R^4$, $R^5$, $R^6$, $L^1$, $L^2$, $L^4$, and s are as defined herein.

In another aspect of the invention are compounds of formula (II)

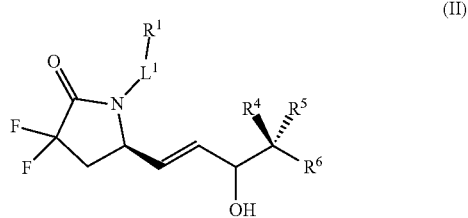

(II)

or a pharmaceutically acceptable salt thereof, wherein $R^1$, $R^4$, $R^5$, $R^6$, and $L^1$ are as defined herein.

Another aspect of the present invention relates to pharmaceutical compositions comprising therapeutically effective amounts of a compound described herein or a pharmaceutically acceptable salt, solvate, salt of a solvate, or solvate of a salt thereof, in combination with a pharmaceutically acceptable carrier.

In another aspect, the invention provides compounds that bind to the $EP_4$ receptor with high affinity and agonist activity. In certain embodiments, compounds of the invention may possess selectivity for the $EP_4$ receptor versus other EP receptors.

In another aspect, the present invention provides a method of treating a disease or disorder related to the $EP_4$ receptor by administering to a patient a therapeutically effective amount of a compound or composition of formula (I), (Ia), or (II). Such diseases or disorders include those related to elevated intraocular pressure such as glaucoma. Other diseases or conditions treatable by the compounds and compositions of the invention include those associated with excessive bone loss, such as osteoporosis.

The present invention also provides methods of preparing compounds of formula (I), (IA), or (II).

In another aspect, the invention provides intermediates useful in the preparation of $EP_4$ agonists. In still another aspect, the invention provides methods of preparing the intermediates.

Further provided herein are the use of the present compounds or pharmaceutically acceptable salts, solvates, salts of solvates, or solvates of salts thereof, in the manufacture of a medicament for the treatment of the diseases or conditions described herein, alone or in combination with one or more pharmaceutically acceptable carrier(s).

BRIEF DESCRIPTION OF THE DRAWINGS

FIG. 1 depicts data showing the effect of Compound 2C on stimulation of bone growth in the rat calvarial defect model.

DETAILED DESCRIPTION

Definition of Terms

The term "agonist" as used herein refers to a compound, the biological effect of which is to mimic the action of the natural agonist PGE2. An agonist may have full efficacy (i.e., equivalent to PGE2), partial efficacy (lower maximal efficacy compared to PGE2), or super maximal efficacy (higher maximal efficacy compared to PGE2). An agonist with partial efficacy is referred to as a "partial agonist." An agonist with super maximal efficacy is referred to as a "super agonist."

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, means a straight or branched chain hydrocarbon and containing at least one carbon-carbon triple bond. Representative examples include propynyl, butynyl, pentynyl, and the like.

The term "alkylene," as used herein, means a divalent group derived from a straight or branched chain hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and —CH$_2$CH(CH$_3$)CH(CH$_3$)CH$_2$—.

The term "alkenylene," as used herein, means a divalent group derived from a straight or branched chain hydrocarbon and containing at least one carbon-carbon double bond. Representative examples of alkenylene include, but are not limited to —CH═CH—, —CH$_2$CH═CH—, and —CH$_2$CH═CH(CH$_3$)—.

The term "alkynylene," as used herein, means a divalent group derived from a straight or branched chain hydrocarbon and containing at least one carbon-carbon triple bond. Representative examples of alkynylene include, but are not limited to —CH$_2$—C≡C—, —CH$_2$CH$_2$—C≡C—, and —C≡C—CH$_2$CH(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkylcarbonyl" as used herein, means an alkyl group, as defined herein, appended to the parent molecular moiety through a C(O) group.

The terms "haloalkyl," "haloalkenyl," and "haloalkynyl" as used herein, mean, respectively an alkyl, alkenyl, or alkynyl group, as defined herein, in which one, two, three, four, five, six, or seven hydrogen atoms are replaced by halogen. For example, representative examples of haloalkyl include, but are not limited to, 2-fluoroethyl, 2,2-difluoroethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "heteroaryl," as used herein, means a monocyclic heteroaryl or a fused bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is an 8- to 12-membered ring system having a monocyclic heteroaryl fused to an additional ring; wherein the additional ring may be aromatic or partially saturated, and may contain additional heteroatoms. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, furopyridinyl, indolyl, indazolyl, isoquinolinyl, naphthyridinyl, oxazolopyridine, quinolinyl, thienopyridinyl, 5,6,7,8-tetrahydroquinolinyl, 6,7-dihydro-5H-cyclopenta[b]pyridinyl, and 2,3-dihydrofuro[3,2-b]pyridinyl. The monocyclic and the bicyclic heteroaryl groups are connected to the parent molecular moiety through any substitutable carbon atom or any substitutable nitrogen atom contained within the groups.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

The term "heterocycle" or "heterocyclic" as used herein, refers to a monocyclic heterocycle, a bicyclic heterocycle, or a spirocyclic heterocycle. The monocyclic heterocycle is a 3, 4, 5, 6, 7, or 8-membered ring containing at least one heteroatom selected from O, N, or S. The 3 or 4 membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The bicyclic heterocycle is a 5-12-membered ring system having a monocyclic heterocycle fused to a phenyl, a saturated or partially saturated carbocyclic ring, or another monocyclic heterocycle ring. Representative examples of bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4-, 5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. Examples of a spiroheterocycle include, but are not limited to, 5-oxaspiro[3,4]octane and 8-azaspiro[4.5]decane. The monocyclic and bicyclic heterocycle groups of the present invention may contain an alkylene bridge of 1, 2, 3, or 4 carbon atoms, linking two non-adjacent atoms of the group. Examples of such a bridged heterocycle include, but are not limited to, 2-azabicyclo[2.2.1]heptanyl, 2-azabicyclo[2.2.2]octanyl, 1,2,3,4-tetrahydro-1,4-methanoisoquinolinyl, and oxabicyclo[2.2.1]heptanyl. The monocyclic, bicyclic, and spirocyclic heterocycle groups are connected to the parent molecular moiety through any substitutable carbon atom or any substitutable nitrogen atom contained within the group.

Terms such as "alkyl," "cycloalkyl," "alkylene," etc. may be preceded by a designation indicating the number of atoms present in the group in a particular instance (e.g., "$C_3$-$C_{10}$alkyl," "$C_3$-$C_{10}$cycloalkyl," "$C_2$-$C_6$alkynylene," "$C_2$-$C_6$alkenylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_3$-$C_{10}$," the members of the group that follows may have any number of carbon atoms falling within the recited range. A "$C_3$-$C_{10}$alkyl," for example, is an alkyl group having from 3 to 10 carbon atoms, however arranged.

Compounds

According to a general aspect of the present invention, there are provided compounds useful as $EP_4$ receptor agonists, as well as compositions and methods relating thereto. Compounds of the invention have the structure set forth in formula (I), (Ia), or (II).

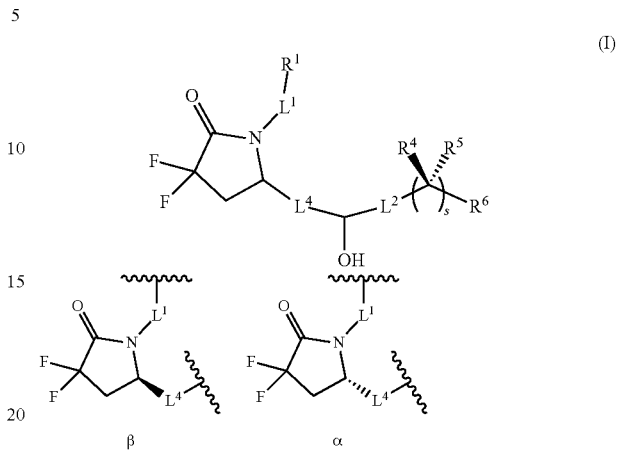

Formula (I) refers to compounds having either β stereochemistry or a substantially equal mixture of β and α stereochemistries at the γ-position of the lactam ring. Excluded are compounds having pure or substantially pure α stereochemistry at the γ-position, as compounds possessing the α stereochemistry at the γ-position have been found to lack appreciable activity as $EP_4$ receptor agonists.

In some embodiments of the invention, $L^1$ is $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents. In other embodiments, $L^1$ is $C_3$-$C_7$alkylene, optionally substituted. In some groups of compounds, $L^1$ is n-pentylene, n-hexylene, or n-heptylene each optionally substituted with 1, 2, 3, or 4 fluoro substituents. In subgroups of compounds, $L^1$ is n-hexylene.

In other embodiments, $L^1$ is —$(CH_2)_t$-G-$(CH_2)_p$—; wherein t, p, and G are as defined herein. In some groups of compounds, t and p are both 0. In other groups of compounds, t is 0 and p is 0, 1, 2, or 3. In still other groups of compounds, p is 0 and t is 0, 1, or 2.

In other embodiments, $L^1$ is —$(CH_2)_n$-$G^1$-$(CH_2)_p$—, wherein $G^1$ is as defined herein, n is 1, 2, 3, 4, or 5 and p is 1, 2, or 3.

In still other embodiments, $L^1$ is —$(CH_2)_n$-$G^2$-$(CH_2)_p$—, —$(CH_2)_n$—C≡C-$G^2$-, or —$(CH_2)_n$—C(H)=C(H)-$G^2$- wherein $G^2$, n and p are as defined herein.

In still other embodiments, $L^1$ is —$(CH_2)_3$-$G^2$-$(CH_2)_p$—, —$CH_2$—C≡C-$G^2$-, or —$CH_2$—C(H)=C(H)-$G^2$-.

In still other embodiments, $L^1$ is —$(CH_2)_3$-$G^2$-, —$CH_2$—C≡C-$G^2$-, or —$CH_2$—C(H)=C(H)-$G^2$-.

In some embodiments $L^1$ is —$(CH_2)_n$-$G^2$-$(CH_2)_n$—. For example, in some groups of compounds, $G^2$ is

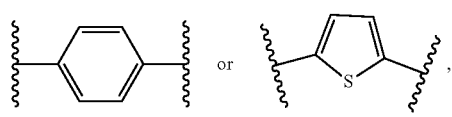

n is 2 and p is 0. In other groups, $G^2$ is

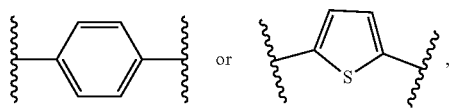

n is 3 and p is 0. In still other groups, $G^2$ is

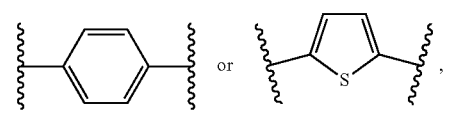 [SMILES: *c1ccc(*)cc1 ; *c1ccc(*)s1]

n is 2 and p is 0, 1, 2, or 3. In yet other groups, $G^2$ is

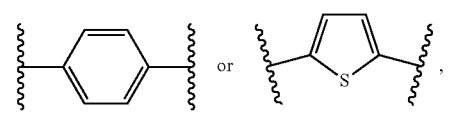 [SMILES: *c1ccc(*)cc1 ; *c1ccc(*)s1]

p is 0, and n is 2, 3, 4, or 5. In some subgroups, $G^2$ is

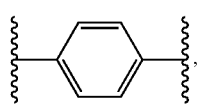

n is 2 and p is 0. In other subgroups, $G^2$ is

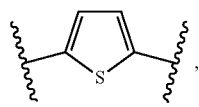 [SMILES: *c1ccc(*)s1]

n is 3 and p is 0. In other subgroups, $G^2$ is

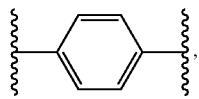

n is 1 and p is 1.

In still other embodiments, $L^1$ is —$(CH_2)_n$—C≡C-$G^2$- or —$(CH_2)_n$—C(H)═C(H)-$G^2$-. For example, in some groups of compounds $G^2$ is

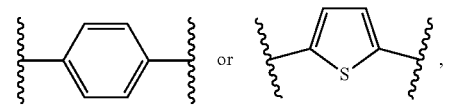

and n is 1. In certain subgroups of compounds $G^2$ is

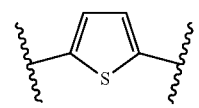 [SMILES: *c1ccc(*)s1]

and n is 1. In other subgroups, $L^1$ is —$(CH_2)_n$—C≡C-$G^2$-, $G^2$ is

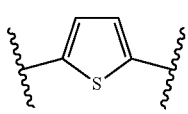 [SMILES: *c1ccc(*)s1]

and n is 1. In still other subgroups, $L^1$ is —$(CH_2)_n$—C(H)═C(H)-$G^2$-, $G^2$ is

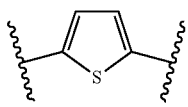 [SMILES: *c1ccc(*)s1]

and n is 1.

In compounds of formula (I), (Ia), or (II), $R^1$ is $COOR^{10}$, $CONR^{10}R^{11}$, $CH_2OR^{10}$, $SO_3R^{10}$, $SO_2NR^{10}R^{11}$, $PO(OR^{10})_2$, or tetrazol-5-yl; wherein $R^{10}$ is H, $C_1$-$C_4$ alkyl (e.g., methyl, ethyl) or aryl (e.g., phenyl) and $R^{11}$ is H, $C_1$-$C_4$ alkyl (e.g., methyl, ethyl), $COR^{12}$, $OR^{10}$, or $SO_2R^{12}$; wherein $R^{12}$ is $C_1$-$C_4$ alkyl (e.g., methyl, ethyl). In one group of compounds, $R^1$ is COOH or $COOCH_3$. In another group of compounds, $R^1$ is COOH.

In compounds of formula (I) or (Ia), $L^4$ is —$C(R^2)_2$—$C(R^3)_2$—, —$C(R^2)$═$C(R^3)$—, C≡C—, or

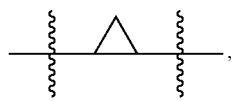

wherein $R^2$ and $R^3$ are each H, $CH_3$, fluoro, or chloro. In some embodiments, $L^4$ is —$C(R^2)_2$—$C(R^3)_2$— and $R^2$ and $R^3$ are each hydrogen. In other embodiments, $L^4$ is —$C(R^2)$═$C(R^3)$— and $R^2$ and $R^3$ are each independently H, $CH_3$, fluoro or chloro. In some groups of compounds, $L^4$ is —$C(R^2)$═$C(R^3)$— and $R^2$ and $R^3$ are hydrogen. In certain subgroups, $L^4$ is In other embodiments, $L^4$ is —C≡C—. In yet other embodiments, $L^4$ is In compounds of formula (I) or (Ia), $L^2$ is —$CH_2$— or a bond. In some embodiments, $L^2$ is a bond.

In compounds of formula (I), (Ia), or (II), $R^4$ and $R^5$ are each independently H, F, $CF_3$, or $C_1$-$C_4$ alkyl (e.g., methyl, ethyl, etc.); or $R^4$ and $R^5$ together with the carbon to which they are attached form a $C_3$-$C_5$ cycloalkyl (e.g., cyclopropyl),

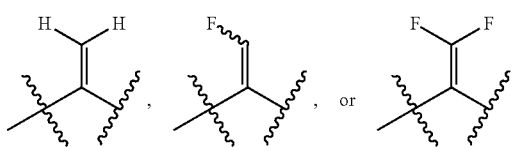

In some embodiments, $R^4$ and $R^5$ are each independently hydrogen or $CH_3$. In other embodiments $R^4$ is $C_1$-$C_4$ alkyl (e.g., methyl, ethyl, etc.) and $R^5$ is hydrogen. In yet other embodiments, $R^4$ is hydrogen and $R^5$ is $C_1$-$C_4$ alkyl (e.g., methyl, ethyl, etc.). In still other embodiments, $R^4$ and $R^5$ are fluoro. In some embodiments, $R^4$ is methyl and $R^5$ is hydrogen. In other embodiments, $R^4$ is hydrogen and $R^5$ is methyl.

In the compounds of formula (I), (Ia), or (II), the stereochemistry of the hydroxyl group on the lower chain may be either α or β or a mixture of α and β.

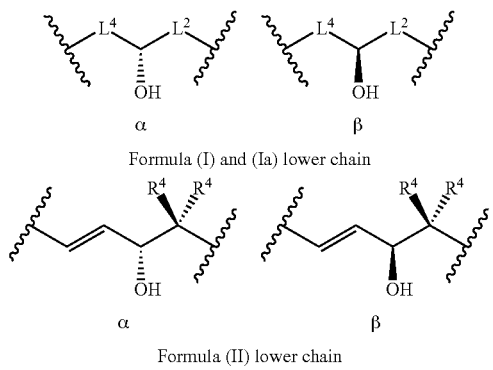

Formula (I) and (Ia) lower chain

Formula (II) lower chain

In some embodiments of the invention, $R^6$ is aryl or heteroaryl, each optionally substituted as described herein. In some groups of compounds, $R^6$ is aryl, optionally substituted as described herein. In some groups of compounds, $R^6$ is phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$). In other embodiments of the invention, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, each optionally substituted as described herein. In other embodiments, $R^6$ is $C_3$-$C_{10}$alkyl (e.g., propyl, butyl, pentyl, octyl, etc.). In some groups of compounds, $R^6$ is n-propyl, n-butyl, or n-pentyl. In a particular subgroups of compounds, $R^6$ is n-butyl. In other embodiments, $R^6$ is $C_3$-$C_{10}$alkynyl (e.g., propynyl, butynyl, pentynyl, hexynyl, etc.). In some groups of compounds, $R^6$ is but-2-yn-1-yl, pent-2-yn-1-yl, or hex-2-yn-1-yl. In particular subgroups, $R^6$ is pent-2-yn-1-yl.

In some embodiments, $R^6$ is $L^3$-$R^7$, where $L^3$ and $R^7$ are as defined herein. In other embodiments, $L^3$ is $C_1$-$C_6$alkylene, $C_2$-$C_6$alkenylene, or $C_2$-$C_6$alkynylene. The $C_1$-$C_6$alkylene, $C_2$-$C_6$alkenylene, and $C_2$-$C_6$alkynylene are optionally substituted with 1, 2, 3, or 4 fluoro substituents. In further embodiments, $L^3$ is $C_1$-$C_6$alkylene (e.g., propylene, butylene, pentylene, etc.), optionally substituted. In further embodiments, $L^3$ is $C_1$-$C_6$alkylene, where the $C_1$-$C_6$alkylene is a straight chain alkylene group. For, example, in some groups of compounds, $L^3$ is n-propylene, n-butylene, or n-pentylene. In still other embodiments, $L^3$ is $C_2$-$C_6$alkenylene (e.g., propenylene, butenylene, etc.). In other embodiments $L^3$ is $C_2$-$C_6$alkynylene (e.g., propynylene, butynylene, etc.). In other embodiments, $L^3$ is —$CH_2$—C≡C—.

In still further embodiments $L^3$ is —$(CH_2)_m$-$G^3$-$(CH_2)_q$—, —$(CH_2)_m$-$G^4$-$(CH_2)_q$—, or -$G^5$-C≡C—; wherein m and q are each independently 0, 1, 2, or 3 and m+q=0, 1, 2, 3, or 4. In one embodiment, $L^3$ is —$(CH_2)_m$-$G^3$-$(CH_2)_q$— and m, q, and $G^3$ are as defined herein. In another embodiment, $L^3$ is —$(CH_2)_m$-$G^4$-$(CH_2)_q$— and m, q, and $G^4$ are as defined herein. In one embodiment, $G^4$ is

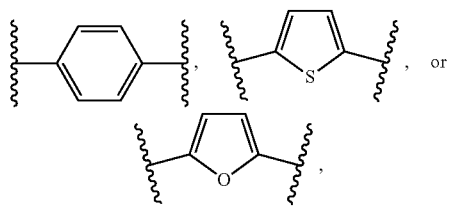

each optionally substituted as described herein. In another embodiment, $G^4$ is

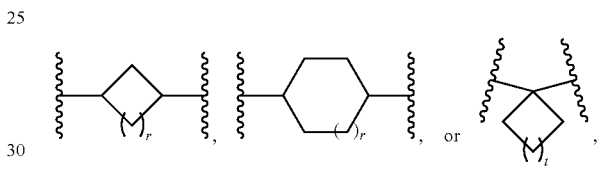

each optionally substituted as described herein. In another embodiment, $L^3$ is -$G^5$-C≡C—, wherein $G^5$ is as defined herein. In one embodiment, $G^5$ is

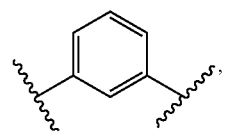 [SMILES: *c1cccc(*)c1]

optionally substituted as described herein. In another embodiment, $G^5$ is

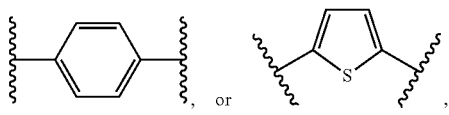 [SMILES: *c1ccc(*)cc1 ; *c1ccc(*)s1]

each optionally substituted as described herein. In another embodiment, $G^5$ is

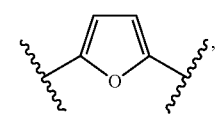 [SMILES: *c1ccc(*)o1]

optionally substituted as described herein.

In compounds of formula (I), (Ia), or (II), $R^7$ is $C_3$-$C_5$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein $R^7$ is optionally substituted as described herein. In some embodiments, $R^7$ is aryl, optionally substituted. In other embodiments, $R^7$ is phenyl, optionally substituted. In some groups of compounds, $R^7$ is phenyl.

In one aspect of the invention are compounds of formula (I), (Ia), or (II), wherein $L^1$-$R^1$ is $C_3$-$C_7$alkylene-$R^1$, wherein the $C_3$-$C_7$alkylene is optionally substituted with 1, 2, 3, or 4 fluoro substituents; or $L^1$-$R^1$ is —$(CH_2)_n$-$G^2$-$(CH_2)_p$—$R^1$, —$(CH_2)_n$—C≡C-$G^2$-$R^1$, or —$(CH_2)_n$—C(H)=C(H)-$G^2$-$R^1$, wherein n is 1, 2, 3, 4, or 5, p is 0, 1, 2, or 3, and n+p=1, 2, 3, 4, 5, or 6; $G^2$ is

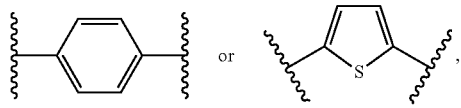

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy; $R^1$ is COOR$^{10}$; and $R^{10}$ is H or $C_1$-$C_4$ alkyl. In one embodiment of this aspect of the invention $L^1$-$R^1$ is n-hexylene-COOR$^{10}$, —$(CH_2)_n$-$G^2$-$(CH_2)_p$—COOR$^{10}$, —$(CH_2)_n$—C≡C-$G^2$-COOR$^{10}$, or —$(CH_2)_n$—C(H)=C(H)-$G^2$-COOR$^{10}$; wherein n is 1, 2 or 3, p is 0 or 1; $G^2$ is

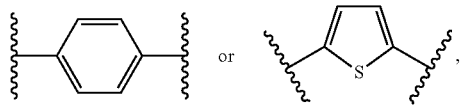 [SMILES: *c1ccc(*)cc1 ; *c1ccc(*)s1]

and $R^{10}$ is H or $CH_3$.

In one embodiment of this aspect of the invention, $L^1$-$R^1$ is $C_3$-$C_7$alkylene-$R^1$ and the $C_3$-$C_7$alkylene is optionally substituted with 1-4 fluoro substituents. In one group of compounds, for example, $L^1$-$R^1$ is n-pentylene-COOR$^{19}$, n-hexylene-COOR$^{10}$, n-heptylene-COOR$^{10}$, etc., and $R^{19}$ is H or $CH_3$. In one embodiment, $L^1$-$R^1$ is n-hexylene-COOH or n-hexylene-COOCH$_3$.

In another embodiment of this aspect of the invention, $L^1$-$R^1$ is —$(CH_2)_n$-$G^2$-$(CF_{12})_p$—$R^1$; and $G^2$ is

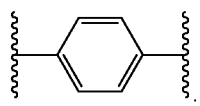 [SMILES: *c1ccc(*)cc1]

In another embodiment, $L^1$-$R^1$ is —$(CH_2)_n$-$G^2$-COOR$^{19}$ (i.e., p is 0), $G^2$ is

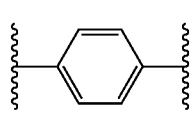

n is 2 or 3, and $R^{10}$ is H or $CH_3$. In one embodiment, $L^1$-$R^1$ is

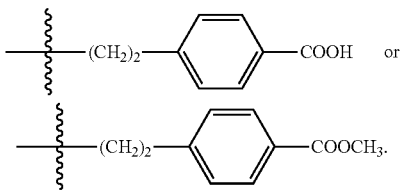

In another embodiment, $L^1$-$R^1$ is

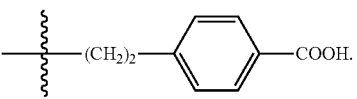

In another embodiment of this aspect of the invention $L^1$-$R^1$ is —$(CH_2)_n$-$G^2$-$(CH_2)_p$—$R^1$ and $G^2$ is

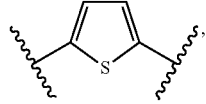 [SMILES: *c1ccc(*)s1]

In another embodiment, $L^1$-$R^1$ is —$(CH_2)_n$-$G^2$-COOR$^{19}$ (i.e., p is 0), $G^2$ is

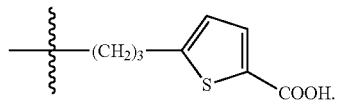

n is 2 or 3; and $R^{19}$ is H or $CH_3$. In still another embodiment, $L^1$-$R^1$ is

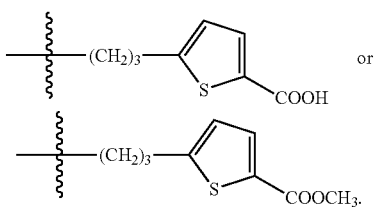

In yet another embodiment, $L^1$-$R^1$ is

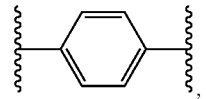 [SMILES: *c1ccc(*)cc1]

In another embodiment, $L^1$-$R^1$ is —$CH_2$-$G^2$-$CH_2$—COOR$^{19}$, $G^2$ is and $R^{10}$ is H or $CH_3$. In another embodiment, $L^1$-$R^1$ is —$CH_2$-$G^2$-$CH_2$—$COOR^{10}$, $G^2$ is

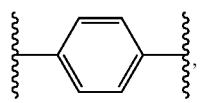

and $R^9$ is H.

In still another embodiment of this aspect of the invention, $L^1$-$R^1$ is —$(CH_2)_n$—C≡C-$G^2$-$COOR^{19}$ and $G^2$ is

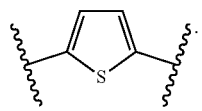 [SMILES: *c1ccc(*)s1]

In yet another embodiment, $L^1$-$R^1$ is —$(CH_2)_n$—C≡C-$G^2$-$COOR^{10}$, $G^2$ is

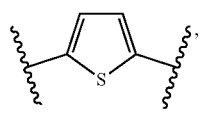 [SMILES: *c1ccc(*)s1]

n is 1, and $R^{10}$ is H or $CH_3$. In another embodiment, $L^1$-$R^1$ is —$(CH_2)_n$—C≡C-$G^2$-$COOR^{10}$, $G^2$ is

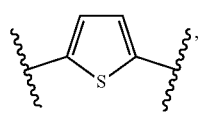

n is 1, and $R^{10}$ is H.

In another embodiment of this aspect of the invention, $L^1$-$R^1$ is —$(CH_2)_n$—C(H)=C(H)-$G^2$-$COOR^{10}$ and $G^2$ is

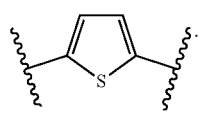 [SMILES: *c1ccc(*)s1]

In another embodiment, $L^1$-$R^1$ is —$(CH_2)_n$—C(H)=C(H)-$G^2$-$COOR^{10}$, $G^2$ is

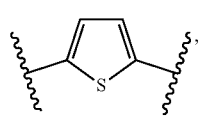

n is 1, and $R^{10}$ is H or $CH_3$. In another embodiment, $L^1$-$R^1$ is —$(CH_2)_n$—C(H)=C(H)-$G^2$-$COOR^{10}$, $G^2$ is

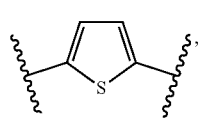

n is 1, and $R^{10}$ is H.

In another aspect of the invention are compounds of formula (I) or (Ia), wherein

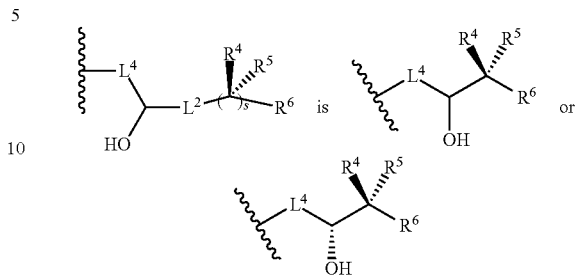

(i.e., $L^2$ is a bond and s is 1), $R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, (each optionally substituted as described herein) and $L^4$, $R^4$, and $R^5$ are as defined herein. In a first embodiment of this aspect of the invention, $L^4$ is

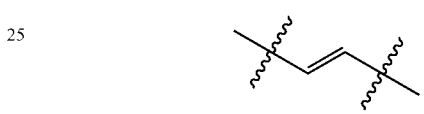

and $R^4$ and $R^5$ are independently H or $CH_3$. In one group of compounds according to the first embodiment, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl. In another group of compounds of this embodiment, $R^6$ is $C_3$-$C_{10}$alkyl (e.g., propyl, butyl, pentyl, octyl, etc.). In a subgroup of compounds, $R^6$ is n-propyl, n-butyl, or n-pentyl. In another subgroup, $R^6$ is n-butyl. In another group of compounds of the first embodiment, $R^6$ is $C_3$-$C_{10}$alkynyl (e.g., propynyl, butynyl, pentynyl, hexynyl, etc.). In a subgroup of compounds, $R^6$ is but-2-yn-1-yl, pent-2-yn-1-yl, or hex-2-yn-1-yl. In another subgroup, $R^6$ is pent-2-yn-1-yl. In another group of compounds according to the first embodiment, $R^6$ is aryl or heteroaryl, each optionally substituted as described herein. In one group of compounds, $R^6$ is phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$). In a second embodiment of this aspect of the invention, $L^4$ is —$CH_2$—$CH_2$— and $R^4$ and $R^5$ are independently H or $CH_3$. In a third embodiment of this aspect of the invention $L^4$ is —C≡C— and $R^4$ and $R^5$ are independently H or $CH_3$. In a fourth embodiment of this aspect of the invention, $L^4$ is

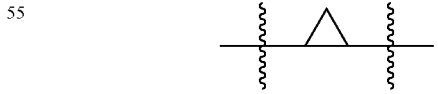

and $R^4$ and $R^5$ are independently H or $CH_3$. Groups of compounds according to the second, third, and fourth embodiments include those where $R^6$ is $C_3$-$C_{10}$alkyl (e.g., propyl, butyl, pentyl, octyl, etc.), $C_3$-$C_{10}$alkynyl (e.g., propynyl, butynyl, pentynyl, hexynyl, etc.), or phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$).

In another aspect of the invention are compounds of formula (I) or (Ia), wherein

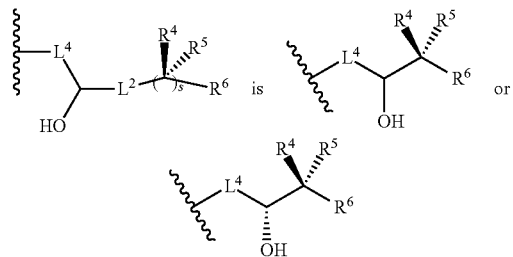 is (i.e., $L^2$ is a bond, s is 1, and $R^4$ and $R^5$ are fluoro), $R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, (each optionally substituted as described herein), and $L^4$ is as defined herein. In a first embodiment according to this aspect of the invention, $L^4$ is

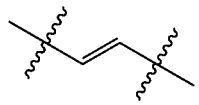 [SMILES: */C=C/*]

and $R^6$ is aryl, optionally substituted as describe herein. In one group of compounds according to the first embodiment $R^6$ is phenyl, optionally substituted. In another group of compounds $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl.

In another aspect of the invention are compounds of formula (I) or (Ia), wherein

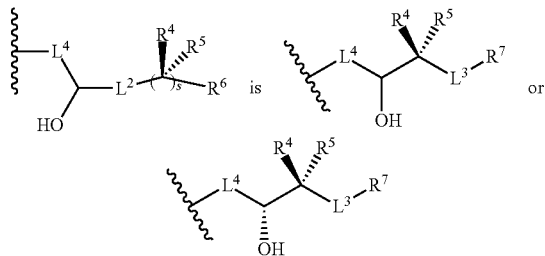

(i.e., $L^2$ is a bond, s is 1, and $R^6$ is $L^3$-$R^7$), $L^3$ is $C_1$-$C_6$alkylene, $C_2$-$C_6$alkenylene, or $C_2$-$C_6$alkynylene (each optionally substituted with 1, 2, 3, or 4 fluoro substituents), and $L^4$, $R^4$, $R^5$, and $R^7$ are as defined herein. In a first embodiment of this aspect of the invention, $L^4$ is

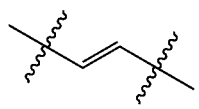 [SMILES: */C=C/*]

and $R^4$ and $R^5$ are independently H or $CH_3$. In one group of compounds according to the first embodiment, $R^7$ is $C_3$-$C_8$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein $R^7$ is optionally substituted as described herein. In one group of compounds of this embodiment, $L^3$ is $C_1$-$C_6$alkylene (e.g., propylene, butylene, pentylene, etc.) and $R^7$ is phenyl, naphthyl, thienyl, or cyclohexyl, each optionally substituted. In another group of compounds of this embodiment, $L^3$ is $C_1$-$C_6$alkylene (e.g., propylene, butylene, pentylene, etc.), where the $C_1$-$C_6$alkylene is a straight chain alkylene group, and $R^7$ is phenyl optionally substituted. In a subgroup of compounds $L^3$ is n-propylene, n-butylene, or n-pentylene and $R^7$ is phenyl. In another group of compounds of this embodiment, $L^3$ is $C_2$-$C_6$alkenylene (e.g., propenylene, butenylene, etc.) and $R^7$ is phenyl, naphthyl, thienyl, or cyclohexyl, each optionally substituted. In another group of compounds of this embodiment, $L^3$ is $C_2$-$C_6$alkynylene (e.g., propynylene, butynylene, etc.) and $R^7$ is phenyl, naphthyl, thienyl, or cyclohexyl, each optionally substituted. In a subgroup of compounds, $L^3$ is —$CH_2$—C≡C—, and $R^7$ is phenyl. In a second embodiment of this aspect of the invention, $L^4$ is —$CH_2$—$CH_2$— and $R^4$ and $R^5$ are independently H or $CH_3$. In a third embodiment of this aspect of the invention $L^4$ is —C≡C— and $R^4$ and $R^5$ are independently H or $CH_3$. In a fourth embodiment of this aspect of the invention, $L^4$ is

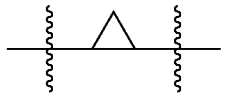 [SMILES: *C1CC1*]

and $R^4$ and $R^5$ are independently H or $CH_3$. Groups of compounds according to the second, third, and fourth embodiments include those where $L^3$ is $C_2$-$C_6$alkylene (e.g., propylene, butylene, pentylene, etc.), $C_2$-$C_6$alkenylene (e.g., propenylene, butenylene, etc.), or $C_2$-$C_6$alkynylene (e.g., propynyl, butynyl, etc.), and $R^7$ is phenyl, naphthyl, thienyl, or cyclohexyl, each optionally substituted.

In another aspect of the invention,

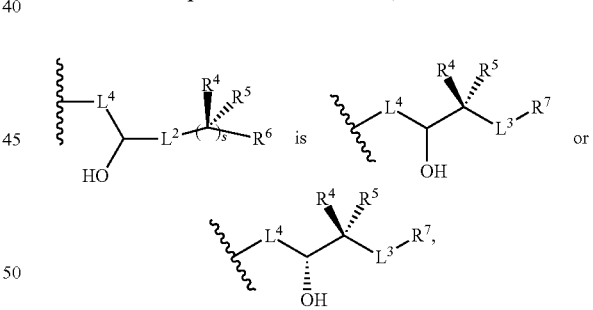

$L^3$ is —$(CH_2)_m$-$G^3$-$(CH_2)_q$—, —$(CH_2)_m$-$G^4$-$(CH_2)_q$—, or -$G^5$-C≡C—; and $L^4$, $G^3$, $G^4$, $G^5$, $R^4$, $R^5$, $R^7$, m, and q are as defined herein. In a first embodiment of this aspect of the invention, $L^4$ is

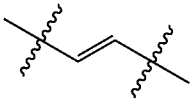 [SMILES: */C=C/*]

and $R^4$ and $R^5$ are independently H or $CH_3$. In one group of compounds according to the first embodiment, $L^3$ is -$G^5$-C≡C—, $G^5$ is

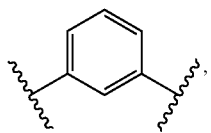 [SMILES: *c1cccc(*)c1]

and R$^7$ is C$_3$-C$_8$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein R$^7$ is optionally substituted as described herein.

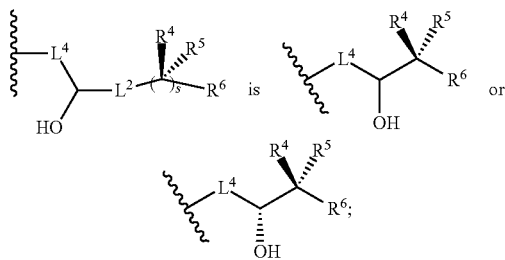

In another aspect of the invention,

L$^4$ is —C(R$^2$)=C(R$^3$)—; R$^2$ and R$^3$ are each hydrogen; R$^4$ and R$^5$ are independently H or C$_1$-C$_4$ alkyl; R$^6$ is C$_3$-C$_{10}$alkyl, C$_3$-C$_{10}$alkynyl, or L$^3$-R$^7$; L$^3$ is C$_1$-C$_6$alkylene or C$_2$-C$_6$alkynylene; wherein the C$_1$-C$_5$alkylene and C$_2$-C$_6$alkynylene are optionally substituted with 1, 2, 3, or 4 fluoro substituents; and R$^7$ is aryl, wherein R$^7$ is optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy, and —C$_1$-C$_3$alkylene-C$_1$-C$_3$alkoxy.

In another aspect of the invention are compounds of formula (I) or (Ia), wherein:

L$^1$-R$^1$ is C$_3$-C$_7$alkylene-R$^1$, wherein the C$_3$-C$_7$alkylene is optionally substituted with 1, 2, 3, or 4 fluoro substituents; or L$^1$-R$^1$ is —(CH$_2$)$_n$-G$^2$-(CH$_2$)$_p$—R$^1$, —(CH$_2$)$_n$—, —C≡C-G$^2$-R$^1$, or —(CH$_2$)$_n$—C(H)=C(H)-G$^2$-R$^1$, wherein n is 1, 2, 3, 4, or 5, p is 0, 1, 2, or 3, and n+p=1, 2, 3, 4, 5, or 6; G$^2$ is

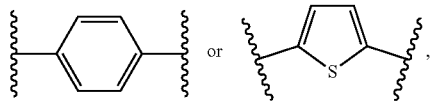

wherein G$^2$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy; R$^1$ is COOR$^{10}$; R$^{10}$ is H or 01-04 alkyl; and

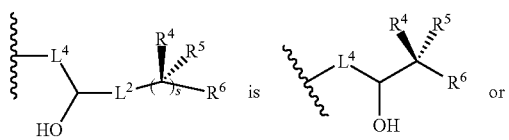

-continued

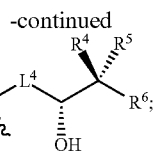

L$^4$ is —C(R$^2$)$_2$—C(R$^3$)$_2$—, —C(R$^2$)=C(R$^3$)—, —C≡C—, or

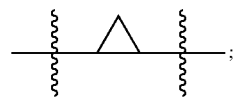

wherein R$^2$ and R$^3$ are each H, CH$_3$, fluoro, or chloro; R$^4$ and R$^5$ are each independently H, F, CF$_3$, or C$_1$-C$_4$ alkyl; or R$^4$ and R$^5$ together with the carbon to which they are attached form a C$_3$-C$_5$ cycloalkyl; R$^6$ is aryl, C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, C$_3$-C$_{10}$haloalkynyl, or L$^3$-R$^7$; L$^3$ is C$_1$-C$_6$alkylene, C$_2$-C$_6$alkenylene, or C$_2$-C$_6$alkynylene wherein the C$_1$-C$_6$alkylene, C$_2$-C$_6$alkenylene, and C$_2$-C$_6$alkynylene are optionally substituted with 1, 2, 3, or 4 fluoro substituents; and R$^7$ is aryl, wherein R$^7$ is optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy, and —C$_1$-C$_3$alkylene-C$_1$-C$_3$alkoxy.

In one embodiment according to the foregoing aspect of the invention, L$^4$ is

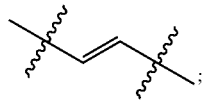 [SMILES: */C=C/*]

R$^4$ and R$^5$ are independently H or C$_1$-C$_4$ alkyl; R$^6$ is C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, C$_3$-C$_{10}$haloalkynyl, or L$^3$-R$^7$; L$^3$ is C$_1$-C$_6$alkylene, C$_2$-C$_6$alkenylene, or C$_2$-C$_6$alkynylene; wherein the C$_1$-C$_6$alkylene, C$_2$-C$_6$alkenylene, and C$_2$-C$_6$alkynylene are optionally substituted with 1, 2, 3, or 4 fluoro substituents; and R$^7$ is aryl, wherein R$^7$ is optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy, and —C$_1$-C$_3$alkylene-C$_1$-C$_3$alkoxy.

In one group of compounds according to the foregoing embodiment, L$^1$-R$^1$ is C$_3$-C$_7$alkylene-R$^1$; or L$^1$-R$^1$ is —(CF$_{12}$)$_n$-G$^2$-(CH$_2$)$_p$—R$^1$, —(CH$_2$)$_n$—C≡C-G$^2$-R$^1$, or —(CH$_2$)$_n$—C(H)=C(H)-G$^2$-R$^1$, wherein n is 1, 2 or 3, p is 0, 1, or 2, and n+p=1, 2, 3 or 4; G$^2$ is

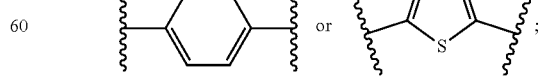

R$^1$ is COOR$^{10}$; R$^{10}$ is H or C$_1$-C$_4$ alkyl; R$^4$ and R$^5$ are independently H or CH$_3$; L$^3$ is ethynylene, propynylene, or butynylene; and R$^6$ is phenyl or C$_1$-C$_6$alkyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

In one group of compounds according to the foregoing embodiment, $L^1$-$R^1$ is $C_3$-$C_7$alkylene-$R^1$; or $L^1$-$R^1$ is —$(CH_2)_n$-$G^2$-$(CH_2)_p$—$R^1$, wherein n is 2 or 3 and p is 0; $G^2$ is

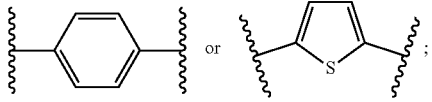

$R^1$ is $COOR^{10}$; and $R^{10}$ is H or $C_1$-$C_4$ alkyl.

In one group of compounds according to the foregoing embodiment, $R^4$ and $R^5$ are independently H or $CH_3$; $R^6$ is $C_3$-$C_{10}$alkyl, $C_3$-$C_{10}$alkynyl, or $L^3$-$R^7$; $L^3$ is $C_1$-$C_6$alkylene or $C_2$-$C_6$alkynylene; wherein the $C_1$-$C_6$alkylene and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy. In one subgroup of compounds, $L^1$ is $C_3$-$C_7$alkylene or —$(CH_2)_n$-$G^2$-$(CH_2)_p$—, wherein n is 2 or 3 and p is 0; and $G^2$ is

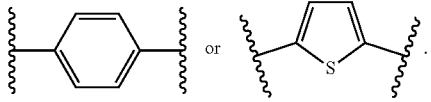

In another subgroup of compounds, $L^1$ is $C_3$-$C_7$alkylene or —$(CH_2)_n$-$G^2$-; n is 2 or 3; $G^2$ is

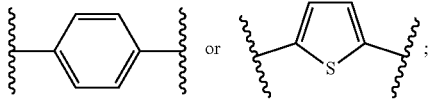

$R^6$ is propyl, butyl, pentyl, propynyl, butynyl, pentynyl, hexynyl, or $L^3$-$R^7$; $L^3$ is propylene, butylene, pentylene, propynylene, or butynylene; and $R^7$ is phenyl or phenyl optionally substituted. In another subgroup of compounds, $L^1$ is $C_3$-$C_7$alkylene and $R^6$ is propyl, butyl, pentyl, propynyl, butynyl, pentynyl, or hexynyl. In another subgroup of compounds, $L^1$ is $C_3$-$C_7$alkylene and $R^6$ is $L^3$-$R^7$; $L^3$ is propylene, butylene, pentylene, propynylene, or butynylene; and $R^7$ is phenyl or phenyl optionally substituted. In another subgroup of compounds, $L^1$ is —$(CH_2)_n$-$G^2$-, wherein n is 2 or 3; $G^2$ is

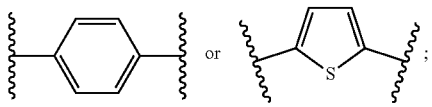 [SMILES: *c1ccc(*)cc1 ; *c1ccc(*)s1]

and $R^6$ is propyl, butyl, pentyl, propynyl, butynyl, pentynyl, or hexynyl. In another subgroup of compounds, $L^1$ is —$(CH_2)_n$-$G^2$-, wherein n is 2 or 3; $G^2$ is

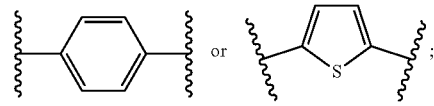 [SMILES: *c1ccc(*)cc1 ; *c1ccc(*)s1]

and $R^6$ is $L^3$-$R^7$; $L^3$ is propylene, butylene, pentylene, propynylene, or butynylene; and $R^7$ is phenyl or phenyl optionally substituted. In a further subgroup, $L^1$ is n-hexylene or —$(CH_2)_n$-$G^2$-, wherein n is 2 or 3; $G^2$ is

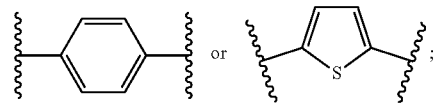

$R^1$ is $COOR^{10}$; $R^{10}$ is H or $CH_3$; $R^6$ is n-butyl, but-2-yn-1-yl, pent-2-yn-1-yl, hex-2-yn-1-yl, or $L^3$-$R^7$; $L^3$ is n-propylene, n-butylene, or n-pentylene or —$CH_2$—$C≡C$—; and $R^7$ is phenyl or phenyl optionally substituted. In another subgroup of compounds, $L'$ is n-hexylene; $R^1$ is $COOR^{10}$; $R^{10}$ is H or $CH_3$; and $R^6$ is n-butyl, but-2-yn-1-yl, pent-2-yn-1-yl, or hex-2-yn-1-yl. In another subgroup of compounds, $L^1$ is n-hexylene; $R^1$ is $COOR^{10}$; $R^{10}$ is H or $CH_3$; and $R^6$ is $L^3$-$R^7$; $L^3$ is n-propylene, n-butylene, n-pentylene or —$CH_2$—$C≡C$—; and $R^7$ is phenyl or phenyl optionally substituted. In another subgroup of compounds, $L^1$ is —$(CH_2)_n$-$G^2$-, wherein n is 2 or 3; $G^2$ is

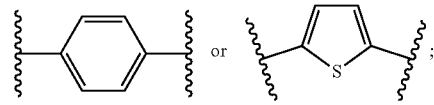 [SMILES: *c1ccc(*)cc1 ; *c1ccc(*)s1]

$R^1$ is $COOR^{10}$; $R^{10}$ is H or $CH_3$; and $R^6$ is n-butyl, but-2-yn-1-yl, pent-2-yn-1-yl or hex-2-yn-1-yl. In another subgroup of compounds, $L^1$ is —$(CH_2)_n$-$G^2$-, wherein n is 2 or 3; $G^2$ is

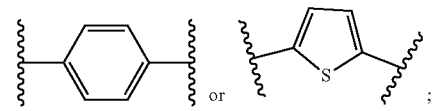

$R^1$ is $COOR^{10}$; $R^{10}$ is H or $CH_3$; and $R^6$ is $L^3$-$R^7$; $L^3$ is n-propylene, n-butylene, n-pentylene or —$CH_2$—$C≡C$—; and $R^7$ is phenyl or phenyl optionally substituted.

In another group of compounds according to the foregoing embodiment, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl. In a subgroup of compounds, $L^1$ is $C_3$-$C_7$alkylene, wherein the alkylene is optionally substituted with 1, 2, 3, or 4 fluoro substituents. In a further subgroup, $R^6$ is $C_3$-$C_{10}$alkyl, $C_3$-$C_{10}$alkenyl, or $C_3$-$C_{10}$alkynyl; and $L^1$ is $C_3$-$C_7$alkylene. In another subgroup, $L^1$ is —$(CH_2)_n$-$G^2$-$(CH_2)_p$—, —$(CH_2)_n$—$C≡C$-$G^2$-, or —$(CH_2)_n$—$C(H)=C(H)$-$G^2$-, wherein n is 1, 2, 3, 4, or 5, p is 0, 1, 2, or 3, and n+p=1, 2, 3, 4, 5, or 6; and $G^2$ is

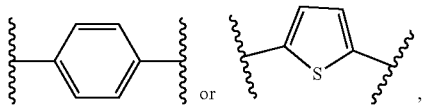 , wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In a further subgroup, $R^6$ is $C_3$-$C_{10}$alkyl, $C_3$-$C_{10}$alkenyl, or $C_3$-$C_{10}$alkynyl; and $L^1$ is —$(CH_2)_n$-$G^2$-$(CH_2)_p$—, wherein n is 2 or 3 and p is 0; and $G^2$ is

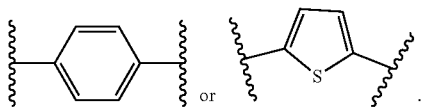 [SMILES: *c1ccc(*)cc1 ; *c1ccc(*)s1] .

In yet another group of compounds according to the foregoing embodiment, $R^6$ is $L^3$-$R^7$; $L^3$ is $C_1$-$C_6$alkylene, $C_2$-$C_6$alkenylene, or $C_2$-$C_6$alkynylene; wherein the $C_1$-$C_6$alkylene, $C_2$-$C_6$alkenylene, and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy. In one subgroup of compounds, $L^1$ is $C_3$-$C_7$alkylene, wherein the $C_3$-$C_7$alkylene is optionally substituted with 1, 2, 3, or 4 fluoro substituents. In a further subgroup of compounds, $R^6$ is $L^3$-$R^7$; $L^3$ is $C_1$-$C_6$alkylene, $C_2$-$C_6$alkenylene, or $C_2$-$C_6$alkynylene; $R^7$ is aryl or optionally substituted aryl; and $L^1$ is $C_3$-$C_7$alkylene. In still another subgroup $R^6$ is $L^3$-$R^7$; $L^3$ is $C_1$-$C_6$alkylene, $C_2$-$C_6$alkenylene, or $C_2$-$C_6$alkynylene; $R^7$ is phenyl or phenyl optionally substituted; and $L^1$ is $C_3$-$C_7$alkylene. In another subgroup, $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

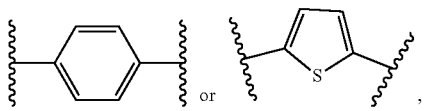 , wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In a further subgroup of compounds, $R^6$ is $L^3$-$R^7$; $L^3$ is $C_1$-$C_6$alkylene, $C_2$-$C_6$alkenylene, or $C_2$-$C_5$alkynylene; $R^7$ is aryl; $L^1$ is —$(CH_2)_n$-$G^2$-$(CH_2)_p$—, wherein n is 2 or 3, and p is 0; and $G^2$ is

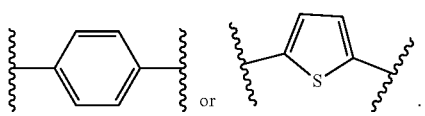 [SMILES: *c1ccc(*)cc1 ; *c1ccc(*)s1] .

In still another subgroup $R^6$ is $L^3$-$R^7$; $L^3$ is $C_1$-$C_6$alkylene, $C_2$-$C_6$alkenylene, or $C_2$-$C_6$alkynylene; $R^7$ is phenyl or phenyl optionally substituted; and $L^1$ is —$(CH_2)_n$-$G^2$-$(CH_2)_p$—, wherein n is 2 or 3, p is 0; and $G^2$ is

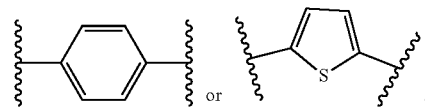 ,

In still another group of compounds according to the foregoing embodiment, $L^1$ is $C_3$-$C_7$alkylene, wherein the $C_3$-$C_7$alkylene is optionally substituted with 1, 2, 3, or 4 fluoro substituents.

In another group of compounds according to the foregoing embodiment, $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

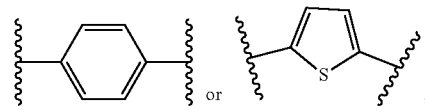 , wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In one subgroup of compounds, $L^1$ is —$(CH_2)_n$-$G^2$-$(CH_2)_p$—, wherein n is 2 or 3, p is 0, and $G^2$ is

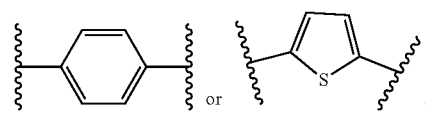 .

In another aspect of the invention are compounds of formula (II)

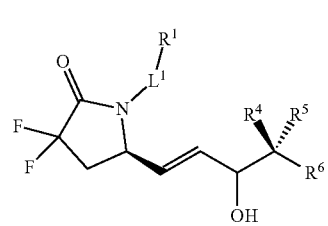

(II)

wherein:

$L^1$ is a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;

b) —$(CH_2)_t$-G-$(CH_2)_p$—; wherein t is 0, 1, or 2, p is 0, 1, 2, or 3, and t+p=0, 1, 2, 3, or 4; or c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{13}$)=C($R^{13}$)-$G^2$-, wherein n is 1, 2, 3, 4, or 5, p is 0, 1, 2, or 3, and n+p=1, 2, 3, 4, 5, or 6;

G is

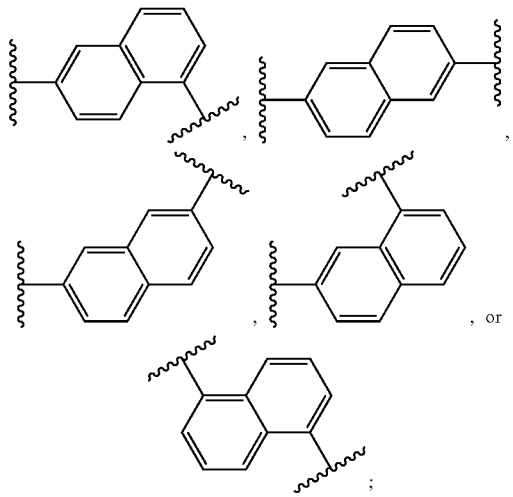
;

$G^1$ is O, C(O), S, S(O), S(O)$_2$, or NR$^8$; wherein R$^8$ is H, C$_1$-C$_4$ alkyl, or C$_1$-C$_4$alkylcarbonyl;
$G^2$ is

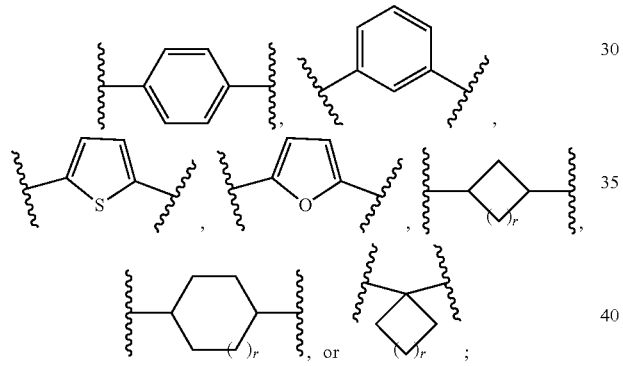

wherein $G^2$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;
R$^1$ is COOR$^{10}$, CONR$^{18}$R$^{11}$, CH$_2$OR$^{10}$, SO$_3$R$^{10}$, SO$_2$NR$^{10}$R$^{11}$, PO(OR$^{10}$)$_2$, or tetrazol-5-yl;
R$^{10}$ is H, C$_1$-C$_4$ alkyl, or aryl;
R$^{11}$ is H, C$_1$-C$_4$ alkyl, COR$^{12}$, OR$^{10}$, or SO$_2$R$^{12}$;
R$^{12}$ is C$_1$-C$_4$ alkyl;
R$^{13}$, at each occurrence, is independently H or C$_1$-C$_4$alkyl;
R$^4$ and R$^5$ are each independently H, F, CF$_3$, or C$_1$-C$_4$ alkyl; or R$^4$ and R$^5$ together with the carbon to which they are attached form a C$_3$-C$_5$ cycloalkyl,

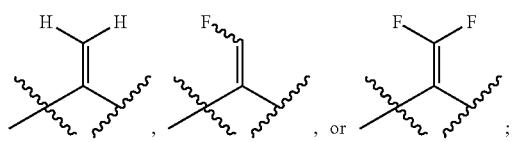

R$^6$ is aryl, heteroaryl, C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, C$_3$-C$_{10}$haloalkynyl, or L$^3$-R$^7$; wherein the aryl and heteroaryl are optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy; and —C$_1$-C$_3$alkylene-C$_1$-C$_3$alkoxy; and wherein the C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, and C$_3$-C$_{10}$haloalkynyl are optionally substituted with a substituent selected from the group consisting of COOR$^{10}$, CONR$^{10}$R$^{11}$, CH$_2$OR$^{10}$, SO$_3$R$^{10}$, SO$_2$NR$^{10}$R$^{11}$, PO(OR$^{10}$)$_2$, and tetrazol-5-yl;
L$^3$ is C$_1$-C$_5$alkylene, C$_2$-C$_6$alkenylene, C$_2$-C$_6$alkynylene, —(CH$_2$)$_m$-G$^3$-(CH$_2$)$_q$—, —(CH$_2$)$_m$-G$^4$-(CH$_2$)$_q$—, or -G$^5$-C≡C—; wherein the C$_1$-C$_5$alkylene, C$_2$-C$_6$alkenylene, and C$_2$-C$_6$alkynylene are optionally substituted with 1, 2, 3, or 4 fluoro substituents; and wherein m and q are each independently 0, 1, 2, or 3 and m+q=0, 1, 2, 3, or 4;
G$^3$ is O, C(O), S, S(O), S(O)$_2$, or NR$^9$; wherein R$^9$ is H, C$_1$-C$_4$ alkyl, or C$_1$-C$_4$alkylcarbonyl;
G$^4$ is

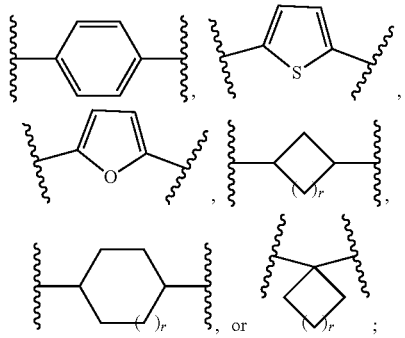

wherein G$^4$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;
G$^5$ is

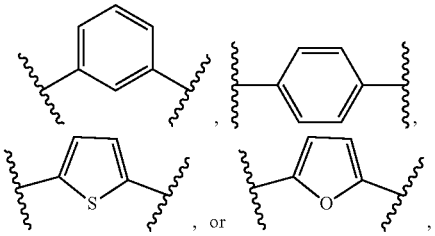

wherein G$^5$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;
R$^7$ is C$_3$-C$_8$cycloalkyl, aryl, heteroaryl, or heterocyclyl; wherein R$^7$ is optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy, and —C$_1$-C$_3$alkylene-C$_1$-C$_3$alkoxy; and r is 0 or 1.

In one embodiment according to the foregoing aspect, L$^1$ is C$_3$-C$_7$alkylene, —(CH$_2$)$_n$-G$^2$-(CH$_2$)$_p$—, —(CH$_2$)$_n$—

C≡C-G$^2$-, or —(CH$_2$)$_n$—C(H)═C(H)-G$^2$-, wherein n is 1, 2, 3, 4, or 5, p is 0, 1, 2, or 3, and n+p=1, 2, 3, 4, 5, or 6; G$^2$ is

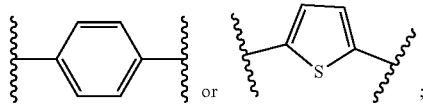 [SMILES: *c1ccc(*)cc1 ; *c1ccc(*)s1]

R$^1$ is COOR$^{10}$; R$^{10}$ is H or C$_1$-C$_4$ alkyl; R$^4$ and R$^5$ are each independently H or C$_1$-C$_4$ alkyl; R$^6$ is C$_3$-C$_{10}$alkyl, C$_3$-C$_{10}$alkenyl, C$_3$-C$_{10}$alkynyl, or L$^3$-R$^7$; L$^3$ is C$_1$-C$_6$alkylene, C$_2$-C$_6$alkynylene, or C$_2$-C$_6$alkynylene; and R$^7$ is aryl, optionally substituted as described herein.

In another embodiment according to the foregoing aspect, L$^1$ is C$_3$-C$_7$alkylene or —(CH$_2$)$_n$-G$^2$-(CH$_2$)$_p$—, wherein n is 2, 3, 4, or 5, p is 0, 1, 2, or 3, and n+p=2, 3, 4, 5, or 6; G$^2$ is

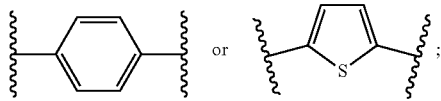 [SMILES: *c1ccc(*)cc1 ; *c1ccc(*)s1]

R$^1$ is COOR$^{10}$; R$^{10}$ is H or C$_1$-C$_4$ alkyl; R$^4$ and R$^5$ are each independently H or C$_1$-C$_4$ alkyl; R$^6$ is C$_3$-C$_{10}$alkyl, C$_3$-C$_{10}$alkenyl, C$_3$-C$_{10}$alkynyl, or L$^3$-R$^7$; L$^3$ is C$_1$-C$_6$alkylene, C$_2$-C$_6$alkynylene, or C$_2$-C$_6$alkynylene; and R$^7$ is aryl, optionally substituted as described herein.

In another embodiment, L$^1$ is C$_3$-C$_7$alkylene or —(CH$_2$)$_n$-G$^2$-(CH$_2$)$_p$—, wherein n is 2 or 3, p is 0; G$^2$ is

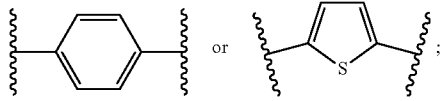 [SMILES: *c1ccc(*)cc1 ; *c1ccc(*)s1]

R$^1$ is COOR$^{10}$; R$^{10}$ is H or C$_1$-C$_4$ alkyl; R$^4$ and R$^5$ are each independently H or C$_1$-C$_4$ alkyl; R$^6$ is C$_3$-C$_{10}$alkyl, C$_3$-C$_{10}$alkynyl, or L$^3$-R$^7$; L$^3$ is C$_1$-C$_6$alkylene, C$_2$-C$_6$alkynylene, or C$_2$-C$_6$alkynylene; and R$^7$ is aryl, optionally substituted as described herein.

In another aspect, the invention provides a compound selected from the group consisting of:
methyl 7-((5R)-3,3-difluoro-5-((E)-3-hydroxy-4-methyloct-1-en-6-yn-1-yl)-2-oxopyrrolidin-1-yl)heptanoate;
methyl 7-((5R)-3,3-difluoro-5-((3S,E)-3-hydroxy-4-methyloct-1-en-6-yn-1-yl)-2-oxopyrrolidin-1-yl)heptanoate;
methyl 7-((R)-3,3-difluoro-5-((3S,4S,E)-3-hydroxy-4-methyloct-1-en-6-yn-1-yl)-2-oxopyrrolidin-1-yl)heptanoate;
methyl 7-((R)-3,3-difluoro-5-((3S,4R,E)-3-hydroxy-4-methyloct-1-en-6-yn-1-yl)-2-oxopyrrolidin-1-yl)heptanoate;
methyl 7-((5R)-3,3-difluoro-5-((3R,E)-3-hydroxy-4-methyloct-1-en-6-yn-1-yl)-2-oxopyrrolidin-1-yl) heptanoate;
methyl 7-((R)-3,3-difluoro-5-((3R,4S,E)-3-hydroxy-4-methyloct-1-en-6-yn-1-yl)-2-oxopyrrolidin-1-yl)heptanoate;
methyl 7-((R)-3,3-difluoro-5-((3R,4R,E)-3-hydroxy-4-methyloct-1-en-6-yn-1-yl)-2-oxopyrrolidin-1-yl)heptanoate;
7-((R)-3,3-difluoro-5-((3S,4S,E)-3-hydroxy-4-methyloct-1-en-6-yn-1-yl)-2-oxopyrrolidin-1-yl)heptanoic acid;
7-((R)-3,3-difluoro-5-((3S,4R,E)-3-hydroxy-4-methyloct-1-en-6-yn-1-yl)-2-oxopyrrolidin-1-yl)heptanoic acid;
7-((R)-3,3-difluoro-5-((3R,4S,E)-3-hydroxy-4-methyloct-1-en-6-yn-1-yl)-2-oxopyrrolidin-1-yl)heptanoic acid;
7-((R)-3,3-difluoro-5-((3R,4R,E)-3-hydroxy-4-methyloct-1-en-6-yn-1-yl)-2-oxopyrrolidin-1-yl)heptanoic acid;
methyl 7-((R)-3,3-difluoro-5-((3S,4S,E)-3-hydroxy-4-methylnon-1-en-6-yn-1-yl)-2-oxopyrrolidin-1-yl)heptanoate;
methyl 7-((R)-3,3-difluoro-5-((3R, 4S,E)-3-hydroxy-4-methylnon-1-en-6-yn-1-yl)-2-oxopyrrolidin-1-yl)heptanoate;
7-((R)-3,3-difluoro-5-((3S,4S,E)-3-hydroxy-4-methylnon-1-en-6-yn-1-yl)-2-oxopyrrolidin-1-yl)heptanoic acid;
7-((R)-3,3-difluoro-5-((3R,4S,E)-3-hydroxy-4-methylnon-1-en-6-yn-1-yl)-2-oxopyrrolidin-1-yl)heptanoic acid;
methyl 7-((5R)-3,3-difluoro-5-((E)-3-hydroxy-4-methyldec-1-en-6-yn-1-yl)-2-oxopyrrolidin-1-yl)heptanoate;
methyl 7-((R)-3,3-difluoro-5-((3S,4S,E)-3-hydroxy-4-methyldec-1-en-6-yn-1-yl)-2-oxopyrrolidin-1-yl)heptanoate;
7-((R)-3,3-difluoro-5-((3S,4S,E)-3-hydroxy-4-methyldec-1-en-6-yn-1-yl)-2-oxopyrrolidin-1-yl)heptanoic acid;
methyl 7-((5R)-3,3-difluoro-5-((E)-3-hydroxy-4-methyl-7-phenylhept-1-en-6-yn-1-yl)-2-oxopyrrolidin-1-yl)heptanoate;
methyl 7-((R)-3,3-difluoro-5-((3S,4S,E)-3-hydroxy-4-methyl-7-phenylhept-1-en-6-yn-1-yl)-2-oxopyrrolidin-1-yl)heptanoate;
7-((R)-3,3-difluoro-5-((3S,4S,E)-3-hydroxy-4-methyl-7-phenylhept-1-en-6-yn-1-yl)-2-oxopyrrolidin-1-yl)heptanoic acid;
methyl 7-((5R)-3,3-difluoro-5-((E)-3-hydroxy-4-methyloct-1-en-1-yl)-2-oxopyrrolidin-1-yl)heptanoate;
methyl 7-((R)-3,3-difluoro-5-((3S,4S,E)-3-hydroxy-4-methyloct-1-en-1-yl)-2-oxopyrrolidin-1-yl)heptanoate;
7-((R)-3,3-difluoro-5-((3S,4S,E)-3-hydroxy-4-methyloct-1-en-1-yl)-2-oxopyrrolidin-1-yl)heptanoic acid;
methyl 7-((5R)-3,3-difluoro-5-((E)-3-hydroxy-4-methyl-7-phenylhept-1-en-1-yl)-2-oxopyrrolidin-1-yl)heptanoate;
methyl 7-((5R)-3,3-difluoro-5-((3S,E)-3-hydroxy-4-methyl-7-phenyl hept-1-en-1-yl)-2-oxopyrrolidin-1-yl)heptanoate;
methyl 7-((R)-3,3-difluoro-5-((3S,4S,E)-3-hydroxy-4-methyl-7-phenylhept-1-en-1-yl)-2-oxopyrrolidin-1-yl) heptanoate;
methyl 7-((R)-3,3-difluoro-5-((3S,4R,E)-3-hydroxy-4-methyl-7-phenyl hept-1-en-1-yl)-2-oxopyrrolidin-1-yl) heptanoate;
methyl 7-((5R)-3,3-difluoro-5-((3R,E)-3-hydroxy-4-methyl-7-phenylhept-1-en-1-yl)-2-oxopyrrolidin-1-yl) heptanoate;
7-((R)-3,3-difluoro-5-((3S,4S,E)-3-hydroxy-4-methyl-7-phenylhept-1-en-1-yl)-2-oxopyrrolidin-1-yl)heptanoic acid;
7-((R)-3,3-difluoro-5-((3S,4R,E)-3-hydroxy-4-methyl-7-phenylhept-1-en-1-yl)-2-oxopyrrolidin-1-yl)heptanoic acid;
7-((5R)-3,3-difluoro-5-((3R,E)-3-hydroxy-4-methyl-7-phenylhept-1-en-1-yl)-2-oxopyrrolidin-1-yl)heptanoic acid;
methyl 7-((5R)-3,3-difluoro-5-((E)-3-hydroxynon-1-en-6-yn-1-yl)-2-oxopyrrolidin-1-yl)heptanoate;
methyl 7-((5R)-3,3-difluoro-5-((3S,E)-3-hydroxynon-1-en-6-yn-1-yl)-2-oxopyrrolidin-1-yl)heptanoate;
7-((5R)-3,3-difluoro-5-((3S,E)-3-hydroxynon-1-en-6-yn-1-yl)-2-oxopyrrolidin-1-yl)heptanoic acid;
methyl 7-((5R)-3,3-difluoro-5-((E)-3-hydroxy-7-phenylhept-1-en-6-yn-1-yl)-2-oxopyrrolidin-1-yl)heptanoate;

methyl 7-((5R)-3,3-difluoro-5-((3S,E)-3-hydroxy-7-phenyl-hept-1-en-6-yn-1-yl)-2-oxopyrrolidin-1-yl)heptanoate;
7-((5R)-3,3-difluoro-5-((3S,E)-3-hydroxy-7-phenylhept-1-en-6-yn-1-yl)-2-oxopyrrolidin-1-yl)heptanoic acid;
methyl 7-((5R)-3,3-difluoro-5-((E)-3-hydroxyoct-1-en-1-yl)-2-oxopyrrolidin-1-yl)heptanoate;
methyl 7-((R)-3,3-difluoro-5-((S,E)-3-hydroxyoct-1-en-1-yl)-2-oxopyrrolidin-1-yl)heptanoate;
methyl 7-((R)-3,3-difluoro-5-((R,E)-3-hydroxyoct-1-en-1-yl)-2-oxopyrrolidin-1-yl)heptanoate;
7-((R)-3,3-difluoro-5-((S,E)-3-hydroxyoct-1-en-1-yl)-2-oxopyrrolidin-1-yl)heptanoic acid;
7-((R)-3,3-difluoro-5-((R,E)-3-hydroxyoct-1-en-1-yl)-2-oxopyrrolidin-1-yl)heptanoic acid;
methyl 7-((5R)-3,3-difluoro-5-((E)-3-hydroxy-7-phenyl-hept-1-en-1-yl)-2-oxopyrrolidin-1-yl)heptanoate;
methyl 7-((R)-3,3-difluoro-5-((S,E)-3-hydroxy-7-phenyl-hept-1-en-1-yl)-2-oxopyrrolidin-1-yl)heptanoate;
methyl 7-((R)-3,3-difluoro-5-((R,E)-3-hydroxy-7-phenyl-hept-1-en-1-yl)-2-oxopyrrolidin-1-yl)heptanoate;
7-((R)-3,3-difluoro-5-((S,E)-3-hydroxy-7-phenylhept-1-en-1-yl)-2-oxopyrrolidin-1-yl)heptanoic acid;
7-((R)-3,3-difluoro-5-((R,E)-3-hydroxy-7-phenylhept-1-en-1-yl)-2-oxopyrrolidin-1-yl)heptanoic acid;
4-(2-((R)-3,3-difluoro-5-((3S,4S,E)-3-hydroxy-4-methyl-oct-1-en-6-yn-1-yl)-2-oxopyrrolidin-1-yl)ethyl)benzoic acid;
methyl 4-(2-((5R)-3,3-difluoro-5-((E)-3-hydroxy-4-methyl-non-1-en-6-yn-1-yl)-2-oxopyrrolidin-1-yl)ethyl)benzoate;
methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate;
methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate;
methyl 4-(2-((5R)-3,3-difluoro-5-((3R,E)-3-hydroxy-4-methylnon-1-en-6-yn-1-yl)-2-oxopyrrolidin-1-yl)ethyl)benzoate;
4-(2-((R)-3,3-difluoro-5-((3S,4S,E)-3-hydroxy-4-methyl-non-1-en-6-yn-1-yl)-2-oxopyrrolidin-1-yl)ethyl)benzoic acid;
4-(2-((R)-3,3-difluoro-5-((3S,4R,E)-3-hydroxy-4-methyl-non-1-en-6-yn-1-yl)-2-oxopyrrolidin-1-yl)ethyl)benzoic acid;
4-(2-((5R)-3,3-difluoro-5-((3R,E)-3-hydroxy-4-methylnon-1-en-6-yn-1-yl)-2-oxopyrrolidin-1-yl)ethyl)benzoic acid;
4-(2-((R)-3,3-difluoro-5-((3S,4S,E)-3-hydroxy-4-methyl-dec-1-en-6-yn-1-yl)-2-oxopyrrolidin-1-yl)ethyl)benzoic acid;
4-(2-((R)-3,3-difluoro-5-((3S,4S,E)-3-hydroxy-4-methyl-7-phenylhept-1-en-6-yn-1-yl)-2-oxopyrrolidin-1-yl)ethyl)benzoic acid;
4-(2-((R)-3,3-difluoro-5-((3S,4S,E)-3-hydroxy-4-methyl-oct-1-en-1-yl)-2-oxopyrrolidin-1-yl)ethyl)benzoic acid;
4-(2-((R)-3,3-difluoro-5-((3S,4S,E)-3-hydroxy-4-methyl-7-phenylhept-1-en-1-yl)-2-oxopyrrolidin-1-yl)ethyl)benzoic acid;
4-(2-((R)-3,3-difluoro-5-((S,E)-3-hydroxyoct-1-en-6-yn-1-yl)-2-oxopyrrolidin-1-yl)ethyl)benzoic acid;
4-(2-((R)-3,3-difluoro-5-((S,E)-3-hydroxynon-1-en-6-yn-1-yl)-2-oxopyrrolidin-1-yl)ethyl)benzoic acid;
4-(2-((R)-3,3-difluoro-5-((S,E)-3-hydroxydec-1-en-6-yn-1-yl)-2-oxopyrrolidin-1-yl)ethyl)benzoic acid;
4-(2-((R)-3,3-difluoro-5-((S,E)-3-hydroxy-7-phenylhept-1-en-6-yn-1-yl)-2-oxopyrrolidin-1-yl)ethyl)benzoic acid;
methyl 4-(2-((5R)-3,3-difluoro-5-((E)-3-hydroxyoct-1-en-1-yl)-2-oxopyrrolidin-1-yl)ethyl)benzoate;
methyl 4-(2-((R)-3,3-difluoro-5-((S,E)-3-hydroxyoct-1-en-1-yl)-2-oxopyrrolidin-1-yl)ethyl)benzoate;
methyl 4-(2-((R)-3,3-difluoro-5-((R,E)-3-hydroxyoct-1-en-1-yl)-2-oxopyrrolidin-1-yl)ethyl)benzoate;
4-(2-((R)-3,3-difluoro-5-((S,E)-3-hydroxyoct-1-en-1-yl)-2-oxopyrrolidin-1-yl)ethyl)benzoic acid;
4-(2-((R)-3,3-difluoro-5-((R,E)-3-hydroxyoct-1-en-1-yl)-2-oxopyrrolidin-1-yl)ethyl)benzoic acid;
4-(2-((R)-3,3-difluoro-5-((S,E)-3-hydroxy-7-phenylhept-1-en-1-yl)-2-oxopyrrolidin-1-yl)ethyl)benzoic acid;
5-(3-((R)-3,3-difluoro-5-((3S,4S,E)-3-hydroxy-4-methyl-oct-1-en-6-yn-1-yl)-2-oxopyrrolidin-1-yl)propyl)thiophene-2-carboxylic acid;
methyl 5-(3-((5R)-3,3-difluoro-5-((E)-3-hydroxy-4-methyl-non-1-en-6-yn-1-yl)-2-oxopyrrolidin-1-yl)propyl)thiophene-2-carboxylate;
methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate;
methyl 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylate;
methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate;
5-(3-((R)-3,3-difluoro-5-((3S,4S,E)-3-hydroxy-4-methyl-non-1-en-6-yn-1-yl)-2-oxopyrrolidin-1-yl)propyl)thiophene-2-carboxylic acid;
5-(3-((R)-3,3-difluoro-5-((3S,4R,E)-3-hydroxy-4-methyl-non-1-en-6-yn-1-yl)-2-oxopyrrolidin-1-yl)propyl)thiophene-2-carboxylic acid;
5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylic acid;
5-(3-((R)-3,3-difluoro-5-((3S,4S,E)-3-hydroxy-4-methyl-dec-1-en-6-yn-1-yl)-2-oxopyrrolidin-1-yl)propyl)thiophene-2-carboxylic acid;
5-(3-((R)-3,3-difluoro-5-((3S,4S,E)-3-hydroxy-4-methyl-7-phenylhept-1-en-6-yn-1-yl)-2-oxopyrrolidin-1-yl)propyl)thiophene-2-carboxylic acid;
5-(3-((R)-3,3-difluoro-5-((3S,4S,E)-3-hydroxy-4-methyl-oct-1-en-1-yl)-2-oxopyrrolidin-1-yl)propyl)thiophene-2-carboxylic acid;
5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid;
5-(3-((R)-3,3-difluoro-5-((S,E)-3-hydroxyoct-1-en-6-yn-1-yl)-2-oxopyrrolidin-1-yl)propyl)thiophene-2-carboxylic acid;
5-(3-((R)-3,3-difluoro-5-((S,E)-3-hydroxynon-1-en-6-yn-1-yl)-2-oxopyrrolidin-1-yl)propyl)thiophene-2-carboxylic acid;
5-(3-((R)-3,3-difluoro-5-((S,E)-3-hydroxydec-1-en-6-yn-1-yl)-2-oxopyrrolidin-1-yl)propyl)thiophene-2-carboxylic acid;
5-(3-((R)-3,3-difluoro-5-((S,E)-3-hydroxy-7-phenylhept-1-en-6-yn-1-yl)-2-oxopyrrolidin-1-yl)propyl)thiophene-2-carboxylic acid;
methyl 5-(3-((5R)-3,3-difluoro-5-((E)-3-hydroxyoct-1-en-1-yl)-2-oxopyrrolidin-1-yl)propyl)thiophene-2-carboxylate;
methyl 5-(3-((R)-3,3-difluoro-5-((S,E)-3-hydroxyoct-1-en-1-yl)-2-oxopyrrolidin-1-yl)propyl)thiophene-2-carboxylate;

methyl 5-(3-((R)-3,3-difluoro-5-((R,E)-3-hydroxyoct-1-en-1-yl)-2-oxopyrrolidin-1-yl)propyl)thiophene-2-carboxylate;
5-(3-((R)-3,3-difluoro-5-((S,E)-3-hydroxyoct-1-en-1-yl)-2-oxopyrrolidin-1-yl)propyl)thiophene-2-carboxylic acid;
5-(3-((R)-3,3-difluoro-5-((R,E)-3-hydroxyoct-1-en-1-yl)-2-oxopyrrolidin-1-yl)propyl)thiophene-2-carboxylic acid;
5-(3-((R)-3,3-difluoro-5-((S,E)-3-hydroxy-7-phenylhept-1-en-1-yl)-2-oxopyrrolidin-1-yl)propyl)thiophene-2-carboxylic acid;
methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate;
methyl 5-(3-((R)-3,3-difluoro-5-((3S,4R,E)-3-hydroxy-4-methyl-7-phenylhept-1-en-1-yl)-2-oxopyrrolidin-1-yl)propyl)thiophene-2-carboxylate;
5-(3-((R)-3,3-difluoro-5-((3S,4R,E)-3-hydroxy-4-methyl-7-phenylhept-1-en-1-yl)-2-oxopyrrolidin-1-yl)propyl)thiophene-2-carboxylic acid;
methyl 5-(3-((S)-3,3-difluoro-5-((3R,4S)-3-hydroxy-4-methyl-7-phenylheptyl)-2-oxopyrrolidin-1-yl)propyl)thiophene-2-carboxylate;
methyl 5-(3-((S)-3,3-difluoro-5-((3R,4R)-3-hydroxy-4-methyl-7-phenyl heptyl)-2-oxopyrrolidin-1-yl)propyl)thiophene-2-carboxylate;
5-(3-((S)-3,3-difluoro-5-((3R,4R)-3-hydroxy-4-methyl-7-phenylheptyl)-2-oxopyrrolidin-1-yl)propyl)thiophene-2-carboxylic acid;
methyl 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylate;
methyl 5-(3-((R)-3,3-difluoro-5-((3S,4R,E)-3-hydroxy-4-methyl-6-phenylhex-1-en-1-yl)-2-oxopyrrolidin-1-yl)propyl)thiophene-2-carboxylate;
5-(3-((R)-3,3-difluoro-5-((3S,4R,E)-3-hydroxy-4-methyl-6-phenylhex-1-en-1-yl)-2-oxopyrrolidin-1-yl)propyl)thiophene-2-carboxylic acid;
methyl 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylate;
5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylic acid;
5-(3-((R)-3,3-difluoro-5-((3S,4R,E)-3-hydroxy-4-methyl-8-phenyloct-1-en-1-yl)-2-oxopyrrolidin-1-yl)propyl)thiophene-2-carboxylic acid;
methyl 5-(3-((S)-3,3-difluoro-5-((3R,4S)-3-hydroxy-4-methyl-8-phenyloctyl)-2-oxopyrrolidin-1-yl)propyl)thiophene-2-carboxylate;
methyl 5-(3-((S)-3,3-difluoro-5-((3R,4R)-3-hydroxy-4-methyl-8-phenyloctyl)-2-oxopyrrolidin-1-yl)propyl)thiophene-2-carboxylate;
5-(3-((S)-3,3-difluoro-5-((3R,4S)-3-hydroxy-4-methyl-8-phenyloctyl)-2-oxopyrrolidin-1-yl)propyl)thiophene-2-carboxylic acid;
5-(3-((S)-3,3-difluoro-5-((3R,4R)-3-hydroxy-4-methyl-8-phenyloctyl)-2-oxopyrrolidin-1-yl)propyl)thiophene-2-carboxylic acid;
methyl 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylate;
methyl 5-(3-((R)-3,3-difluoro-5-((3S,4R,E)-3-hydroxy-4-methyl-9-phenylnon-1-en-1-yl)-2-oxopyrrolidin-1-yl)propyl)thiophene-2-carboxylate;
5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylic acid;
5-(3-((R)-3,3-difluoro-5-((3S,4R,E)-3-hydroxy-4-methyl-9-phenylnon-1-en-1-yl)-2-oxopyrrolidin-1-yl)propyl)thiophene-2-carboxylic acid;
methyl 5-(3-((S)-3,3-difluoro-5-((3R,4S)-3-hydroxy-4-methyl-9-phenylnonyl)-2-oxopyrrolidin-1-yl)propyl)thiophene-2-carboxylate;
methyl 5-(3-((S)-3,3-difluoro-5-((3R,4R)-3-hydroxy-4-methyl-9-phenylnonyl)-2-oxopyrrolidin-1-yl)propyl)thiophene-2-carboxylate;
5-(3-((S)-3,3-difluoro-5-((3R,4S)-3-hydroxy-4-methyl-9-phenylnonyl)-2-oxopyrrolidin-1-yl)propyl)thiophene-2-carboxylic acid;
5-(3-((S)-3,3-difluoro-5-((3R,4R)-3-hydroxy-4-methyl-9-phenylnonyl)-2-oxopyrrolidin-1-yl)propyl)thiophene-2-carboxylic acid;
methyl 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylate;
methyl 5-(3-((R)-3,3-difluoro-5-((3S,4R,E)-3-hydroxy-4-methyl-5-phenylpent-1-en-1-yl)-2-oxopyrrolidin-1-yl)propyl)thiophene-2-carboxylate;
5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylic acid;
5-(3-((R)-3,3-difluoro-5-((3S,4R,E)-3-hydroxy-4-methyl-5-phenylpent-1-en-1-yl)-2-oxopyrrolidin-1-yl)propyl)thiophene-2-carboxylic acid;
methyl 5-(3-((R)-3,3-difluoro-5-((S,E)-3-hydroxy-7-phenylhept-1-en-1-yl)-2-oxopyrrolidin-1-yl)propyl)thiophene-2-carboxylate;
methyl 5-(3-((R)-3,3-difluoro-5-((S,E)-3-hydroxy-7-phenylhept-1-en-6-yn-1-yl)-2-oxopyrrolidin-1-yl)propyl)thiophene-2-carboxylate;
methyl 5-(3-((S)-3,3-difluoro-5-((S)-3-hydroxy-7-phenylheptyl)-2-oxopyrrolidin-1-yl)propyl)thiophene-2-carboxylate;
5-(3-((S)-3,3-difluoro-5-((S)-3-hydroxy-7-phenylheptyl)-2-oxopyrrolidin-1-yl)propyl)thiophene-2-carboxylic acid;
methyl 7-((S)-3,3-difluoro-5-((3R,4S)-3-hydroxy-4-methyl-7-phenylheptyl)-2-oxopyrrolidin-1-yl)heptanoate;
methyl 7-((S)-3,3-difluoro-5-((3R,4R)-3-hydroxy-4-methyl-7-phenylheptyl)-2-oxopyrrolidin-1-yl)heptanoate;
7-((S)-3,3-difluoro-5-((3R,4S)-3-hydroxy-4-methyl-7-phenyl heptyl)-2-oxopyrrolidin-1-yl)heptanoic acid;
7-((S)-3,3-difluoro-5-((3R,4R)-3-hydroxy-4-methyl-7-phenylheptyl)-2-oxopyrrolidin-1-yl)heptanoic acid;
methyl 7-((S)-3,3-difluoro-5-((3R,4S)-3-hydroxy-4-methyl-8-phenyloctyl)-2-oxopyrrolidin-1-yl)heptanoate;
methyl 7-((S)-3,3-difluoro-5-((3R,4R)-3-hydroxy-4-methyl-8-phenyloctyl)-2-oxopyrrolidin-1-yl)heptanoate;
7-((S)-3,3-difluoro-5-((3R,4S)-3-hydroxy-4-methyl-8-phenyloctyl)-2-oxopyrrolidin-1-yl)heptanoic acid;
7-((S)-3,3-difluoro-5-((3R,4R)-3-hydroxy-4-methyl-8-phenyloctyl)-2-oxopyrrolidin-1-yl)heptanoic acid;
methyl 7-((S)-3,3-difluoro-5-((3R,4S)-3-hydroxy-4-methyl-9-phenylnonyl)-2-oxopyrrolidin-1-yl)heptanoate;
methyl 7-((S)-3,3-difluoro-5-((3R,4R)-3-hydroxy-4-methyl-9-phenylnonyl)-2-oxopyrrolidin-1-yl)heptanoate;
7-((S)-3,3-difluoro-5-((3R,4S)-3-hydroxy-4-methyl-9-phenylnonyl)-2-oxopyrrolidin-1-yl)heptanoic acid;
7-((S)-3,3-difluoro-5-((3R,4R)-3-hydroxy-4-methyl-9-phenylnonyl)-2-oxopyrrolidin-1-yl)heptanoic acid;
methyl 5-(3-((R)-3,3-difluoro-5-((3S,4S,E)-3-hydroxy-4-methyl-8-phenyloct-1-en-6-yn-1-yl)-2-oxopyrrolidin-1-yl)propyl)thiophene-2-carboxylate;

methyl 5-(3-((R)-3,3-difluoro-5-((3S,4R,E)-3-hydroxy-4-methyl-8-phenyloct-1-en-6-yn-1-yl)-2-oxopyrrolidin-1-yl)propyl)thiophene-2-carboxylate;
5-(3-((R)-3,3-difluoro-5-((3S,4S,E)-3-hydroxy-4-methyl-8-phenyloct-1-en-6-yn-1-yl)-2-oxopyrrolidin-1-yl)propyl)thiophene-2-carboxylic acid;
5-(3-((R)-3,3-difluoro-5-((3S,4R,E)-3-hydroxy-4-methyl-8-phenyloct-1-en-6-yn-1-yl)-2-oxopyrrolidin-1-yl)propyl)thiophene-2-carboxylic acid;
methyl 5-(3-((R)-3,3-difluoro-5-((3S,4S,E)-3-hydroxy-4-methyl-9-phenylnon-1-en-6-yn-1-yl)-2-oxopyrrolidin-1-yl)propyl)thiophene-2-carboxylate;
methyl 5-(3-((R)-3,3-difluoro-5-((3S,4R,E)-3-hydroxy-4-methyl-9-phenylnon-1-en-6-yn-1-yl)-2-oxopyrrolidin-1-yl)propyl)thiophene-2-carboxylate;
5-(3-((R)-3,3-difluoro-5-((3S,4S,E)-3-hydroxy-4-methyl-9-phenylnon-1-en-6-yn-1-yl)-2-oxopyrrolidin-1-yl)propyl)thiophene-2-carboxylic acid;
5-(3-((R)-3,3-difluoro-5-((3S,4R,E)-3-hydroxy-4-methyl-9-phenylnon-1-en-6-yn-1-yl)-2-oxopyrrolidin-1-yl)propyl)thiophene-2-carboxylic acid;
(R)-1-(6-(1H-tetrazol-5-yl)hexyl)-3,3-difluoro-5-((3S,4S,E)-3-hydroxy-4-methyl-7-phenylhept-1-en-1-yl)pyrrolidin-2-one;
7-((R)-3,3-difluoro-5-((3S,4S,E)-3-hydroxy-4-methyl-7-phenyl hept-1-en-1-yl)-2-oxopyrrolidin-1-yl)-N-ethylheptanamide;
7-((R)-3,3-difluoro-5-((3S,4S,E)-3-hydroxy-4-methyl-7-phenyl hept-1-en-1-yl)-2-oxopyrrolidin-1-yl)-N-(methylsulfonyl)heptanamide;
7-((S)-3,3-difluoro-5-((3R,4R,E)-3-hydroxy-4-methyl-7-phenyl hept-1-en-1-yl)-2-oxopyrrolidin-1-yl)heptanoic acid;
7-((R)-3,3-difluoro-5-((3S,4S,Z)-3-hydroxy-4-methyl-7-phenyl hept-1-en-1-yl)-2-oxopyrrolidin-1-yl)heptanoic acid;
3-(3-((R)-3,3-difluoro-5-((3S,4S,E)-3-hydroxy-4-methyl-7-phenylhept-1-en-1-yl)-2-oxopyrrolidin-1-yl) propyl)benzoic acid;
7-((R)-3,3-difluoro-5-((3S,4S,E)-3-hydroxy-4-methyl-7-phenyl hept-1-en-1-yl)-2-oxopyrrolidin-1-yl) hept-5-ynoic acid;
(Z)-7-((R)-3,3-difluoro-5-((3S,4S,E)-3-hydroxy-4-methyl-7-phenylhept-1-en-1-yl)-2-oxopyrrolidin-1-yl) hept-5-enoic acid;
5-(3-((R)-3,3-difluoro-5-((3S,4S,E)-3-hydroxy-4-methyl-7-phenylhept-1-en-1-yl)-2-oxopyrrolidin-1-yl) prop-1-yn-1-yl)thiophene-2-carboxylic acid;
4-((2-((R)-3,3-difluoro-5-((3S,4S,E)-3-hydroxy-4-methyl-7-phenyl hept-1-en-1-yl)-2-oxopyrrolidin-1-yl)ethyl)thio)butanoic acid;
7-((S)-3,3-difluoro-5-((3R,4S)-3-hydroxy-4-methyl-7-phenylheptyl)-2-oxopyrrolidin-1-yl)heptanoic acid;
5-(3-((S)-3,3-difluoro-5-((3R,4S)-3-hydroxy-4-methyl-7-phenylheptyl)-2-oxopyrrolidin-1-yl)propyl)thiophene-2-carboxylic acid;
4-(2-((S)-3,3-difluoro-5-((3R,4S)-3-hydroxy-4-methyl-7-phenylheptyl)-2-oxopyrrolidin-1-yl)ethyl)benzoic acid;
3-(3-((S)-3,3-difluoro-5-((3R,4S)-3-hydroxy-4-methyl-7-phenylheptyl)-2-oxopyrrolidin-1-yl)propyl)benzoic acid;
4-((2-((S)-3,3-difluoro-5-((3R,4S)-3-hydroxy-4-methyl-7-phenylheptyl)-2-oxopyrrolidin-1-yl)ethyl)thio)butanoic acid;
7-((R)-3,3-difluoro-5-((3S,4S)-3-hydroxy-4-methyl-7-phenylhept-1-yn-1-yl)-2-oxopyrrolidin-1-yl)heptanoic acid;
7-((R)-3,3-difluoro-5-((3R,4S,E)-3-hydroxy-4-phenylpent-1-en-1-yl)-2-oxopyrrolidin-1-yl)heptanoic acid;
7-((R)-3,3-difluoro-5-((3S,4S,E)-3-hydroxy-4-methyl-5-phenylpent-1-en-1-yl)-2-oxopyrrolidin-1-yl)heptanoic acid;
7-((R)-3,3-difluoro-5-((3S,4S,E)-3-hydroxy-4-methyl-6-phenylhex-1-en-1-yl)-2-oxopyrrolidin-1-yl)heptanoic acid;
7-((R)-3,3-difluoro-5-((3S,4S,E)-3-hydroxy-4-methyl-8-phenyloct-1-en-1-yl)-2-oxopyrrolidin-1-yl)heptanoic acid;
7-((R)-3,3-difluoro-5-((3S,4S,E)-3-hydroxy-4-methyl-9-phenylnon-1-en-1-yl)-2-oxopyrrolidin-1-yl)heptanoic acid;
7-((R)-5-((3S,4S,E)-7-cyclohexyl-3-hydroxy-4-methylhept-1-en-1-yl)-3,3-difluoro-2-oxopyrrolidin-1-yl)heptanoic acid;
7-((R)-3,3-difluoro-5-((3S,4S,E)-3-hydroxy-4-methyl-7-(naphthalen-2-yl)hept-1-en-1-yl)-2-oxopyrrolidin-1-yl)heptanoic acid;
7-((R)-3,3-difluoro-5-((3S,4S,E)-3-hydroxy-4-methyl-7-(naphthalen-1-yl)hept-1-en-1-yl)-2-oxopyrrolidin-1-yl)heptanoic acid;
7-((R)-3,3-difluoro-5-((3S,4S,E)-7-(3-fluorophenyl)-3-hydroxy-4-methylhept-1-en-1-yl)-2-oxopyrrolidin-1-yl)heptanoic acid;
7-((R)-3,3-difluoro-5-((3S,4S,E)-3-hydroxy-4-methyl-7-(m-tolyl)hept-1-en-1-yl)-2-oxopyrrolidin-1-yl)heptanoic acid;
7-((R)-5-((3S,4S,E)-7-(3-chlorophenyl)-3-hydroxy-4-methylhept-1-en-1-yl)-3,3-difluoro-2-oxopyrrolidin-1-yl)heptanoic acid;
7-((R)-3,3-difluoro-5-((3S,4S,E)-3-hydroxy-7-(3-methoxyphenyl)-4-methylhept-1-en-1-yl)-2-oxopyrrolidin-1-yl)heptanoic acid;
7-((R)-3,3-difluoro-5-((3S,4S,E)-3-hydroxy-7-(3-(methoxymethyl)phenyl)-4-methylhept-1-en-1-yl)-2-oxopyrrolidin-1-yl)heptanoic acid;
7-((R)-3,3-difluoro-5-((3S,4S,E)-3-hydroxy-4-methyl-6-(phenylthio)hex-1-en-1-yl)-2-oxopyrrolidin-1-yl)heptanoic acid;
7-((R)-3,3-difluoro-5-((3S,4S,E)-3-hydroxy-4-methyl-6-phenoxyhex-1-en-1-yl)-2-oxopyrrolidin-1-yl)heptanoic acid;
7-((R)-5-((3S,4S,E)-4-ethyl-3-hydroxy-7-phenylhept-1-en-1-yl)-3,3-difluoro-2-oxopyrrolidin-1-yl)heptanoic acid;
7-((R)-3,3-difluoro-5-((3R,4R,E)-3-hydroxy-4-isopropyl-7-phenylhept-1-en-1-yl)-2-oxopyrrolidin-1-yl)heptanoic acid;
7-((R)-3,3-difluoro-5-((3R,4S,E)-3-hydroxy-7-phenyl-4-(trifluoromethyl)hept-1-en-1-yl)-2-oxopyrrolidin-1-yl)heptanoic acid;
7-((R)-5-((R,E)-4,4-difluoro-3-hydroxy-7-phenylhept-1-en-1-yl)-3,3-difluoro-2-oxopyrrolidin-1-yl)heptanoic acid;
7-((R)-3,3-difluoro-5-((R,E)-3-hydroxy-4-methylene-7-phenylhept-1-en-1-yl)-2-oxopyrrolidin-1-yl)heptanoic acid;
7-((R)-5-((R,E)-4-(difluoromethylene)-3-hydroxy-7-phenylhept-1-en-1-yl)-3,3-difluoro-2-oxopyrrolidin-1-yl)heptanoic acid; and
7-((R)-3,3-difluoro-5-((R,E)-3-hydroxy-3-(1-(3-phenylpropyl)cyclobutyl)prop-1-en-1-yl)-2-oxopyrrolidin-1-yl)heptanoic acid; or
a pharmaceutically acceptable salt thereof.

Compounds described herein may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The various stereoisomers (including enantiomers and diastereomers) and mixtures thereof of the compounds described are also contemplated. Individual stereoisomers of compounds described may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. All various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae within this specification can represent only one of the possible tautomeric forms. It is to be understood that encompassed herein are any tautomeric form, and mixtures thereof, and is not to be limited merely to any one tautomeric form utilized within the naming of the compounds or formulae.

Additionally, unless otherwise stated, the structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in a biological assay, or as $EP_4$ receptor agonists.

Also contemplated as part of the invention are compounds formed by synthetic means or formed in vivo by biotransformation or by chemical means. For example, certain compounds of the invention may function as prodrugs that are converted to other compounds of the invention upon administration to a subject.

Methods of Treatment

The compounds of the invention are $EP_4$ receptor agonists and are useful in treating or preventing conditions or diseases responsive to an $EP_4$ receptor agonist. Conditions or diseases treatable with compounds of the invention include elevated intraocular pressure, glaucoma, ocular hypertension, dry eye, macular edema, macular degeneration, alopecia (alone or in combination with, for example, an L-PGDS inhibitor or an H-PGDS inhibitor or in combination with both an L-PGDS inhibitor and H-PGDS inhibitor; Garza, L. A. et al, *Science Translational Medicine*, 2012, 4(126), 126ra34), cerebralvascular accident (Liang, X. et al, *Journal of Clinical Investigation*, 2011, 121(11), 4362-4371), brain damage due to trauma, neuropathic pain (e.g., diabetic neuropathy, sciatica, post-herpetic neuralgia, HIV-related neuropathy, trigeminal neuralgia, ductus arteriosis, chemotherapy-induced pain), low bone density due to osteoporosis (Cameron, K. O. et al, *Bioorganic and Medicinal Chemistry Letters*, 2006, 16, 1799-1802) or glucocorticoid treatment, bone fracture, and bone loss due to periodontal disease, surgical procedures, cancer, or trauma. Further uses of the compounds of the invention include use in increasing bone density in preparation of bone for receiving dental or orthopedic implants, coating of implants for enhanced osseointegration, and use in all forms of spinal fusion.

The present invention provides methods of treatment comprising administering to a patient in need thereof: (i) a therapeutically effective amount of a compound of formula (I), (Ia), or (II) or a pharmaceutically acceptable salt thereof, or a solvate of either; or (ii) a composition comprising any of the foregoing compound, salt, or solvate and a pharmaceutically acceptable carrier.

In one aspect, the invention provides a method of treating glaucoma, osteoporosis, bone fracture, low bone density due to periodontal disease, or neuropathic pain.

In another aspect, the invention provides a method of stimulating bone formation. According to this aspect of the invention, one embodiment provides a method of treating osteoporosis, bone fracture, and periodontal disease. In another embodiment, the compound or composition of the invention is administered alone. In still another embodiment, the compound or composition is administered in combination with one or more additional therapeutic agents to treat bone loss or osteoporosis. Compounds of the invention can be used in combination with other agents useful in treating or preventing bone loss such as an organic bisphosphonate (e.g., alendronic acid or sodium alendronate); a cathepsin K inhibitor; an estrogen or an estrogen receptor modulator; calcitonin; an inhibitor of osteoclast proton ATPase; an inhibitor of HMG-CoA reductase; an integrin receptor antagonist; a RANKL inhibitor such as denosumab; a bone anabolic agent, such as PTH; a bone morphogenetic agent such as BMP-2, BMP-4, and BMP-7; Vitamin D or a synthetic Vitamin D analogue such as ED-70; an androgen or an androgen receptor modulator; a SOST inhibitor; and the pharmaceutically acceptable salts and mixtures thereof. A preferred combination is a compound of the present invention and an organic bisphosphonate.

In another aspect, the invention provides a method of lowering intraocular pressure. According to this aspect of the invention, one embodiment provides a method of treating glaucoma. In another embodiment, the compound or composition of the invention is administered alone. In still another embodiment, the compound or composition is administered in combination with one or more additional therapeutic agents that lower intraocular pressure such as a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, or para-aminoclonidine, a carbonic anhydrase inhibitor such as dorzolamide, acetazolamide, metazolamide or brinzolamide; and a prostaglandin such as latanoprost, travaprost, or unoprostone, and the pharmaceutically acceptable salts and mixtures thereof.

In still another aspect, the invention provides a method of treating neuropathic pain. According to this aspect of the invention, one embodiment provides a method of treating diabetic neuropathy, sciatica, post-herpetic neuralgia, HIV-related neuropathy, trigeminal neuralgia, or chemotherapy-induced pain. In another embodiment, the compound or composition of the invention is administered alone. In still another embodiment, the compound or composition is administered in combination with one or more additional therapeutic agents that treat neuropathic pain such as gabapentin, pregabalin, duloxetine, and lamotrigine, and the pharmaceutically acceptable salts and mixtures thereof.

Compounds described herein can be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions may require such repeated or chronic administration of the compounds. Compounds described herein may become more effective upon repeated or chronic administration such that the therapeutically effective doses on repeated or chronic administration can be lower than the therapeutically effective dose from a single administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

In one aspect of the invention, compounds of the invention, or a pharmaceutically acceptable salt thereof, or a solvate of either; or (ii) a composition comprising any of the foregoing compound, salt, or solvate and a pharmaceutically acceptable carrier are administered as the active pharmaceutical agent. In another aspect, compounds of the invention or a pharmaceutically acceptable salt thereof, or a solvate of either; or (ii) a composition comprising any of the foregoing compound, salt, or solvate and a pharmaceutically acceptable carrier are administered to a subject and the administered compounds are converted to the active pharmaceutical agent in the subject by chemical or biotransformation.

Ophthalmic formulations of compounds of the invention may contain from 0.001 to 5% and especially 0.001 to 0.1% of active agent. Higher dosages as, for example, up to about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

Compounds may be administered orally once or several times per day each in an amount of from 0.001 mg to 100 mg per adult, preferably about 0.01 to about 10 mg per adult. Compounds may also be administered parenterally once or several times per day each in an amount of from 0.1 ng to 10 mg per adult or continuously administered into a vein for 1 hour to 24 hours per day. Compounds may also be administered locally to stimulate bone formation in an amount from 0.0001 µg to 500 µg.

Pharmaceutical Compositions

Pharmaceutical compositions comprise compounds described herein, pharmaceutically acceptable salts thereof, or solvates of either. The pharmaceutical compositions comprising the compound, salt, or solvate described herein can be formulated together with one or more non-toxic pharmaceutically acceptable carriers, either alone or in combination with one or more other medicaments as described hereinabove.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The pharmaceutical compositions can be administered to humans, other mammals, and birds orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The pharmaceutical compositions can further be administered to humans, other mammals, and birds locally to the desired site of action; for example, into a bone void such as a tooth socket defect, adjacent to an alveolar bone, or a bone defect caused by surgery, trauma, or disease.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate;

agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, poly(lactic-co-glycolic acid), microcrystalline cellulose, aluminum metahydroxide, bentonite, agar-agar, tragacanth, collagen sponge, demineralized bone matrix, and mixtures thereof.

The compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to compounds described herein, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., Methods in Cell Biology, Volume XIV, Academic Press, New York, N.Y. (1976), p. 33 et seq.

Dosage forms for topical administration of compounds described herein include powders, sprays, ointments and inhalants. The active compounds can be mixed under sterile conditions with a pharmaceutically acceptable carrier and any needed preservatives, buffers or propellants which can be required. Opthalmic formulations, eye ointments, powders and solutions are also contemplated as being within the scope.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Compounds described herein can exist in unsolvated as well as solvated forms, including hydrated forms, such as hemi-hydrates. In general, the solvated forms, with pharmaceutically acceptable solvents such as water and ethanol, among others, are equivalent to the unsolvated forms.

Chemistry and Examples

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well-known and commonly used in the art.

It will be appreciated that the synthetic schemes and specific examples are illustrative and are not to be read as limiting the scope of the invention. Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. The skilled artisan will also appreciate that not all of the substituents in the compounds of formula (I) will tolerate certain reaction conditions employed to synthesize the compounds. Routine experimentation, including appropriate manipulation of the reaction conditions, reagents and sequence of the synthetic route, protection and deprotection may be required in the case of particular compounds. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3 d ed.), John Wiley & Sons, NY (1999), which is incorporated herein by reference in its entirety.

Furthermore, the skilled artisan will appreciate that in some cases, the order in which moieties are introduced may vary. The particular order of steps required to produce the compounds of formula (I) is dependent upon the particular compounds being synthesized, the starting compound, and the relative stability of the substituted moieties. Thus, synthesis of the present compounds may be accomplished by methods analogous to those described in the synthetic schemes described herein and in the specific examples, with routine experimentation (e.g., manipulation of the reaction conditions, reagents, and sequence of the synthetic steps).

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Systematic names of compound structures have been generated by the Convert-Structure-to-Name function of Chem & Bio Draw 12.0 Ultra by CambridgeSoft®, which uses the Cahn-Ingold-Prelog rules for stereochemistry. When discussing individual atomic positions of compound structures, an alternative continuous numbering scheme for the lactams as described below may be used.

When used in the present application, the following abbreviations have the meaning set out below:

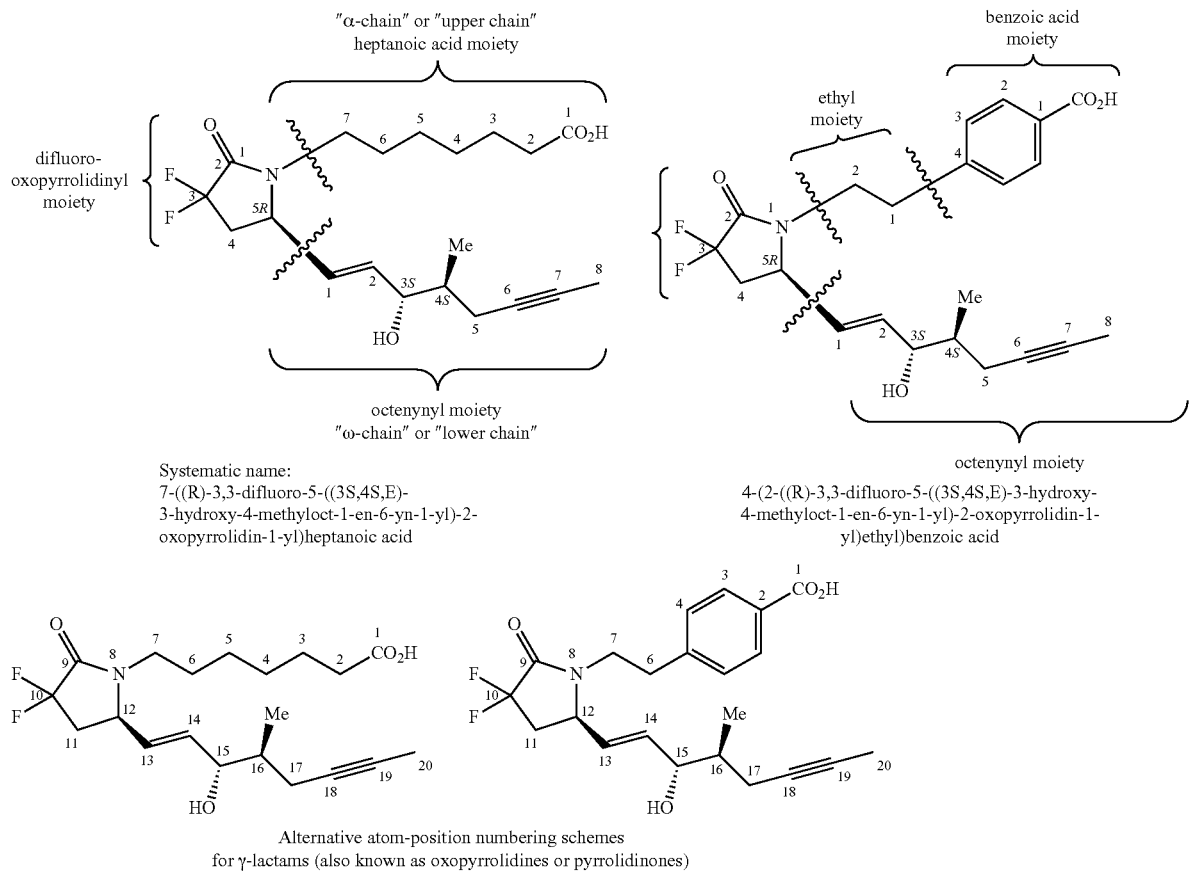

Alternative atom-position numbering schemes for γ-lactams (also known as oxopyrrolidines or pyrrolidinones)

Liquid chromatography-mass spectra (LC/MS) were obtained using an Agilent LC/MSD G1946D or an Agilent 1100 Series LC/MSD Trap G1311A or G2435A. Quantifications were obtained on a Cary 50 Bio UV-visible spectrophotometer.

$^1H$, $^{13}C$, and $^{19}F$ Nuclear magnetic resonance (NMR) spectra were obtained using a Varian INOVA nuclear magnetic resonance spectrometer at 400, 100, and 376 MHz, respectively.

High performance liquid chromatography (HPLC) analytical separations were performed on an Agilent 1100 or Agilent 1200 HPLC analytical system and followed by an Agilent Technologies G1315B Diode Array Detector set at or near the $UV_{max}$ @ 260 nm.

High performance liquid chromatography (HPLC) preparatory separations were performed on a Gilson preparative HPLC system or an Agilent 1100 preparative HPLC system and followed by an Agilent Technologies G1315B Diode Array Detector set at or near the $UV_{max}$ @ 260 nm.

Analytical chiral HPLC separations were performed on an Agilent 1100 analytical system and followed by an Agilent Technologies G1315B Diode Array Detector set at or near the $UV_{max}$ @ 260 nm.

Thin layer chromatography (TLC) analyses were performed on Uniplate™ 250□ silica gel plates (Analtech, Inc. Catalog No. 02521) and were typically developed for visualization using 50 volume % concentrated sulfuric acid in water spray unless otherwise indicated.

Ac is acetyl;
ACN is acetonitrile;
$BBr_3$ is boron tribromide;
Bn is benzyl;
$BnNH_2$ is benzylamine;
BSA is bovine serum albumin;
$CH_2Cl_2$ is dichloromethane;
$CHCl_3$ is chloroform;
$CDCl_3$ is deuterochloroform;
CSA is camphorsulfonic acid;
DCC is N,N'-dicyclohexylcarbodiimide;
DME is 1,2-dimethoxyethane;
DMF is N,N-dimethylformamide;
DMP is 2,2-dimethoxypropane (also called, acetone dimethyl acetal);
DMSO is dimethyl sulfoxide;
DBU is 1,8-diazabicyclo[5.4.0]undec-7-ene;
DIA is diisopropylamine;
DMAP is 4-dimethylaminopyridine;
EDC/EDAC is N-(3-dimethylaminopropyl)-N-ethylcarbodiimide hydrochloride;
EDTA is ethylenediaminetetraacetic acid;
EE is ethoxyeth-1-yl;
ee is enantiomeric excess;
EIA is enzyme immunoassay;
Et is ethyl;
EtOAc is ethyl acetate;
EtOH is ethanol;

Et$_3$N is triethylamine;
HCl is hydrogen chloride;
HOBt is 1-hydroxybenzotriazole;
Me is methyl;
MeOH is methanol;
MTBE is methyl tert-butyl ether;
NaOMe is sodium methoxide;
nBuLi or n-BuLi is n-butyllithium;
NFSi is N-fluorobenzenesulfonimide;
NHS is N-hydroxysuccinimide;
NMP is 1-methyl-2-pyrrolidinone;
PG is a protecting group;
Ph is phenyl;
Pd(PPh$_3$)$_4$ is tetrakis(triphenylphosphine)palladium;
PhMe is toluene;
rt is room temperature;
TBAF is tetrabutylammonium fluoride;
TBS or TBDMS is tert-butyldimethylsilyl;
tBu or t-Bu is tert-butyl;
TEA is triethylamine;
TFA is trifluoroacetic acid;
THF is tetrahydrofuran;
TMS is trimethylsilyl; and
Tris-HCl is 2-amino-2-(hydroxymethyl)-1,3-propanediol hydrochloride.

The γ-lactam scaffold common to the compounds of the present invention may be derived from the difluorooxopyrrolidinyl intermediate, (R)-3,3-difluoro-5-(hydroxymethyl)pyrrolidin-2-one ((R)-8), which may be prepared from commercially available (R)-(+)-5-oxopyrrolidine-2-carboxylic acid (D-pyroglutamic acid) (1) as illustrated in Scheme 1.

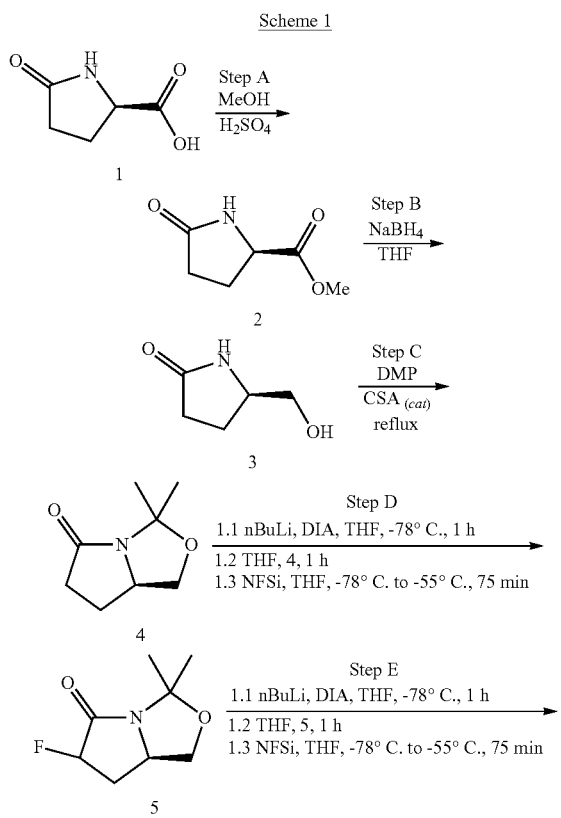

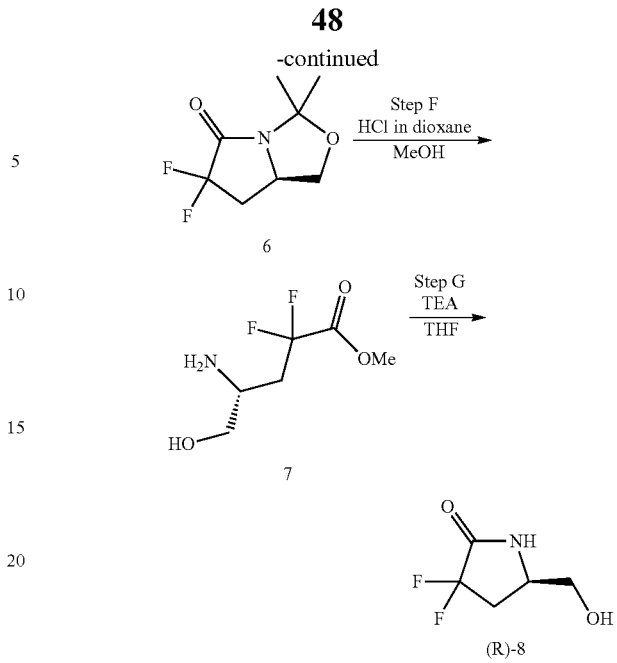

D-pyroglutamic acid (1) may undergo acid-catalyzed esterification in an alcohol solvent, such as methanol, as illustrated in Step A. The resulting ester intermediate (2) may be reduced with sodium borohydride in a solvent, such as THF, to the alcohol intermediate (R)-5-(hydroxymethyl)pyrrolidin-2-one (3) as shown for Step B. The followings Steps C, D, E, F, and G may be carried out according to the procedures described in US 2009/0275537. Simultaneous protection of the alcohol and amide groups of intermediate 3 by the acid-catalyzed addition of 2,2-dimethoxypropane (Step C) provides protected intermediate 4. Subsequent repeat stepwise deprotonation followed by addition of electrophilic fluorine using NFSi (Steps D and E) affords the α,α-difluoropyrrolidone intermediate 6. Treatment of intermediate 6 with HCl in 1,4-dioxane and methanol (Step F) removes the protecting group and opens the lactam ring to provide intermediate 7. Annulation (Step G) is achieved with the use of a base, such as triethylamine, to provide (R)-3,3-difluoro-5-(hydroxymethyl)pyrrolidin-2-one ((R)-8).

An alternative preparation of (R)-8 is illustrated in Scheme 1A.

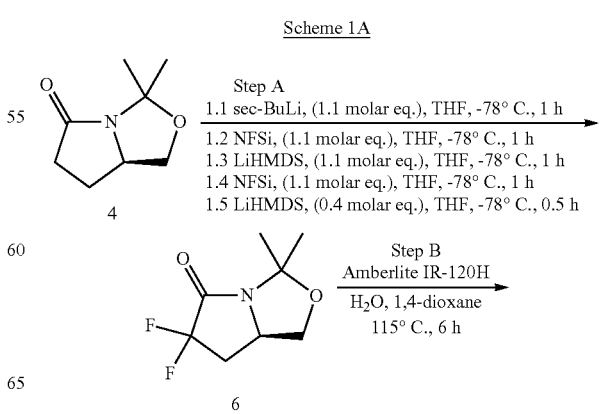

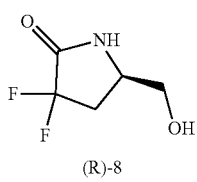

(R)-8

Intermediate (R)-3,3-dimethyltetrahydro-3H,5H-pyrrolo[1,2-c]oxazol-5-one (4) may be converted directly to its difluoro analog (R)-6,6-difluoro-3,3-dimethyltetrahydro-3H,5H-pyrrolo[1,2-c]oxazol-5-one (6) in a one-pot method (Step A) comprising the addition of a solution comprising sec-butyllithium in (about 1.1 molar equivalents of sec-butyllithium) to a solution comprising 4 (limiting reagent) in THF at −78° C., stirring for about an hour at −78° C., subsequent addition of a solution comprising NFSi (about 1.1 molar equivalents of NFSi), stirring for about another hour at −78° C., addition of a solution comprising LiHMDS (about 1.1 molar equivalents), stirring for about another hour at −78° C., subsequent addition of a solution comprising NFSi (about 1.1 molar equivalents of NFSi), stirring for about another hour at −78° C., addition of a solution comprising LiHMDS (about 0.4 molar equivalent), and stirring for about 30 minutes. Intermediate 5 may subsequently be converted directly to (R)-8 by treatment (Step B) with a strongly acid gel-type ion-exchange resin.

Compounds of the present invention may be prepared from 8 or 0-protected 8 by general routes illustrated in Scheme 2.

Compounds of the present invention, (I), may be prepared from 8 or protected 8, for example, by a process that comprises first installing the upper chain with a nitrogen-carbon bond forming reaction (using 8 or an O-protected 8), wherein the nitrogen atom of the γ-lactam ring of 8 forms a covalent bond with the appropriate upper chain carbon atom to provide the corresponding 8+upper chain intermediate shown in Scheme 2. In some aspects of the present invention, the nitrogen-carbon forming reaction comprises an alkylation reaction between 8 or an oxygen-protected analog of 8 and an alkylating agent comprising the upper chain moiety and a leaving group as illustrated in Scheme 2A. In some aspects of the present invention, the alkylating agent is an alkyl halide such as an alkyl iodide, alkyl bromide, or alkyl triflate. In other aspects of the present invention, the alkylating agent is an allyl bromide. In other aspects of the present invention, the alkylating agent is a propargyl halide such as a propargyl bromide.

Scheme 2A

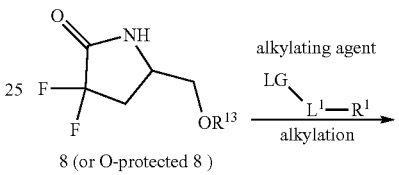

8 (or O-protected 8)

Scheme 2

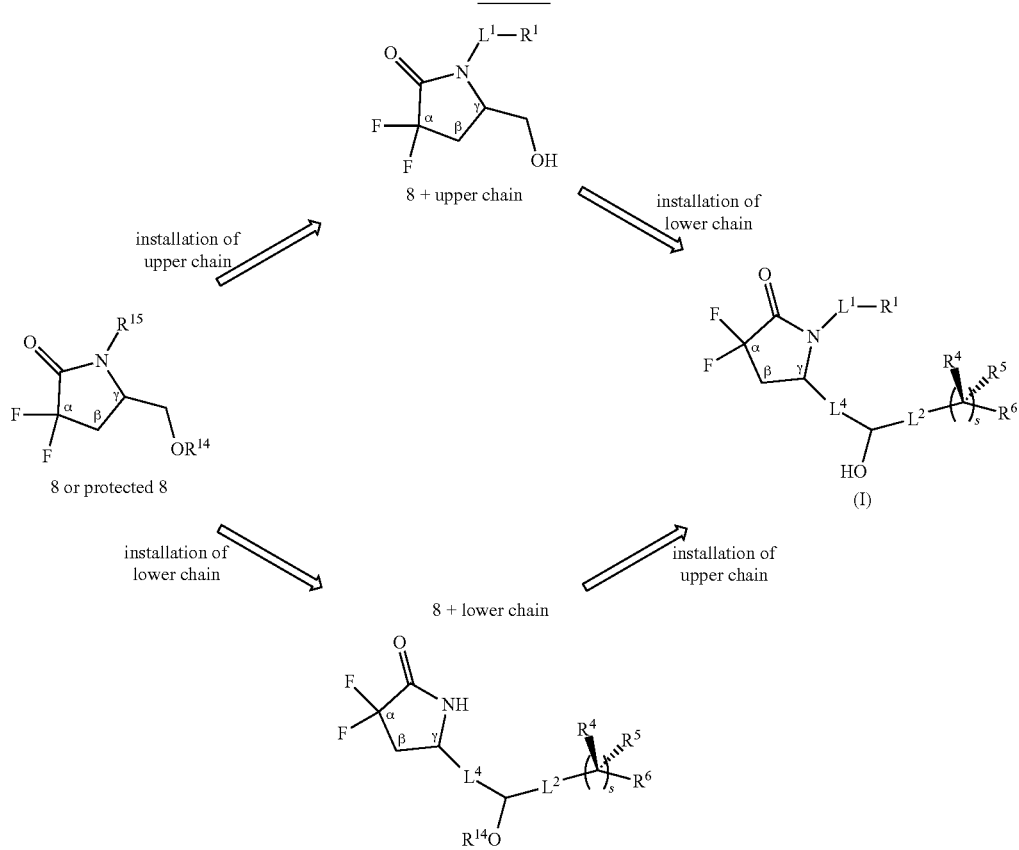

$R^{14}$ is hydrogen or an oxygen protecting group.
$R^{15}$ is hydrogen or a nitrogen protecting group.

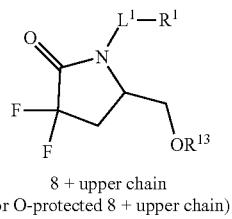

8 + upper chain
(or O-protected 8 + upper chain)

Leaving group "LG" is, for example, iodo, bromo, chloro, trifluoromethanesulfonyl, methanesulfonylate toluenesulfonylate, or 4-nitrobenzenesulfonylate. $R^{13}$ is hydrogen or an oxygen protecting group.

The installation of the upper chain may be followed by a process that comprises installation of the lower chain by way of a carbon-carbon bond forming reaction, wherein the hydroxymethyl group carbon atom attached to the γ-position of the lactam ring of intermediate 8+upper chain forms a covalent bond (carbon-carbon single, double, or triple bond) with the appropriate lower chain carbon atom to provide the corresponding compound (I). In some aspects of the present invention, the intermediate 8+upper chain (directly from the alkylation reaction or its O-protected analog having undergone subsequent deprotection) is oxidized to the corresponding aldehyde intermediate, which may be subsequently subjected to Horner-Wadsworth-Emmons reaction conditions in the presence of a β-keto phosphonate ester coupling partner to, after subsequent reduction of the resulting ketone to the corresponding alcohol, provide compounds (I) of the present invention, wherein $L^4$ is a carbon-carbon double bond, as illustrated in Scheme 1B.

tion, wherein the nitrogen atom of the γ-lactam ring of 8+lower chain forms a covalent bond with the appropriate upper chain carbon atom to provide the corresponding compound (I).

In some aspects of the present invention, the synthetic route to a compound (I) comprises a process wherein certain intermediates 8+upper chain may undergo chemical reaction or a series of chemical reactions, which are known in the art or disclosed herein, that chemically modify the upper chain such that chemical installation and/or modification of the lower chain is facilitated.

In further aspects of the present invention, the synthetic route to a compound (I) comprises a process wherein a certain intermediate 8+upper chain may undergo chemical reaction or a series of chemical reactions, which are known in the art or disclosed herein, that chemically modify the upper chain such that at least one particular functional group or other structural feature not incorporated into said intermediate is incorporated into the structure of invention compound (I).

In some aspects of the present invention, the synthetic route to a compound (I) comprises a process wherein certain intermediates 8+lower chain may undergo chemical reaction or a series of chemical reactions, which are known in the art or disclosed herein, that chemically modify the lower chain such that chemical installation and/or modification of the upper chain is facilitated.

In further aspects of the present invention, the synthetic route to a compound (I) comprises a process wherein a certain intermediate 8+lower chain may undergo chemical reaction or a series of chemical reactions, which are known in the art or disclosed herein, that chemically modify the lower chain such that at least one particular functional group or other structural feature not incorporated into said intermediate is incorporated into the structure of invention compound (I). For some embodiments of compound (I) wherein $L^4$ is a carbon-carbon single bond, the synthesis may comprise a sequence of steps as shown in Scheme 2C.

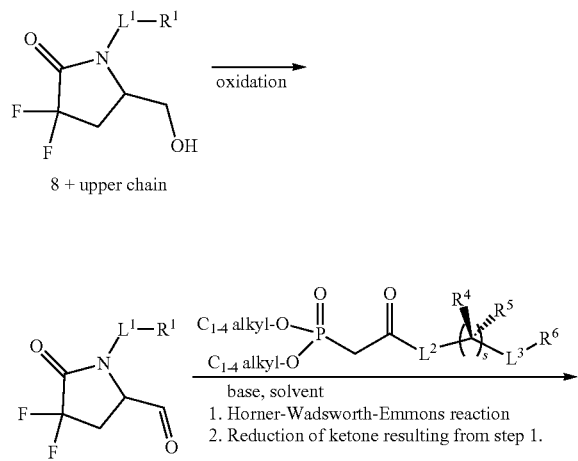

Alternatively, compounds of the present invention, (I), may be prepared from 8 or protected 8, for example, by a process that comprises first installing the lower chain with a carbon-carbon bond forming reaction (using 8 or an N-protected 8), wherein the hydroxymethyl group carbon atom attached to the γ-position of the lactam ring of intermediate 8 forms a covalent bond (carbon-carbon single, double, or triple bond) with the appropriate lower chain carbon atom to provide the corresponding 8+lower chain intermediate shown in Scheme 2. The installation of the lower chain may be followed by a process that comprises installation of the upper chain by way of nitrogen-carbon bond forming reac-

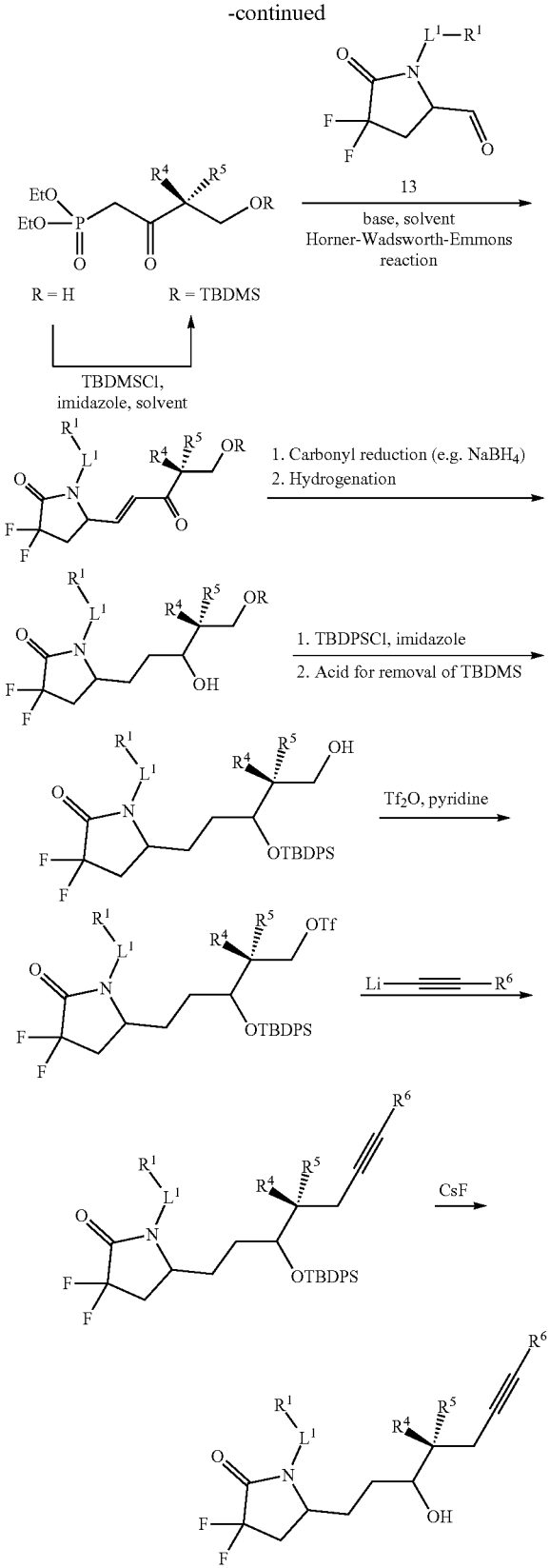

Omission of the hydrogenation step of Scheme 2C may provide compounds of Formula (I) wherein $L^4$ is a carbon-carbon double bond and wherein various $R^4$ and $R^5$ may be incorporated. In some aspects, $R^4$ and $R^5$ are determined by the starting ketone used in the chemical route sequence. Some ketones that may be utilized for this purpose and are commercially available include butan-2-one, pentan-2-one, 3-methyl-2-butanone (Aldrich), cyclopropyl methyl ketone (Aldrich), cyclobutyl methyl ketone (Aldrich), and 1-cyclopentyl-ethanone (Aldrich). Starting ketones and substituted acetylenes may also be available according to published procedures or methods well known to those skilled in the art.

Synthetic routes utilized to prepare compounds of the present invention typically proceed through a carbon-carbon double bond formation (olefination) step to install the compound's lower chain. The olefination may be accomplished by the interaction of an appropriate aldehyde intermediate with an appropriate nucleophilic carbanion species. Such methods may include Wittig reactions, wherein the nucleophilic carbanion species is an appropriate organic phosphonium ylide. Another carbon-carbon bond forming reaction that may be employed is a Horner-Wadsworth-Emmons reaction, wherein the coupling partner with the aldehyde is an appropriate organic phosphonate carbanion. Published reviews describing the general scope and mechanism along with various protocols for these types of olefination reactions include the following:

Boutagy, J. and Thomas, R. *Chemical Reviews*, 1974, 74, 87-99.

Wadsworth, W. S., Jr. *Organic Reactions*, 1977, 25, 73-253.

Walker, B. J. in *Organophosphorous Reagents in Organic Synthesis*, Cadogan, J. I. G., Ed.; Academic Press: New York, 1979, pp. 155-205.

Schlosser, M. et al., *Phosphorous and Sulfur and the Related Elements*, 1983, 18(2-3), 171-174.

Maryanoff, B. E. and Reitz, A. B. *Chemical Reviews*, 1989, 89(4), 863-927.

Kelly, S. E. in *Comprehensive Organic Synthesis*, Trost, B. M. and Fleming, I. Ed.; Pergamon: Oxford, 1991, Vol. 1, pp. 729-817.

Kolodiazhnyi, O. I., *Phosphorus Ylides, Chemistry and Application in Organic Synthesis*; Wiley-VCH: New York, 1999.

Another carbon-carbon bond forming reaction that may be used to install the lower chain is the Peterson olefination reaction, which is reviewed by Ager, D. J. *Organic Reactions*, 1990, 38, 1-223.

Aldehydes that may be used in the olefination step involved in preparation of compounds of the present invention include, but are not limited to, intermediates 13a-f, which can be generally prepared from (R)-3,3-difluoro-5-(hydroxymethyl)pyrrolidin-2-one ((R)-8), as shown in Scheme 3.

Scheme 3

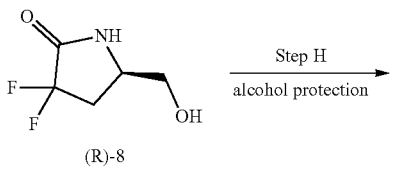

(R)-8

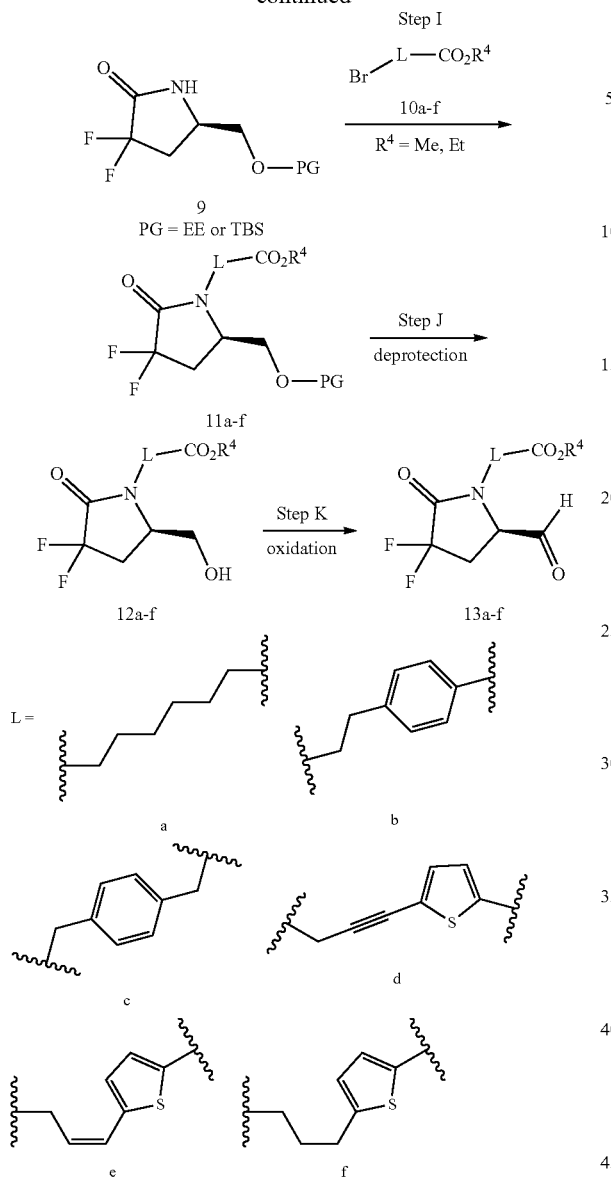

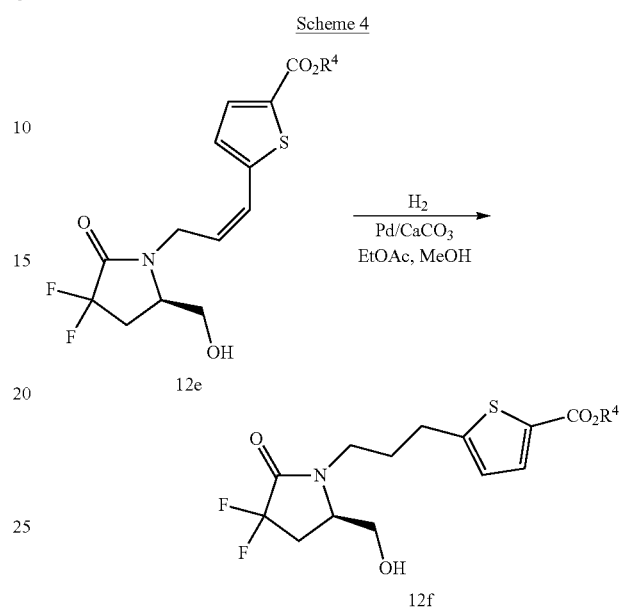

12f followed by the controlled oxidation of the alcohol affords aldehyde intermediate 13f as illustrated in Scheme 3, Step K.

The hydroxyl moiety of intermediate (R)-8 may be protected (Step H) by reacting with ethyl vinyl ether (EVE) in the presence of TFA or tert-butyldimethylsilyl chloride (TBDMSCl) in the presence of a base, such as imidazole, to provide the EE-protected or TBS-protected species (9), respectively. N-alkylation of one of the protected α,α-difluoropyrrolidone intermediates (9) with an alkylating agent, such as one of 10a-f, affords the corresponding intermediate 11a-f (Step I). Alcohol deprotection (Step J) and subsequent controlled alcohol oxidation (Step K) provides the corresponding aldehyde intermediates 13a-f that may be employed in the subsequent olefination step.

Aldehyde intermediate 13f may alternatively be acquired by the hydrogenation of protected alcohol intermediates 11d or 11e to 11f or the unprotected alcohol intermediates 12d or 12e to 12f, followed by the subsequent deprotection (for 11f) and controlled oxidation to 13f. One hydrogenation reaction example is illustrated in Scheme 4. Palladium-catalyzed reduction of the internal carbon-carbon double bond of intermediate 12e (Scheme 4) to provide alcohol intermediate Detailed procedures for preparing the aldehyde intermediates is described below.

Preparation of (R)-methyl 7-(3,3-difluoro-5-formyl-2-oxopyrrolidin-1-yl)heptanoate (13a)

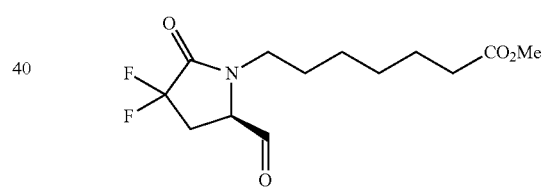

Scheme 1, Step A: Preparation of (R)-methyl 5-oxopyrrolidine-2-carboxylate (2) from (R)-5-oxopyrrolidine-2-carboxylic acid (1)

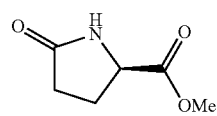

To a solution consisting of (R)-5-oxopyrrolidine-2-carboxylic acid (1,D-pyroglutamic acid from Chem-Impex International, 12.6 g, 97.4 mmol) in methanol (100 mL) was added sulfuric acid (1 mL) and the mixture was stirred at room temperature for 24 hours. The solvent was evaporated from the mixture, and the residue was purified by silica gel chromatography. Elution with acetone-dichloromethane (3:7 v/v) afforded the title intermediate (13.3 g, 95%) as a clear oil; TLC $R_f$ 0.42 (solvent system: 3:7 v/v acetone-dichloromethane); $^1$H-NMR (CDCl$_3$) δ 4.25 (t, 1H), 3.73 (s, 3H), 2.5-2.2 (m, 4H).

Scheme 1, Step B: Preparation of (R)-5-(hydroxymethyl) pyrrolidin-2-one (3)

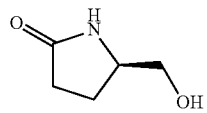

To a solution consisting of (R)-methyl 5-oxopyrrolidine-2-carboxylate (intermediate 2, 13.2 g, 115 mmol) in methanol (100 mL) at 0° C. was added sodium borohydride (10.5 g, 278 mmol) in portions. The reaction mixture was stirred at 0° C. until completion, at which time, acetic acid (3 mL) was added. The reaction mixture was concentrated and the residue was purified on silica gel, eluting with methanol-chloroform (1:9 v/v) to afford the title intermediate (12.9 g, 97%) as a colorless solid; TLC R/0.33 (solvent system: 1:9 v/v methanol-chloroform); $^1$H-NMR (CDCl$_3$) δ 7.17 (s, 1H), 3.92 (s, 1H), 3.85-3.75 (m, 1H), 3.64-3.40 (m, 2H), 2.42-2.35 (m, 2H), 2.2-2.05 (m, 1H), 1.88-1.7 (m, 1H).

Scheme 1, Step C: Preparation of (R)-3,3-dimethyltetrahydropyrrolo[1,2-c]oxazol-5(3H)-one (4)

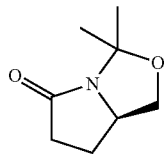

To a solution consisting of (R)-5-hydroxymethyl-2-pyrrolidinone (Alfa Aesar, 5.3 g, 46 mmol) in 2,2-dimethoxypropane (DMP) (40 mL, 326 mmol) was added camphorsulfonic acid (530 mg). The mixture was brought to reflux at 75° C. for 4 hours, and was subsequently concentrated in vacuo. Fresh DMP (40 mL) was then added and the mixture was brought to reflux overnight. After concentration, the remaining residue was purified by silica gel chromatography. Elution with ethyl acetate-heptanes (1:2 v/v) afforded the title intermediate (3.6 g) as a clear oil; TLC R$_f$ 0.20 (solvent system 50:50 v/v heptanes:ethyl acetate); $^1$H-NMR (CDCl$_3$) δ 4.3-4.2 (1H, m), 4.1 (1H, dd), 3.5 (1H, t), 2.9-2.7 (1H, m), 2.6-2.5 (1H, m), 2.2-2.1 (1H, m), 1.9-1.7 (1H, m), 1.7 (3H, s), 1.5 (3H, s); MS (ESI$^+$) m/z 156.2 (M+1).

Scheme 1, Step C: First alternative preparation of (R)-3,3-dimethyltetrahydropyrrolo[1,2-c]oxazol-5(3H)-one (4)

To a mixture consisting of (R)-5-hydroxymethyl-2-pyrrolidinone (20 g, 174 mmol) in 2,2-dimethoxypropane (1.4 L, 11,400 mmol) was added camphorsulfonic acid (1.0 g, 4.3 mmol). The stirring mixture was heated to 75° C. for 20 hours. The reaction mixture was treated with a saturated aqueous solution of sodium bicarbonate, diluted with water, and extracted with ethyl acetate. The combined organic phase was washed with a saturated aqueous solution of sodium chloride, dried over sodium sulfate, filtered, and concentrated. The residue was purified by silica gel chromatography. Elution with methanol-dichloromethane (1:70 v/v) afforded the title compound as a white solid (21.2 g, 78%); TLC R$_f$ 0.6 (solvent system: 25:75 v/v ethyl acetate-hexane); MS (ESI$^+$) m/z 156.1 (M+H)$^+$, 178.1 (M+Na)$^+$; $^1$H-NMR (CDCl$_3$) δ 4.3-4.2 (1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Scheme 1, Step C: Second alternative preparation of (R)-3,3-dimethyltetrahydropyrrolo[1,2-c]oxazol-5(3H)-one (4)

To a mixture consisting of (R)-5-hydroxymethyl-2-pyrrolidinone (50.0 g, 434 mmol) in 2,2-dimethoxypropane (533 mL, 4300 mmol) was added camphorsulfonic acid (2.85 g, 10.8 mmol). The stirring mixture was brought to reflux at 88° C. for 1.5 hours, while removing methanol by distillation. The reaction mixture was subsequently heated to 95° C. for one hour, cooled to room temperature, treated with triethylamine (5 mL), and stirred for 5 minutes. The mixture was then diluted with hexanes-ethyl acetate (500 mL, 1:3 v/v) and washed sequentially with a 50% aqueous solution of sodium chloride and a saturated aqueous solution of sodium chloride. The organic phase was dried over sodium sulfate, filtered, and concentrated. The residue was purified by crystallization from hexanes to afford the title compound as white crystalline solid (30.48 g, 45%); TLC R/0.4 (solvent system: 5:95 v/v methanol:dichloromethane) MS (ESI$^+$) m/z 156.1 (M+H)$^+$, 178.1 (M+Na)$^+$; $^1$H-NMR (CDCl$_3$) δ 4.3-4.2 (m, 1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Scheme 1, Step D: Preparation of (R)-6-fluoro-3,3-dimethyltetrahydropyrrolo [1,2-c]oxazol-5(3$^1$-O-one (5)

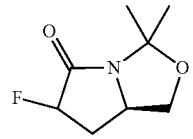

To a mixture consisting of diisopropylamine (6.5 mL, 46 mmol) and THF (75 mL) at −78° C. was added dropwise a solution of nBuLi (2.5 M in hexanes, 18 mL, 44 mmol), and the resulting solution stirred for one hour. A solution consisting of (R)-3,3-dimethyltetrahydropyrrolo[1,2-c]oxazol-5 (3H)-one (intermediate 4, 3.6 g, 23 mmol) in THF (25 mL) was added dropwise, and the resulting solution stirred for one hour. A solution consisting of N-fluorobenzenesulfonimide (9.5 g, 30 mmol) in THF (50 mL) was added dropwise, and the resulting solution was allowed to stir for 75 minutes below −55° C., and was subsequently quenched with the addition of a saturated aqueous ammonium chloride solution and warmed to room temperature. The organic material was extracted twice with ethyl acetate. The combined organic phase was dried over anhydrous sodium sulfate, filtered, and concentrated. The residue was dissolved in ethyl acetate, filtered, and the filtrate was concentrated to a gold oil, which was purified by silica gel chromatography. Elution with ethyl acetate:heptanes (1:3 v/v) afforded an approximately 1:1 mixture of the diastereomers of the title intermediate (1.54 g) as a clear oil; TLC R$_f$ 0.40 (solvent system 50:50 v/v heptanes:ethyl acetate); $^1$H-NMR (CDCl$_3$) δ 5.4-5.2 (m, 1H), 5.2-5.0 (m, 1H), 4.5-4.4 (m, 1H), 4.2-4.1 (m, 2H), 4.0-3.9 (m, 1H), 3.5 (t, 1H), 3.4 (t, 1H), 2.8-2.7 (m, 1H), 2.5-2.3 (m, 1H), 2.1-1.8 (m, 2H), 1.7 (s, 3H), 1.7 (s, 3H), 1.5 (s, 3H) 1.5 (s, 3H); $^{19}$F-NMR (CDCl$_3$, 376 MHz) δ−102.2 (dd, −0.5F, J=264.2, 13.2 Hz), −103.5 (ddd, −0.5F, J=264.3, 26.5, 14.6 Hz); MS (ESI$^+$) m/z 174.1 (M+1).

Scheme 1, Step D: Alternative preparation of (7aR)-6-fluoro-3,3-dimethyltetrahydropyrrolo[1,2-c]oxazol-5(3H)-one (5)

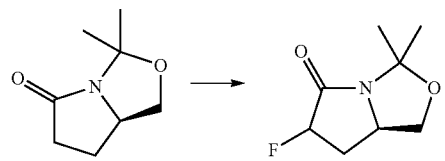

To a solution consisting of (R)-3,3-dimethyltetrahydropyrrolo[1,2-c]oxazol-5(3H)-one (intermediate 4, 18.5 g, 119 mmol) in dry THF (400 mL) at −75° C. was added lithium diisopropylamide (74.5 mL, 149 mmol, 2 M in heptanes/THF/ethylbenzene from Sigma Aldrich) dropwise over 20 minutes, then stirred for one hour. The reaction mixture was then treated with a solution consisting of N-fluorobenzenesulfonimide (56.6 g, 167 mmol, NFSi, from Oakwood Chemical) in THF (300 mL) with steady addition over 30 minutes, and the resulting mixture was stirred for 16 hours, warming to room temperature. To the reaction mixture was added a saturated aqueous solution of ammonium chloride. The organic material was extracted twice with ethyl acetate. The organic layer was washed with a 50% aqueous solution of sodium chloride, followed by a saturated solution of sodium chloride, and dried over sodium sulfate, filtered, and concentrated. The residue was redissolved in ethyl acetate (200 mL) and treated with heptane (200 mL), causing the formation of a white precipitate. The precipitate was filtered and washed with 50% ethyl acetate in heptane. The combined filtrate was concentrated. The residue was dissolved in ethyl acetate (200 mL) and treated with heptane (200 mL), forming a second precipitate. The second precipitate was filtered and washed with 50% ethyl acetate in heptane. The filtrate was concentrated and the residue (31 g) was purified by silica gel chromatography. Elution with ethyl acetate-hexanes (1:3 v/v) afforded pure samples of each of the two diastereomers of the title compound as tan solids (4.1 g of each) and a portion of mixed diastereomers (3.8 g of an approximately 1:1 ratio). The total mass of the two diastereomer products isolated was 12.0 g (65% total yield).

(6S,7aR)-6-fluoro-3,3-dimethyltetrahydropyrrolo[1,2-c]oxazol-5(3H)-one (5.1α) and (6R,7aR)-6-fluoro-3,3-dimethyltetrahydropyrrolo[1,2-c]oxazol-5(3H)-one (5.1β)

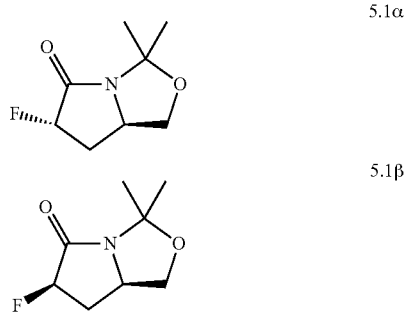

5.1α

5.1β

Separation of the two isomers by chromatography, as described above, provided the two pure diastereomers.

(5.1α) TLC R$_f$ 0.55 (solvent system: 60:40 v/v ethyl acetate-hexanes); HPLC on an Agilent 1100 instrument, ultraviolet detector at 210 nm, stationary phase Gemini 3μ C18, 50×2 mm column, mobile phase, water-methanol-acetic acid gradient over 4 min (90:10:0.1 to 10:90:0.1), retention time 2.33 minutes; MS (ESI⁺) m/z 174.1 (M+H)⁺; 1H-NMR (CDCl$_3$) δ 5.085 (ddd, J=51.6, 6.0, 0.8 Hz, 1H) 4.5-4.4 (m, 1H), 4.15 (dd, 1H), 3.4 (dd, 1H), 2.5-2.3 (m, 1H), 2.1-1.7 (m, 1H), 1.65 (s, 3H), 1.5 (s, 3H); ¹⁹F-NMR (CDCl$_3$, 376 MHz) δ−184.5 (ddd, J=52, 41, 22 Hz, 1F).

(5.1β) TLC R$_f$ 0.45 (solvent system: 60:40 v/v ethyl acetate-hexanes); HPLC on an Agilent 1100 instrument, ultraviolet detector at 210 nm, stationary phase Gemini 3μ C18, 50×2 mm column, mobile phase, water-methanol-acetic acid gradient over 4 min (90:10:0.1 to 10:90:0.1), retention time 1.69 minutes; MS (ESI⁺) m/z 174.1 (M+H)⁺; 1H-NMR (CDCl$_3$) δ 5.325 (ddd, J=52.4, 9.9, 7.7 Hz, 1H) 4.2 (dd, 1H), 4.0-3.9 (m, 1H), 3.5 (dd, 1H), 2.8-2.7 (m, 1H), 2.0-1.9 (m, 1H), 1.7 (s, 3H), 1.5 (s, 3H); ¹⁹F-NMR (CDCl$_3$, 376 MHz) δ−185.9 (dd, J=52, 23 Hz, 1F).

Scheme 1, Step E: Preparation of (R)-6,6-difluoro-3,3-dimethyltetrahydropyrrolo [1,2-c]oxazol-5(31-1)-one (6)

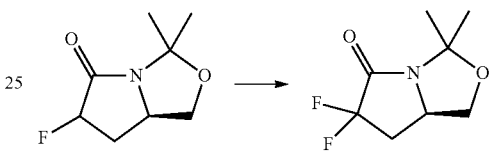

To a solution consisting of (7aR)-6-fluoro-3,3-dimethyltetrahydropyrrolo[1,2-c]oxazol-5(3H)-one (8.0 g, 46.2 mmol, mixture of diastereomers of 5.1) in dry THF (300 mL) at −75° C. was added lithium bis(trimethylsilyl)amide (50.8 mL, 50.8 mmol, LiHMDS 1 M in THF) dropwise over ten minutes, then stirred for one hour. The reaction mixture was then treated with a solution consisting of N-fluorobenzenesulfonimide (17.5 g, 55.4 mmol) in THF (100 mL) with steady addition over ten minutes. The resulting mixture was stirred for 30 minutes. Lithium bis(trimethylsilyl)amide (10.0 mL, 10 mmol) was added, and the reaction stirred for 16 hours, warming to room temperature. To the reaction mixture was added a 50% aqueous solution of ammonium chloride. The organic material was extracted with ethyl acetate-heptane (5:1). The organic layer was washed sequentially with a 50% aqueous solution of sodium chloride, water, and a saturated solution of sodium chloride, then dried over sodium sulfate, filtered, and concentrated. The residue was purified by silica gel chromatography. Elution with ethyl acetate-hexanes (1:5 v/v) afforded the title compounds as a tan solid (7.39 g; 79%); TLC R$_f$ 0.70 (solvent system: 50:50 v/v ethyl acetate-hexanes); ¹H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 1, Step E: Preparation of (R)-6,6-difluoro-3,3-dimethyltetrahydropyrrolo [1,2-c]oxazol-5(3H)-one (6)

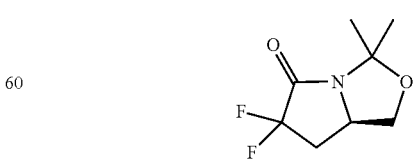

To a mixture consisting of diisopropylamine (2.2 mL, 8.9 mmol) and THF (40 mL) at −78° C. was added dropwise a solution of nBuLi (2.5 M in hexanes, 6.0 mL, 15 mmol), and the resulting solution stirred for one hour. A solution consisting of (7aR)-6-fluoro-3,3-dimethyltetrahydropyrrolo[1,2-c]oxazol-5(3H)-one (intermediate 5, 1.54 g, 8.90 mmol) in THF (25 mL) was added dropwise, and the resulting solution stirred for one hour. A solution consisting of N-fluorobenzenesulfonimide (3.5 g, 11 mmol) in THF (25 mL) was added dropwise, and the resulting mixture was allowed to stir for 75 minutes below −55° C. The reaction mixture was subsequently quenched with the addition of a saturated aqueous ammonium chloride solution and warmed to room temperature. The organic material was extracted twice with ethyl acetate. The combined organic phase was dried over anhydrous sodium sulfate, filtered, and concentrated. The residue was dissolved in ethyl acetate, filtered, and the filtrate was concentrated to a gold oil which was purified by silica gel chromatography. Elution with ethyl acetate:heptanes (1:5 v:v) afforded the title intermediate (1.28 g, 75%) as a clear oil; TLC $R_f$ 0.60 (solvent system 50:50 v/v heptanes:ethyl acetate); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H); MS (ESI$^+$) m/z 192.1 (M+1).

Scheme 1A, Step A: Alternative Preparation of (R)-6,6-difluoro-3,3-dimethyltetrahydropyrrolo [1,2-c]oxazol-5(3H)-one (6)

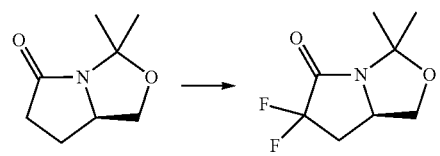

To a mixture consisting of (R)-3,3-dimethyltetrahydropyrrolo[1,2-c]oxazol-5(31-1)-one (4) (15.5 g, 100 mmol) in dry THF (300 mL) at −78° C. was added sec-butyllithium (78.5 mL, 110 mmol, 1.4 M in cyclohexane, from Sigma Aldrich) dropwise over 5 minutes. The resulting reaction mixture was stirred for one hour and was subsequently treated with a mixture consisting of N-fluorobenzene sulfonimide (35 g, 111 mmol, NFSi, from Oakwood) in THF (100 mL) with steady addition over five minutes. The resulting reaction mixture was stirred for another hour, after which time a lithium bis(trimethylsilyl)amide solution (LiHMDS, 110 mL, 110 mmol, 1.0 M in THF, from Sigma Aldrich) was added dropwise over five minutes. The resulting reaction mixture was stirred for another hour, after which time a mixture consisting of NFSi (34.4 g, 109 mmol) in THF (100 mL) was added over five minutes. The resulting reaction mixture was stirred for two hours, after which time was added lithium bis(trimethylsilyl)amide (40 mL, 40 mmol, 1M in THF) to the −78° C. reaction mixture, which was subsequently stirred for 30 minutes. The cooling bath was removed and a saturated aqueous solution of ammonium chloride added. The reaction mixture was allowed to warm to room temperature, and the organic material was extracted with ethyl acetate. The organic layer was sequentially washed with water, a 50% saturated aqueous solution of sodium chloride, and a saturated solution of sodium chloride, dried over sodium sulfate, filtered, and concentrated. The residue was purified by silica gel chromatography. Elution with ethyl acetate-hexanes (1:3 v/v) afforded the title compound as a solid (11.64 g; 61%); TLC $R_f$ 0.4 (solvent system: 5:95 v/v methanol-dichloromethane); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 1, Step F: Preparation of (R)-methyl 4-amino-2,2-difluoro-5-hydroxypentanoate (7)

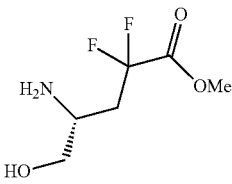 [SMILES: COC(=O)C(F)(F)C[C@@H](N)CO]

To an ice-cooled solution consisting of (R)-6,6-difluoro-3,3-dimethyltetrahydropyrrolo[1,2-c]oxazol-5(3H)-one (intermediate 6, 1.28 g, 6.70 mmol) in methanol (20 mL) was added dropwise 4N HCl in dioxane (3.0 mL, 12 mmol) and stirred at room temperature for 16 hours. The resulting mixture was concentrated and the product concentrate used without purification; TLC $R_f$ 0.60 (solvent system 93:7 v/v dichloromethane-methanol).

Scheme 1, Step G: Preparation of (R)-3,3-difluoro-5-(hydroxymethyl)pyrrolidin-2-one ((R)-8)

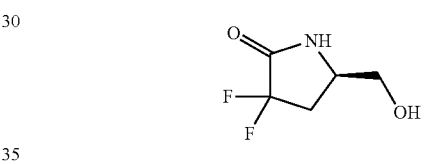

To a solution consisting of (R)-methyl 4-amino-2,2-difluoro-5-hydroxypentanoate (intermediate 7, 6.70 mmol) in THF (25 mL) was added triethylamine (6 mL) and the reaction mixture was stirred overnight. The reaction mixture was concentrated to give a crude residue, which was purified by silica gel chromatography. Elution with methanol:dichloromethane (1:20 v/v) afforded the title intermediate (540 mg) as a clear oil; TLC $R_f$ 0.40 (solvent system 93:7 v/v dichloromethane:methanol); $^1$H-NMR (CDCl$_3$) δ 3.7-3.6 (w, 1H), 3.6-3.4 (m, 2H), 3.4-3.2 (m, 1H), 2.7-2.4 (m, 1H), 2.4-2.1 (m, 1H); MS (ESI$^+$) m/z 152.1 (M+1); (ESI$^-$) m/z 150.1 (M−1).

Scheme 1A, Step B: Alternative preparation of (R)-3,3-difluoro-5-(hydroxymethyl)pyrrolidin-2-one ((R)-8)

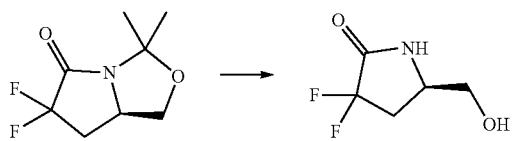

To a solution consisting of (R)-6,6-difluoro-3,3-dimethyltetrahydropyrrolo[1,2-c]oxazol-5(3H)-one (intermediate 6, 12.5 g, 65.4 mmol) in water-1,4-dioxane (300 mL, 1:1 v/v) was added Amberlite IR-120H* (6.23 g). The reaction mixture was heated to 115° C. for 6 hours and was subsequently filtered through Celite and washed with methanol.

The filtrate was concentrated under reduced pressure, using toluene and ethanol additives to help drive off water, to provide a residue. The residue was washed with diethyl ether to afford the title compound as a tan solid (8.8 g; 89%), which was carried on without further purification; TLC $R_f$ 0.25 (solvent system: 70:30 v/v ethyl acetate:hexanes). Amberlite IR-120H ion-exchange resin, strongly acid gel-type resin with sulfonic acid functionality, CAS: 39389-20-3. 75 g of Amberlite was washed and decanted three times with deionized water. The fourth wash was filtered using suction filtration and the semi-dry resin was quickly washed with 2-propanol then diethyl ether. The resin was dried to give 54 g of free flowing dark brown bead resin.

Scheme 3, Step H: Preparation of (5R)-5-((1-ethoxyethoxy)methyl)-3,3-difluoropyrrolidin-2-one (9; PG=EE)

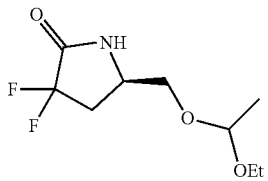

To a solution consisting of (R)-3,3-difluoro-5-(hydroxymethyl)pyrrolidin-2-one (intermediate 8, 540 mg, 3.57 mmol) in dichloromethane (20 mL) and THF (10 mL) was added ethyl vinyl ether (1.4 mL, 15 mmol) followed by trifluoroacetic acid (20 mg). The reaction mixture was stirred at room temperature for 16 hours. The reaction mixture was diluted with ethyl acetate (150 mL) and washed with a saturated aqueous solution of sodium bicarbonate (10 mL) and brine (5 mL) before being dried over sodium sulfate, filtered, and concentrated. The residue was purified by silica gel chromatography. Elution with methanol:dichloromethane (1:60 v/v) afforded the title intermediate (726 mg) as a clear oil; TLC $R_f$ 0.60 (solvent system: 93:7 v/v dichloromethane:methanol); $^1$H-NMR (CDCl$_3$) δ 4.8-4.6 (m, 1H), 4.0-3.8 (m, 1H), 3.7-3.5 (m, 2H), 3.5-3.4 (m, 2H), 2.8-2.6 (m, 1H), 2.4-2.2 (m, 1H), 1.3 (d, 3H), 1.2 (t, 3H); MS (ESI$^+$) m/z 241.1 (M+NH$_3$), 246.1 (M+Na); (ESI$^-$) m/z 222.1 (M−1).

Scheme 3, Step H: Preparation of (R)-5-(((tert-butyldimethylsilyl)oxy)methyl)-3,3-difluoropyrrolidin-2-one (9; PG=TBS)

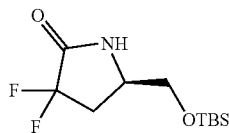 [SMILES: CC(C)(C)[Si](C)(C)OC[C@H]1CC(F)(F)C(=O)N1]

To a solution consisting of (R)-3,3-difluoro-5-(hydroxymethyl)pyrrolidin-2-one (intermediate 8, 880 mg, 3.57 mmol) in DMF (10 mL) and THF (10 mL) was added tert-butyldimethylchlorosilane (1.40 g, 9.23 mmol) followed by imidazole (800 mg, 6.55 mmol). The reaction mixture was stirred at room temperature for 16 hours. The reaction mixture was diluted with water (10 mL) and extracted thrice with ethyl acetate (55 ml, 2×25 ml). The combined organics were washed with 1:1 water:brine (3×10 mL) and brine (5 mL) before being dried over sodium sulfate, filtered, and concentrated. The residue was purified by silica gel chromatography. Elution with methanol:dichloromethane (1:50 v/v) afforded the title intermediate (1528 mg, 99%) as a clear oil; TLC $R_f$ 0.60 (solvent system: 95:5 v/v dichloromethane-methanol); $^1$H-NMR (CDCl$_3$) δ 3.8-3.7 (m, 1H), 3.7-3.6 (m, 1H), 3.5-3.4 (m, 1H), 2.6-2.5 (m, 1H), 2.3-2.1 (m, 1H), 0.8 (s, 9H), 0.0 (s, 6H); MS (ESI$^+$) m/z 266.1 (M+1).

Scheme 3, Step I: Preparation of methyl 7-((5R)-5-((1-ethoxyethoxy)methyl)-3,3-difluoro-2-oxopyrrolidin-1-yl)heptanoate (11a)

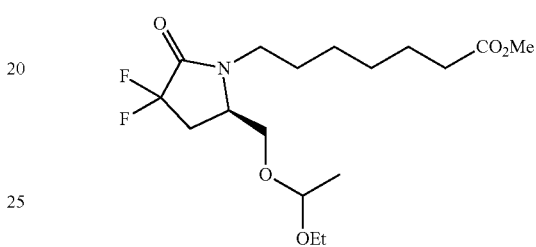

To a suspension consisting of sodium hydride (60% in mineral oil, 18 mg, 0.45 mmol) and sodium iodide (74 mg, 0.49 mmol) in DMF (5 mL) was added dropwise a solution of (5R)-5-((1-ethoxyethoxy)methyl)-3,3-difluoropyrrolidin-2-one (intermediate 9; PG=EE, 100 mg, 0.45 mmol) in DMF (5 mL). The mixture was stirred at room temperature for two hours followed by 50° C. for 30 minutes. To the reaction mixture was added dropwise methyl 7-bromoheptanoate (10a, Alfa Aesar, 120 mg, 0.538 mmol) and stirring continued overnight at 50° C. The mixture was diluted with ethyl acetate (200 mL) and washed sequentially with 0.5N hydrochloric acid (20 mL), a 5% aqueous solution of sodium thiosulfate (10 mL), 50% brine (4×25 mL), and brine (25 mL). The organic phase was dried over sodium sulfate, filtered, and concentrated. The residue was purified by silica gel chromatography. Elution with methanol:dichloromethane (1:100 v/v) afforded the title intermediate (128 mg, 78%) as a clear oil; TLC $R_f$ 0.95 (solvent system: 93:7 v/v dichloromethane:methanol); $^1$H-NMR (CDCl$_3$) δ 4.7 (dq, 1H), 3.85-3.75 (m, 1H), 3.75-3.4 (m, 8H), 3.15-3.05 (m, 1H), 2.65-2.35 (m, 1H), 2.3 (t, 2H), 1.7-1.4 (m, 4H), 1.4-1.3 (m, 4H), 1.3 (d, 3H), 1.2 (t, 3H); MS (ESI$^+$) m/z 383.2 (M+NH$_3$)$^+$, 388.1 (M+Na).

Alternative Preparation of 11a:

To a suspension consisting of sodium hydride (60% in mineral oil, 108 mg, 2.7 mmol) and sodium iodide (450 mg, 3.0 mmol) in DMF (30 mL) was added dropwise a solution consisting of (5R)-5-((1-ethoxyethoxy)methyl)-3,3-difluoropyrrolidin-2-one (intermediate 9; PG=EE, 600 mg, 2.68 mmol) in DMF (30 mL). The reaction mixture was stirred at room temperature for two hours followed by 50° C. for 30 minutes. To the reaction mixture was added dropwise methyl 7-bromoheptanoate (available from Alfa Aesar, 720 mg, 2.23 mmol) and stirring continued overnight at 50° C. The mixture was diluted with ethyl acetate and washed sequentially with 0.5N hydrochloric acid, a 5% aqueous solution of sodium thiosulfate, 50% saturate aqueous solution of sodium chloride, and saturate aqueous solution of sodium chloride. The organic phase was dried over sodium sulfate, filtered, and concentrated. The residue was purified by silica gel chromatography. Elution with methanol:dichloromethane (1:125 v/v) afforded the title intermediate (888 mg, 90%) as a tan solid; TLC R$_f$ 0.95 (solvent system: 93:7 v/v dichloromethane-methanol); MS (ESI$^+$) m/z 383.2 (M+NH$_4$)$^+$, 388.1 (M+Na)$^+$.

Scheme 3, Step J: Preparation of (R)-methyl 7-(3,3-difluoro-5-(hydroxymethyl)-2-oxopyrrolidin-1-yl) heptanoate (12a)

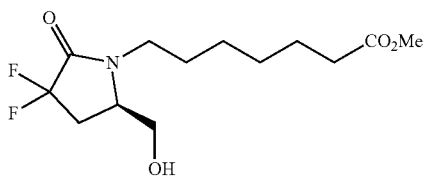 [SMILES: COC(=O)CCCCCCN1C(=O)C(F)(F)C[C@@H]1CO]

To a solution consisting of methyl 7-((5R)-5-((1-ethoxyethoxy)methyl)-3,3-difluoro-2-oxopyrrolidin-1-yl)heptanoate (intermediate 11a, 113 mg, 0.310 mmol) in methanol (10 mL) was added p-toluenesulfonic acid monohydrate (2 mg) and the mixture was stirred at room temperature for 18 hours. The reaction mixture was concentrated to give a crude residue that was purified by silica gel chromatography. Elution with methanol-dichloromethane (1:80 v/v) afforded the title intermediate (86 mg, 95%) as a pale yellow oil; TLC R$_f$ 0.55 (solvent system: 7:93 v/v methanol-dichloromethane); $^1$H-NMR (CDCl$_3$) δ 3.85-3.6 (m, 4H), 3.65 (s, 3H), 3.2-3.1 (m, 1H), 2.6-2.4 (m, 2H), 2.3 (t, 2H), 1.7-1.4 (m, 4H), 1.4-1.2 (m, 4H); MS (ESI$^+$) m/z 311.2 (M+$^+$NH$_4$), 316.1 (M+Na).

Scheme 3, Step K: Preparation of (R)-methyl 7-(3,3-difluoro-5-formyl-2-oxopyrrolidin-1-yl) heptanoate (13a)

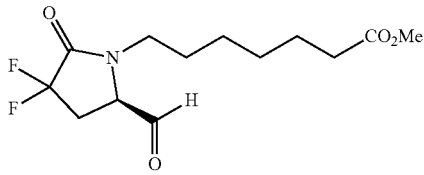 [SMILES: COC(=O)CCCCCCN1C(=O)C(F)(F)C[C@@H]1C=O]

To a solution consisting of (R)-methyl 7-(3,3-difluoro-5-(hydroxymethyl)-2-oxopyrrolidin-1-yl)heptanoate (intermediate 12a, 85 mg, 0.29 mmol) in dichloromethane (10 ml) was added Dess-Martin periodinate (150 mg, 0.348 mmol), and the reaction mixture was stirred for four hours. The reaction mixture was filtered and the filtrate was subsequently concentrated. Without further workup, the residue was purified by silica gel chromatography. Elution with methanol-dichloromethane (1:200 v/v) afforded the title intermediate (76.6 mg, 91%) as a pale yellow oil; TLC R$_f$ 0.60 (solvent system: 7:93 v/v methanol-dichloromethane).

Preparation of (R)-methyl 4-(2-(3,3-difluoro-5-formyl-2-oxopyrrolidin-1-yl)ethyl)benzoate (13b)

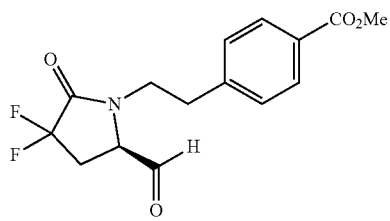 [SMILES: COC(=O)c1ccc(CCN2C(=O)C(F)(F)C[C@@H]2C=O)cc1]

Scheme 3, Step I: Preparation of (R)-methyl 4-(2-(5-(((tert-butyldimethylsilyl)oxy)methyl)-3,3-difluoro-2-oxopyrrolidin-1-yl)ethyl)benzoate (11b; PG=TBS)

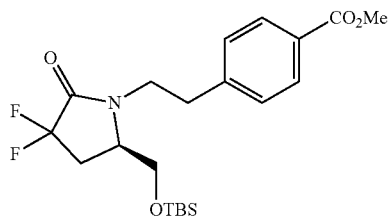 [SMILES: COC(=O)c1ccc(CCN2C(=O)C(F)(F)C[C@@H]2CO[Si](C)(C)C(C)(C)C)cc1]

To a suspension consisting of sodium hydride (60% in mineral oil, 61 mg, 1.5 mmol) and sodium iodide (251 mg, 1.67 mmol) in DMF (40 mL) was added dropwise a solution consisting of (R)-5-(((tert-butyldimethylsilyl)oxy)methyl)-3,3-difluoropyrrolidin-2-one (intermediate 9; PG=TBS, 370 mg, 1.39 mmol) in DMF (5 mL). The mixture was stirred at room temperature for two hours followed by 50° C. for 30 minutes. To the reaction mixture was added dropwise methyl 4-(2-bromoethyl)benzoate (406 mg, 1.67 mmol) in DMF (5 mL), and stirring continued overnight at 50° C. The mixture was diluted with ethyl acetate and washed sequentially with 0.5 N hydrochloric acid, a 5% aqueous solution of sodium thiosulfate, 50% brine, and brine. The organic phase was dried over sodium sulfate, filtered, and concentrated. The residue was purified by silica gel chromatography. Elution with ethyl acetate:heptane (increasing solvent strength, 1:50 v/v to 1:10 v/v) followed by eluting with methanol-dichloromethane (1:50 v/v) afforded the title intermediate (39 mg, 6.6%); TLC R$_f$ 0.6 (solvent system: 70:30 v/v heptane:ethyl acetate); $^1$H-NMR (CDCl$_3$) δ 7.9 (d, 2H), 7.28 (d, 2H), 3.98-3.91 (m, 1H), 3.9 (s, 3H), 3.74-3.48 (m, 2H), 3.46-3.35 (m, 2H), 3.1-2.9 (m, 2H), 2.48-2.18 (m, 2H), 0.8 (s, 9H), 0.0 (s, 6H); MS (ESI$^+$) m/z 445.1 (M+NH$_3$).

Significant improvement of the yield (in relation to (R)-5-(((tert-butyldimethylsilyl)oxy)methyl)-3,3-difluoropyrrolidin-2-one) was realized by repeated additions of sodium hydride and methyl 4-(2-bromoethyl)benzoate to the reaction mixture.

Scheme 3, Step J: (R)-methyl 4-(2-(3,3-difluoro-5-(hydroxymethyl)-2-oxopyrrolidin-1-yl)ethyl)benzoate (12b)

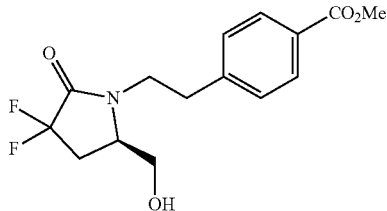 [SMILES: COC(=O)c1ccc(CCN2C(=O)C(F)(F)C[C@@H]2CO)cc1]

To a solution consisting of (R)-methyl 4-(2-(5-(((tert-butyldimethylsilyl)oxy)methyl)-3,3-difluoro-2-oxopyrrolidin-1-yl)ethyl)benzoate (11b, 180 mg, 0.42 mmol) in THF (10 mL) was added tetrabutylammonium fluoride (0.55 mL, 1M in THF), and the reaction mixture was stirred overnight. The reaction mixture was diluted with ethyl acetate and washed with 1:1 brine-water (3×15 mL) and once with brine. The organic phase was dried over sodium sulfate, filtered, and concentrated. The crude residue was purified by silica gel chromatography. Elution with methanol-dichloromethane (increasing solvent strength, 1:200 v/v to 1:30 v/v) afforded the title intermediate (147 mg); TLC $R_f$ 0.5 (solvent system: 5:95 v/v methanol-dichloromethane); $^1$H-NMR (CDCl$_3$) δ 7.9 (d, 2H), 7.24 (d, 2H), 3.98-3.91 (m, 1H), 3.87 (s, 3H), 3.74-3.48 (m, 2H), 3.51-3.46 (m, 2H), 3.1-2.8 (m, 2H), 2.48-2.22 (m, 2H); MS (ESI$^+$) m/z 331 (M+$^+$NH$_4$).

Scheme 3, Step K: Preparation of (R)-methyl 4-(2-(3,3-difluoro-5-formyl-2-oxopyrrolidin-1-yl)ethyl)benzoate (13b)

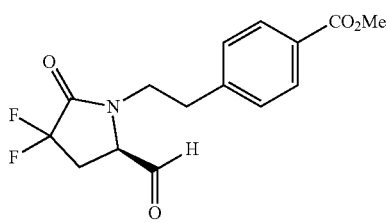 [SMILES: COC(=O)c1ccc(CCN2C(=O)C(F)(F)C[C@@H]2C=O)cc1]

(R)-methyl 4-(2-(3,3-difluoro-5-formyl-2-oxopyrrolidin-1-yl)ethyl)benzoate was prepared from 12b using the oxidation procedure (Step K) described for the preparation of intermediate 13a from intermediate 12a; TLC $R_f$ 0.4 (solvent system: 95:5 v/v dichloromethane-methanol); $^1$H-NMR (CDCl$_3$) δ 9.2 (s, 1H), 7.9 (dd, 2H), 7.24 (dd, 2H), 3.98-3.91 (m, 1H), 3.87 (s, 3H), 3.74-3.48 (m, 2H), 3.51-3.46 (m, 2H), 3.1-2.8 (m, 2H), 2.48-2.22 (m, 2H).

Preparation of (R)-methyl 5-(3-(3,3-difluoro-5-formyl-2-oxopyrrolidin-1-yl)prop-1-yn-1-yl)thiophene-2-carboxylate (13d)

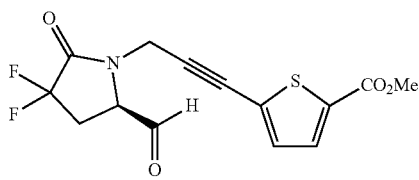 [SMILES: COC(=O)c1ccc(C#CCN2C(=O)C(F)(F)C[C@@H]2C=O)s1]

(R)-Methyl 5-(3-(3,3-difluoro-5-formyl-2-oxopyrrolidin-1-yl)prop-1-yn-1-yl)thiophene-2-carboxylate is prepared in the manner as that described for the preparation of intermediate 13a except that methyl 5-(3-bromoprop-1-yn-1-yl)thiophene-2-carboxylate (10d) is used in Step I instead of methyl 7-bromoheptanoate.

Preparation of (R,Z)-methyl 5-(3-(3,3-difluoro-5-formyl-2-oxopyrrolidin-1-yl)prop-1-en-1-yl)thiophene-2-carboxylate (13e)

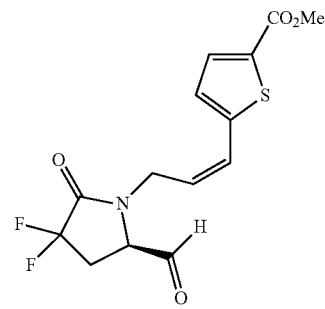 [SMILES: COC(=O)c1ccc(/C=C\CN2C(=O)C(F)(F)C[C@@H]2C=O)s1]

(R,Z)-Methyl 5-(3-(3,3-difluoro-5-formyl-2-oxopyrrolidin-1-yl)prop-1-en-1-yl)thiophene-2-carboxylate is prepared in the manner as that described for the preparation of intermediate 13a except that (Z)-methyl 5-(3-bromoprop-1-en-1-yl)thiophene-2-carboxylate (10e) is used in Step I instead of methyl 7-bromoheptanoate.

Preparation of (R)-methyl 5-(3-(3,3-difluoro-5-formyl-2-oxopyrrolidin-1-yl)propyl)thiophene-2-carboxylate (13f)

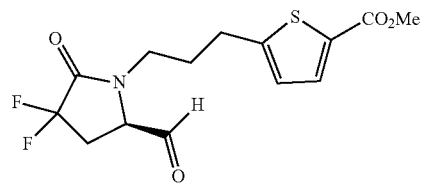 [SMILES: COC(=O)c1ccc(CCCN2C(=O)C(F)(F)C[C@@H]2C=O)s1]

Preparation of methyl 5-bromothiophene-2-carboxylate

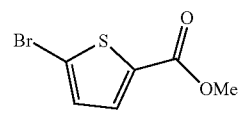

To an iced-cooled solution consisting of 5-bromo-2-thiophene carboxylic acid (Oakwood Products, 5.1 g, 25 mmol) in ethyl acetate (200 mL) and methanol (20 mL) was added TMS diazomethane (2M in diethyl ether, 20 ml, 40 mmol) over 20 minutes. Gas evolution was observed and the reaction mixture was stirred for one hour. The mixture was then allowed to warm to room temperature overnight. The volatile material was removed and the residue was purified by silica gel chromatography. Elution with ethyl acetate-heptane (1:50 v/v) afforded the title intermediate (5.4 g, 98%) as a white solid; TLC IR/0.60 (solvent system 90:10 v/v heptanes:ethyl acetate); $^1$H-NMR (CDCl$_3$) δ 7.5 (d, 1H), 7.1 (d, 1H), 4.9 (s, 3H).

Preparation of methyl 5-(3-hydroxyprop-1-yn-1-yl)thiophene-2-carboxylate

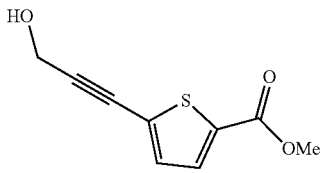 [SMILES: COC(=O)c1ccc(C#CCO)s1]

To a solution consisting of methyl 5-bromo-2-thiophene carboxylate (5.4 g, 24 mmol) in benzene (60 mL) was added tetrakis(triphenylphosphine)palladium (0) (676 mg, 0.6 mmol) and the reaction mixture was stirred for 30 minutes. To the reaction mixture was then added, quickly in one portion, a solution consisting of copper iodide (360 mg, 1.8 mmol) and n-butylamine (5.0 ml, 48 mmol in benzene (10 mL) followed by slow addition of propargyl alcohol (2.2 mL, 36 mmol) in benzene (30 ml) over 15 minutes. The reaction mixture was stirred for five days and was quenched with a saturated solution of ammonium chloride (200 mL). The organic material was extracted with diethyl ether (3×300 mL). The combined organic phase was washed with water (100 mL) and brine (2×50 mL) before drying over sodium sulfate and concentrating to a dark brown oil. The residue was purified by silica gel chromatography. Elution with ethyl acetate-heptane-(1:9 v:v) afforded the title intermediate (4.39 g, 93%); TLC R$_f$ 0.7 (solvent system 50:50 v/v heptanes:ethyl acetate); $^1$H-NMR (CDCl$_3$). δ 7.6 (d, 1H), 7.1 (d, 1H), 4.5 (s, 2H), 3.9 (s, 3H), 2.0 (br t, 1H).

Preparation of methyl 5-(3-hydroxypropyl)thiophene-2-carboxylate

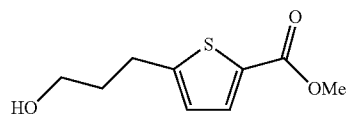 [SMILES: COC(=O)c1ccc(CCCO)s1]

To a solution consisting of methyl 5-(3-hydroxyprop-1-yn-1-yl)thiophene-2-carboxylate (700 mg, 3.57 mmol) in methanol (10 ml) was added palladium on calcium carbonate, 5% (2.0 g). The reaction atmosphere was replaced with hydrogen and the reaction mixture was stirred vigorously for two hours. The mixture was then filtered through Celite and the solvent removed. The residue was purified by silica gel chromatography. Elution with methanol-dichloromethane (1:100 v:v) afforded the title intermediate (650 mg, 91%); TLC R$_f$ 0.60 (solvent system 93:7 v/v dichloromethane-methanol); $^1$H-NMR (CDCl$_3$) δ 7.2 (d, 1H), 6.8 (d, 1H), 3.9 (s, 3H), 3.7 (t, 2H), 2.9 (t, 2H), 2.0-1.9 (m, 2H), 1.8-1.7 (br m, 1H); MS (ESI$^+$) m/z 201.1 (M+1), 223.0 (M+Na).

Preparation of methyl 5-(3-bromopropyl)thiophene-2-carboxylate (10f)

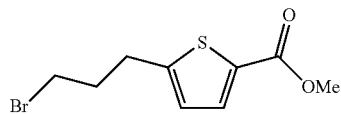 [SMILES: COC(=O)c1ccc(CCCBr)s1]

To a solution consisting of methyl 5-(3-hydroxypropyl) thiophene-2-carboxylate (633 mg, 3.17 mmol) in dichloromethane (25 mL) at 0° C. was added carbon tetrabromide (1.56 g, 4.43 mmol) and triphenylphosphine (1.23 g, 4.43 mmol). The reaction mixture was stirred for two hours. The solvent was removed and the residue was purified by silica gel chromatography. Elution with ethyl acetate-heptane (1:20 v:v) afforded the title intermediate (2.56 g); TLC R$_f$ 0.60 (solvent system 75:25 v/v heptane-ethyl acetate); MS (ESI$^+$) m/z 263.0 (M+1); $^1$H-NMR (CDCl$_3$) δ 7.6 (d, 1H), 6.8 (d, 1H), 3.9 (s, 3H), 3.85 (t, 2H), 2.95 (t, 2H), 2.0-1.9 (m, 2H).

Alternative preparation of methyl 5-(3-bromopropyl)thiophene-2-carboxylate (10f)

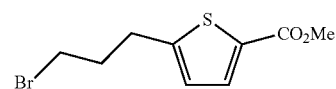 [SMILES: COC(=O)c1ccc(CCCBr)s1]

Preparation of 5-(3-bromopropyl)thiophene-2-carboxylic Acid

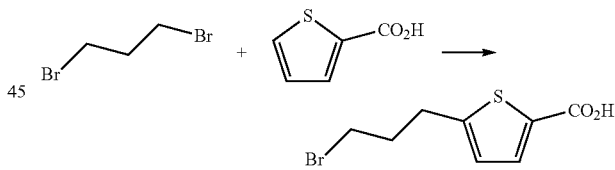

To a solution consisting of thienoic acid (10 g, 78 mmol) in THF (150 mL) at −78° C. was added an LDA solution (85 mL, 170 mmol, 2 M in heptanes/THF/ethylbenzene, Sigma-Aldrich) dropwise over 20 minutes, and the reaction mixture was stirred 40 minutes. To the reaction mixture was then added dibromopropane (23.8 g, 117 mmol) in one portion, and the reaction mixture was allowed to warm to room temperature and was stirred for 3 days. To the reaction mixture was added 50 mL each of a saturated aqueous solution of ammonium chloride, a saturated aqueous solution of sodium chloride, and 6 N HCl. The organic material was extracted with ethyl acetate and the organic layer was dried over sodium sulfate, filtered, and concentrated to afford the title compound as a yellow oil (24.0 g). The product was used without further purification; TLC R$_f$ 0.5 (solvent system: 30:70:1 v/v ethyl acetate-hexanes-acetic acid).

Preparation of methyl 5-(3-bromopropyl)thiophene-2-carboxylate (10f)

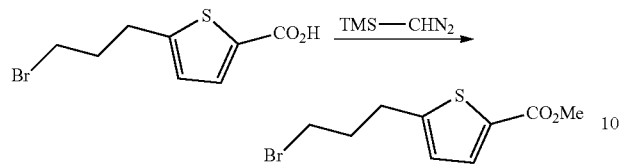

To a solution consisting of 5-(3-bromopropyl) thiophene-2-carboxylic acid (from procedure above, 24 g, 78 mmol) in ethyl acetate (150 mL) and methanol (15 mL) at 0° C. was added TMS-diazomethane (50 mL, 100 mmol, 2 M) dropwise over one hour. The reaction mixture was then allowed to warm to room temperature and was stirred for 16 hours, The reaction mixture was concentrated under reduced pressure without workup. The residue was purified by silica gel chromatography. Elution with ethyl acetate-heptane (1:80 v/v) afforded the title compound as a white solid (4.95 g; 24% over two steps); TLC $R_f$ 0.45 (solvent system: 15:85 v/v ethyl acetate-hexanes); MS (ESI$^+$) m/z 263, 265 (isotopic bromines, each (M+H)+); $^1$HNMR (CDCl$_3$) δ 7.5 (d, 1H), 6.7 (d, 1H), 3.75 (s, 3H), 3.3 (t, 2H), 2.9 (t, 2H), 2.1-2.0 (m, 2H).

Scheme 3, Step I: Preparation of (R)-methyl 5-(3-(5-(((tert-butyldimethylsilyl)oxy)methyl)-3,3-difluoro-2-oxopyrrolidin-1-yl)propyl)thiophene-2-carboxylate (11f; PG=TBS)

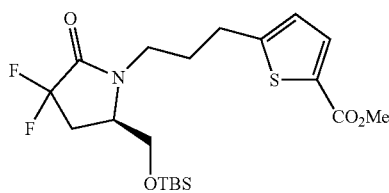 [SMILES: COC(=O)c1ccc(CCCN2C(=O)C(F)(F)C[C@@H]2CO[Si](C)(C)C(C)(C)C)s1]

To a suspension consisting of sodium hydride (60% in mineral oil, 458 mg, 11.5 mmol) and sodium iodide (1.79 g, 12.0 mmol) in DMF (60 mL) was added dropwise a solution consisting of (R)-5-(((tert-butyldimethylsilyl)oxy)methyl)-3,3-difluoropyrrolidin-2-one (5; PG=TBS, 2.9 g, 10.9 mmol) in DMF (10 mL). The mixture was stirred at room temperature for 90 minutes, after which time was added dropwise a mixture consisting of methyl 5-(3-bromopropyl) thiophene-2-carboxylate (10f, 3.16 g, 12.0 mmol, preparation described above) in DMF, and stirring was continued at 50° C. for 16 hours. The mixture was treated with an aqueous solution of ammonium chloride and extracted with 2:1 ethyl acetate-heptane. The combined organics were washed with a 50% saturated aqueous solution of sodium chloride, followed by a saturated aqueous solution of sodium chloride, and was dried over sodium sulfate. The residue was purified by silica gel chromatography. Elution with ethyl acetate-heptane (1:5 v/v) afforded the title intermediate (4.6 g; 93%); TLC $R_f$ 0.30 (solvent system: 75:25 v/v heptanes:ethyl acetate); $^1$H-NMR (CDCl$_3$) δ 7.6 (d, 1H), 6.8 (d, 1H), 3.8 (s, 3H), 3.7-3.6 (m, 1H), 3.6-3.5 (m, 1H), 3.3-3.1 (m, 1H), 2.8 (t, 2H), 2.6-2.4 (m, 1H), 2.4-2.2 (m, 1H), 2.0 (s, 3H), 1.2 (t, 1H), 0.8 (s, 9H), 0.0 (s, 6H); MS (ESI$^+$) m/z 465.1 (M+NH$_4$)$^+$.

Scheme 3, Step J: Preparation of (R)-methyl 5-(3-(3,3-difluoro-5-(hydroxymethyl)-2-oxopyrrolidin-1-yl)propyl)thiophene-2-carboxylate (12f)

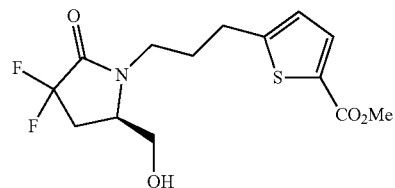 [SMILES: COC(=O)c1ccc(CCCN2C(=O)C(F)(F)C[C@@H]2CO)s1]

To a solution consisting of (R)-methyl 5-(3-(5-(((tert-butyldimethylsilyl)oxy)methyl)-3,3-difluoro-2-oxopyrrolidin-1-yl)propyl)thiophene-2-carboxylate (11f; PG=TBS, 5.15 g, 11.5 mmol) in THF (20 mL) was added TBAF (1 M in THF, 14.96 mL, 14.96 mmol) over two hours and the mixture was stirred at room temperature for 16 hours. The mixture was treated with an aqueous solution of ammonium chloride and extracted with ethyl acetate. The combined organic phase was washed with a 50% saturated aqueous solution of sodium chloride, followed by a saturated aqueous solution of sodium chloride and was dried over sodium sulfate, filtered, and concentrated. The residue was purified by silica gel chromatography. Elution with methanol-dichloromethane (1:80 v/v) afforded the title intermediate as a pale yellow oil (3.4 g; 88%); TLC $R_f$ 110.5 (solvent system: 5:95 v/v methanol-dichloromethane); $^1$H-NMR (CDCl$_3$) δ 7.6 (d, 1H), 6.8 (d, 1H), 3.85 (s, 3H), 3.8-3.6 (m, 4H), 3.3-3.1 (m, 1H), 2.85 (t, 2H), 2.6-2.4 (m, 2H), 2.1-1.9 (m, 2H); MS (ESI$^+$) m/z 351.0 (M+NH$_4$)$^+$.

Scheme 3, Step J: Alternative preparation of (R)-methyl 5-(3-(3,3-difluoro-5-(hydroxymethyl)-2-oxopyrrolidin-1-yl)propyl)thiophene-2-carboxylate (12f)

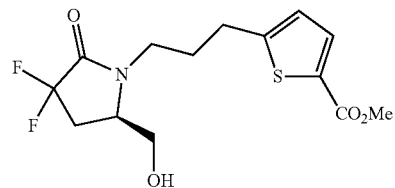 [SMILES: COC(=O)c1ccc(CCCN2C(=O)C(F)(F)C[C@@H]2CO)s1]

To a solution consisting of (R)-methyl 5-(3-(5-(((tert-butyldimethylsilyl)oxy)methyl-3,3-difluoro-2-oxopyrrolidin-1-yl)propyl)thiophene-2-carboxylate (11f; PG=TBS, 305 mg, 0.682 mmol) in methanol (10 mL) was added 1 M HCl (1 mL) and the reaction mixture was stirred overnight. The mixture was concentrated under reduced pressure to provide a residue, which was purified by silica gel chromatography. Elution with 5:95 (v/v) methanol-dichloromethane afforded the title intermediate (178 mg, 78.4%) as an oil; TLC $R_f$ 0.4, solvent system: 5:95 (v/v) methanol-dichloromethane.

Scheme 3, Step K: Preparation of (R)-methyl 5-(3-(3,3-difluoro-5-formyl-2-oxopyrrolidin-1-propyl)thiophene-2-carboxylate (13f)

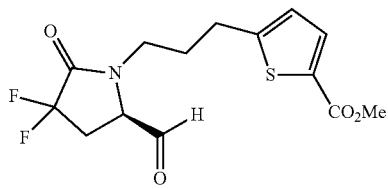 [SMILES: COC(=O)c1ccc(CCCN2C(=O)C(F)(F)C[C@@H]2C=O)s1]

(R)-Methyl 5-(3-(3,3-difluoro-5-formyl-2-oxopyrrolidin-1-yl)propyl)thiophene-2-carboxylate was prepared from 12f using the oxidation procedure (Step K) described for the preparation of intermediate 13a from intermediate 12a to afford the title intermediate (80 mg) as a pale yellow oil; TLC $R_f$ 0.60 (solvent system: 7:93 v/v methanol-dichloromethane).

Organic β-keto phosphonate esters such as

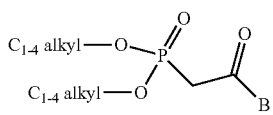

(15)

may be used as reaction coupling partners with aldehydes such as 13a-f in a Horner-Emmons-Wadsworth-type process to install the lactam lower-chain scaffold. Such β-keto phosphonate esters may be prepared by coupling an appropriate carboxylic ester

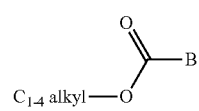

(14)

with lithiated/deprotonated dialkyl methylphosphonate according to the general reaction illustrated in Scheme 6 and variations thereof. Tables A-P/Q of Lower Chains (below) describe various lower-chain components B of the exemplary embodiments.

Carboxylic esters 14 may be commercially available or prepared from commercially-available starting materials as shown in Schemes 7a-g. The numbering system, comprising various numerical, lower-case alphabetical, and lower-case Roman numeral descriptors, for intermediates comprising component B, such as carboxylic esters 14, β-keto phosphonate esters 15, NHS esters 18, amides 19, carboxylic acids 20, and (S)-3-(B-carbonyl)-4-benzyloxazolidin-2-ones 21 found in Schemes, Tables, and Examples herein shall be interpreted in the following manner. Intermediates comprising component B, such as in the formulae shown below,

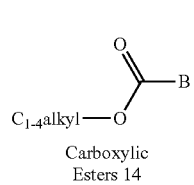

Carboxylic Esters 14

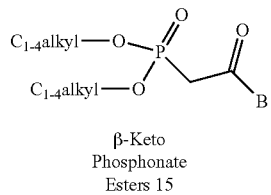

β-Keto Phosphonate Esters 15

-continued

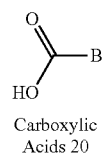

Carboxylic Acids 20

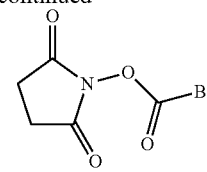

NHS Esters 18

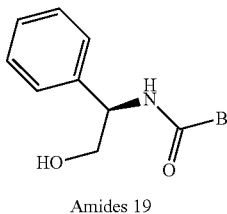

Amides 19

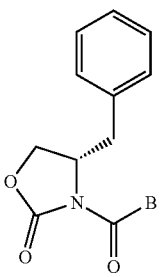

(S)-3-(B-Carbonyl)-4-benzyloxazolidin-2-ones 21 wherein: B = 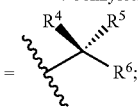

shall be expressed as a formula having three or four moieties which define the functionality of the intermediate and the $R^4$, $R^5$ and $R^6$ substituents of B comprising the intermediate. The first moiety is expressed as an Arabic numeral which represents the type of intermediate with its compound structure in accordance with the descriptions herein (e.g., 14 is a carboxylic ester; 15 is a β-keto phosphonate ester; 18 is an NHS ester; 19 is an amide; 20 is a carboxylic acid, etc.). The second moiety is expressed as a lower case letter that represents the structure of the $R^6$ group in accordance with the descriptions herein. A particular genus of intermediates having a range of $R^6$ substituents is shown by replacing the first moiety by a letter range enclosed within parentheses (e.g., (a-o)). The third moiety is expressed as a lower case letter that represents the nature of the $R^4$ and $R^5$ substitutions as follows: a (wherein both $R^4$ and $R^5$ are hydrogen); b (wherein $R^4$ is $C_1$-$C_4$ alkyl, $R^5$ is hydrogen); c (wherein $R^4$ is hydrogen, $R^5$ is $C_1$-$C_4$ alkyl; d (wherein both $R^4$ and $R^5$ are $C_1$-$C_4$ alkyl; and e (wherein $R^4$ and $R^5$ with the carbon to which they are bound form a $C_3$-$C_5$ cycloalkyl. In addition, a third moiety designation of "b/c" represents a mixture of the b and c stereoisomers. The fourth moiety is expressed as a lower-case Roman numeral in parentheses that represents the size and structure of the $R^4$ and/or $R^5$ $C_1$-$C_4$ alkyl group or groups, if present, or the size of the $C_3$-$C_5$ cycloalkyl ring, if present, in accordance with the descriptions herein. In the case where both $R^4$ and $R^5$ are hydrogen (e.g. 14aa), no lower-case Roman numeral in parentheses is present. This descriptor only takes into account embodiments for which only one of $R^4$ and $R^5$ is $C_1$-$C_4$ alkyl, both $R^4$ and $R^5$ are identical $C_1$-$C_4$ alkyl, or $R^4$ and $R^5$ with the carbon to which they are bound form a $C_3$-$C_5$ cycloalkyl, and does not take into account embodiments for which both $R^4$ and $R^5$ are $C_1$-$C_4$ alkyl that are different one from another. However, $R^4$ and $R^5$ may both be C1-C4 alkyl groups that are not the same. Although no examples of these embodiments are represented in these tables, their absence infers no limitation in scope. Table A lists some intermediates with defined B substituents ($R^4$, $R^5$ and $R^6$) as well as indicating the partial formulae notations for each listed combination of $R^4$, $R^5$ and $R^6$. By way of example, a carboxylic ester of formula 14 with $R^4$ as H, $R^5$ as Me and $R^6$ as

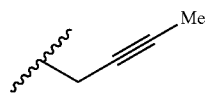 [SMILES: *CC#CC]

is expressed as 14ac(i) when the hereinabove defined notations are used. Similarly, a genus of carboxylic esters wherein $R^4$ and $R^5$ are each H and $R^6$ is varied can be envisaged when expressed by the formula 14(a-o)a in view of Tables A through O as provided herein.

A carboxylic ester, 14(a-o) or 14(a-o)b/c(i-viii), may be prepared in two steps from commercially available diethyl malonate or an appropriate commercially available diethyl 2-($C_1$-$C_4$ alkyl) malonate starting material. Reaction of the malonate starting material with an appropriate lithium amide base, such as LDA or LiHMDS, or an appropriate hydride base, such as sodium hydride, or alkoxide base, such as sodium ethoxide, followed with an appropriate alkylating agent $R^6$—$X^1$, as illustrated in Scheme 7a, Step A, affords the corresponding 2-$R^6$-substituted diethyl malonate 16. Subsequent decarboxylation (Step B) provides the corresponding carboxylic ester intermediate 14, wherein both $R^4$ and $R^5$ are hydrogen, or wherein one of $R^4$ and $R^5$ is a $C_1$-$C_4$ alkyl group (alkyl groups (i) through (viii) represent methyl, ethyl, n-propyl, 2-propyl, n-butyl, iso-butyl, sec-butyl, and tert-butyl, respectively) and the other is a hydrogen. Examples of commercially available diethyl ($C_1$-$C_4$ alkyl) malonates include diethyl methyl malonate, diethyl ethyl malonate, diethyl isopropyl malonate, diethyl n-propyl malonate, diethyl n-butyl malonate (all from Sigma-Aldrich, Acros Organics, or Alfa Aesar), diethyl isobutyl malonate, and diethyl sec-butyl malonate (both from Alfa Aesar). Methods for preparing the starting diethyl ($C_1$-$C_4$ alkyl) malonates are known in the art; for example, diethyl malonate may be combined with a base such as potassium carbonate and an appropriate alkylating agent such as methyl iodide, ethyl iodide, n-propyl bromide, or n-butyl bromide under microwave irradiation in the method described by Keglevich et al. in *Letters in Organic Chemistry*, 2008, 5(3), 224-228 and in *Green Chemistry*, 2006, 8(12), 1073-1075. Other methods that may be used to prepare the diethyl (01-04 alkyl) malonates include the reaction of diethyl malonate with an appropriate alkylating agent such as ethyl iodide, isopropyl bromide, isobutyl bromide, or sec-butyl bromide in the presence of a base such as sodium ethoxide in an organic solvent such as ethanol as described in Patel and Ryono in *Bioorganic and Medicinal Chemistry Letters*, 1992, 2(9), 1089-1092 and elsewhere.

Carboxylic ester intermediates 14 possessing a gem-dimethyl substitution at the carbon atom a to the ester carbonyl group (both $R^4$ and $R^5$ are methyl), such as 14(a-o)d(i), may be prepared by the methylation of the corresponding mono-α-methyl ester intermediate (stereochemical mixture) 14(a-o)b/c(i) as shown in Scheme 7b and reported in Shibasaki, M. et al, in *Chemical and Pharmaceutical Bulletin*, 1989, 37(6), 1647-1649.

Scheme 7c illustrates mono-alkylations of commercially available or prepared carboxylic esters 14(a-o)a with an alkylating agent $R^4/R^5$—$X^1$, wherein the $R^4/R^5$ group is a $C_1$-$C_4$ alkyl group and $X^1$ is a leaving group such as iodide or bromide to provide the corresponding mono-alkylated analogs 14(a-o)b/c, respectively. The mono-alkylated carboxylic ester analogs may be alkylated a second time; for example, mono-methylated carboxylic acid esters (stereochemical mixture) 14(a-o)b/c(i) may be methylated a second time to provide the corresponding gem-dimethyl substituted esters 14(a-o)d(i), as illustrated in Scheme 7d.

Scheme 7e illustrates the preparation of 1-$R^6$-substituted $C_3$-$C_5$ cycloalkylcarboxylic acids and their $C_1$-$C_4$ alkyl esters 14(a-o)e(ix-xi). Similar transformations are described in Yang, D. et. al. in *Journal of Organic Chemistry*, 2009, 74(22), 8726-8732; Cowling, S. J. and Goodby, J. W. in *Chemical Communications* (Cambridge, United Kingdom), 2006, 39, 4107-4709; Araldi, G. L. et. al. in WO 2003/103604; and others.

Stereopure carboxylic esters 14(a-o)b(i-viii) and their stereoisomers, 14(a-o)c(i-viii) may be prepared according to the route illustrated in Scheme 7f. Alkylation of an appropriately-substituted carboxylic acid starting material, such as propionic acid ($R^4/R^5$ is a methyl group), at the carbon position alpha to the acid carbonyl group by treatment of the acid with an appropriate base, such as lithium diisopropylamide (about two molar equivalents) in the presence of a suitable solvent, such as THF, with an alkylating agent $R^6$—$X^1$ (Step A) provides the corresponding carboxylic acid intermediates 20(a-o)b/c(i-viii). Subsequent coupling of the carboxylic acid intermediate with N-hydroxysuccinimide (NHS) forms the corresponding NHS ester (an activated ester) stereoisomeric mixture 18(a-o)b/c(i-viii) (Step B). Treatment of the activated ester stereoisomeric mixture 18(a-o)b/c(i-viii) with (R)-2-amino-2-phenylethanol in THF results in the mixture of two amide diastereomers 19(a-o)b(i-viii) and 19(a-o)c(i-viii) (Step C), which may be separated by chromatography to provide each pure diastereomer (Step D). Recrystallization of the individual diastereomers may provide amides with even greater de purity. Amide hydrolysis of each diastereomer to its corresponding carboxylic acid 20(a-o)b(i-viii) and 20(a-o)c(i-viii), respectively (Step E), and subsequent esterification (Step F) provides corresponding individual carboxylic ester stereoisomers 14(a-o)b(i-viii) and 14(a-o)c(i-viii), respectively.

Scheme 7g shows a synthetic pathway to stereopure carboxylic esters 14(a-o)b(i-vii) ($R^5$ is hydrogen) employing the use of the chiral auxiliary to generate "(S)-3-(B-carbonyl)-4-benzyloxazolidin-2-ones" 21(a-o)a (both $R^4$ and $R^5$ are hydrogen) for more-efficient (asymmetric) alkylation in Step C to provide the corresponding alkylated. "(S)-3-(B-carbonyl)-4-benzyloxazolidin-2-ones" analogs enriched in the 21(a-o)b(i-vii) stereoisomer over the 21(a-o)c(i-vii) stereoisomer. Removal of the chiral auxiliary (Step D) following alkylation and subsequent chiral amide derivatization (Steps E and F) provides the diastereomers 19(a-o)b(i-vii) separable by chromatography and further purified by crystallization (Step G). Acid-catalyzed amide hydrolysis (Step H) to the corresponding stereopure carboxylic acid 20(a-o)b(i-vii) and subsequent esterification (Step I) provide the desired stereopure carboxylic ester intermediates 14(a-o)b(i-vii), which can be carried onto their corresponding stereopure β-keto phosphonate esters 15(a-o)b(i-vii).

Scheme 8 illustrates the conversions of acetylenic carboxylic esters 14(a-f)a and 14(a-f)(b-e)(i-xi) to the corresponding β-keto phosphonates by the previously-described general manner (Step A) and subsequent catalytic hydrogenation (Step B) to provide the corresponding saturated analogs.

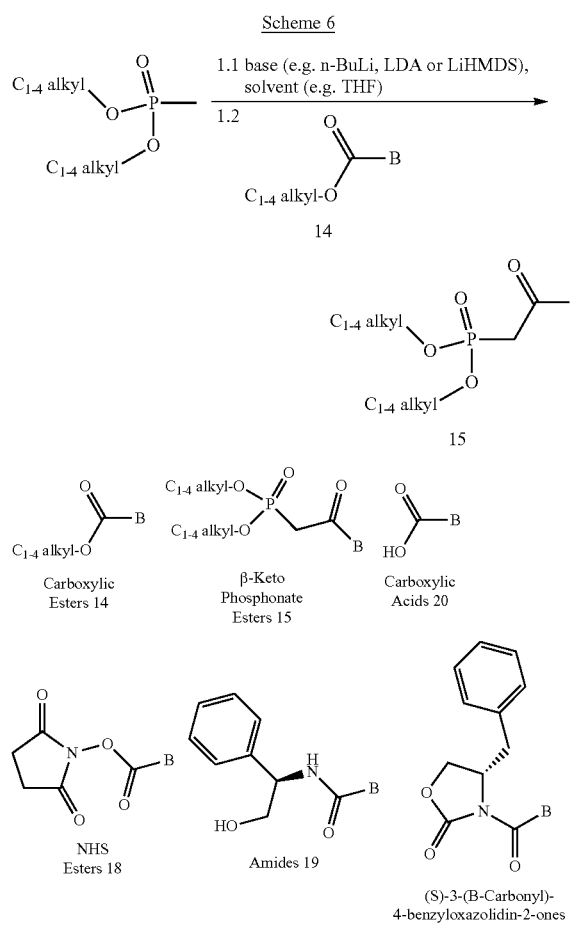

TABLE A

| | | of Lower Chains | |
|---|---|---|---|
| B | R⁴ | R⁵ | R⁶ |
| aa | H | H | |
| ab(i) | Me | H | |
| ac(i) | H | Me | ⸺≡⸺Me |
| ad(i) | Me | Me | |
| ab(ii) | Et | H | |
| ac(ii) | H | Et | |
| ad(ii) | Et | Et | |
| ab(iii) | n-Pr | H | |
| ac(iii) | H | n-Pr | |
| ad(iii) | n-Pr | n-Pr | |
| ab(iv) | i-Pr | H | |
| ac(iv) | H | i-Pr | |
| ad(iv) | i-Pr | i-Pr | |
| ab(v) | n-Bu | H | |
| ac(v) | H | n-Bu | |
| ad(v) | n-Bu | n-Bu | |
| ab(vi) | i-Bu | H | |
| ac(vi) | H | i-Bu | |
| ad(vi) | i-Bu | i-Bu | |
| ab(vii) | sec-Bu | H | |
| ac(vii) | H | sec-Bu | |
| ad(vii) | sec-Bu | sec-Bu | |
| ab(viii) | tert-Bu | H | |
| ac(viii) | H | tert-Bu | |
| ad(viii) | tert-Bu | tert-Bu | |

TABLE A-continued

| | | of Lower Chains | |
|---|---|---|---|
| B | R⁴ | R⁵ | R⁶ |
| ae(ix) | | —CH₂—CH₂— | |
| ae(x) | | —(CH₂)₂—CH₂— | |
| ae(xi) | | —(CH₂)₃—CH₂— | |

Carboxylic Esters 14

β-Keto Phosphonate Esters 15

Carboxylic Acids 20

NHS Esters 18

Amides 19

(S)-3-(B-Carbonyl)-4-benzyloxazolidin-2-ones 21

TABLE A-continued of Lower Chains

| B | R⁴ | R⁵ | R⁶ |
|---|---|---|---|

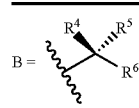

R⁴ and/or R⁵ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu

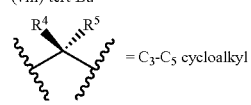 = $C_3$-$C_5$ cycloalkyl (ix) cyclopropyl
(x) cyclobutyl
(xi) cyclopentyl

*R⁴ and R⁵ may both be $C_1$-$C_4$ alkyl groups that are not the same. Although no examples of these embodiments are represented in these tables, their absence infers no limitation in scope.

TABLE B of Lower Chains

| B | R⁴ | R⁵ | R⁶ |
|---|---|---|---|
| ba | H | H | |
| bb(i) | Me | H | |
| bc(i) | H | Me | |
| bd(i) | Me | Me | |
| bb(ii) | Et | H | |
| bc(ii) | H | Et | |
| bd(ii) | Et | Et | |
| bb(iii) | n-Pr | H | |
| bc(iii) | H | n-Pr | |
| bd(iii) | n-Pr | n-Pr | |
| bb(iv) | i-Pr | H | |
| bc(iv) | H | i-Pr | |
| bd(iv) | i-Pr | i-Pr | |
| bb(v) | n-Bu | H | |
| bc(v) | H | n-Bu | |
| bd(v) | n-Bu | n-Bu | |
| bb(vi) | i-Bu | H | |
| bc(vi) | H | i-Bu | |
| bd(vi) | i-Bu | i-Bu | |
| bb(vii) | sec-Bu | H | |
| bc(vii) | H | sec-Bu | |
| bd(vii) | sec-Bu | sec-Bu | |
| bb(viii) | tert-Bu | H | |
| bc(viii) | H | tert-Bu | |
| bd(viii) | tert-Bu | tert-Bu | |
| be(ix) | 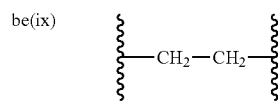 | | |
| be(x) | 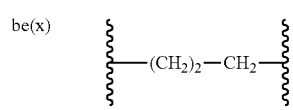 | | |
| be(xi) | 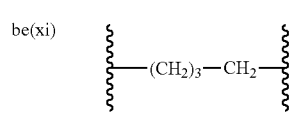 | | |

TABLE B-continued of Lower Chains

| B | R⁴ | R⁵ | R⁶ |
|---|---|---|---|

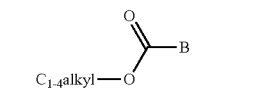

Carboxylic Esters 14

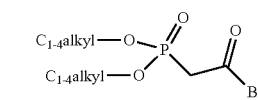

β-Keto Phosphonate Esters 15

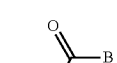

Carboxylic Acids 20

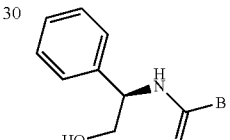

NHS Esters 18

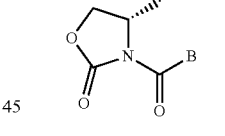

Amides 19

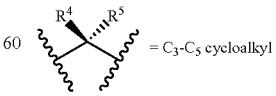

(S)-3-(B-Carbonyl)-4-benzyloxazolidin-2-ones 21

R⁴ and/or R⁵ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu

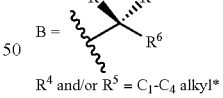 = $C_3$-$C_5$ cycloalkyl (ix) cyclopropyl
(x) cyclobutyl
(xi) cyclopentyl

*R⁴ and R⁵ may both be $C_1$-$C_4$ alkyl groups that are not the same. Although no examples of these embodiments are represented in these tables, their absence infers no limitation in scope.

TABLE C of Lower Chains

| B | R⁴ | R⁵ | R⁶ |
|---|---|---|---|
| ca | H | H | |
| cb(i) | Me | H | |
| cc(i) | H | Me | |
| cd(i) | Me | Me | |
| cb(ii) | Et | H | |
| cc(ii) | H | Et | |
| cd(ii) | Et | Et | |
| cb(iii) | n-Pr | H | |
| cc(iii) | H | n-Pr | |
| cd(iii) | n-Pr | n-Pr | |
| cb(iv) | i-Pr | H | |
| cc(iv) | H | i-Pr | |
| cd(iv) | i-Pr | i-Pr | |
| cb(v) | n-Bu | H | |
| cc(v) | H | n-Bu | |
| cd(v) | n-Bu | n-Bu | |
| cb(vi) | i-Bu | H | |
| cc(vi) | H | i-Bu | |
| cd(vi) | i-Bu | i-Bu | |
| cb(vii) | sec-Bu | H | |
| cc(vii) | H | sec-Bu | |
| cd(vii) | sec-Bu | sec-Bu | |
| cb(viii) | tert-Bu | H | |
| cc(viii) | H | tert-Bu | |
| cd(viii) | tert-Bu | tert-Bu | |
| ce(ix) | | | —CH₂—CH₂— |
| ce(x) | | | —(CH₂)₂—CH₂— |
| ce(xi) | | | —(CH₂)₃—CH₂— |

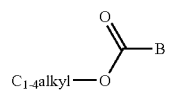

Carboxylic Esters 14

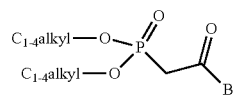

β-Keto Phosphonate Esters 15

Carboxylic Acids 20

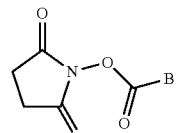

NHS Esters 18

TABLE C-continued of Lower Chains

| B | R⁴ | R⁵ | R⁶ |
|---|---|---|---|

Amides 19 — structure: PhCH(NHC(O)B)CH₂OH (S)-3-(B-Carbonyl)-4-benzyloxazolidin-2-ones 21 — (S)-4-benzyl-3-(B-carbonyl)oxazolidin-2-one B = $\mathrm{C}(R^4)(R^5)(R^6)$ $R^4$ and/or $R^5$ = $C_1$–$C_4$ alkyl*

(i) Me
(ii) Et
(iii) n-Pr
(iv) i-Pr
(v) n-Bu
(vi) i-Bu
(vii) sec-Bu
(viii) tert-Bu $R^4, R^5$ together = $C_3$–$C_5$ cycloalkyl (ix) cyclopropyl
(x) cyclobutyl
(xi) cyclopentyl

*$R^4$ and $R^5$ may both be $C_1$–$C_4$ alkyl groups that are not the same. Although no examples of these embodiments are represented in these tables, their absence infers no limitation in scope.

TABLE D of Lower Chains

| B | R⁴ | R⁵ | R⁶ |
|---|---|---|---|
| da | H | H | |
| db(i) | Me | H | |
| dc(i) | H | Me | |
| dd(i) | Me | Me | |
| db(ii) | Et | H | |
| dc(ii) | H | Et | |
| dd(ii) | Et | Et | |
| db(iii) | n-Pr | H | |
| dc(iii) | H | n-Pr | |
| dd(iii) | n-Pr | n-Pr | |
| db(iv) | i-Pr | H | |
| dc(iv) | H | i-Pr | |
| dd(iv) | i-Pr | i-Pr | |
| db(v) | n-Bu | H | |
| dc(v) | H | n-Bu | |
| dd(v) | n-Bu | n-Bu | |
| db(vi) | i-Bu | H | |
| dc(vi) | H | i-Bu | |
| dd(vi) | i-Bu | i-Bu | |
| db(vii) | sec-Bu | H | |
| dc(vii) | H | sec-Bu | |
| dd(vii) | sec-Bu | sec-Bu | |

R⁶ (for da–dd series): CH₂–C≡C–C₆H₅ (phenylpropargyl)

TABLE D-continued of Lower Chains

| B | R⁴ | R⁵ | R⁶ |
|---|---|---|---|
| db(viii) | tert-Bu | H | |
| dc(viii) | H | tert-Bu | |
| dd(viii) | tert-Bu | tert-Bu | |
| de(ix) | 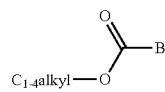 | | |
| de(x) | 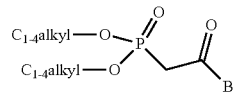 | | |
| de(xi) | | | |

Carboxylic
Esters 14

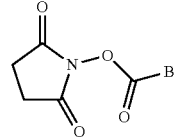

β-Keto
Phosphonate
Esters 15

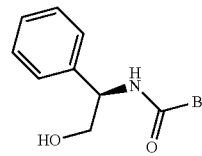

Carboxylic
Acids 20

NHS
Esters 18

Amides 19

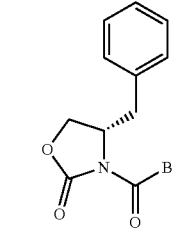

(S)-3-(B-Carbonyl)-
4-benzyloxazolidin-2-ones 21

TABLE D-continued of Lower Chains

| B | R⁴ | R⁵ | R⁶ |
|---|---|---|---|

B = (structure with R⁴, R⁵, R⁶)

R⁴ and/or R⁵ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu (R⁴/R⁵ structure) = $C_3$-$C_5$ cycloalkyl (ix) cyclopropyl
(x) cyclobutyl
(xi) cyclopentyl

*R⁴ and R⁵ may both be $C_1$-$C_4$ alkyl groups that are not the same. Although no examples of these embodiments are represented in these tables, their absence infers no limitation in scope.

TABLE E of Lower Chains

| B | R⁴ | R⁵ | R⁶ |
|---|---|---|---|
| ea | H | H | (pent-2-ynyl-phenyl group) |
| eb(i) | Me | H | |
| ec(i) | H | Me | |
| ed(i) | Me | Me | |
| eb(ii) | Et | H | |
| ec(ii) | H | Et | |
| ed(ii) | Et | Et | |
| eb(iii) | n-Pr | H | |
| ec(iii) | H | n-Pr | |
| ed(iii) | n-Pr | n-Pr | |
| eb(iv) | i-Pr | H | |
| ec(iv) | H | i-Pr | |
| ed(iv) | i-Pr | i-Pr | |
| eb(v) | n-Bu | H | |
| ec(v) | H | n-Bu | |
| ed(v) | n-Bu | n-Bu | |
| eb(vi) | i-Bu | H | |
| ec(vi) | H | i-Bu | |
| ed(vi) | i-Bu | i-Bu | |
| eb(vii) | sec-Bu | H | |
| ec(vii) | H | sec-Bu | |
| ed(vii) | sec-Bu | sec-Bu | |
| eb(viii) | tert-Bu | H | |
| ec(viii) | H | tert-Bu | |
| ed(viii) | tert-Bu | tert-Bu | |
| ee(ix) | —CH₂—CH₂— | | |
| ee(x) | —(CH₂)₂—CH₂— | | |
| ee(xi) | —(CH₂)₃—CH₂— | | |

TABLE E-continued of Lower Chains

| B | R⁴ | R⁵ | R⁶ |
|---|----|----|----|

[Structure: $C_{1-4}$alkyl—O—C(=O)—B]
Carboxylic Esters 14

[Structure: $C_{1-4}$alkyl—O, $C_{1-4}$alkyl—O, P(=O)—CH₂—C(=O)—B]
β-Keto Phosphonate Esters 15

[Structure: HO—C(=O)—B]
Carboxylic Acids 20

[Structure: NHS ester with succinimide ring—O—C(=O)—B]
NHS Esters 18

[Structure: phenyl-CH(NH—C(=O)—B)—CH₂OH]
Amides 19

[Structure: (S)-4-benzyl-oxazolidin-2-one N—C(=O)—B]
(S)-3-(B-Carbonyl)-4-benzyloxazolidin-2-ones 21

B = [R⁴, R⁵, R⁶ on central carbon]

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu

[Structure with R⁴, R⁵ on ring] = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

TABLE F of Lower Chains

| B | R⁴ | R⁵ | R⁶ |
|---|----|----|-----|
| fa | H | H | [R⁶ = –CH₂–C≡C–CH₂–CH₂–phenyl (shown spanning all rows)] |
| fb(i) | Me | H | |
| fc(i) | H | Me | |
| fd(i) | Me | Me | |
| fb(ii) | Et | H | |
| fc(ii) | H | Et | |
| fd(ii) | Et | Et | |
| fb(iii) | n-Pr | H | |
| fc(iii) | H | n-Pr | |
| fd(iii) | n-Pr | n-Pr | |
| fb(iv) | i-Pr | H | |
| fc(iv) | H | i-Pr | |
| fd(iv) | i-Pr | i-Pr | |
| fb(v) | n-Bu | H | |
| fc(v) | H | n-Bu | |
| fd(v) | n-Bu | n-Bu | |
| fb(vi) | i-Bu | H | |
| fc(vi) | H | i-Bu | |
| fd(vi) | i-Bu | i-Bu | |
| fb(vii) | sec-Bu | H | |
| fc(vii) | H | sec-Bu | |
| fd(vii) | sec-Bu | sec-Bu | |
| fb(viii) | tert-Bu | H | |
| fc(viii) | H | tert-Bu | |
| fd(viii) | tert-Bu | tert-Bu | |
| fe(ix) | —CH₂—CH₂— (cyclic linker) | | |
| fe(x) | —(CH₂)₂—CH₂— (cyclic linker) | | |
| fe(xi) | —(CH₂)₃—CH₂— (cyclic linker) | | |

[Structure: $C_{1-4}$alkyl—O—C(=O)—B]
Carboxylic Esters 14

[Structure: $C_{1-4}$alkyl—O, $C_{1-4}$alkyl—O, P(=O)—CH₂—C(=O)—B]
β-Keto Phosphonate Esters 15

[Structure: HO—C(=O)—B]
Carboxylic Acids 20

[Structure: NHS ester with succinimide ring—O—C(=O)—B]
NHS Esters 18

TABLE F-continued of Lower Chains

| B | R⁴ | R⁵ | R⁶ |
|---|----|----|----|

Amides 19 (structure: HO-CH2-CH(Ph)-NH-C(=O)-B)

(S)-3-(B-Carbonyl)-4-benzyloxazolidin-2-ones 21 (benzyl-substituted oxazolidinone with N-C(=O)-B)

$$B = \begin{matrix} R^4 & R^5 \\ & R^6 \end{matrix}$$

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu $\begin{matrix} R^4 & R^5 \end{matrix}$ = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

TABLE G of Lower Chains

| B | R⁴ | R⁵ | R⁶ |
|---|----|----|----|
| ga | H | H | (n-pentyl-like chain) |
| gb(i) | Me | H | |
| gc(i) | H | Me | |
| gd(i) | Me | Me | |
| gb(ii) | Et | H | |
| gc(ii) | H | Et | |
| gd(ii) | Et | Et | |
| gb(iii) | n-Pr | H | |
| gc(iii) | H | n-Pr | |
| gd(iii) | n-Pr | n-Pr | |
| gb(iv) | i-Pr | H | |
| gc(iv) | H | i-Pr | |
| gd(iv) | i-Pr | i-Pr | |
| gb(v) | n-Bu | H | |
| gc(v) | H | n-Bu | |
| gd(v) | n-Bu | n-Bu | |
| gb(vi) | i-Bu | H | |
| gc(vi) | H | i-Bu | |
| gd(vi) | i-Bu | i-Bu | |
| gb(vii) | sec-Bu | H | |
| gc(vii) | H | sec-Bu | |
| gd(vii) | sec-Bu | sec-Bu | |

TABLE G-continued of Lower Chains

| B | R⁴ | R⁵ | R⁶ |
|---|----|----|----|
| gb(viii) | tert-Bu | H | |
| gc(viii) | H | tert-Bu | |
| gd(viii) | tert-Bu | tert-Bu | |
| ge(ix) | —CH₂—CH₂— | | |
| ge(x) | —(CH₂)₂—CH₂— | | |
| ge(xi) | —(CH₂)₃—CH₂— | | |

$C_{1-4}$alkyl—O—C(=O)—B

Carboxylic Esters 14

$C_{1-4}$alkyl—O—P(=O)(O—$C_{1-4}$alkyl)—CH₂—C(=O)—B

β-Keto Phosphonate Esters 15

HO—C(=O)—B

Carboxylic Acids 20

NHS Esters 18 (N-hydroxysuccinimide ester with —O—C(=O)—B)

Amides 19 (structure: HO-CH2-CH(Ph)-NH-C(=O)-B)

(S)-3-(B-Carbonyl)-4-benzyloxazolidin-2-ones 21

TABLE G-continued of Lower Chains

| B | R⁴ | R⁵ | R⁶ |
|---|----|----|----|

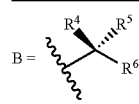

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu

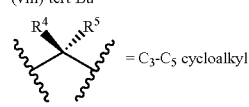 = C₃-C₅ cycloalkyl (ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

TABLE H of Lower Chains

| B | R⁴ | R⁵ | R⁶ |
|---|----|----|----|
| ha | H | H | |
| hb(i) | Me | H | |
| hc(i) | H | Me | |
| hd(i) | Me | Me | |
| hb(ii) | Et | H | |
| hc(ii) | H | Et | |
| hd(ii) | Et | Et | |
| hb(iii) | n-Pr | H | |
| hc(iii) | H | n-Pr | |
| hd(iii) | n-Pr | n-Pr | |
| hb(iv) | i-Pr | H | |
| hc(iv) | H | i-Pr | |
| hd(iv) | i-Pr | i-Pr | |
| hb(v) | n-Bu | H | |
| hc(v) | H | n-Bu | |
| hd(v) | n-Bu | n-Bu | |
| hb(vi) | i-Bu | H | |
| hc(vi) | H | i-Bu | |
| hd(vi) | i-Bu | i-Bu | |
| hb(vii) | sec-Bu | H | |
| hc(vii) | H | sec-Bu | |
| hd(vii) | sec-Bu | sec-Bu | |
| hb(viii) | tert-Bu | H | |
| hc(viii) | H | tert-Bu | |
| hd(viii) | tert-Bu | tert-Bu | |
| he(ix) | —CH₂—CH₂— | | |
| he(x) | —(CH₂)₂—CH₂— | | |
| he(xi) | —(CH₂)₃—CH₂— | | |

TABLE H-continued of Lower Chains

| B | R⁴ | R⁵ | R⁶ |
|---|----|----|----|

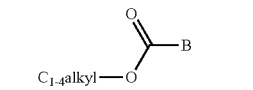

Carboxylic Esters 14

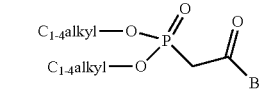

β-Keto Phosphonate Esters 15

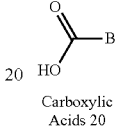

Carboxylic Acids 20

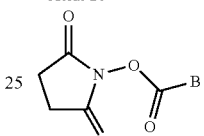

NHS Esters 18

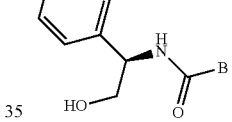

Amides 19

(S)-3-(B-Carbonyl)-4-benzyloxazolidin-2-ones 21

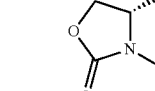

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu

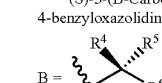 = C₃-C₅ cycloalkyl (ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

TABLE I of Lower Chains

| B | R⁴ | R⁵ | R⁶ |
|---|---|---|---|
| ia | H | H | |
| ib(i) | Me | H | |
| ic(i) | H | Me | |
| id(i) | Me | Me | |
| ib(ii) | Et | H | 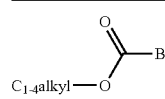 |
| ic(ii) | H | Et | |
| id(ii) | Et | Et | |
| ib(iii) | n-Pr | H | |
| ic(iii) | H | n-Pr | |
| id(iii) | n-Pr | n-Pr | |
| ib(iv) | i-Pr | H | |
| ic(iv) | H | i-Pr | |
| id(iv) | i-Pr | i-Pr | |
| ib(v) | n-Bu | H | |
| ic(v) | H | n-Bu | |
| id(v) | n-Bu | n-Bu | |
| ib(vi) | i-Bu | H | |
| ic(vi) | H | i-Bu | |
| id(vi) | i-Bu | i-Bu | |
| ib(vii) | sec-Bu | H | |
| ic(vii) | H | sec-Bu | |
| id(vii) | sec-Bu | sec-Bu | |
| ib(viii) | tert-Bu | H | |
| ic(viii) | H | tert-Bu | |
| id(viii) | tert-Bu | tert-Bu | |
| ie(ix) | | —CH₂—CH₂— | |
| ie(x) | | —(CH₂)₂—CH₂— | |
| ie(xi) | | —(CH₂)₃—CH₂— | |

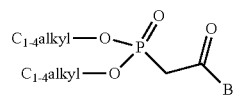

Carboxylic Esters 14

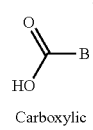

β-Keto Phosphonate Esters 15

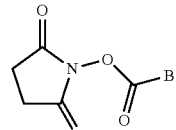

Carboxylic Acids 20

NHS Esters 18

TABLE I-continued of Lower Chains

| B | R⁴ | R⁵ | R⁶ |
|---|---|---|---|

Amides 19

(S)-3-(B-Carbonyl)-4-benzyloxazolidin-2-ones 21

B =

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu = C₃-C₅ cycloalkyl (ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

TABLE J of Lower Chains

| B | R⁴ | R⁵ | R⁶ |
|---|---|---|---|
| ja | H | H | |
| jb(i) | Me | H | |
| jc(i) | H | Me | |
| jd(i) | Me | Me | |
| jb(ii) | Et | H | |
| jc(ii) | H | Et | |
| jd(ii) | Et | Et | |
| jb(iii) | n-Pr | H | |
| jc(iii) | H | n-Pr | |
| jd(iii) | n-Pr | n-Pr | |
| jb(iv) | i-Pr | H | |
| jc(iv) | H | i-Pr | |
| jd(iv) | i-Pr | i-Pr | |
| jb(v) | n-Bu | H | |
| jc(v) | H | n-Bu | |
| jd(v) | n-Bu | n-Bu | |
| jb(vi) | i-Bu | H | |
| jc(vi) | H | i-Bu | |
| jd(vi) | i-Bu | i-Bu | |
| jb(vii) | sec-Bu | H | |
| jc(vii) | H | sec-Bu | |
| jd(vii) | sec-Bu | sec-Bu | |

TABLE J-continued of Lower Chains

| B | R⁴ | R⁵ | R⁶ |
|---|---|---|---|
| jb(viii) | tert-Bu | H | |
| jc(viii) | H | tert-Bu | |
| jd(viii) | tert-Bu | tert-Bu | |
| je(ix) | —CH₂—CH₂— | | |
| je(x) | —(CH₂)₂—CH₂— | | |
| je(xi) | —(CH₂)₃—CH₂— | | |

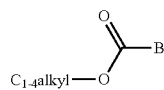

Carboxylic Esters 14

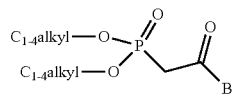

β-Keto Phosphonate Esters 15

Carboxylic Acids 20

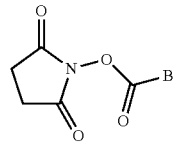

NHS Esters 18

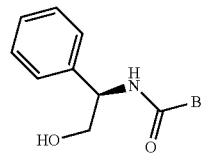

Amides 19

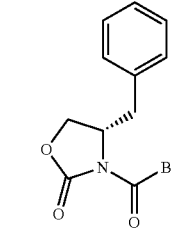

(S)-3-(B-Carbonyl)-4-benzyloxazolidin-2-ones 21

TABLE J-continued of Lower Chains

| B | R⁴ | R⁵ | R⁶ |
|---|---|---|---|

B = (R⁴, R⁵, R⁶ on central C)

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu (R⁴R⁵ ring) = C₃-C₅ cycloalkyl (ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

TABLE K of Lower Chains

| B | R⁴ | R⁵ | R⁶ |
|---|---|---|---|
| ka | H | H | 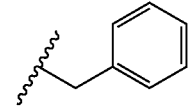 |
| kb(i) | Me | H | |
| kc(i) | H | Me | |
| kd(i) | Me | Me | |
| kb(ii) | Et | H | |
| kc(ii) | H | Et | |
| kd(ii) | Et | Et | |
| kb(iii) | n-Pr | H | |
| kc(iii) | H | n-Pr | |
| kd(iii) | n-Pr | n-Pr | |
| kb(iv) | i-Pr | H | |
| kc(iv) | H | i-Pr | |
| kd(iv) | i-Pr | i-Pr | |
| kb(v) | n-Bu | H | |
| kc(v) | H | n-Bu | |
| kd(v) | n-Bu | n-Bu | |
| kb(vi) | i-Bu | H | |
| kc(vi) | H | i-Bu | |
| kd(vi) | i-Bu | i-Bu | |
| kb(vii) | sec-Bu | H | |
| kc(vii) | H | sec-Bu | |
| kd(vii) | sec-Bu | sec-Bu | |
| kb(viii) | tert-Bu | H | |
| kc(viii) | H | tert-Bu | |
| kd(viii) | tert-Bu | tert-Bu | |
| ke(ix) | —CH₂—CH₂— | | |
| ke(x) | —(CH₂)₂—CH₂— | | |
| ke(xi) | —(CH₂)₃—CH₂— | | |

TABLE K-continued of Lower Chains

| B | R⁴ | R⁵ | R⁶ |
|---|----|----|----|

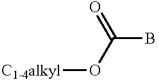

Carboxylic Esters 14

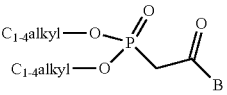

β-Keto Phosphonate Esters 15

Carboxylic Acids 20

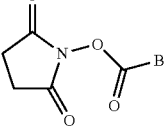

NHS Esters 18

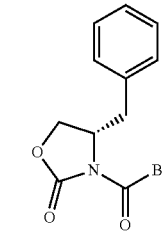

Amides 19

(S)-3-(B-Carbonyl)-4-benzyloxazolidin-2-ones 21

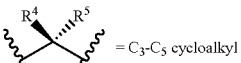

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu

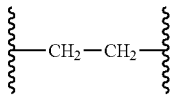 = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

TABLE L of Lower Chains

| B | R⁴ | R⁵ | R⁶ |
|---|----|----|----|
| la | H | H | |
| lb(i) | Me | H | |
| lc(i) | H | Me | |
| ld(i) | Me | Me | |
| lb(ii) | Et | H | |
| lc(ii) | H | Et | |
| ld(ii) | Et | Et | |
| lb(iii) | n-Pr | H | |
| lc(iii) | H | n-Pr | |
| ld(iii) | n-Pr | n-Pr | |
| lb(iv) | i-Pr | H | |
| lc(iv) | H | i-Pr | |
| ld(iv) | i-Pr | i-Pr | |
| lb(v) | n-Bu | H | |
| lc(v) | H | n-Bu | |
| ld(v) | n-Bu | n-Bu | |
| lb(vi) | i-Bu | H | |
| lc(vi) | H | i-Bu | |
| ld(vi) | i-Bu | i-Bu | |
| lb(vii) | sec-Bu | H | |
| lc(vii) | H | sec-Bu | |
| ld(vii) | sec-Bu | sec-Bu | |
| lb(viii) | tert-Bu | H | |
| lc(viii) | H | tert-Bu | |
| ld(viii) | tert-Bu | tert-Bu | |
| le(ix) |  | | |
| le(x) | 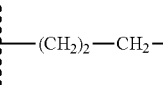 | | |
| le(xi) |  | | |

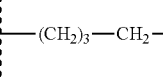

Carboxylic Esters 14

β-Keto Phosphonate Esters 15

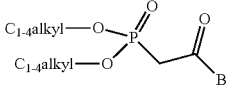

Carboxylic Acids 20

NHS Esters 18

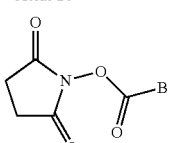

TABLE L-continued of Lower Chains

| B | R⁴ | R⁵ | R⁶ |
|---|----|----|-----|

Amides 19 (structure: phenyl-CH(CH2OH)-NH-C(=O)-B)

(S)-3-(B-Carbonyl)-4-benzyloxazolidin-2-ones 21

B = (structure with R⁴, R⁵, R⁶)

$R^4$ and/or $R^5$ = $C_1$-$C_4$ alkyl*
- (i) Me
- (ii) Et
- (iii) n-Pr
- (iv) i-Pr
- (v) n-Bu
- (vi) i-Bu
- (vii) sec-Bu
- (viii) tert-Bu (structure) = $C_3$-$C_5$ cycloalkyl
- (ix) cyclopropyl
- (x) cyclobutyl
- (xi) cyclopentyl

*$R^4$ and $R^5$ may both be $C_1$-$C_4$ alkyl groups that are not the same. Although no examples of these embodiments are represented in these tables, their absence infers no limitation in scope.

TABLE M of Lower Chains

| B | R⁴ | R⁵ | R⁶ |
|---|-----|-----|-----|
| ma | H | H | |
| mb(i) | Me | H | |
| mc(i) | H | Me | |
| md(i) | Me | Me | (4-phenylbutyl group) |
| mb(ii) | Et | H | |
| mc(ii) | H | Et | |
| md(ii) | Et | Et | |
| mb(iii) | n-Pr | H | |
| mc(iii) | H | n-Pr | |
| md(iii) | n-Pr | n-Pr | |
| mb(iv) | i-Pr | H | |
| mc(iv) | H | i-Pr | |
| md(iv) | i-Pr | i-Pr | |
| mb(v) | n-Bu | H | |
| mc(v) | H | n-Bu | |
| md(v) | n-Bu | n-Bu | |
| mb(vi) | i-Bu | H | |
| mc(vi) | H | i-Bu | |
| md(vi) | i-Bu | i-Bu | |
| mb(vii) | sec-Bu | H | |
| mc(vii) | H | sec-Bu | |
| md(vii) | sec-Bu | sec-Bu | |
| mb(viii) | tert-Bu | H | |
| mc(viii) | H | tert-Bu | |
| md(viii) | tert-Bu | tert-Bu | |
| me(ix) | —CH₂—CH₂— | | |
| me(x) | —(CH₂)₂—CH₂— | | |
| me(xi) | —(CH₂)₃—CH₂— | | |

Carboxylic Esters 14 ($C_{1-4}$alkyl—O—C(=O)—B)

β-Keto Phosphonate Esters 15 ($C_{1-4}$alkyl—O)₂P(=O)—CH₂—C(=O)—B

Carboxylic Acids 20 (HO—C(=O)—B)

NHS Esters 18 (N-hydroxysuccinimide ester of B)

Amides 19 (phenyl-CH(CH₂OH)-NH-C(=O)-B)

TABLE M-continued of Lower Chains

| B | R⁴ | R⁵ | R⁶ |
|---|----|----|----|

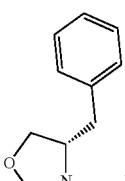

(S)-3-(B-Carbonyl)-
4-benzyloxazolidin-2-ones 21

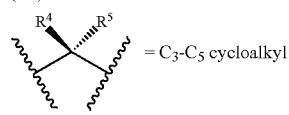

R⁴ and/or R⁵ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu

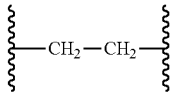 = $C_3$-$C_5$ cycloalkyl (ix) cyclopropyl
(x) cyclobutyl
(xi) cyclopentyl

*R⁴ and R⁵ may both be $C_1$-$C_4$ alkyl groups that are not the same. Although no examples of these embodiments are represented in these tables, their absence infers no limitation in scope.

TABLE N of Lower Chains

| B | R⁴ | R⁵ | R⁶ |
|---|----|----|----|
| na | H | H | 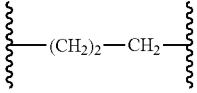 |
| nb(i) | Me | H | |
| nc(i) | H | Me | |
| nd(i) | Me | Me | |
| nb(ii) | Et | H | |
| nc(ii) | H | Et | |
| nd(ii) | Et | Et | |
| nb(iii) | n-Pr | H | |
| nc(iii) | H | n-Pr | |
| nd(iii) | n-Pr | n-Pr | |
| nb(iv) | i-Pr | H | |
| nc(iv) | H | i-Pr | |
| nd(iv) | i-Pr | i-Pr | |
| nb(v) | n-Bu | H | |
| nc(v) | H | n-Bu | |
| nd(v) | n-Bu | n-Bu | |
| nb(vi) | i-Bu | H | |
| nc(vi) | H | i-Bu | |
| nd(vi) | i-Bu | i-Bu | |
| nb(vii) | sec-Bu | H | |
| nc(vii) | H | sec-Bu | |
| nd(vii) | sec-Bu | sec-Bu | |
| nb(viii) | tert-Bu | H | |
| nc(viii) | H | tert-Bu | |
| nd(viii) | tert-Bu | tert-Bu | |

TABLE N-continued of Lower Chains

| B | R⁴ | R⁵ | R⁶ |
|---|----|----|----|
| ne(ix) | 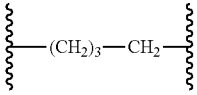 | | |
| ne(x) |  | | |
| ne(xi) | 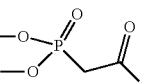 | | |

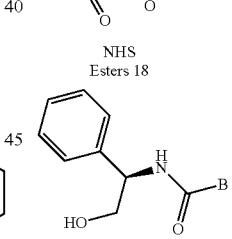

Carboxylic Esters 14

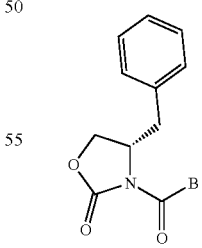

β-Keto Phosphonate Esters 15

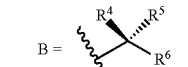

Carboxylic Acids 20

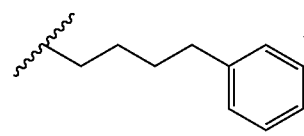 [SMILES: *CCCCc1ccccc1]

NHS Esters 18

Amides 19

(S)-3-(B-Carbonyl)-
4-benzyloxazolidin-2-ones 21

R⁴ and/or R⁵ = $C_1$-$C_4$ alkyl*
(i) Me

TABLE N-continued of Lower Chains

| B | R⁴ | R⁵ | R⁶ |
|---|----|----|----|
| (ii) Et | | | |
| (iii) n-Pr | | | |
| (iv) i-Pr | | | |
| (v) n-Bu | | | |
| (vi) i-Bu | | | |
| (vii) sec-Bu | | | |
| (viii) tert-Bu | | | |

 = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

TABLE O of Lower Chains

| B | R⁴ | R⁵ | R⁶ |
|---|----|----|----|
| oa | H | H | |
| ob(i) | Me | H | |
| oc(i) | H | Me | |
| od(i) | Me | Me | |
| ob(ii) | Et | H | |
| oc(ii) | H | Et | |
| od(ii) | Et | Et | |
| ob(iii) | n-Pr | H | |
| oc(iii) | H | n-Pr | |
| od(iii) | n-Pr | n-Pr | |
| ob(iv) | i-Pr | H | |
| oc(iv) | H | i-Pr | |
| od(iv) | i-Pr | i-Pr | |
| ob(v) | n-Bu | H | |
| oc(v) | H | n-Bu | |
| od(v) | n-Bu | n-Bu | |
| ob(vi) | i-Bu | H | |
| oc(vi) | H | i-Bu | |
| od(vi) | i-Bu | i-Bu | |
| ob(vii) | sec-Bu | H | |
| oc(vii) | H | sec-Bu | |
| od(vii) | sec-Bu | sec-Bu | |
| ob(viii) | tert-Bu | H | |
| oc(viii) | H | tert-Bu | |
| od(viii) | tert-Bu | tert-Bu | |
| oe(ix) | —CH₂—CH₂— | | |
| oe(x) | —(CH₂)₂—CH₂— | | |
| oe(xi) | —(CH₂)₃—CH₂— | | |

The R⁶ column shows: 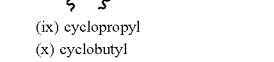

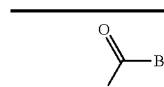

Carboxylic Esters 14

TABLE O-continued of Lower Chains

| B | R⁴ | R⁵ | R⁶ |
|---|----|----|----|

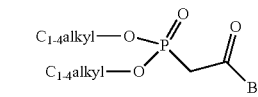

β-Keto Phosphonate Esters 15

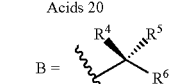

Carboxylic Acids 20

B = 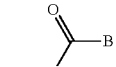

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu

 = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

TABLE P/Q of Lower Chains

| | B |
|---|---|
| p |  |
| q |  |

Scheme 7a

Step A 1.1 base (e.g. LDA or LiHMDS), solvent (e.g. THF)

1.2 $R^6$—$X^1$

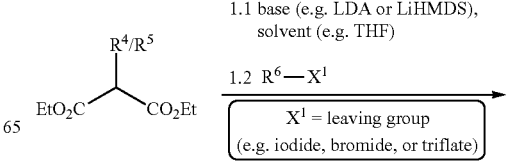

$X^1$ = leaving group (e.g. iodide, bromide, or triflate)

-continued

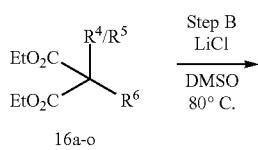

Step B
LiCl
DMSO
80° C.

16a-o → 14(a-o)a or 14(a-o)b/c(i-viii)

Scheme 7e

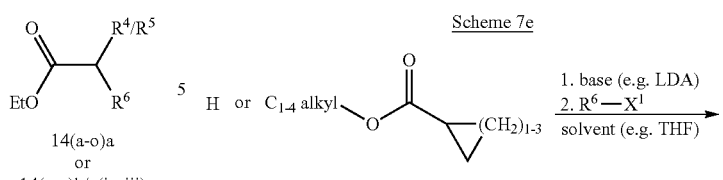

1. base (e.g. LDA)
2. $R^6$—$X^1$
solvent (e.g. THF)

14(a-o)e(ix-xi)

Scheme 7b

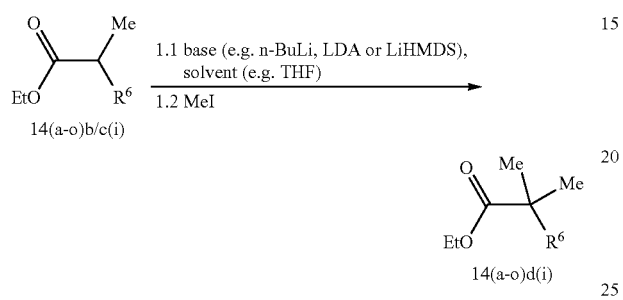

1.1 base (e.g. n-BuLi, LDA or LiHMDS), solvent (e.g. THF)
1.2 MeI

14(a-o)b/c(i) → 14(a-o)d(i)

Scheme 7f
Step A

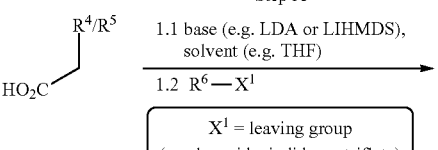

1.1 base (e.g. LDA or LiHMDS), solvent (e.g. THF)
1.2 $R^6$—$X^1$ $X^1$ = leaving group (e.g. bromide, iodide, or triflate)

Scheme 7c

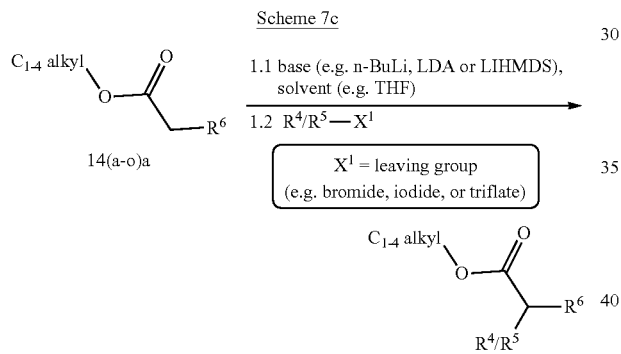

1.1 base (e.g. n-BuLi, LDA or LiHMDS), solvent (e.g. THF)
1.2 $R^4/R^5$—$X^1$ $X^1$ = leaving group (e.g. bromide, iodide, or triflate)

14(a-o)a → 14(a-o)b/c(i-vii)

Step B

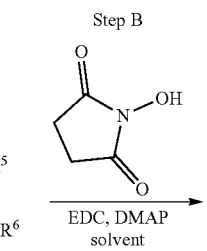

EDC, DMAP
solvent

20(a-o)b/c(i-viii)

Scheme 7d

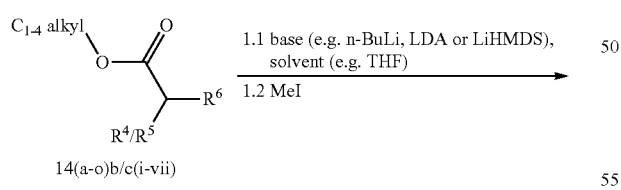

1.1 base (e.g. n-BuLi, LDA or LiHMDS), solvent (e.g. THF)
1.2 MeI

14(a-o)b/c(i-vii) → 14(a-o)d(i, etc.)

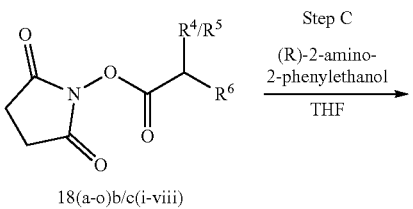

Step C
(R)-2-amino-2-phenylethanol
THF

18(a-o)b/c(i-viii)

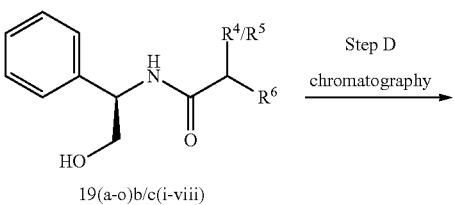

Step D
chromatography

19(a-o)b/c(i-viii)

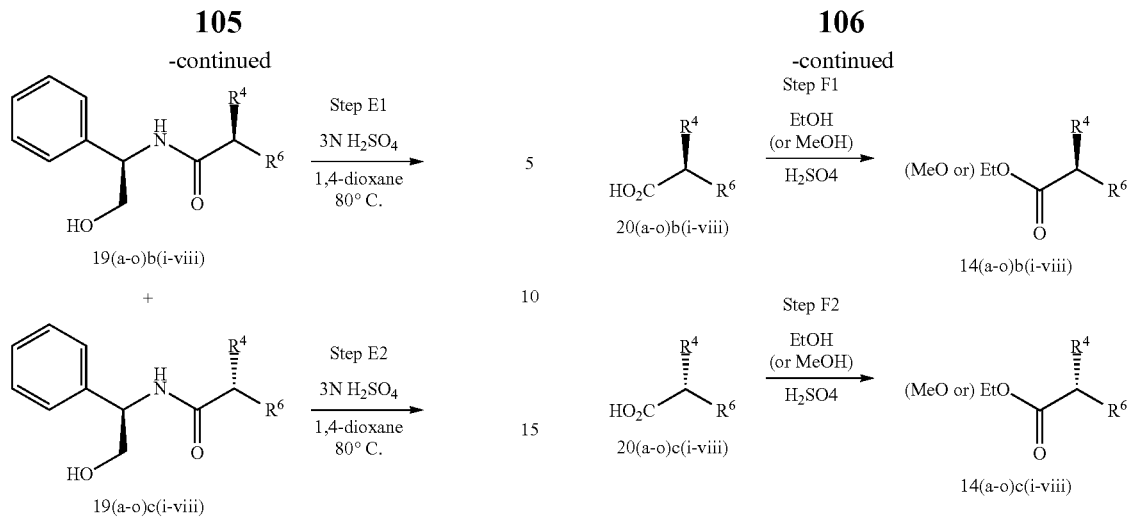
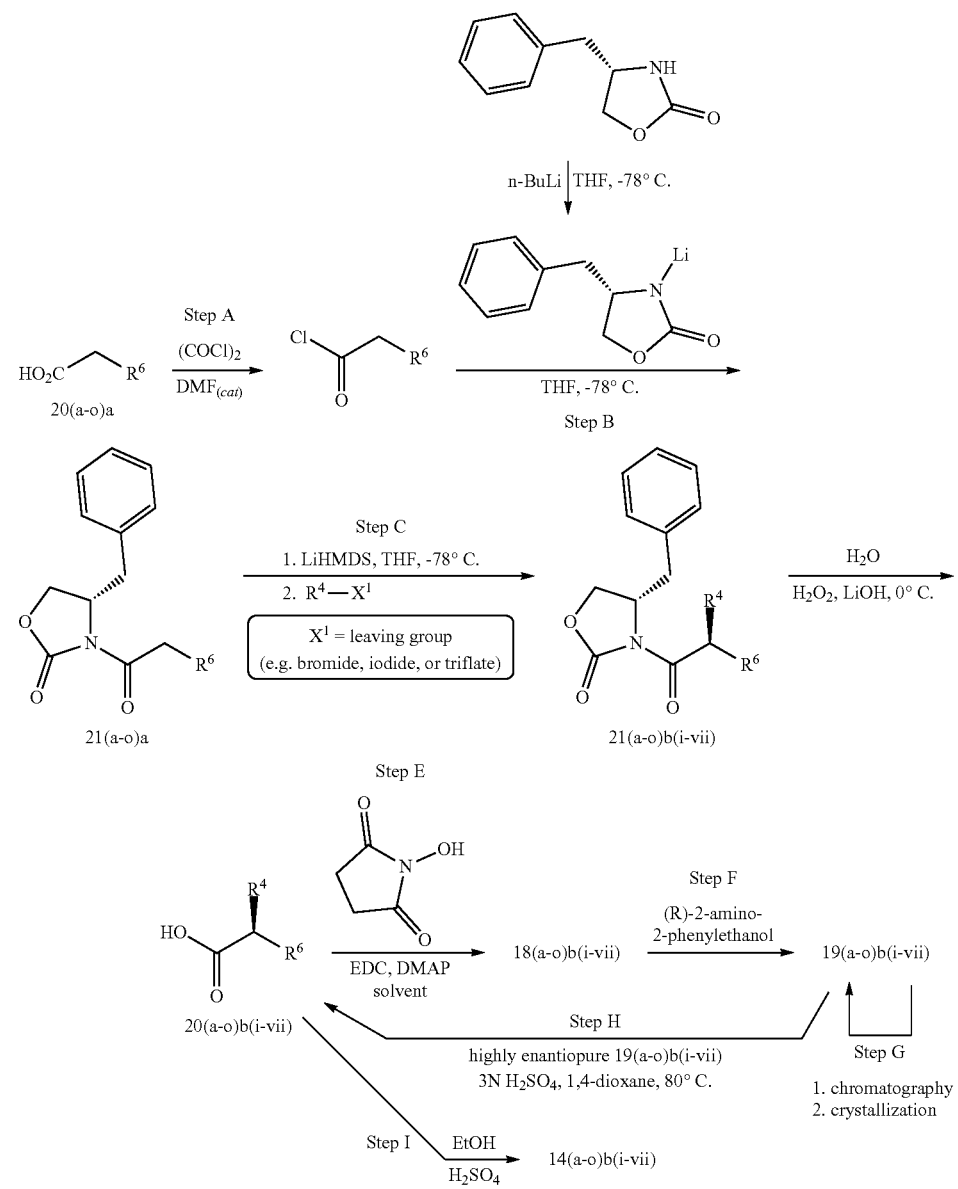
Scheme 7g

Scheme 8

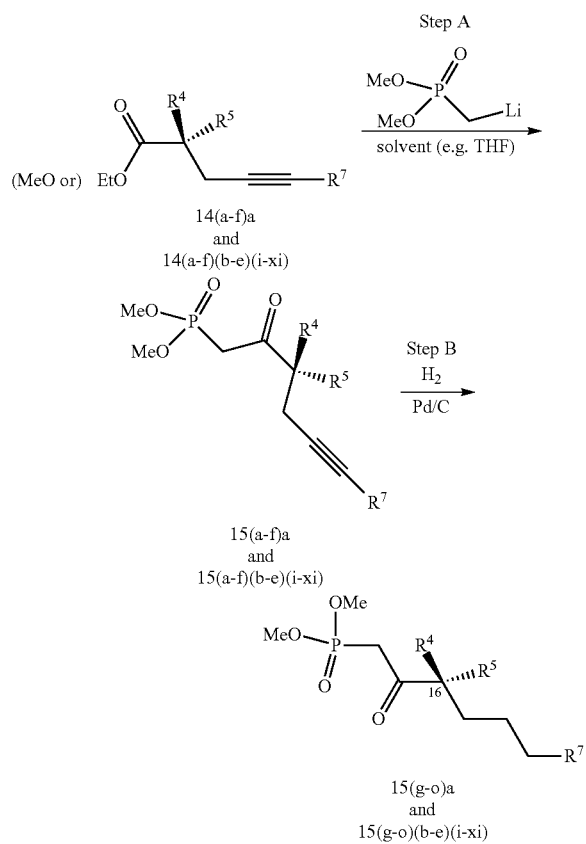

(±)-Dimethyl (3-methyl-2-oxohept-5-yn-1-yl)phosphonate (15ab(i)/15ac(i))

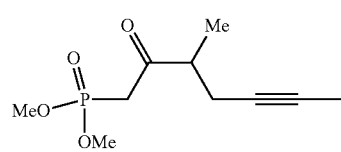

Scheme 7a, Step A: Preparation of diethyl 2-(but-2-yn-1-yl)-2-methylmalonate (16a(i))

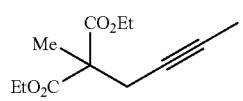

To a stirring mixture consisting of diethyl 2-methylmalonate (Sigma-Aldrich, 34.8 g, 200 mmol) in THF (50 mL) at −78° C. was added lithium bis-(trimethylsilyl)amide (1M in THF, 200 mL, 200 mmol) and the resulting reaction mixture was stirred at −78° C. for 30 minutes. To the reaction mixture was added a mixture consisting of 1-bromobut-2-yne (GFS, 25 g, 190 mmol) in THF (50 mL), and the mixture was stirred for another hour at −78° C., and was then allowed to warm to room temperature. The mixture was treated with 10% aqueous sodium hydrogen sulfate, diluted with brine (800 mL), and extracted with ethyl acetate (300 mL). The organic phase was washed with brine (2×250 mL), dried over sodium sulfate, filtered, and concentrated. The residue (brown oil) was purified by silica gel chromatography. Elution with ethyl acetate-hexane (1:9 v/v) afforded the title intermediate (41.5 g, 97.6%); TLC $R_f$ 0.52 (solvent system: 1:9 v/v ethyl acetate-hexane).

Scheme 7a, Step B: Preparation of (±)-ethyl 2-methylhex-4-ynoate (14ab(i)/14ac(i))

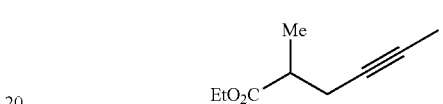

To a mixture consisting of diethyl-2-(but-2-yn-1-yl)-methylmalonate (41.5 g, 184 mmol) in DMSO (150 mL) was added lithium chloride (8.05 g, 190 mmol) and water (6.2 mL), and the stirring mixture was heated at 160° C. overnight. The reaction mixture was cooled and diluted with brine, and the organic material was extracted with ethyl acetate (250 mL). The organic phase was washed with brine (2×200 mL), dried over sodium sulfate, filtered, and concentrated. The residue (dark brown oil) was filtered through a pad of silica gel, using ethyl acetate-hexane (1:4 v/v) to flush the column. The filtrate was concentrated to give the title intermediate (22.3 g, 78.9%) as a colorless oil; TLC $R_f$ 0.37 (solvent system: 1:4 v/v ethyl acetate:hexanes).

Scheme 8, Step A: Preparation of (±)-dimethyl (3-methyl-2-oxohept-5-yn-1-yl)phosphonate (15ab(i)/15ac(i))

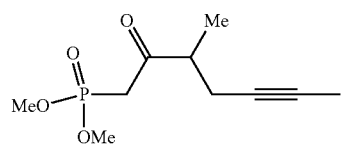

To a stirring mixture consisting of dimethyl methylphosphonate (21.7 g, 175 mmol) in THF (200 mL) at −78° C. was added n-butyllithium (1.6 M in hexanes, 106.2 mL, 169.9 mmol) and the mixture was allowed to continue stirring at −78° C. for one hour. To the reaction mixture was added dropwise (±)-ethyl 2-methylhex-4-ynoate (22.3 g, 145 mmol) and the resulting mixture was stirred at −78° C. for three hours. The reaction mixture was treated with 10% sodium hydrogen sulfate to achieve pH 4, diluted with brine (800 mL), and extracted with ethyl acetate (250 mL). The organic phase was washed with brine (2×150 mL), dried over sodium sulfate, filtered, and concentrated. The residue was purified by silica gel chromatography. Elution with ethyl acetate afforded the title intermediate (24.12 g, 71.6%) as a colorless oil; TLC $R_f$ 0.31 (solvent system: ethyl acetate); MS (ESI$^+$) m/z 233 (M+1).

Preparation of (S)-(+)-dimethyl (3-methyl-2-oxo-hept-5-yn-1-yl)phosphonate (15ab(i))

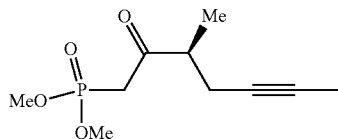

(S)-(+)-Dimethyl (3-methyl-2-oxohept-5-yn-1-yl)phosphonate was prepared in the same manner as that described for the preparation of intermediate 15bb(i) except that intermediate (S)-2-methylhex-4-ynoic acid was prepared instead of (S)-2-methylhept-4-ynoic acid and used to complete the synthesis of the title compound 15ab(i) as a clear oil; TLC $R_f$ 0.27 (solvent system: 4:1 v/v ethyl acetate-hexane); $^1$H-NMR (CDCl$_3$) δ 3.80 (s, 3H), 3.77 (s, 3H), 3.11-3.27 (m, 2H), 2.86-2.95 (m, 1H), 2.23-2.42 (m, 2H), 1.71-1.77 (m, 3H), 1.18 (d, 3H); MS (ESI$^+$) m/z 233 (M+1); $[α]^{20}_D$=+44° (c=1, CHCl$_3$).

Preparation of (±)-dimethyl (3-methyl-2-oxooct-5-yn-1-yl)phosphonate (15bb(i)/15bc(i))

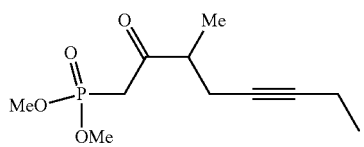 [SMILES: CCC#CCC(C)C(=O)CP(=O)(OC)OC]

(±)-Dimethyl (3-methyl-2-oxooct-5-yn-1-yl)phosphonate was prepared in the same manner as that described for the preparation of intermediate 15ab(i)/15ac(i) except that 1-bromopent-2-yne was used instead of 1-bromobut-2-yne; chiral analytical HPLC (stationary phase: Chiralcel OJ-H normal phase 250×4.6 mm; mobile phase: 85:15 hexane/1-propanol; flow rate: 1 mL/min): two peaks each of essentially equal area, fast peak having retention time of 5.8 min, slow peak having a retention time of 6.5 min; MS (ESI$^+$) m/z 247.1 (M+1).

Preparation of (S)-(+)-dimethyl (3-methyl-2-oxooct-5-yn-1-yl)phosphonate (15bb(i))

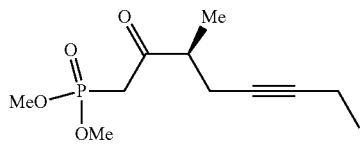 [SMILES: CCC#CC[C@H](C)C(=O)CP(=O)(OC)OC]

(S)-(+)-Dimethyl (3-methyl-2-oxooct-5-yn-1-yl)phosphonate was prepared by following the sequence of reaction steps described in Scheme 7a, 7f and Scheme 8, Step A. The intermediate 2-methylhept-4-ynoic acid was prepared according to a method described in WO 2011/003058 A1. (S)-(+)-Diethyl (3-methyl-2-oxooct-5-yn-1-yl)phosphonate was prepared according to the method described in the Journal of Medicinal Chemistry, 1986, 29(3), 313-315, except that 2,5-dioxopyrrolidin-1-yl 2-methylhept-4-ynoate (N-hydroxysuccinimide 2-methylhept-4-ynoate) was prepared as an activated acyl species (activated ester) instead of 2-methylhept-4-ynoyl chloride to make the intermediate diastereomeric pair N—((R)-2-hydroxy-1-phenylethyl)-2-methylhept-4-ynamide. The diastereomers were separated by silica gel chromatography and the desired diastereomer was manipulated as described to afford the title intermediate as a clear oil. The absolute stereochemistry of the title intermediate was proven by determination of its specific rotation. $[α]^T_λ$=α/cl, $[α]^{21.9}_D$=+0.574/(0.025 g/1 mL) (0.5)=+45.83° (c=1, CHCl$_3$). Literature reported specific rotation from Liebigs Annalen der Chemie, 1989, 11, 1081-1083; $[α]^{20}_D$=+37.7° (c=1, CHCl$_3$); chiral analytical HPLC (stationary phase: Chiralcel OJ-H normal phase 250×4.6 mm; mobile phase: 85:15 hexane/1-propanol; flow rate: 1 mL/min) retention time 6.4 min, 100% purity; TLC $R_f$ 0.32 (solvent system: 4:1 v/v ethyl acetate-hexane); $^1$H-NMR (CDCl$_3$) δ 3.76-3.80 (m, 6H), 3.11-3.29 (m, 2H), 2.86-2.95 (m, 1H), 2.36-2.44 (m, 1H), 2.26-2.33 (m, 1H), 2.09-2.16 (m, 2H), 1.16-1.20 (m, 3H), 1.06-1.11 (m, 3H); MS (ESI$^+$) m/z 247 (M+1).

A second preparation of the title intermediate by the same process described above afforded the title intermediate wherein the specific rotation (c=1, CHCl$_3$) is +49°.

Preparation of (±)-dimethyl (3-methyl-2-oxonon-5-yn-1-yl)phosphonate (15cb(i)/15cc(i))

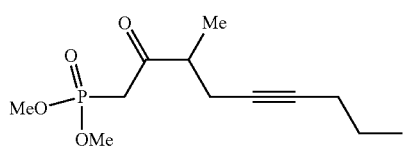 [SMILES: CCCC#CCC(C)C(=O)CP(=O)(OC)OC]

(±)-Dimethyl (3-methyl-2-oxonon-5-yn-1-yl)phosphonate was prepared in the same manner as that described for the preparation of intermediate 15ab(i)/15ac(i) except that 1-bromohex-2-yne (prepared from the corresponding commercially available alcohol using PBr$_3$/pyridine) was used instead of 1-bromobut-2-yne; MS (ESI$^+$) m/z 261 (M+1).

Preparation of (S)-(+)-dimethyl (3-methyl-2-oxonon-5-yn-1-yl)phosphonate (15cb(i))

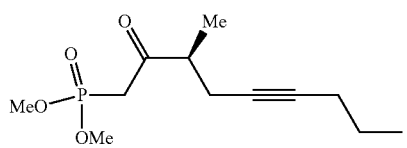 [SMILES: CCCC#CC[C@H](C)C(=O)CP(=O)(OC)OC]

(S)-(+)-Dimethyl (3-methyl-2-oxonon-5-yn-1-yl)phosphonate was prepared in the same manner as that described for the preparation of intermediate 15bb(i) except that intermediate (S)-2-methyloct-4-ynoic acid was prepared instead of (S)-2-methylhept-4-ynoic acid and used to complete the synthesis of the title compound 15cb(i) as a clear oil; TLC $R_f$ 0.12 (solvent system: 3:2 v/v ethyl acetate-hexane); $^1$H-NMR (CDCl$_3$) δ 3.76-3.80 (m, 6H), 3.11-3.29 (m, 2H), 2.86-2.95 (m, 1H), 2.27-2.45 (m, 2H), 2.04-2.12 (m, 2H), 1.39-1.55 (m, 2H), 1.13-1.24 (m, 3H), 0.94 (m, 3H); MS (ESI$^+$) m/z 261 (M+1); $[α]^{20}_D$=+48.8° (c=1, CHCl$_3$).

Preparation of (±)-dimethyl (3-methyl-2-oxo-6-phenylhex-5-yn-1-yl)phosphonate (15db(i)/15dc(i))

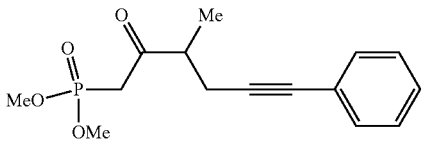 [SMILES: COP(=O)(CC(=O)C(C)CC#Cc1ccccc1)OC]

(±)-Dimethyl (3-methyl-2-oxo-6-phenylhex-5-yn-1-yl)phosphonate was prepared in the same manner as that described for the preparation of intermediate 15ab(i)/15ac(i) except that (3-bromoprop-1-yn-1-yl)benzene (prepared from the corresponding commercially available alcohol using PBr$_3$/pyridine) was used instead of 1-bromobut-2-yne to afford 2.4 g of a clear oil; $^1$H-NMR (CDCl$_3$) δ 7.35-7.45 (m, 2H), 7.2-7.3 (m, 3H), 3.85-3.75 (m, 6H), 3.25 (d, 2H), 3.0-3.2 (m, 1H), 2.5-2.7 (m, 2H), 1.25 (d, 3H); MS (ESI$^+$) m/z 295.1 (M+1).

Preparation of (S)-(+)-dimethyl (3-methyl-2-oxo-6-phenylhex-5-yn-1-yl)phosphonate (15db(i))

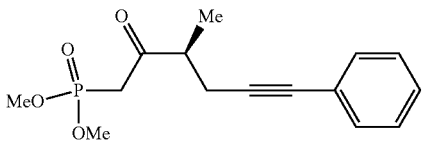 [SMILES: COP(=O)(CC(=O)[C@@H](C)CC#Cc1ccccc1)OC]

(S)-(+)-Dimethyl (3-methyl-2-oxo-6-phenylhex-5-yn-1-yl)phosphonate was prepared in the same manner as that described for the preparation of intermediate 15bb(i) except that intermediate (S)-2-methyl-5-phenylpent-4-ynoic acid was prepared instead of (S)-2-methylhept-4-ynoic acid and used to complete the synthesis of the title compound 15db(i) as a clear oil; TLC R$_f$ 0.22 (solvent system: 4:1 v/v ethyl acetate-hexane); MS (ESI$^+$) m/z 295 (M+1).

Preparation of (±)-dimethyl (3-methyl-2-oxo-6-phenylhexyl)phosphonate (15mb(i)/15mc(i))

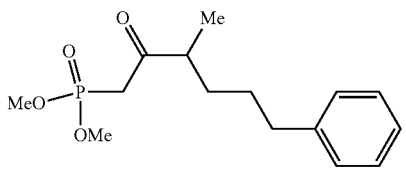 [SMILES: COP(=O)(CC(=O)C(C)CCCc1ccccc1)OC]

A mixture consisting of (±)-dimethyl (3-methyl-2-oxo-6-phenylhex-5-yn-1-yl)phosphonate (15db(i)/15dc(i)), (1.0 g, 3.4 mmol) and 10% palladium on activated carbon (15 mg) in methanol (30 mL) was stirred under an atmosphere of hydrogen overnight. The hydrogen was evacuated and the mixture was filtered through a micropore filter. The filtrate was concentrated in vacuo to afford the title compound (1.0 g, quantitative yield) as a clear oil; $^1$H-NMR (CDCl$_3$) δ 7.3-7.25 (m, 2H), 7.2-7.1 (m, 3H), 3.8-3.7 (m, 6H), 3.1 (d, 2H), 2.8-2.75 (m, 1H), 2.7-2.5 (m, 2H), 1.8-1.65 (m, 1H), 1.65-1.5 (m, 2H), 1.4-1.3 (m, 1H), 1.1 (d, 3H); MS (ESI$^+$) m/z 299 (M+1).

Preparation of (S)-(+)-dimethyl (3-methyl-2-oxo-6-phenylhexyl)phosphonate (15mb(i))

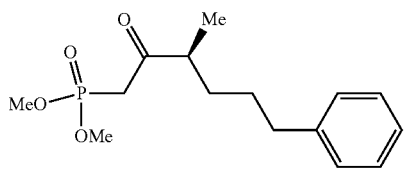 [SMILES: COP(=O)(CC(=O)[C@@H](C)CCCc1ccccc1)OC]

(S)-(+)-Dimethyl (3-methyl-2-oxo-6-phenylhexyl)phosphonate was prepared as a clear oil in the same manner as that described for the preparation of phosphonate 15mb(i)/15mc(i); $^1$H-NMR (CDCl$_3$) δ 7.3-7.2 (m, 2H), 7.2-7.1 (m, 3H), 3.8-3.7 (m, 6H), 3.12 (s, 1H), 3.07 (s, 1H), 2.8-2.7 (m, 1H), 2.7-2.5 (m, 2H), 1.8-1.7 (m, 2H), 1.7-1.5 (m, 2H), 1.1 (d, 3H); MS (ESI$^+$) m/z 299 (M+1).

Alternative preparation of (S)-(+)-dimethyl (3-methyl-2-oxo-6-phenylhexyl)phosphonate (15mb(i))

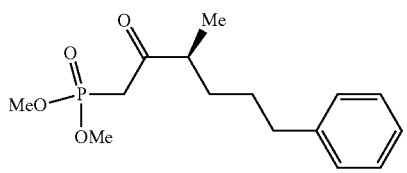 [SMILES: COP(=O)(CC(=O)[C@@H](C)CCCc1ccccc1)OC]

Scheme 7f, Step A: Preparation of (±)-2-methyl-5-phenylpentanoic acid (20mb(i)/20mc(i))

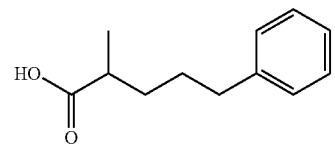

To a solution consisting of diisopropylamine (218.25 mL, 1557.3 mmol) in THF (400 mL) at −50° C. was added an n-butyllithium solution (628 mL, 393 mmol, 1.6 M solution in hexane). The reaction mixture was stirred for five minutes and was then allowed to warm to −20° C. To the reaction mixture was added dropwise a solution consisting of propionic acid (44.67 g, 603 mmol) in HMPA (102 mL). The reaction mixture was stirred at room temperature for 30 minutes, and subsequently cooled to 0° C., after which a mixture consisting of 1-bromo-3-phenylpropane (100 g, 502 mmol) in THF (200 mL) was added. The resulting reaction mixture stirred at room temperature for two hours. The reaction mixture was diluted with water and extracted with ethyl acetate. The aqueous layer was separated and then acidified with 2 M HCl until acidic. The aqueous layer was then extracted three times with ethyl acetate, and the organic layers were combined and dried over sodium sulfate, filtered, and concentrated to afford the title intermediate (105 g, quantitative yield) as a clear oil; TLC R$_f$ 0.44 (solvent system: 25:75:1 v/v/v ethyl acetate-heptane-acetic acid.

Scheme 7f, Step B: Preparation of (±)-2,5-dioxopyrrolidin-1-yl 2-methyl-5-phenylpentanoate (18mb(i))

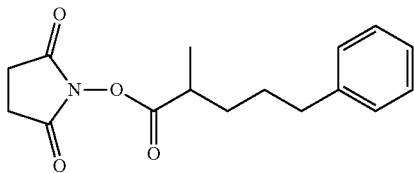 [SMILES: CC(CCCc1ccccc1)C(=O)ON1C(=O)CCC1=O]

To a mixture consisting of (±)-2-methyl-5-phenylpentanoic acid (20mb(i)/20mc(i), 105.6 g, 549.1 mmol) in dichloromethane (800 mL) was added N-hydroxysuccinimide (69.5 g, 604 mmol), 4-dimethylaminopyridine (73.8 g, 604 mmol) and 1-ethyl-(3-dimethylaminopropyl) carbodiimide hydrochloride (115.8 g, 604.0 mmol) and the reaction mixture was stirred overnight at room temperature. The reaction mixture was extracted with dichloromethane and washed twice with brine, dried over sodium sulfate, filtered, and concentrated under vacuum. The residue was purified by silica gel chromatography. Elution with ethyl acetate-heptane (30:70 v/v) afforded the title intermediate (85.6 g, 54%); TLC $R_f$ 0.32 (solvent system 25:75 v/v ethyl acetate-heptane.

Scheme 7f, Steps C and D: Preparation of (S)—N—((R)-2-hydroxy-1-phenylethyl)-2-methyl-5-phenylpentanamide (19mb(i))

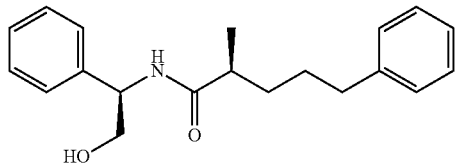 [SMILES: C[C@@H](CCCc1ccccc1)C(=O)N[C@@H](CO)c1ccccc1]

To a solution consisting of (±)-2,5-dioxopyrrolidin-1-yl 2-methyl-5-phenyl pentanoate (18mb(i), 85.6 g, 296 mmol) in THF (3000 mL) at 48° C. was added R-(−)-2-phenylglycinol (65.9 g, 480 mmol, Bridge Organics) in portions. The resulting reaction mixture was stirred at 48° C. for 40 hours. A white precipitate formed, which was filtered from the reaction mixture and washed with THF. The filtrate was concentrated under vacuum and the residue, comprising the diastereomeric pair, was chromatographed on silica gel. Elution with ethyl acetate-heptane (50:50 v/v) afforded the pure diastereomer title compound (31.3 g, 34%) as a colorless solid; TLC $R_f$ 0.205 (solvent system: 50:50 v/v ethyl acetate-heptane); HPLC retention time 15.1 minutes, stationary phase: Gemini 5µ C18 250×4.6 mm, ultraviolet detector at 210 nm, mobile phase: 1 mL/min, 60:40:0.1 v/v methanol-water-acetic acid.

Scheme 7f, Step E1: Preparation of (S)-(+)-2-methyl-5-phenylpentanoic acid (20mb(i))

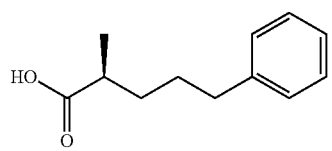

To a solution consisting of (S)—N—((R)-2-hydroxy-1-phenylethyl)-2-methyl-5-phenylpentanamide (19mb(i), 3.5 g, 11.24 mmol) in 1,4-dioxane (80 mL) was added aqueous sulfuric acid (36 mL, 3 N solution) and the mixture was stirred overnight at 80° C. The reaction mixture was extracted with ethyl acetate three times and the organic layers were combined, dried over sodium sulfate, filtered, and concentrated under vacuum. The residue was purified by silica gel chromatography. Elution with ethyl acetate-heptane-acetic acid (30:70:0.4 v/v/v) afforded the title compound (2.4 g, quantitative yield) as a clear oil; $R_f$ 0.48 (solvent system: 30:70:0.4 v/v/v ethyl acetate-heptane-acetic acid; HPLC retention time 26.0 minutes; Chiralpak IA, 5µ, 4.6×25 mm, ultraviolet detector at 208 nm 0.75 ml/min 99:1:0.5 v/v heptanes-2-propanol-acetic acid; MS (ESI$^-$) m/z 191.1 (M−H)$^-$; $^1$H-NMR (CDCl$_3$) δ 7.33-7.27 (m, 2H), 7.22-7.16 (m, 3H), 2.67-2.60 (m, 2H), 2.56-2.46 (m, 1H), 1.80-1.60 (m, 3H), 1.59-1.36 (m, 1H), 1.25-1.14 (m, 3H); $[\alpha]^T_\lambda=[\alpha]^{21.9}_D=+0.089/(0.01501$ g/1.5 mL)(0.5)=+17.79° (c=1, CHCl$_3$).

Scheme 7f, Step F1: Preparation of (S)-(+)-ethyl 2-methyl-5-phenylpentanoate (14mb(i))

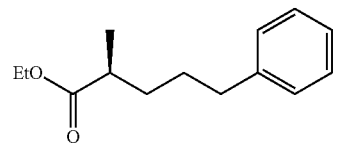 [SMILES: CCOC(=O)[C@@H](C)CCCc1ccccc1]

To a solution consisting of (S)-(+)-2-methyl-5-phenylpentanoic acid (20mb(i), 2.3 g, 12 mmol) in ethanol (200 mL) was added 4 drops of concentrated sulfuric acid. The stirring reaction mixture was brought to reflux overnight and was subsequently cooled and concentrated under vacuum. The residue was diluted with ethyl acetate and washed twice with brine. The organic layer was dried over sodium sulfate, filtered, and concentrated under vacuum to afford the title compound (2.4 g, 91%) as a clear oil; TLC $R_f$ 0.66 (solvent system: 15:85:1 v/v/v ethyl acetate-heptane-acetic; MS (ESI$^-$) m/z 221.2 (M+H)$^+$; $^1$H-NMR (CDCl$_3$) δ 7.29-7.25 (m, 2H), 7.21-7.13 (m, 3H), 4.12 (q, J=6.96 Hz, 2H), 2.64-2.57 (m, 2H), 2.48-2.39 (m, 1H), 1.75-1.54 (m, 3H), 1.52-1.41 (m, 1H), 1.24 (t, J=7.14 Hz, 3H) 1.16-1.11 (m, 3H); $[\alpha]T_\lambda=a/cl$, $[\alpha]^{21.9}_D=+0.101/(0.01506$ g/1.5 ml) (0.5)=+20.12° (c=1, CHCl$_3$).

Scheme 6: Preparation of (S)-(+)-dimethyl (3-methyl-2-oxo-6-phenylhexyl)phosphonate (15mb(i))

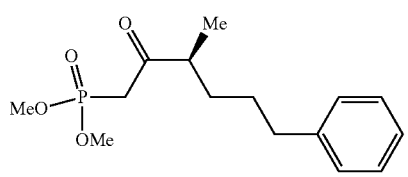 [SMILES: COP(=O)(CC(=O)[C@@H](C)CCCc1ccccc1)OC]

To a stirring solution consisting of dimethyl methylphosphonate (23.37 g, 188.4 mmol) in THF (400 mL) at −78° C. was slowly added n-butyllithium solution (112 mL, 179 mmol, 1.6 M solution in hexane). The reaction mixture was stirred for 30 minutes, after which time, (S)-(+)-ethyl 2-methyl-5-phenylpentanoate (14mb(i), 28.1 g, 94.2 mmol) in THF (100 mL) was slowly added. The resulting reaction mixture was stirred at −78° C. for two hours and was then allowed to rise to room temperature overnight. The reaction mixture was treated with 5% KHSO₄ and extracted with ethyl acetate three times. The organic layer was washed twice with 50:50 water-brine and the organic layer was dried over sodium sulfate, filtered, and concentrated under vacuum. The residue was purified by silica gel chromatography. Elution with ethyl acetate-heptane (60:40 v/v) afforded the title compound (11.9 g, 42%) as a clear oil, pure of unrelated components; TLC R$_f$ 0.22 (solvent system: 60:40 v/v ethyl acetate-heptane); HPLC retention time 14.5 minutes, 5μ Chiralpak IA 250×4.6 mm, ultraviolet detector at 210 nm, 1 mL/min, chiral purity 97.8% (S), 2.19% (R); MS (ESI⁻) m/z 297.1 (M−H)⁻; ¹H NMR (CDCl₃) δ 7.28-7.21 (m, 2H), 7.17-7.12 (m, 3H), 3.76-3.71 (m, 6H), 3.10 (d, J=2.20 Hz, 1H), 3.04 (d, J=2.20 Hz, 1H), 2.79-2.70 (m, 1H), 2.54-2.62 (m, 2H), 1.74-1.54 (m, 3H), 1.42-1.24 (m, 1H), 1.07 (d, J=6.96 Hz, 3H); [α]$^T_λ$=α/cl, [α]$^{21.9}_D$=+0.084/ (0.0169 g/1.5 mL)(0.5)=+14.91° (c=1.13, CHCl₃).

The chromatography also provided additional title compound (8.3 g) with approximately 95% chemical purity based on visual observation of TLC; chiral purity 98.19% (S), 1.81% (R).

Second alternative preparation of (S)-(+)-dimethyl (3-methyl-2-oxo-6-phenylhexyl)phosphonate (15mb(1))

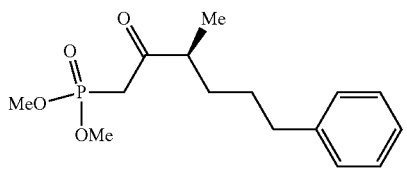 [SMILES: COP(=O)(CC(=O)[C@@H](C)CCCc1ccccc1)OC]

Scheme 7g, Step B: Preparation of (S)-4-benzyl-3-(5-phenylpentanoyl)oxazolidin-2-one (21ma)

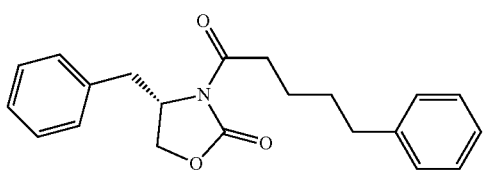 [SMILES: O=C(CCCCc1ccccc1)N1C(=O)OC[C@@H]1Cc1ccccc1]

To a stirring solution consisting of (S)-4-benzyloxazolidin-2-one (0.9 g, 5.08 mmol) in THF (20 mL) at −78° C. was slowly added n-butyllithium solution (3.5 mL, 5.6 mmol, 1.6 M solution in hexane). The reaction mixture was stirred at −78° C. for two hours, after which time 5-phenylpentanoyl chloride (1 g, 5 mmol, prepared by treatment of 5-phenylpentanoic acid with oxalyl chloride and catalytic DMF) was slowly added. The reaction mixture was stirred at −78° C. for two hours and was then allowed to rise to room temperature overnight. The reaction mixture was acidified with 5% KHSO₄ and extracted twice with ethyl acetate. The organic phase was washed with brine, dried over sodium sulfate, filtered, and concentrated under vacuum. The residue was purified by silica gel chromatography. Elution with ethyl acetate-heptane (25:75 v/v) afforded the title compound (1.4 g, 82%) as a clear oil; TLC R$_f$ 0.40 (solvent system: 25:75 v/v ethyl acetate-heptane); MS (ESI⁺) m/z 337.4 (M+H)⁺, 360.2 (M+Na)+.

Scheme 7g, Step C: Preparation of (S)-4-benzyl-3-((S)-2-methyl-5-phenylpentanoyl)oxazolidin-2-one (21 mb(i))

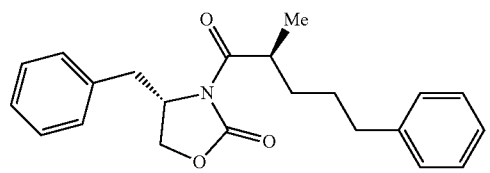 [SMILES: C[C@@H](CCCc1ccccc1)C(=O)N1C(=O)OC[C@@H]1Cc1ccccc1]

To a stirring solution consisting of (S)-4-benzyl-3-(5-phenylpentanoyl)oxazolidin-2-one (21ma, 1.24 g, 3.68 mmol) in THF (20 mL) at −78° C. was slowly added lithium bis-(trimethylsilyl)amide solution (4.41 mL, 4.41 mmol, 1 M solution in THF). The reaction mixture was stirred at −78° C. for one hour, after which time iodomethane (0.27 mL, 4.2 mmol) was slowly added. The resulting reaction mixture was allowed to rise to room temperature with stirring overnight. The mixture was acidified with 5% KHSO₄ and extracted twice with ethyl acetate. The organic layer was washed twice with brine, dried over sodium sulfate, filtered, and concentrated under vacuum. The residue was purified by silica gel chromatography. Elution with ethyl acetate-heptane (25:75 v/v) afforded the title compound (563 mg, 43.6%) as a clear oil; TLC R$_f$ 0.53 (solvent system: 25:75 v/v ethyl acetate-heptane; MS (ESI⁺) m/z 352.3 (M+H)⁺ 374.2 (M+Na)⁺.

Scheme 7g, Step D: Preparation of (S)-2-methyl-5-phenylpentanoic acid (20mb(i))

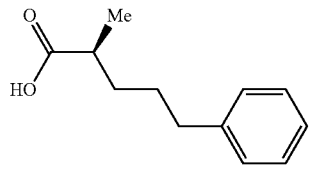 [SMILES: C[C@@H](CCCc1ccccc1)C(=O)O]

To a stirring aqueous mixture cooled to 0° C. comprising (S)-4-benzyl-3-((S)-2-methyl-5-phenylpentanoyl)oxazolidin-2-one (21mb(i), 563 mg, 1.60 mmol) was added hydrogen peroxide and lithium hydroxide. The resulting reaction mixture was stirred for four hours. The reaction mixture was acidified with 5% KHSO₄ and extracted twice with ethyl acetate, the organic layer was washed twice with brine, dried over sodium sulfate, and concentrated under vacuum. The residue was purified by silica gel chromatography. Elution with ethyl acetate-heptane-acetic acid (25:75:0.4) afforded the title compound (293 mg, 95%) as a colorless oil; TLC R$_f$ 0.35 (solvent system: 25:75:0.4 v/v/v ethyl acetate-heptane-acetic acid); HPLC retention time 12.08 min, stationary phase: Chiralpak IA 4.6×25 mm 5μ, ultraviolet detector at 210 nm, mobile phase: 1 mL/min 99:1:0.1 heptane: 2-propanol: acetic acid, 97.22% (S), 2.78% (R).

Scheme 7g, Step E: Preparation of (S)-2,5-dioxopyrrolidin-1-yl 2-methyl-5-phenylpentanoate (18mb(i))

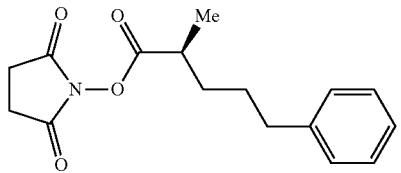 [SMILES: C[C@@H](CCCc1ccccc1)C(=O)ON1C(=O)CCC1=O]

To a mixture consisting of (S)-2-methyl-5-phenylpentanoic acid (20mb(i), 290 mg, 1.51 mmol) in dichloromethane (20 mL) was added N-hydroxysuccinimide (191 mg, 1.66 mmol), 4-dimethylaminopyridine (203 mg, 1.66 mmol) and 1-ethyl-(3-dimethylaminopropyl)carbodiimide hydrochloride (318 mg, 1.66 mmol). The resulting reaction mixture was stirred for two hours at room temperature. The reaction mixture comprising 18mb(i) was carried on directly to the next step.

Scheme 7g, Step F and G: Preparation of (S)—N—((R)-2-hydroxy-1-phenylethyl)-2-methyl-5-phenylpentanamide (19mb(i))

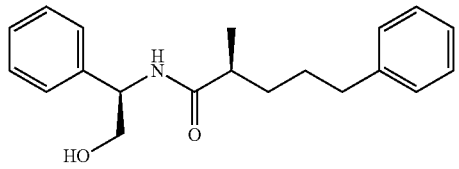 [SMILES: C[C@@H](CCCc1ccccc1)C(=O)N[C@@H](CO)c1ccccc1]

To the reaction mixture comprising 18mb(i) prepared as described above was added R-(−)-2-phenylglycinol, and the resulting reaction mixture was stirred overnight. The mixture was filtered and washed with THF. The combined filtrate and THF wash was concentrated under vacuum. The residue was purified by silca gel chromatography. Elution with ethyl acetate-heptane (60:40 v/v) provided a solid, which was crystallized from ethyl acetate-heptane to afford the highly-stereopure title compound (198 mg, 42%) as a white solid; TLC $R_f$ 0.21 (solvent system: 60:40 v/v ethyl acetate-heptane; HPLC retention time 14.68 minutes, stationary phase: Gemini, 5μ C18 250×4.6 mm, ultraviolet wavelength of 210 nm, mobile phase: 1 mL/min, 60:40:0.1 methanol-water-acetic acid, 100% (S); MS (ESI$^+$) m/z 312.2 (M+H)$^+$, 334.1 (M+Na)$^+$.

Preparation of (S)-(+)-dimethyl (3-methyl-2-oxo-6-phenylhexyl)phosphonate (15mb(i))

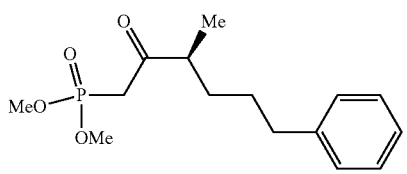 [SMILES: COP(=O)(CC(=O)[C@@H](C)CCCc1ccccc1)OC]

(S)-(+)-Dimethyl (3-methyl-2-oxo-6-phenylhexyl)phosphonate (15mb(i)) is prepared in three steps from the highly stereopure (S)—N—((R)-2-hydroxy-1-phenylethyl)-2-methyl-5-phenylpentanamide (19mb(i)) prepared by the Scheme 7g route as it is from the 19mb(i) derived from the reaction sequence of Scheme 7f starting from (±)-2-methyl-5-phenylpentanoic acid (20mb(i)/20mc(i)).

Preparation of (R)-(−)-dimethyl (3-methyl-2-oxo-6-phenylhexyl)phosphonate (15mc(i))

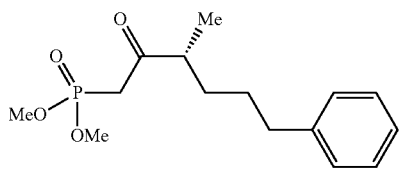 [SMILES: COP(=O)(CC(=O)[C@H](C)CCCc1ccccc1)OC]

Preparation of (−)-(R)—N—((R)-2-hydroxy-1-phenylethyl)-2-methyl-5-phenylpentanamide (19mc(i))

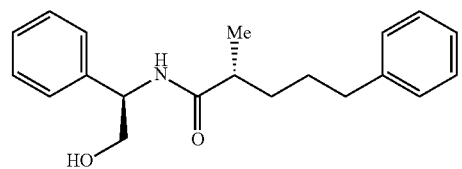 [SMILES: C[C@H](CCCc1ccccc1)C(=O)N[C@@H](CO)c1ccccc1]

(−)-(R)—N—((R)-2-Hydroxy-1-phenylethyl)-2-methyl-5-phenylpentanamide was prepared from (±)-2-methyl-5-phenylpentanoic acid (20mb(i)/20mc(i)) in the same manner as (S)—N—((R)-2-hydroxy-1-phenylethyl)-2-methyl-5-phenylpentanamide (19mb(i)) described above. Silica gel chromatography provided separation of the title compound from its diastereomer (19mb(i)) to provide the desired product (30.2 g, 33%) as a white solid; TLC $R_f$ 0.33 (solvent system: 50:50 v/v ethyl acetate-heptane); HPLC retention time 13.25 minutes, Gemini 5μ C18 250×4.6 mm, at ultraviolet wavelength of 210 nm, 1 mL/min, 60:40:0.1 methanol-water-acetic acid, purity 99.36% (R), 0.64% (S); $[\alpha]^T_\lambda = \alpha/cl$, $[\alpha]^{21.9}_D = -0.066/(0.01573$ g/2 mL)(0.5)= −16.78° (c=0.7865, CHCl$_3$).

Preparation of (R)-(−)-2-methyl-5-phenylpentanoic acid (20mc(i))

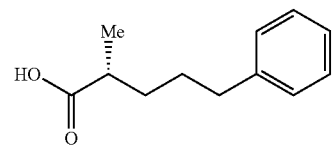 [SMILES: C[C@H](CCCc1ccccc1)C(=O)O]

R)-(−)-2-Methyl-5-phenylpentanoic acid was prepared from 19mc(i) (30 g) in the same manner (S)-(+)-2-methyl-5-phenylpentanoic acid was prepared from 19mb(i) as described above. The residue was purified by silica gel chromatography. Elution with ethyl acetate-heptane-acetic acid (20:80:0.4 v/v/v) afforded the title compound (20.8 g) as a clear oil; TLC $R_f$ 0.51 (solvent system: 30:70:1 v/v/v ethyl aceate-hepatane-acetic acid; HPLC retention time 24.46 min; Chiralpak IA 4.6×25 mm 5μ, at a wavelength of 208 nm 0.75 mL/min, 99:1:0.5 heptane: 2-propanol: acetic acid, chiral purity 99.32% (R), 0.68% (S); MS (ESI⁻) m/z 191.1 (M−H)⁻; $^1$H-NMR (CDCl$_3$) δ 7.31-7.26 (m, 2H), 7.21-7.15 (m, 3H), 2.67-2.57 (m, 2H), 2.54-2.44 (m, 1H), 1.79-1.59 (m, 3H) 1.58-1.41 (m, 1H), 1.18 (d, J=6.96 Hz, 3H).

Preparation of (R)-(−)-ethyl 2-methyl-5-phenylpentanoate (14mc(i))

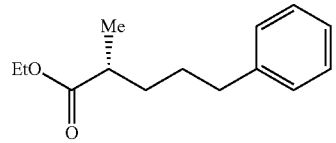 [SMILES: CCOC(=O)[C@H](C)CCCc1ccccc1]

(R)-(−)-Ethyl 2-methyl-5-phenylpentanoate was prepared from 20mc(i) (20.8 g) in the same manner (S)-(+)-ethyl 2-methyl-5-phenylpentanoate was prepared from 20mb(i) as described above. The residue was purified by silica gel chromatography. Elution with ethyl acetate-heptane (5:95 v/v) afforded the title compound (21.0 g, 88%) as a clear oil; TLC R$_f$ 0.66 (solvent system: 15:85:1 v/v/v ethyl acetate-heptane-acetic acid); MS (ESI⁺) m/z 221.2 (M+H)⁺; $^1$H-NMR (CDCl$_3$) δ 7.32-7.26 (m, 2H), 7.20-7.14 (m, 3H), 4.11 (q, J=7.32 Hz, 2H), 2.64-2.57 (m, 2H), 2.48-2.39 (m, 1H), 1.75-1.53 (m, 3H), 1.52-1.41 (m, 1H), 1.27-1.21 (m, 3H), 1.13 (d, J=6.96 Hz, 3H,); [α]$^T_λ$=α/cl, [α]$^{21.9}_D$=−0.114/ (0.01771 g/1.5 mL)(0.5)=−19.31° (c=1.18, CHCl$_3$).

Preparation of (R)-(−)-dimethyl (3-methyl-2-oxo-6-phenylhexyl)phosphonate (15mc(i))

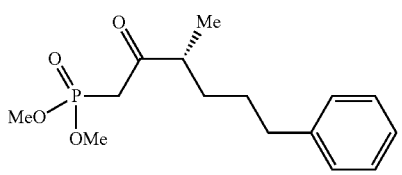 [SMILES: COP(=O)(CC(=O)[C@H](C)CCCc1ccccc1)OC]

(R)-(−)-Dimethyl (3-methyl-2-oxo-6-phenylhexyl)phosphonate was prepared from 14mc(i) (93 mg) in the same manner (S)-(+)-dimethyl (3-methyl-2-oxo-6-phenylhexyl) phosphonate was prepared from 14mb(i) as described above. The residue was purified by silica gel chromatography. Elution with ethyl acetate-heptane (70:30 v/v) afforded the title compound (83 mg, 66%) as a colorless oil; TLC R$_f$ 0.22 (solvent system: 70:30 v/v ethyl acetate-heptane); HPLC retention time 12.36 min, 5μ Chiralpak OJ-H 4.6×250 mm, at ultraviolet wavelength of 210 nm, 90:10:0.1 heptane-ethanol: acetic acid) 1 mL/min, chiral purity 100% (R); MS (ESI⁻) m/z 297.1 (M−H)⁻; $^1$H NMR (CDCl$_3$) δ 7.29 (d, J=6.51 Hz, 2H,), 7.22-7.16 (m, 3H), 3.77 (d, J=11.35 Hz, 3H), 3.78 (d, J=11.35 Hz, 3H), 3.13 (d, J=1.83 Hz, 1H), 3.08 (d, J=1.83 Hz, 1H), 2.78 (d, J=6.96 Hz, 1H), 2.67-2.56 (m, 2H), 1.61-1.52 (m, 3H), 1.45-1.32 (m, 1H), 1.11 (d, J=6.96 Hz, 3H); [α]$^T_λ$=α/cl, [α]$^{21.9}_D$=−0.0801 (0.01742 g/1.5 mL) (0.5)=−13.78° (c=1.16, CHCl$_3$).

Dimethyl (2-oxohept-5-yn-1-yl)phosphonate (15aa)

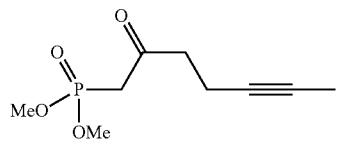

Scheme 7a, Step A: Preparation of diethyl 2-(but-2-yn-1-yl)malonate (16a)

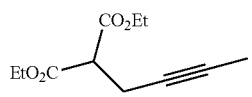

To a stirring mixture consisting of diethyl malonate (24.3 g, 141 mmol) in THF (140 mL) was added sodium hydride (60% dispersion in oil, 2.8 g, 70 mmol) and the resulting reaction mixture was stirred for 50 minutes. To the reaction mixture was added 1-bromobut-2-yne (GFS, 6.2 g, 47 mmol), and the mixture was stirred for two hours. The reaction mixture was treated carefully with 0.5 N HCl and extracted with ethyl acetate. The organic phase was washed with water, then brine, dried over magnesium sulfate, filtered, and concentrated. The residue was purified by silica gel chromatography. Elution with ethyl acetate-heptane (5:95 to 15:85 v/v) afforded the title intermediate (11.5 g, quantitative yield) as a clear oil.

Preparation of dimethyl (2-oxohept-5-yn-1-yl)phosphonate (15aa)

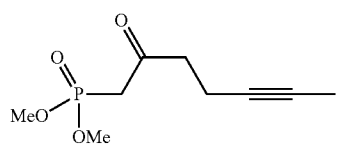

Dimethyl (2-oxohept-5-yn-1-yl)phosphonate was prepared in two steps from diethyl 2-(but-2-yn-1-yl)malonate in the same manner as that described for intermediate 15ab(i)/ 15ac(i) to afford the title phosphonate intermediate (2.5 g) as a clear oil; $^1$H-NMR (CDCl$_3$) δ 3.78 (d, 6H, J=11.5 Hz), 3.1 (d, 2H, J=22.5 Hz), 2.80 (t, 2H), 2.42-2.35 (m, 2H), 1.73 (t, 3H).

Preparation of dimethyl (2-oxooct-5-yn-1-yl)phosphonate (15ba)

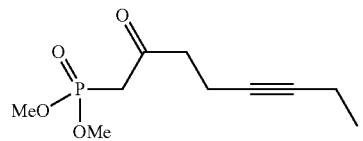

Dimethyl (2-oxooct-5-yn-1-yl)phosphonate was prepared in the same manner as that described for the preparation of intermediate 15aa except that 1-bromopent-2-yne (GFS, 6.9 g, 47 mmol) was used instead of 1-bromobut-2-yne to afford the title phosphonate intermediate (4.0 g) as a clear oil; $^1$H-NMR (CDCl$_3$) δ 3.78 (d, 6H, J=11.1 Hz), 3.11 (d, 2H, J=22.8 Hz), 2.81 (t, 2H), 2.45-2.38 (m, 2H), 2.28-2.36 (m, 2H), 1.08 (t, 3H).

Preparation of dimethyl (2-oxonon-5-yn-1-yl)phosphonate (15ca)

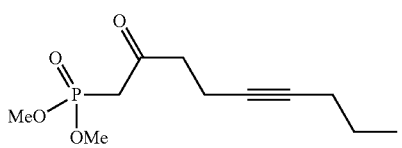 [SMILES: CCCC#CCCC(=O)CP(=O)(OC)OC]

Dimethyl (2-oxonon-5-yn-1-yl)phosphonate is prepared in the same manner as that described for the preparation of intermediate 15aa except that 1-bromohex-2-yne is used instead of 1-bromobut-2-yne.

Preparation of dimethyl (2-oxo-6-phenylhex-5-yn-1-yl)phosphonate (15da)

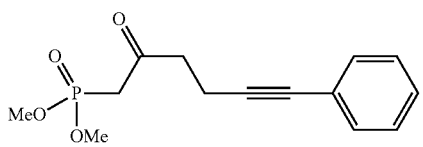 [SMILES: COP(=O)(CC(=O)CCC#Cc1ccccc1)OC]

Scheme 7a, Step A: Preparation of diethyl 2-(hex-2-yn-1-yl)malonate (16d)

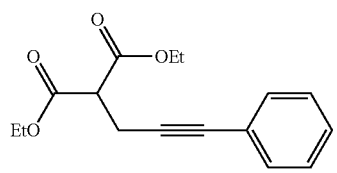 [SMILES: CCOC(=O)C(CC#Cc1ccccc1)C(=O)OCC]

To a stirring suspension consisting of sodium hydride (1.22 g, 51.3 mmol) in THF (100 mL) at 0° C. was added dropwise a solution consisting of diethyl malonate (12.3 g, 76.9 mmol) in THF (20 mL) and the reaction mixture was stirred for 30 minutes. To the 0° C. reaction mixture was added a solution consisting of (3-bromoprop-1-yn-1-yl)benzene (5.0 g, 26 mmol, prepared from the corresponding commercially available alcohol using PBr$_3$/pyridine) in THF (30 mL) and the mixture was allowed to warm to room temperature for one hour. The reaction mixture was quenched with an aqueous solution of sodium chloride (500 mL) and extracted with diethyl ether (500 mL). The organic phase was washed with brine (300 mL), dried over sodium sulfate, filtered, and concentrated to afford the title intermediate (10.6 g) which was used as is in the next step immediately below; TLC R$_f$ 0.47 (solvent system: 1:5 v/v ethyl acetate-heptane).

Preparation of dimethyl (2-oxo-6-phenylhex-5-yn-1-yl)phosphonate (15da)

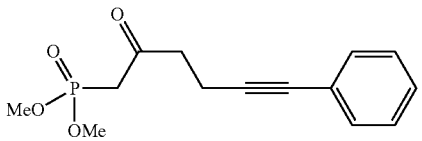 [SMILES: COP(=O)(CC(=O)CCC#Cc1ccccc1)OC]

Dimethyl (2-oxo-6-phenylhex-5-yn-1-yl)phosphonate was prepared in two steps from diethyl 2-(hex-2-yn-1-yl)malonate in the same manner as that described for the preparation of intermediate 15ab(i)/15ac(i) to afford 2.12 g; TLC R$_f$ 0.22 (solvent system: 4:1 v/v ethyl acetate-heptane); $^1$H-NMR (CDCl$_3$) δ 7.31-7.41 (m, 2H), 6.68-7.28 (m, 3H), 3.76-3.81 (m, 6H), 3.17 (s, 1H), 3.12 (s, 1H), 2.92-2.98 (m, 2H), 2.65-2.71 (m, 2H); MS (ESI$^+$) m/z 281 (M+1).

Preparation of dimethyl (2-oxo-6-phenylhexyl)phosphonate (15ma)

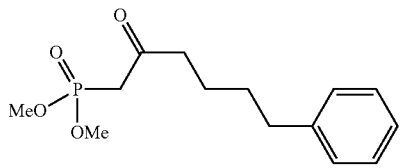 [SMILES: COP(=O)(CC(=O)CCCCc1ccccc1)OC]

Dimethyl (2-oxo-6-phenylhexyl)phosphonate was prepared in the same manner as that described for the preparation of intermediate 15ab(i)/15ac(i) except that methyl 5-phenylpentanoate (Sigma-Aldrich) was used instead of (±)-ethyl 2-methylhex-4-ynoate; $^1$H-NMR (CDCl$_3$) δ 7.29-7.23 (m, 2H), 7.19-7.13 (m, 3H), 3.76 (d, 6H, J=11.1 Hz), 3.06 (d, 2H, J=22.6 Hz), 2.55-2.7 (m, 4H), 1.55-1.7 (m, 4H).

Scheme 6: Preparation of dimethyl (3,3-dimethyl-2-oxoheptyl)phosphonate (15hd(i))

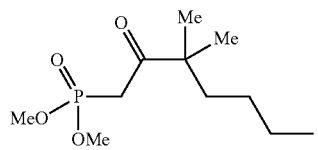

Dimethyl (3,3-dimethyl-2-oxoheptyl)phosphonate was prepared in the same manner as that described for the preparation of intermediate 15ab(i)/15ac(i) except that methyl 2,2-dimethylhexanoate (prepared by the acid (p-toluenesulfonic acid) catalyzed esterification of 2,2-dimethylhexanoic acid) was used instead of (±)-ethyl 2-methylhex-4-ynoate; MS (ESI$^+$) m/z 251 (M+1).

Scheme 6: Preparation of dimethyl (2-oxohex-3-yn-1-yl)phosphonate (15p)

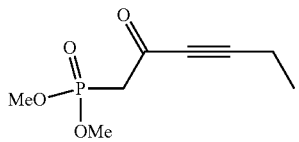

Dimethyl (2-oxohex-3-yn-1-yl)phosphonate was prepared in the same manner as that described for the preparation of intermediate 15ab(i)/15ac(i) except that ethyl pent-2-ynoate was used instead of (±)-ethyl 2-methylhex-4-ynoate; MS (ESI$^+$) m/z 205 (M+1).

Scheme 6: Preparation of dimethyl (2-oxo-4-phenylbut-3-yn-1-yl)phosphonate (15q)

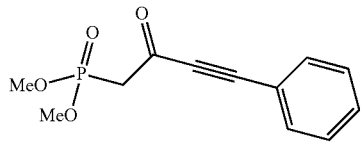 [SMILES: COP(=O)(CC(=O)C#Cc1ccccc1)OC]

Dimethyl (2-oxo-4-phenylbut-3-yn-1-yl)phosphonate was prepared in the same manner as that described for the preparation of intermediate 15ab(i)/15ac(i) except that ethyl 3-phenylpropiolate was used instead of (±)-ethyl 2-methyl-hex-4-ynoate; MS (ESI$^+$) m/z 253 (M+1).

(S)-dimethyl (2-oxo-3-phenylbutyl)phosphonate (15jb(i))

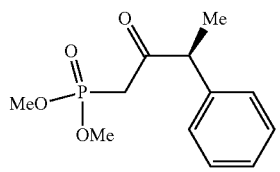 [SMILES: COP(=O)(CC(=O)[C@@H](C)c1ccccc1)OC]

Preparation of (S)-ethyl 2-phenylpropanoate (15jb(i))

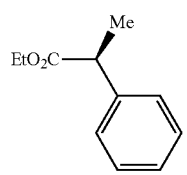 [SMILES: CCOC(=O)[C@@H](C)c1ccccc1]

To a solution consisting of (S)-2-phenylpropanoic acid (1.0 g, 6.7 mmol, from Chem-Impex) in ethanol (30 mL) was added concentrated sulfuric acid (4 drops). The reaction mixture was stirred at reflux overnight in a vessel equipped with a Dean-Stark condenser. To the mixture was added solid sodium bicarbonate and the resulting mixture was filtered and concentrated under vacuum to afford the title compound (1.0 g, 84%) as a colorless oil; TLC R$_f$ 0.5 (solvent system: 15:85:1 v/v/v ethyl acetate-heptane-acetic acid). The product was carried directly onto the next step without further purification.

Preparation of (S)-(+)-dimethyl (2-oxo-3-phenylbutyl)phosphonate (15jb(i))

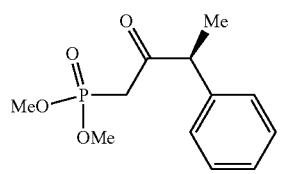 [SMILES: COP(=O)(CC(=O)[C@@H](C)c1ccccc1)OC]

To a stirring solution consisting of dimethyl methylphosphonate (1.392 g, 11.22 mmol) in THF (20 mL) at −78° C. was slowly added n-butyllithium solution (6.6 mL, 11 mmol, 1.6 M solution in hexane). The mixture was stirred for 30 minutes, after which time a mixture consisting of (S)-ethyl 2-phenylpropanoate (1.0 g, 5.6 mmol) in THF (10 mL) was slowly added, and the mixture stirred at −78° C. for two hours before being allowed to rise to room temperature overnight. The reaction mixture was treated with 5% aqueous KHSO$_4$ and extracted with ethyl acetate three times. The combined organic layer was twice washed with a solution of 50:50 water-brine, dried over sodium sulfate, and concentrated under vacuum. The residue was purified by silica gel chromatography. Elution with ethyl acetate-heptane (80:20 v/v) afforded the title compound (1.03 g, 72%) as a colorless oil; TLC R/0.4 (solvent system 80:20 v/v ethyl acetate-heptane); MS (ESI$^+$) m/z 257.1 (M+H)$^+$; $^1$H NMR (CD$_3$OD) δ 7.37-7.22 (m, 5H), 4.01 (q, J=6.71 Hz, 1H), 3.74-3.69 (m, 6H), 3.27-3.2 (m, 1H), 3.09-2.97 (m, 1H), 1.37-1.34 (m, 3H); $[\alpha]^T_\lambda = \alpha/cl$, $[\alpha]^{21.9}_D = 0.946/(0.01859\ g/1.5\ mL)(0.5) = +152.6°$ (c=1.24, CHCl$_3$).

(S)-(+)-dimethyl (3-methyl-2-oxo-4-phenylbutyl)phosphonate (15kb(i))

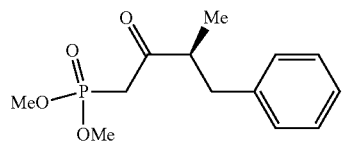 [SMILES: COP(=O)(CC(=O)[C@@H](C)Cc1ccccc1)OC]

(S)-(+)-Dimethyl (3-methyl-2-oxo-4-phenylbutyl)phosphonate was prepared in the same manner as the second alternative preparation of (S)-(+)-dimethyl (3-methyl-2-oxo-6-phenylhexyl)phosphonate (15mb(i)) using the same sequence of reactions except that benzyl bromide was used instead of (3-bromopropyl)benzene. The crude product was purified by silica gel chromatography. Elution with ethyl acetate-heptane (80:20 v/v) afforded the title compound (680 mg) as a colorless oil; TLC R$_f$ 0.35 (solvent system: 80:20 v/v ethyl acetate: heptanes; MS (ESI$^+$) m/z 271.1 (M+H)$^+$; $^1$H-NMR (CDCl$_3$) δ 7.29-7.14 (m, 5H), 3.71 (dd, 6H, J=10.99, 19.04 Hz), 3.12-2.89 (m, 4H), 2.58 (dd, 1H, J=7.69, 13.55 Hz), 1.11 (d, 3H, J=6.96 Hz); $[\alpha]^T_\lambda = \alpha/cl$, $[\alpha]^{21.9}_D = 0.249/(0.01501\ g/1.5\ mL)(0.5) = +49.8°$ (c=1, CHCl$_3$).

Preparation of (S)-(+)-dimethyl (3-methyl-2-oxo-5-phenylpentyl)phosphonate (15lb(i))

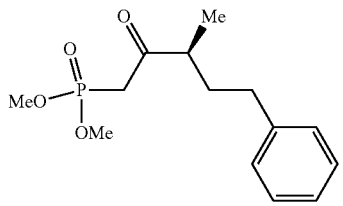 [SMILES: COP(=O)(CC(=O)[C@@H](C)CCc1ccccc1)OC]

(S)-Dimethyl (3-methyl-2-oxo-5-phenylpentyl)phosphonate was prepared in the same manner as the second alternative preparation of (S)-(+)-dimethyl (3-methyl-2-oxo-6-phenylhexyl)phosphonate (15mb(i)) using the same sequence of reactions except that (2-bromoethyl)benzene was used instead of (3-bromopropyl)benzene. The crude product was purified by silica gel chromatography. Elution with ethyl acetate-heptane (50:50 v/v) afforded the title compound (460 mg) as a colorless oil; TLC $R_f$ 0.14 (solvent system: 50:50 v/v ethyl acetate: heptanes); MS (ESI$^+$) m/z 285.1 (M+H)$^+$; $^1$H-NMR (CDCl$_3$) δ 7.30-7.24 (m, 2H), 7.21-7.14 (m, 3H), 3.76 (d, J=14.65 Hz, 3H), 3.76 (d, J=8.06 Hz, 3H), 3.16-3.03 (m, 2H), 2.77 (q, J=6.84 Hz, 1H), 2.64-2.56 (m, 2H), 2.03 (ddt, 1H), 1.16 (d, J=6.96 Hz, 3H); $[α]^T_λ$=α/cl, $[α]^{21.9}_D$=0.052/(0.01998 g/1.5 mL)(0.5)=+7.81° (c=CHCl$_3$).

Preparation of (S)-(+)-dimethyl (3-methyl-2-oxo-7-phenylheptyl)phosphonate (15nb(i))

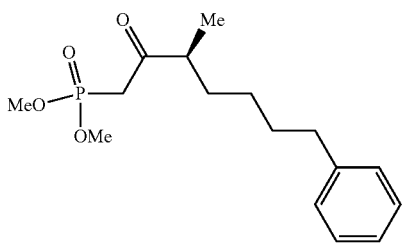 [SMILES: COP(=O)(CC(=O)[C@@H](C)CCCCc1ccccc1)OC]

(S)-Dimethyl (3-methyl-2-oxo-7-phenylheptyl)phosphonate was prepared in the same manner as the second alternative preparation of (S)-(+)-dimethyl (3-methyl-2-oxo-6-phenylhexyl)phosphonate (15mb(i)) using the same sequence of reactions except that (4-bromobutyl)benzene was used instead of (3-bromopropyl)benzene. The crude product was purified by silica gel chromatography. Elution with ethyl acetate-heptane (50:50 v/v) afforded the title compound (2.84 g) as a colorless oil; TLC $R_f$ 0.54 (solvent system: 100 v ethyl acetate); MS (ESI$^+$) m/z 313.1 (M+H)$^+$; $^1$H-NMR (CDCl$_3$) δ 7.22-7.17 (m, 2H), 7.12-7.07 (m, 3H), 3.82-3.68 (m, 6H), 3.07 (s, 1H), 3.01 (s, 1H), 2.71-2.62 (m, 1H), 2.53 (t, J=7.69 Hz, 2H), 1.66-1.47 (m, 4H), 1.28-1.22 (m, 2H), 1.02 (d, J=6.96 Hz, 3H); $[α]T_λ$=α/cl, $[α]^{21.9}_D$=0.052/(0.01998 g/1.5 mL) (0.5)=+7.81° (c=1.017, CHCl$_3$).

Preparation of (S)-(+)-dimethyl (3-methyl-2-oxo-8-phenyloctyl)phosphonate (15ob(i))

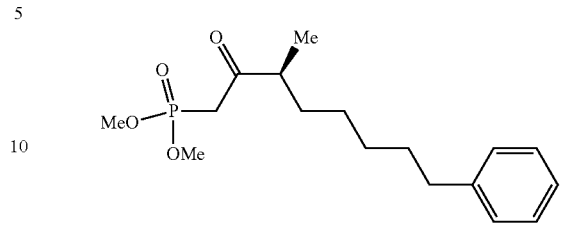

(S)-Dimethyl (3-methyl-2-oxo-8-phenyloctyl)phosphonate was prepared in the same manner as the second alternative preparation of (S)-(+)-dimethyl (3-methyl-2-oxo-6-phenylhexyl)phosphonate (15mb(i)) using the same sequence of reactions except that (5-bromopentyl)benzene was used instead of (3-bromopropyl)benzene. The crude product was purified by silica gel chromatography. Elution with ethyl acetate-heptane (50:50 v/v) afforded the title compound (1.06 g) as a colorless oil; TLC $R_f$ 0.22 (solvent system: 50:50 v/v ethyl acetate: heptanes); MS (ESI$^+$) m/z 327.1 (M+H)$^+$; $^1$H-NMR (CDCl$_3$) δ 7.27-7.24 (m, 2H), 7.19-7.14 (m, 3H), 3.79-3.76 (m, 6H), 3.13 (s, 1H), 3.08 (s, 1H), 2.76-2.68 (m, 1H), 2.61-2.56 (m, 2H), 1.68-1.56 (m, 4H), 1.35-1.28 (m, 4H), 1.09 (d, J=6.96 Hz, 3H); $[α]^T_λ$=α/cl, $[α]^{21.9}_D$=0.074/(0.01534 g/1.5 mL)(0.5)=+14.10° (c=1.02, CHCl$_3$).

Aspects of the present invention may be prepared utilizing a Horner-Emmons-Wadsworth-type procedure, according to the routes described below in Schemes 9 and 10. The coupling of an aldehyde intermediate, such as those for which their preparations are described and illustrated above (13a-f), with an organic phosphonate, such as those that are commercially available or for which their preparations are described and illustrated above (15), by way of Horner-Emmons-Wadsworth olefination reaction, (Scheme 9, Step A) provides an α,β-unsaturated ketone compound intermediate (22a-f). The C15-oxo group may be chemo- and stereoselectively reduced to the corresponding C15-hydroxyl group as stereoisomeric alcohol mixtures (two or more diastereomers, not necessarily of equal quantity) 23a-f (Scheme 9, Step B), which may be subsequently separated by HPLC (Step C) to provide a pure, single C15α-hydroxy diastereomer (24a-f) and a pure, single C15β-hydroxy (25a-f) diastereomers. The ester intermediates resulting from these transformations may be subsequently subjected to deesterification conditions, such as base-catalyzed hydrolysis. Base-catalyzed hydrolysis of the esters provides the corresponding carboxylic acid embodiments (26a-f and 27a-f). Organic □-keto phosphonates bearing a single chiral center, such as any of 15(a-o)b(i-viii) and 15(a-o)c(i-viii), when coupled with aldehydes like 13a-f in Scheme 9, Step A, followed by the stereoselective reduction (Step B), affords a set of four diastereomers which can be separated using HPLC to isolate each of its components (28a-f through 31a-f), C15α-C16β, C15α-C16α, C15β-C16β, and C15β-C16α as illustrated in Scheme 10. The carboxylic acids (32a-f through 35a-f) of each of these four diastereomers may be obtained by base-catalyzed hydrolysis of the corresponding esters using excess lithium hydroxide, potassium hydroxide or sodium hydroxide. Detailed procedures for preparing the sets of diastereomers are described below.

Scheme 9
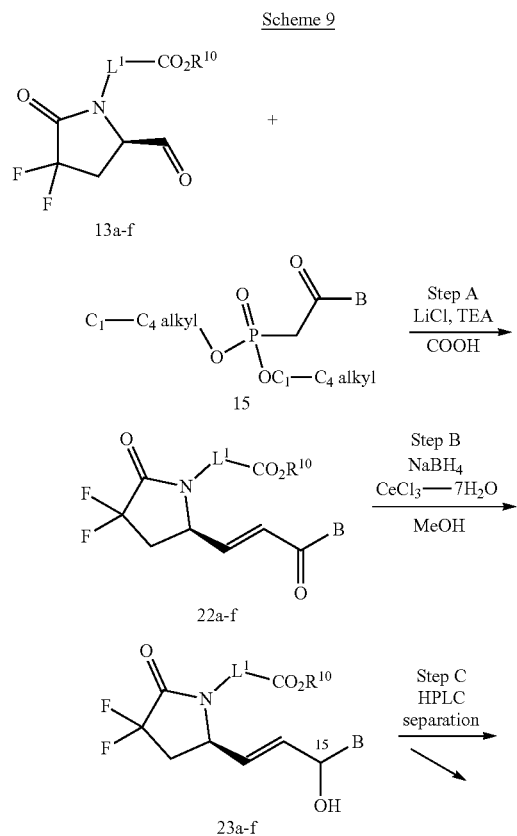
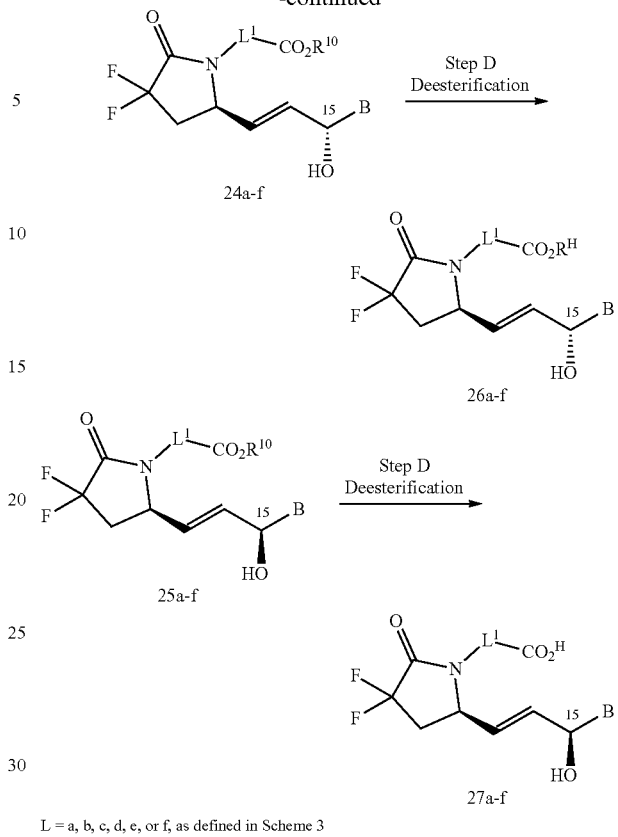
L = a, b, c, d, e, or f, as defined in Scheme 3
Scheme 10
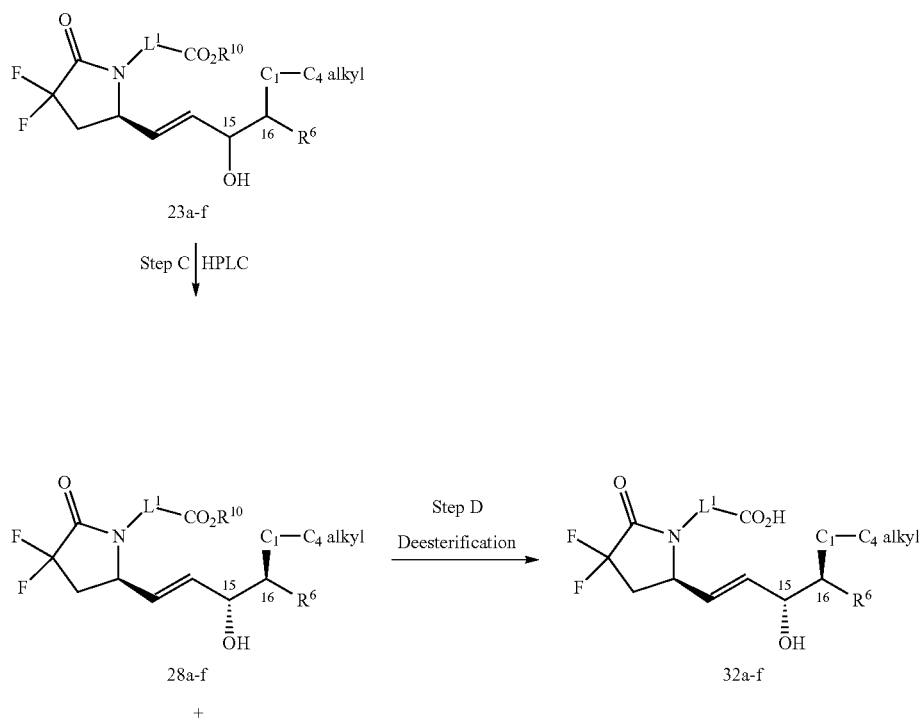

-continued

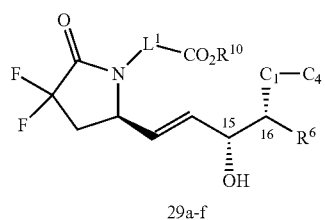
29a-f

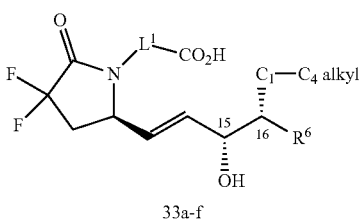
33a-f

+

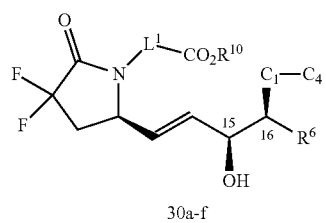
30a-f

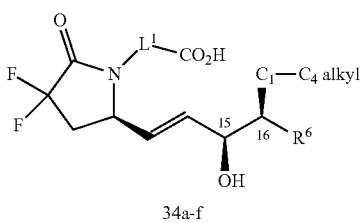
34a-f

+

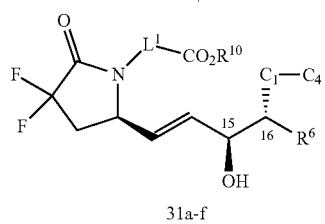
31a-f

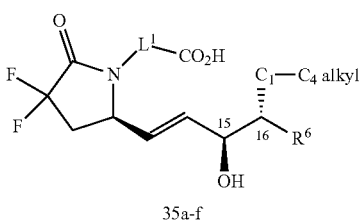
35a-f

Aspects of the present invention may include compounds of formula (I) wherein $R^1$ is a carboxylic acid or carboxylic acid derivative, including, but not limited to, esters, amides, and N-(alkylsulfonyl)amides. Carboxylic acid derivatives may be prepared from the corresponding carboxylic acids by methods known in the art. General methods utilized for carrying out these transformations are illustrated in Scheme 11.

Scheme 11

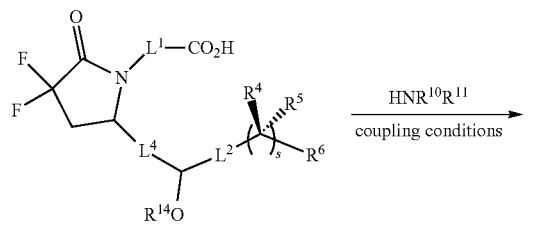

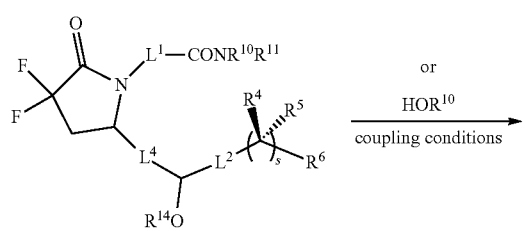

-continued

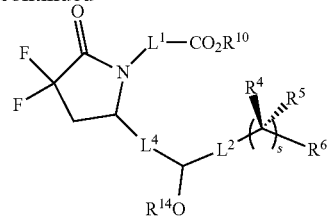

$R^{14}$ is hydrogen or an oxygen protecting group. If $R^{14}$ is an oxygen protecting group, it may be removed after the amide coupling procedure to provide exemplary embodiments Compounds of formula (I), wherein $R^1$ is an amide or N-(alkylsulfonyl)amide, may be prepared from the corresponding compound of formula (I), wherein $R^1$ is a carboxylic acid, by methods known in the art. Methods and strategies for amide bond formation have been reviewed by Montalbetti, G. N. and Falque, V. in *Tetrahedron*, 2005, 61, 10827-10852. Amides and N-(alkylsulfonyl)amides may be prepared from the corresponding carboxylic acids by proceeding through a carboxyl activation and subsequent amide bond formation by methods known in the art. Such procedures may comprise forming a mixture comprising the carboxylic acid (limiting reagent), about one molar equivalent of an amine coupling partner, $HNR^{10}R^{11}$, about one molar equivalent to about a 50% molar excess of a coupling, condensing, or activating agent such as, but not limited to, N,N-dicyclohexylcarbodiimide (DCC), N,N-diisopropylcarbodiimide (DIC), carbonyl diimidazole (CDI), or 1-ethyl-3-(3'-dimethylamino)carbodiimide hydrochloride (EDC or EDAC), benzotriazol-1-yl-oxy-tris-(dimethylamino)-phosphonium hexafluorophosphate (BOP), benzotriazol-1-yl-oxy-tris-pyrrolidino-phosphonium hexafluorophosphate (PyBOP), H-benzotriazol-1-yl)-N,N,N',N'-tetramethyluronium hexafluorophosphate (HBTU), or O-(1H-benzotriazol-1-yl)-N,N,N',N'-tetramethyluronium tetrafluoroborate (TBTU), and a solvent, such as, but not limited to, DMF, NMP, dichloromethane, THF, 1,4-dioxane, acetonitrile, or DME. The mixture may further comprise about one to two molar equivalents of an amine base such as diisopropylethylamine (DIEA), triethylamine (TEA), or pyridine. The mixtures comprising an amine base may further comprise a catalytic amount of an additive such as DMAP. The mixtures comprising DCC, DIC, or EDC may further comprise about one molar equivalent of HOBt. The mixtures may be stirred at room temperature or may be warmed to promote the coupling reaction for the time necessary to effect completion of the desired coupling reaction. Reactions may be worked up and the amide or N-(alkylsulfonyl)amide product purified and isolated by methods known in the art.

Compounds of formula (I), wherein $R^1$ is an ester, may be prepared from the corresponding compound of formula (I), wherein $R^1$ is a carboxylic acid, by methods known in the art. A variety of methods that may be used is described by Larock, R. C. in *Comprehensive Organic Transformations*, VCH Publishers, Inc., New York, 1989, pp. 966-972, and references therein.

Aspects of the present invention may include compounds of formula (I) wherein $R^1$ is tetrazol-5-yl. Compounds of formula (I), wherein $R^1$ is tetrazol-5-yl, may be prepared from the corresponding compound of formula (I), wherein $R^1$ is cyano, by using conditions and methods known in the art, two of which are illustrated in Scheme 12.

Scheme 12

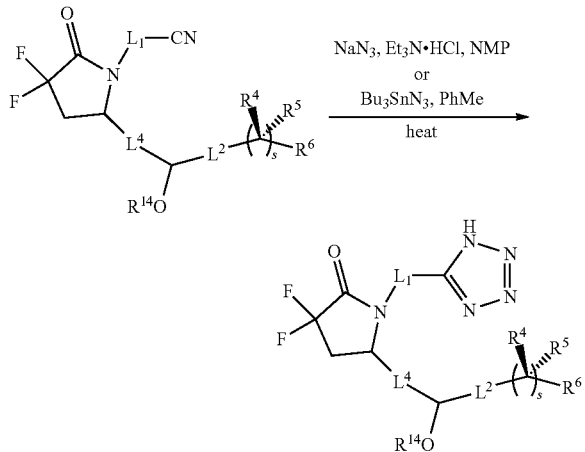

$R^{14}$ is hydrogen or an oxygen protecting group. If $R^{14}$ is an oxygen protecting group, it may be removed after the amide coupling procedure to provide exemplary embodiments.

Aspects of the present invention may include compounds of formula (I) wherein $L^4$ is an ethylene group. These compounds may be obtained by subjecting compounds of formula (I), wherein $L^4$ is ethenylene or ethynylene, to catalytic hydrogenation conditions, such as those known in the art. Catalytic hydrogenation methods have been reviewed by Rylander, P. N. in *Hydrogenation Methods*, Academic Press: New York, 1985, Chapters 2-3.

Aspects of the present invention may further include compounds of formula (I), wherein $L^4$ is —$CH_2$—$CH_2$— (ethylene), and $L^1$ comprises at least one moiety or functional group, such as an alkenyl, alkynyl, or halogen group, that may reduce under typical catalytic hydrogenation conditions. Preparation of these compounds may comprise a synthetic route wherein the lower chain is first installed onto the difluorolactam ring scaffold by, for example, an olefination or alkynylation reaction, as described herein, and the resulting 8+lower chain intermediate, wherein $L^4$ is ethenylene or ethynylene, is subsequently reduced by catalytic hydrogenation to provide the corresponding 8+lower chain intermediate wherein $L^4$ is ethylene. Subsequent installation and, if necessary, chemical modification, of the upper chain would provide the corresponding compound of formula (I) wherein $L^4$ is ethylene.

The following Examples were prepared based on the reaction Schemes 9, Steps A-D and Scheme 10, Steps C and D.

Examples 1A-1I

Step A: Preparation of methyl 7-((5R)-3,3-difluoro-5-((E)-4-methyl-3-oxooct-1-en-6-yn-1-yl)-2-oxopyrrolidin-1-yl)heptanoate

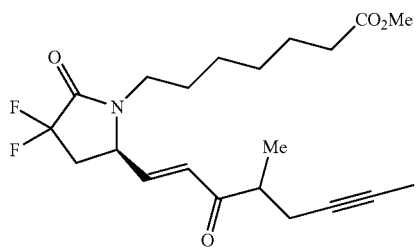 [SMILES: CC#CCC(C)C(=O)/C=C/[C@H]1CC(F)(F)C(=O)N1CCCCCCC(=O)OC]

To an ice cooled mixture consisting of dimethyl (3-methyl-2-oxohept-5-yn-1-yl)phosphonate (76 mg, 0.33 mmol) and (R)-methyl 7-(3,3-difluoro-5-formyl-2-oxopyrrolidin-1-yl) heptanoate (13a, 80 mg, 0.28 mmol) in THF (3 mL) was added lithium chloride (35 mg, 0.83 mmol) followed by triethylamine (55 μL, 0.42 mmol) and the reaction stirred overnight, warming to room temperature. The reaction was quenched with the addition of a saturated solution of aqueous ammonium chloride and extracted with ethyl acetate. The combined organic phase was dried over sodium sulfate and concentrated to a golden oil. The residue was purified by silica gel chromatography. Elution with methanol:dichloromethane (1:300 v/v) to afford the title compound (76.6 mg) as a clear oil; TLC $R_f$ 0.80 (solvent system: 5:95 v/v methanol-dichloromethane); $^1$H-NMR (CDCl$_3$) δ 6.7-6.5 (m, 1H), 6.4 (d, 1H), 4.3-4.2 (m, 2H), 3.0-2.8 (m, 1H), 2.8-2.6 (m, 1H) 2.5-2.2 (m, 6H), 1.8 (s, 3H), 1.7-1.4 (m, 4H), 1.4-1.2 (m, 4H), 1.2 (d, 3H); MS (ESI$^+$) m/z 398.1 (M+1), 420.1 (M+Na), (ESI$^-$) m/z 396.1 (M−1).

Step B: Preparation of four-diastereomer mixture methyl 7-((5R)-3,3-difluoro-5-((E)-3-hydroxy-4-methyloct-1-en-6-yn-1-yl)-2-oxopyrrolidin-1-yl)heptanoate

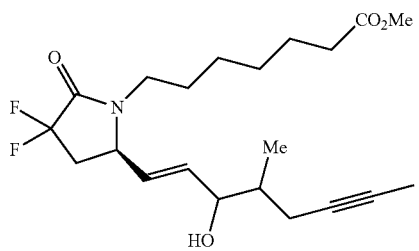 [SMILES: CC#CCC(C)C(O)/C=C/[C@H]1CC(F)(F)C(=O)N1CCCCCCC(=O)OC]

To a −40° C. solution consisting of methyl 7-((5R)-3,3-difluoro-5-((E)-4-methyl-3-oxooct-1-en-6-yn-1-yl)-2-oxopyrrolidin-1-yl)heptanoate (76 mg, 0.20 mmol) in methanol (5 mL) was added cerium chloride heptahydrate (75 mg, 0.20 mmol) in one portion. The reaction mixture was stirred for 15 minutes, and cooled to −78° C. for 20 minutes. Sodium borohydride (15 mg, 0.40 mmol) was added and the reaction was stirred for 3 hours, quenched with equal parts water and saturated ammonium chloride and warmed to room temperature. The reaction mixture was extracted with ethyl acetate. The combined organic phase was dried over sodium sulfate and concentrated to a cloudy white oil. The residue was purified by silica gel chromatography. Elution with methanol-dichloromethane (1:200 v:v) to afford the title compound (70 mg) as a clear oil. $R_f$ 0.50 (solvent system: 5:95 v/v methanol:dichloromethane).

Step C: Preparation of methyl 7-((R)-3,3-difluoro-5-((3S,4S,E)-3-hydroxy-4-methyloct-1-en-6-yn-1-yl)-2-oxopyrrolidin-1-yl)heptanoate (Example 1A), methyl 7-((R)-3,3-difluoro-5-((3S,4R,E)-3-hydroxy-4-methyloct-1-en-6-yn-1-yl)-2-oxopyrrolidin-1-yl)heptanoate (Example 1B), methyl 7-((R)-3,3-difluoro-5-((3R,4S,E)-3-hydroxy-4-methyloct-1-en-6-yn-1-yl)-2-oxopyrrolidin-1-yl)heptanoate (Example 1D) and methyl 7-((R)-3,3-difluoro-5-((3R,4R,E)-3-hydroxy-4-methyloct-1-en-6-yn-1-yl)-2-oxopyrrolidin-1-yl)heptanoate (Example 1E)

From the stereoisomeric mixture comprising the four-diastereomer mixture methyl 7-((5R)-3,3-difluoro-5-((E)-3-hydroxy-4-methyloct-1-en-6-yn-1-yl)-2-oxopyrrolidin-1-yl)heptanoate (70 mg, prepared in Step B of this Example above) were separated the single isomers methyl 7-((R)-3,3-difluoro-5-((3S,4S,E)-3-hydroxy-4-methyloct-1-en-6-yn-1-yl)-2-oxopyrrolidin-1-yl)heptanoate (Example 1A) and methyl 7-((R)-3,3-difluoro-5-((3S,4R,E)-3-hydroxy-4-methyloct-1-en-6-yn-1-yl)-2-oxopyrrolidin-1-yl)heptanoate (Example 1B), and the diastereomeric mixture (at C16) methyl 7-((5R)-3,3-difluoro-5-((3R,E)-3-hydroxy-4-methyloct-1-en-6-yn-1-yl)-2-oxopyrrolidin-1-yl)heptanoate (Example 10) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (96:4 v/v).

Example 1A (7.6 mg); a clear oil; prep HPLC retention time 24.1-25.0 minutes; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Example 1B (5.8 mg); a clear oil; prep HPLC retention time 22.5-23.6 minutes; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Example 1A

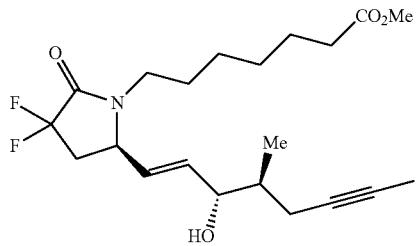

Example 1B

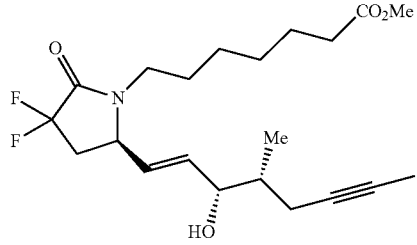

Example 1C

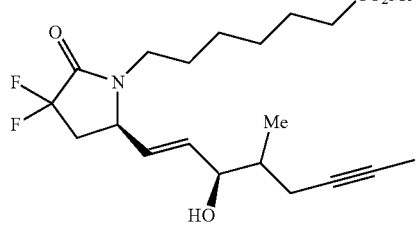

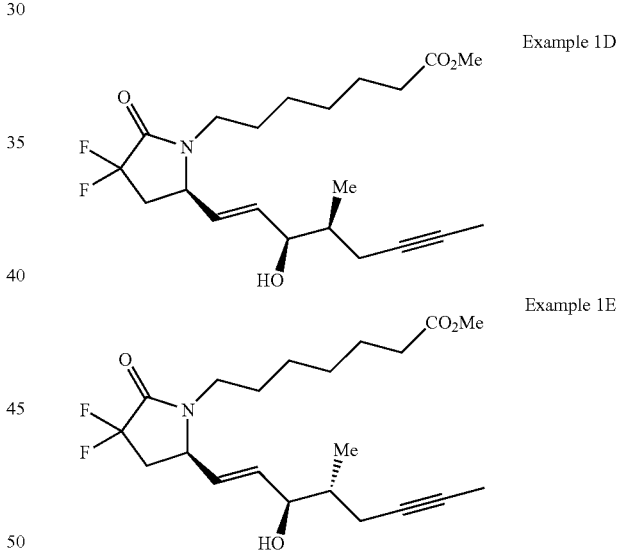

The diastereomeric mixture methyl 7-((5R)-3,3-difluoro-5-((3R,E)-3-hydroxy-4-methyloct-1-en-6-yn-1-yl)-2-oxopyrrolidin-1-yl)heptanoate (Example 1C) was separated to afford the pure diastereomers methyl 7-((R)-3,3-difluoro-5-((3R,4S,E)-3-hydroxy-4-methyloct-1-en-6-yn-1-yl)-2-oxopyrrolidin-1-yl)heptanoate (Example 1D), and methyl 7-((R)-3,3-difluoro-5-((3R,4R,E)-3-hydroxy-4-methyloct-1-en-6-yn-1-yl)-2-oxopyrrolidin-1-yl)heptanoate (Example 1E), by prep HPLC.

Agilent Semi-Prep instrument; ultraviolet detector at 205 nm; Luna Silica 5μ 250×10 mm column; mobile phase of heptanes-ethanol (98:2 v/v).

Example 1D (15.5 mg); a clear oil; HPLC retention time 48.4-55.7 min; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9

(m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI+) m/z 400.2 (M+1), 422.1 (M+Na).

Example 1E (4.3 mg); a clear oil; HPLC retention time 42.7-47.3 min; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI+) m/z 400.2 (M+1), 422.1 (M+Na).

Step D1: Preparation of 7-((R)-3,3-difluoro-5-((3S, 4S,E)-3-hydroxy-4-methyloct-1-en-6-yn-1-yl)-2-oxopyrrolidin-1-yl)heptanoic Acid (Example 1F)

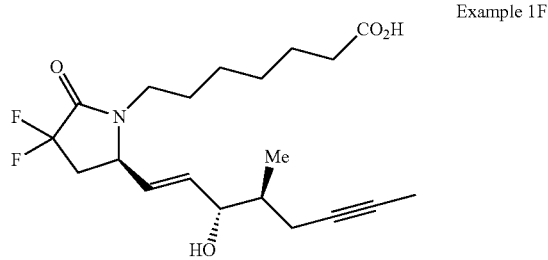 [SMILES: CC#CC[C@H](C)[C@H](O)/C=C/[C@H]1CC(F)(F)C(=O)N1CCCCCCC(=O)O]

Example 1F

To a solution of methyl 7-((R)-3,3-difluoro-5-((3S,4S,E)-3-hydroxy-4-methylnon-1-en-6-yn-1-yl)-2-oxopyrrolidin-1-yl)heptanoate (Example 1A, 5.6 mg, 0.014 mmol) in methanol (0.15 mL) was added lithium hydroxide (1M in H$_2$O, 0.06 mL, 0.06 mmol) and the reaction mixture was stirred overnight. The reaction was quenched with the addition of KHSO$_4$ and brine and the organic material was extracted with ethyl acetate. The organic phase was concentrated, redissolved in ethyl acetate, filtered, and concentrated to give 5.7 mg of a clear oil; TLC R$_f$ 0.45 (solvent system: 90:10:1 v/v dichloromethane-methanol-acetic acid); $^1$H-NMR (CDCl$_3$) δ 6.9-6.8 (m, 1H), 6.6-6.5 (m, 1H), 4.4-4.3 (m, 1H), 4.2-4.1 (m, 1H), 3.6-3.5 (m, 1H) 3.1-2.9 (m, 1H), 2.8-2.6 (br, 1H) 2.4-2.0 (m, 7H), 1.9-1.7 (s, 3H), 1.7-1.4 (m, 4H), 1.4-1.1 (m, 4H), 1.0-0.9 (d, 3H); MS (ESI+) m/z 368.1 (M+1), 408.1 (M+Na).

Step D2: Preparation of 7-((R)-3,3-difluoro-5-((3S, 4R,E)-3-hydroxy-4-methyloct-1-en-6-yn-1-yl)-2-oxopyrrolidin-1-yl)heptanoic Acid (Example 1G)

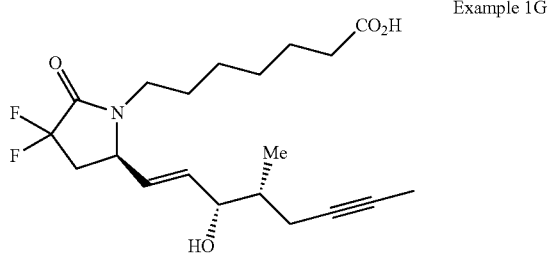 [SMILES: CC#CC[C@@H](C)[C@H](O)/C=C/[C@H]1CC(F)(F)C(=O)N1CCCCCCC(=O)O]

Example 1G

Hydrolysis of methyl 7-((R)-3,3-difluoro-5-((3S,4R,E)-3-hydroxy-4-methyloct-1-en-6-yn-1-yl)-2-oxopyrrolidin-1-yl)heptanoate, done in the same manner as Step D1 above, afforded 5.4 mg of a clear oil; TLC R$_f$ 0.45 (solvent system: 90:10:1 v/v dichloromethane-methanol-acetic acid); $^1$H-NMR (CDCl$_3$) δ 6.9-6.8 (m, 1H), 6.6-6.5 (m, 1H), 4.4-4.3 (m, 1H), 4.2-4.1 (m, 1H), 3.6-3.5 (m, 1H) 3.1-2.9 (m, 1H), 2.8-2.6 (br, 1H) 2.4-2.0 (m, 7H), 1.9-1.7 (s, 3H), 1.7-1.4 (m, 4H), 1.4-1.1 (m, 4H), 1.0-0.9 (d, 3H); MS (ESI+) m/z 368.1 (M+1), 408.1 (M+Na).

Step D3: Preparation of 7-((R)-3,3-difluoro-5-((3R, 4S,E)-3-hydroxy-4-methyloct-1-en-6-yn-1-yl)-2-oxopyrrolidin-1-yl)heptanoic Acid (Example 1H)

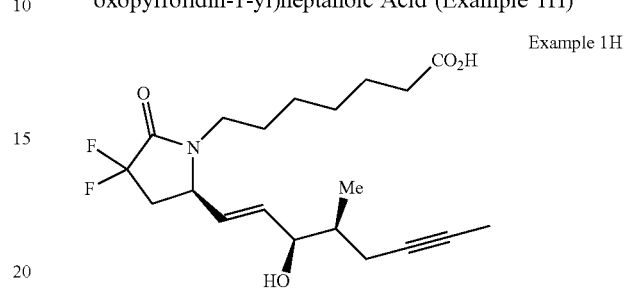

Example 1H

Step D4: Preparation of 7-((R)-3,3-difluoro-5-((3R, 4R,E)-3-hydroxy-4-methyloct-1-en-6-yn-1-yl)-2-oxopyrrolidin-1-yl)heptanoic Acid (Example 1I)

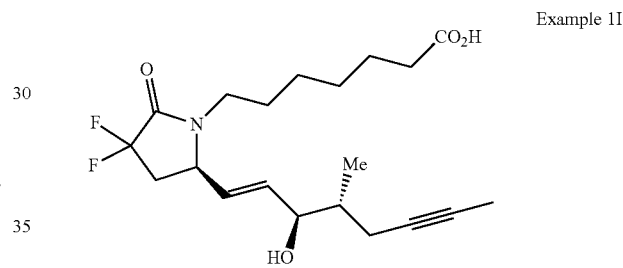

Example 1I

The hydrolysis of each of the following carboxylic ester Examples were performed in the same manner as described in Example 1, Step D1, using aqueous lithium hydroxide (though in some cases sodium hydroxide or potassium hydroxide can and was used instead of lithium hydroxide) to afford the analogous carboxylic acid Examples.

Examples 2A-2D

Step A, B and C, Preparation of methyl 7-((R)-3,3-difluoro-5-((3S,4S,E)-3-hydroxy-4-methylnon-1-en-6-yn-1-yl)-2-oxopyrrolidin-1-yl)heptanoate (Example 2A) and methyl 7-((R)-3,3-difluoro-5-((3R,4S,E)-3-hydroxy-4-methylnon-1-en-6-yn-1-yl)-2-oxopyrrolidin-1-yl)heptanoate (Example 2B)

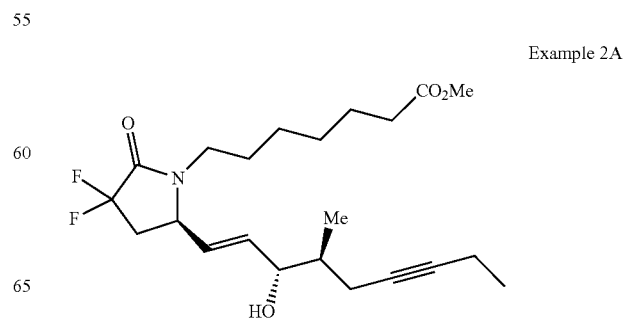

Example 2A

Example 2B

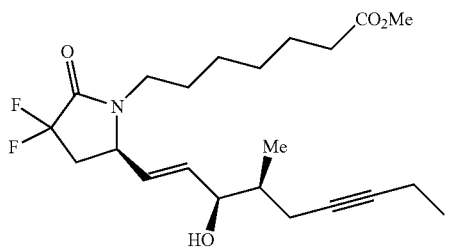

Methyl 7-((5R)-3,3-difluoro-5-((4S,E)-3-hydroxy-4-methylnon-1-en-6-yn-1-yl)-2-oxopyrrolidin-1-yl)heptanoate (61 mg) was prepared by the method described in Example 1, Steps A and B, except that (S)-(+)-dimethyl (3-methyl-2-oxooct-5-yn-1-yl)phosphonate (15bc(i)) was used instead of (±)-dimethyl (3-methyl-2-oxohept-5-yn-1-yl)phosphonate (15ab(i)/15ac(i)) in Step A.

Step C: The pure diastereomers of Example 2A and Example 2B were isolated following separation by prep HPLC.

Agilent Semi-Prep instrument; ultraviolet detector at 233 nm; Chiralpak IA 250×4.6 mm column; mobile phase of heptane-ethanol (98:2 v/v).

Example 2A (8.1 mg); a clear oil; HPLC retention time 57 min; MS (ESI$^+$) m/z 414.1 (M+1) (ESI$^-$) m/z 412.1 (M−1).

Example 2B (20.5 mg); a clear oil; HPLC retention time 42 min; MS (ESI$^+$) m/z 414.1 (M+1) (ESI$^-$) m/z 412.1 (M−1).

Step B: Alternative Preparation of methyl 7-((R)-3,3-difluoro-5-((3S,4S,E)-3-hydroxy-4-methylnon-1-en-6-yn-1-yl)-2-oxopyrrolidin-1-yl)heptanoate (Example 2A) and methyl 7-((R)-3,3-difluoro-5-((3S,4R,E)-3-hydroxy-4-methylnon-1-en-6-yn-1-yl)-2-oxopyrrolidin-1-yl)heptanoate (Example 2B)

To a solution consisting of methyl 7-((R)-3,3-difluoro-5-((S,E)-4-methyl-3-oxonon-1-en-6-yn-1-yl)-2-oxopyrrolidin-1-yl)heptanoate (169 mg, 0.460 mmol) and (R)-Corey-Bakshi-Shibata catalyst (1 M in THF, 0.46 mmol) in dichloromethane (100 mL) at −40° C. was added catechol borane (1 M in THF, 0.46 mmol) dropwise over 10 minutes. The reaction mixture was stirred overnight, warming to room temperature, then quenched with 1 N HCl (10 mL). The reaction mixture was extracted with ethyl acetate. The combined organic phase was dried over sodium sulfate and concentrated to a cloudy brown oil. The residue was purified by silica gel chromatography. Elution with methanol:dichloromethane (1:200 v:v) afforded a mixture of 2A and 2B (52 mg) as a clear oil; R$_f$ 0.65 (solvent system: 7:93 v/v methanol:dichloromethane).

The diastereomers were separated and purified diastereomer 2A (15.2 mg) was isolated using the prep HPLC method described in Step C of the original preparation of this compound above.

Step D1: Preparation of 74(R)-3,3-difluoro-5-((3S,4S,E)-3-hydroxy-4-methylnon-1-en-6-yn-1-yl)-2-oxopyrrolidin-1-yl)heptanoic Acid (Example 2C)

Example 2C

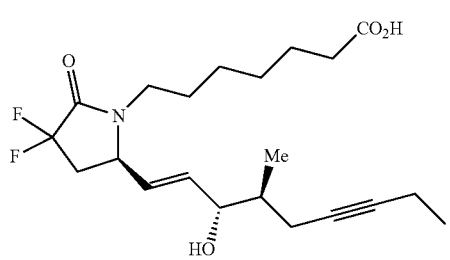

5.9 mg of a clear oil; TLC R$_f$ 0.45 (solvent system: 95:5:1 v/v dichloromethane-methanol-acetic acid); $^1$H-NMR (CDCl$_3$) δ 5.9-5.8 (m, 1H), 5.6-5.5 (m, 1H), 4.2-4.1 (m, 2H), 3.7-3.5 (m, 1H), 3.1-2.9 (m, 1H), 2.8-2.7 (br s, 1H), 2.4-2.3 (t, 2H). 2.3-2.1 (m, 5H), 1.9-1.8 (m, 1H), 1.7-1.5 (m, 5H), 1.4-1.2 (m, 4H), 1.1 (t, 3H), 1.0 (d, 3H); $^{19}$F-NMR (CDCl$_3$) δ−103.5 (d, 1F), −105.5 (d, 1F); MS (ESI$^+$) m/z 400 (M+1), MS (ESI$^-$) m/z 398 (M−1).

Step D2: Preparation of 7-((R)-3,3-difluoro-5-((3R,4S,E)-3-hydroxy-4-methylnon-1-en-6-yn-1-yl)-2-oxopyrrolidin-1-yl)heptanoic Acid (Example 2D)

Example 2D

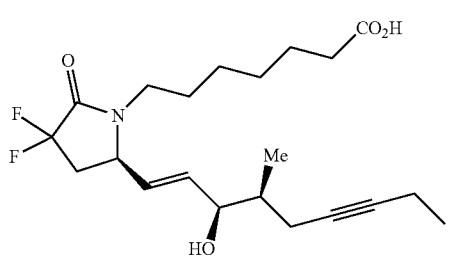

14.8 mg of a clear oil; TLC R$_f$ 0.45 (solvent system: 95:5:1 v/v dichloromethane-methanol-acetic acid); MS (ESI$^+$) m/z 400 (M+1), MS (ESI$^-$) m/z 398 (M−1).

Example 3

Methyl 7-((5R)-3,3-difluoro-5-((E)-3-hydroxy-4-methyldec-1-en-6-yn-1-yl)-2-oxopyrrolidin-1-yl)heptanoate

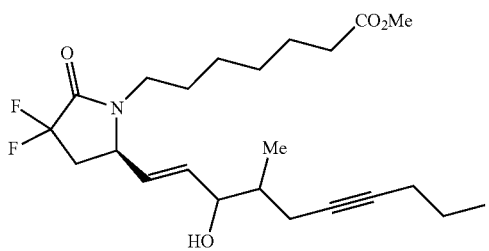 [SMILES: CCCC#CCC(C)C(O)/C=C/[C@H]1CC(F)(F)C(=O)N1CCCCCCC(=O)OC]

Example 4

Methyl 7-((5R)-3,3-difluoro-5-((E)-3-hydroxy-4-methyl-7-phenylhept-1-en-6-yn-1-yl)-2-oxopyrrolidin-1-yl)heptanoate

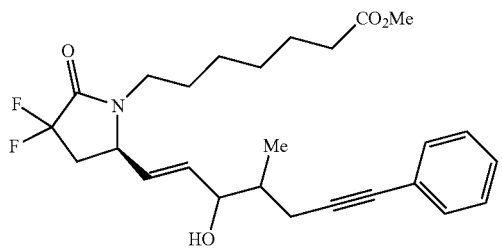 [SMILES: COC(=O)CCCCCCN1C(=O)C(F)(F)C[C@@H]1/C=C/C(O)C(C)CC#Cc1ccccc1]

Example 5

Methyl 7-((5R)-3,3-difluoro-5-((E)-3-hydroxy-4-methyloct-1-en-1-yl)-2-oxopyrrolidin-1-yl)heptanoate

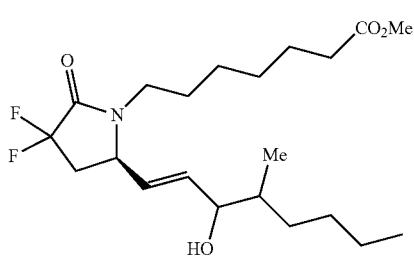 [SMILES: CCCCC(C)C(O)/C=C/[C@H]1CC(F)(F)C(=O)N1CCCCCCC(=O)OC]

Examples 6A-6F

Steps A, B, and C: Preparation of methyl 7-((R)-3,3-difluoro-5-((3S,4S,E)-3-hydroxy-4-methyl-7-phenylhept-1-en-1-yl)-2-oxopyrrolidin-1-yl)heptanoate (Example 6A), methyl 7-((R)-3,3-difluoro-5-((3S,4R,E)-3-hydroxy-4-methyl-7-phenylhept-1-en-1-yl)-2-oxopyrrolidin-1-yl)heptanoate (Example 6B), and methyl 7-((5R)-3,3-difluoro-5-((3R,E)-3-hydroxy-4-methyl-7-phenylhept-1-en-1-yl)-2-oxopyrrolidin-1-yl)heptanoate (Example 6C)

Example 6A

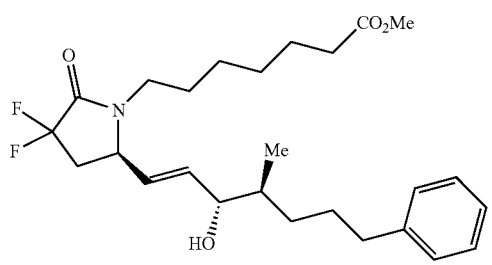

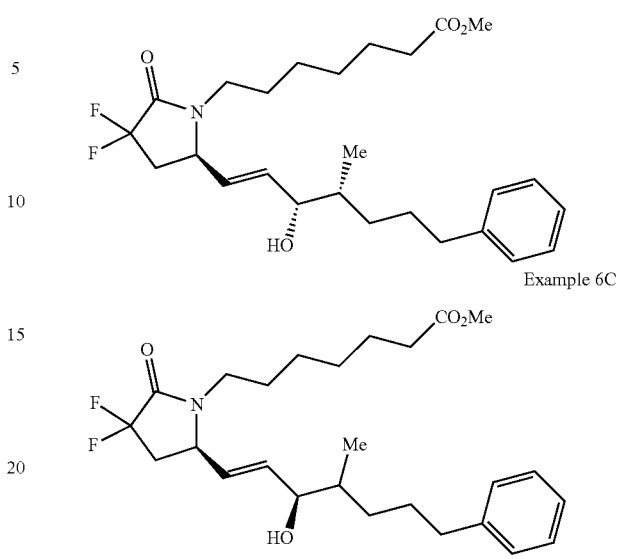

Methyl 7-((5R)-3,3-difluoro-5-((E)-3-hydroxy-4-methyl-7-phenylhept-1-en-1-yl)-2-oxopyrrolidin-1-yl)heptanoate was prepared by the method described in Example 1, Steps A and B, except that (±)-dimethyl (3-methyl-2-oxo-6-phenylhexyl)phosphonate (15mb(i)/15mc(i)) was used instead of (±)-dimethyl (3-methyl-2-oxohept-5-yn-1-yl)phosphonate (15ab(i)/15ac(i)) in Step A.

Step C: From the stereoisomeric mixture comprising the four-diastereomer mixture methyl 7-((5R)-3,3-difluoro-5-((E)-3-hydroxy-4-methyl-7-phenylhept-1-en-1-yl)-2-oxopyrrolidin-1-yl)heptanoate were separated the single isomers methyl 7-((R)-3,3-difluoro-5-((3S,4S,E)-3-hydroxy-4-methyl-7-phenylhept-1-en-1-yl)-2-oxopyrrolidin-1-yl)heptanoate (Example 6A) and methyl 7-((R)-3,3-difluoro-5-((3S,4R,E)-3-hydroxy-4-methyl-7-phenylhept-1-en-1-yl)-2-oxopyrrolidin-1-yl)heptanoate (Example 6B), and the diastereomeric mixture (at $C_{16}$) methyl 7-((5R)-3,3-difluoro-5-((3R,E)-3-hydroxy-4-methyl-7-phenylhept-1-en-1-yl)-2-oxopyrrolidin-1-yl)heptanoate (Example 6C) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (96:4 v/v).

Example 6A (3.3 mg); a clear oil; prep HPLC retention time 20.9-21.8 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI$^+$) m/z 466.4 (M+1), 488.5 (M+Na).

Example 6B (10.1 mg); a clear oil; prep HPLC retention time 19.6-20.7 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI$^+$) m/z 466.4 (M+1), 488.5 (M+Na).

Example 6C (57.7 mg); a clear oil; prep HPLC retention time 16.2-18.6 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI⁺) m/z 466.4 (M+1), 488.5 (M+Na).

Step D1: Preparation of 7-((R)-3,3-difluoro-5-((3S, 4S,E)-3-hydroxy-4-methyl-7-phenylhept-1-en-1-yl)-2-oxopyrrolidin-1-yl)heptanoic Acid (Example 6D)

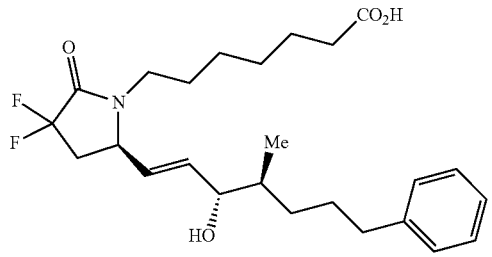 [SMILES: C[C@@H](CCCc1ccccc1)[C@H](O)/C=C/[C@H]1CC(F)(F)C(=O)N1CCCCCCC(=O)O]

3.0 mg of a clear oil; TLC R$_f$ 0.45 (solvent system: 90:10:1 v/v dichloromethane-methanol-acetic acid); ¹H-NMR (CDCl₃) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI⁺) m/z 466.2 (M+1), 488.2 (M+Na).

Step D2: Preparation of 7-((R)-3,3-difluoro-5-((3S, 4R,E)-3-hydroxy-4-methyl-7-phenylhept-1-en-1-yl)-2-oxopyrrolidin-1-yl)heptanoic Acid (Example 6E)

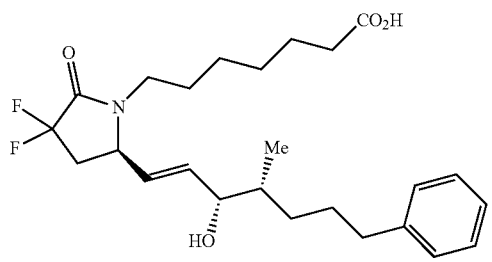 [SMILES: C[C@H](CCCc1ccccc1)[C@H](O)/C=C/[C@H]1CC(F)(F)C(=O)N1CCCCCCC(=O)O]

7.7 mg of a clear oil; TLC R$_f$ 0.45 (solvent system: 90:10:1 v/v dichloromethane-methanol-acetic acid); ¹H-NMR (CDCl₃) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI⁺) m/z 466.2 (M+1), 488.2 (M+Na).

Step D3: Preparation of 7-((5R)-3,3-difluoro-5-((3R,E)-3-hydroxy-4-methyl-7-phenylhept-1-en-1-yl)-2-oxopyrrolidin-1-yl)heptanoic Acid (Example 6F)

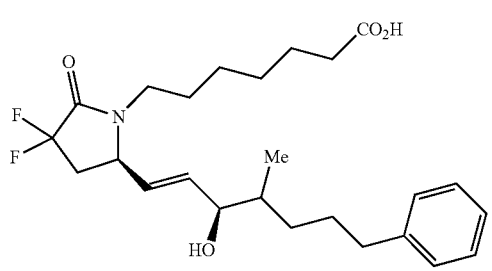 [SMILES: CC(CCCc1ccccc1)[C@@H](O)/C=C/[C@H]1CC(F)(F)C(=O)N1CCCCCCC(=O)O]

8.9 mg of a clear oil; TLC R$_f$ 0.45 (solvent system: 90:10:1 v/v dichloromethane-methanol-acetic acid); ¹H-NMR (CDCl₃) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI⁺) m/z 466.2 (M+1), 488.2 (M+Na).

Example 7

Methyl 7-((5R)-3,3-difluoro-5-((E)-3-hydroxynon-1-en-6-yn-1-yl)-2-oxopyrrolidin-1-yl)heptanoate

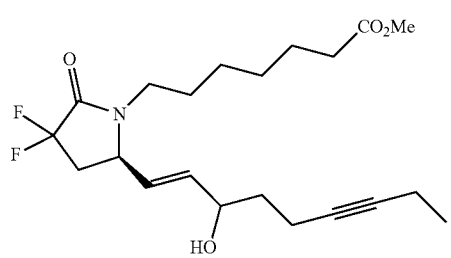 [SMILES: CCC#CCCC(O)/C=C/[C@H]1CC(F)(F)C(=O)N1CCCCCCC(=O)OC]

Example 8

Methyl 7-((5R)-3,3-difluoro-5-((E)-3-hydroxy-7-phenylhept-1-en-6-yn-1-yl)-2-oxopyrrolidin-1-yl)heptanoate

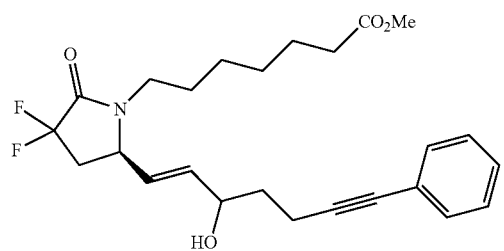 [SMILES: COC(=O)CCCCCCN1C(=O)C(F)(F)C[C@@H]1/C=C/C(O)CCC#Cc1ccccc1]

Examples 9A-9D

Steps A, B, and C: Preparation of methyl 7-((R)-3,3-difluoro-5-((S,E)-3-hydroxyoct-1-en-1-yl)-2-oxopyrrolidin-1-yl)heptanoate (Example 9A) and methyl 7-((R)-3,3-difluoro-5-((R,E)-3-hydroxyoct-1-en-1-yl)-2-oxopyrrolidin-1-yl)heptanoate (Example 9B)

EXample 9A

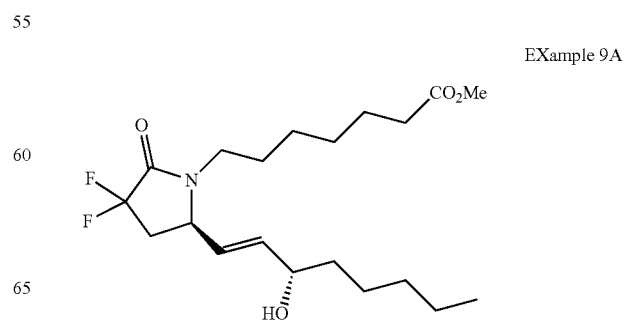

Example 9B

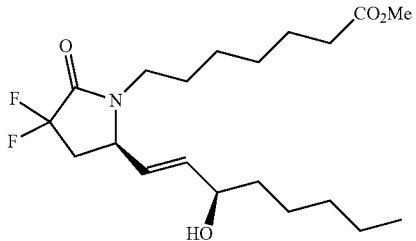

Methyl 7-((5R)-3,3-difluoro-5-((E)-3-hydroxyoct-1-en-1-yl)-2-oxopyrrolidin-1-yl)heptanoate was prepared by the method described in Examples 1, Steps A and B, except that dimethyl (2-oxoheptyl)phosphonate (15ga) was used instead of (±)-dimethyl (3-methyl-2-oxohept-5-yn-1-yl)phosphonate (15ab(i)/15ac(i)) in Step A.

Step C: From the diastereomeric mixture methyl 7-((5R)-3,3-difluoro-5-((E)-3-hydroxyoct-1-en-1-yl)-2-oxopyrrolidin-1-yl)heptanoate were separated the single isomers methyl 7-((R)-3,3-difluoro-5-((S,E)-3-hydroxyoct-1-en-1-yl)-2-oxopyrrolidin-1-yl)heptanoate (Example 9A) and methyl 7-((R)-3,3-difluoro-5-((R,E)-3-hydroxyoct-1-en-1-yl)-2-oxopyrrolidin-1-yl)heptanoate (Example 9B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (93:7 v/v).

Example 9A (21.6 mg); a clear oil; prep HPLC retention time 12.1-12.9 minutes; $^1$H-NMR (CDCl$_3$) δ 6.9-6.8 (m, 1H), 6.6-6.4 (m, 1H), 4.3-4.1 (m, 2H), 3.7 (s, 3H), 3.6-3.5 (m, 1H), 3.1-2.9 (m, 1H), 2.8-2.6 (m, 1H), 2.4-2.1 (m, 4H), 2.0-1.7 (br, 1H) 1.7-1.4 (m, 6H), 1.4-1.2 (m, 10H), 0.9 (t, 3H); MS (ESI$^+$) m/z 390.2 (M+1).

Example 9B (46.5 mg); a clear oil; prep HPLC retention time 10.6-11.5 minutes; 1H-NMR (CDCl$_3$) δ 6.9-6.8 (m, 1H), 6.6-6.4 (m, 1H), 4.3-4.1 (m, 2H), 3.7 (s, 3H), 3.6-3.5 (m, 1H), 3.1-2.9 (m, 1H), 2.8-2.6 (m, 1H), 2.4-2.1 (m, 4H), 2.0-1.7 (br, 1H) 1.7-1.4 (m, 6H), 1.4-1.2 (m, 10H), 0.9 (t, 3H); MS (ESI$^+$) m/z 390.2 (M+1).

Step D1: Preparation of 7-((R)-3,3-difluoro-5-((S,E)-3-hydroxyoct-1-en-1-yl)-2-oxopyrrolidin-1-yl)heptanoic Acid (Example 9C)

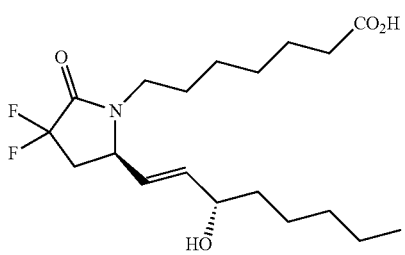 [SMILES: CCCCC[C@H](O)/C=C/[C@H]1CC(F)(F)C(=O)N1CCCCCCC(=O)O]

14.5 mg of a clear oil; TLC R$_f$ 0.40 (solvent system: 90:10:1 v/v dichloromethane-methanol-acetic acid); $^1$H-NMR (CDCl$_3$) δ 6.9-6.8 (m, 1H), 6.5-6.4 (m, 1H), 4.2-4.0 (m, 2H), 3.6-3.5 (m, 1H), 3.1-3.0 (m, 1H), 2.8-2.6 (m, 1H), 2.4-2.0 (m, 4H), 1.7-1.5 (m, 6H), 1.5-1.0 (m, 10H), 0.9 (t, 3H); MS (ESI$^+$) m/z 376.2 (M+1), 398.1 (M+Na).

Step D2: Preparation of 7-((R)-3,3-difluoro-5-((R,E)-3-hydroxyoct-1-en-1-yl)-2-oxopyrrolidin-1-yl)heptanoic Acid (Example 9D)

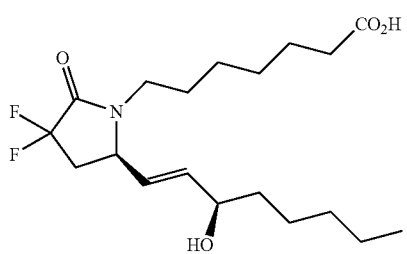 [SMILES: CCCCC[C@@H](O)/C=C/[C@H]1CC(F)(F)C(=O)N1CCCCCCC(=O)O]

14.0 mg of a clear oil; TLC R$_f$ 0.40 (solvent system: 90:10:1 v/v dichloromethane-methanol-acetic acid);); $^1$HNMR (CDCl$_3$) δ 6.9-6.8 (m, 1H), 6.5-6.4 (m, 1H), 4.2-4.0 (m, 2H), 3.6-3.5 (m, 1H), 3.1-3.0 (m, 1H), 2.8-2.6 (m, 1H), 2.4-2.0 (m, 4H), 1.7-1.5 (m, 6H), 1.5-1.0 (m, 10H), 0.9 (t, 3H); MS (ESI$^+$) m/z 376.2 (M+1), 398.1 (M+Na).

Examples 10A-10D

Steps A, B, and C: Preparation of methyl 7-((R)-3,3-difluoro-5-((S,E)-3-hydroxy-7-phenylhept-1-en-1-yl)-2-oxopyrrolidin-1-yl)heptanoate (Example 10A) and methyl 7-((R)-3,3-difluoro-5-((R,E)-3-hydroxy-7-phenylhept-1-en-1-yl)-2-oxopyrrolidin-1-yl)heptanoate (Example 10B)

Example 10A

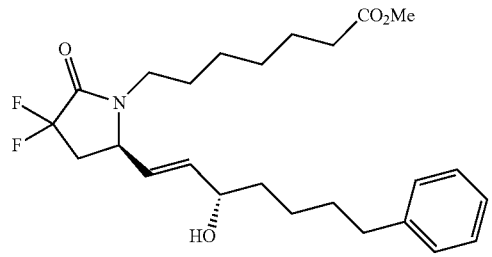 [SMILES: O=C(O)CCCCCCN1C(=O)C(F)(F)C[C@@H]1/C=C/[C@@H](O)CCCCc1ccccc1]

Example 10B

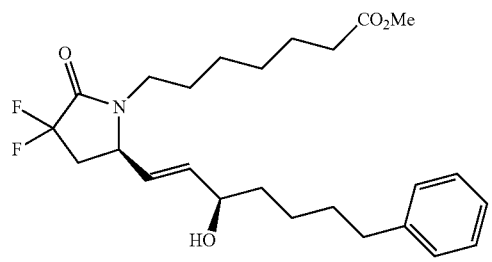 [SMILES: O=C(O)CCCCCCN1C(=O)C(F)(F)C[C@@H]1/C=C/[C@H](O)CCCCc1ccccc1]

Methyl 7-((5R)-3,3-difluoro-5-((E)-3-hydroxy-7-phenylhept-1-en-1-yl)-2-oxopyrrolidin-1-yl)heptanoate was prepared by the method described in Examples 1, Steps A and B, except that dimethyl (2-oxo-6-phenylhexyl)phosphonate (15ma) was used instead of (±)-dimethyl (3-methyl-2-oxohept-5-yn-1-yl)phosphonate (15ab(i)/15ac(i)) in Step A.

Step C: From the diastereomeric mixture methyl 7-((5R)-3,3-difluoro-5-((E)-3-hydroxy-7-phenylhept-1-en-1-yl)-2-oxopyrrolidin-1-yl)heptanoate were separated the single isomers methyl 7-((R)-3,3-difluoro-5-((S,E)-3-hydroxy-7-phenylhept-1-en-1-yl)-2-oxopyrrolidin-1-yl)heptanoate (Example 10A) and methyl 7-((R)-3,3-difluoro-5-((R,E)-3-hydroxy-7-phenylhept-1-en-1-yl)-2-oxopyrrolidin-1-yl) heptanoate (Example 10B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (93:7 v/v).

Example 10A (14.4 mg); a clear oil; prep HPLC retention time 15.8-17.0 minutes; $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.65 (s, 3H), 3.6-3.5 (m, 1H), 3.0-2.9 (m, 1H), 2.6 (t, 3H), 2.3 (t, 3H), 1.9-1.7 (br, 1H), 1.7-1.5 (m, 8H) 1.4-1.2 (m, 6H); $^{19}$F-NMR (CDCl$_3$) δ−103.5 (d, 1F), −105.5 (d, 1F); MS (ESI$^+$) m/z 452.2 (M+1) 474.2 (M+Na).

Example 10B (42.2 mg); a clear oil; prep HPLC retention time 13.7-15.1 minutes; $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.65 (s, 3H), 3.6-3.5 (m, 1H), 3.0-2.9 (m, 1H), 2.6 (t, 3H), 2.3 (t, 3H), 1.9-1.7 (br, 1H), 1.7-1.5 (m, 8H) 1.4-1.2 (m, 6H); $^{19}$F-NMR (CDCl$_3$) δ−103.5 (d, 1F), −105.5 (d, 1F); MS (ESI$^+$) m/z 452.2 (M+1) 474.2 (M+Na).

Step D1: Preparation of 7-((R)-3,3-difluoro-5-((S,E)-3-hydroxy-7-phenlhept-1-en-1-yl)-2-oxopyrrolidin-1-yl)heptanoic Acid (Example 10C)

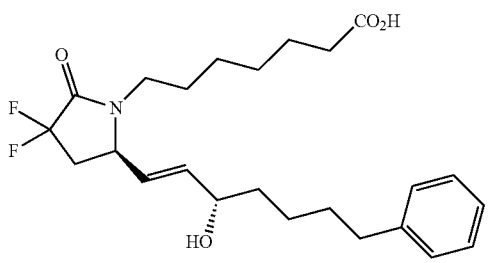

16.5 mg of a clear oil; TLC R$_f$ 0.35 (solvent system: 90:10:1 v/v dichloromethane-methanol-acetic acid); $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.6-3.5 (m, 1H), 3.0-2.9 (m, 1H), 2.6 (t, 3H), 2.2 (t, 3H), 2.2-2.1 (m, 1H), 1.7-1.5 (m, 8H), 1.5-1.1 (m, 6H); $^{19}$F-NMR (CDCl$_3$) δ−103.5 (d, 1F), −105.5 (d, 1F); MS (ESI$^−$) m/z 436.2 (M−1).

Step D2: Preparation of 7-((R)-3,3-difluoro-5-((R,E)-3-hydroxy-7-phenylhept-1-en-1-yl)-2-oxopyrrolidin-1-yl)heptanoic Acid (Example 10D)

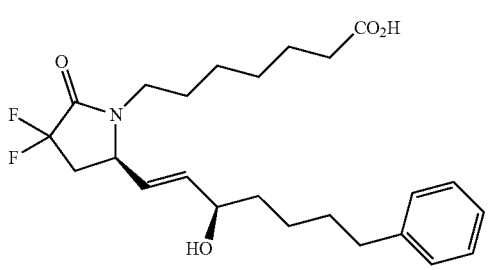

30.3 mg of a clear oil; TLC R$_f$ 0.35 (solvent system: 90:10:1 v/v dichloromethane-methanol-acetic acid); $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.6-3.5 (m, 1H), 3.0-2.9 (m, 1H), 2.6 (t, 3H), 2.2 (t, 3H), 2.2-2.1 (m, 1H), 1.7-1.5 (m, 8H), 1.5-1.1 (m, 6H); $^{19}$F-NMR (CDCl$_3$) δ−103.5 (d, 1F), −105.5 (d, 1F); MS (ESI$^−$) m/z 436.2 (M−1).

Example 11

4-(2-((R)-3,3-Difluoro-5-((3S,4S,E)-3-hydroxy-4-methyloct-1-en-6-yn-1-yl)-2-oxopyrrolidin-1-yl) ethyl)benzoic Acid

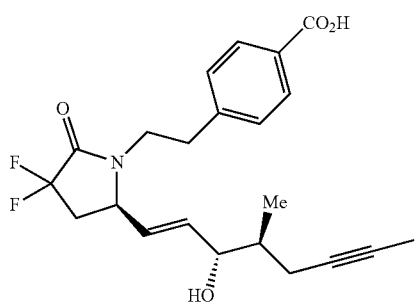 [SMILES: CC#CC[C@H](C)[C@H](O)/C=C/[C@H]1CC(F)(F)C(=O)N1CCc1ccc(C(=O)O)cc1]

Examples 12A-12F

Steps A, B, and C: Preparation of methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate (Example 12A), methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate (Example 12B), and methyl 4-(2-((5R)-3,3-difluoro-5-((3R,E)-3-hydroxy-4-methylnon-1-en-6-yn-1-yl)-2-oxopyrrolidin-1-yl)ethyl)benzoate (Example 12C)

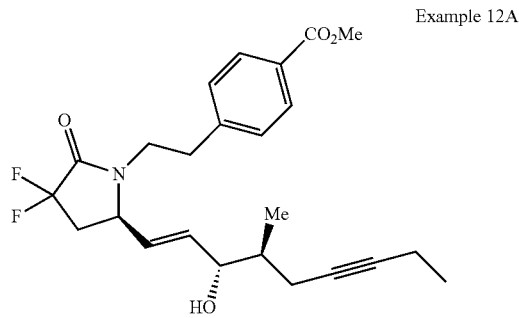

Example 12A

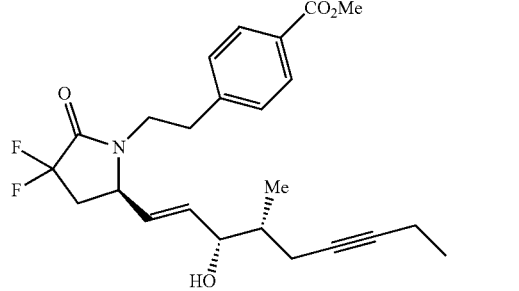

Example 12B

Example 12C

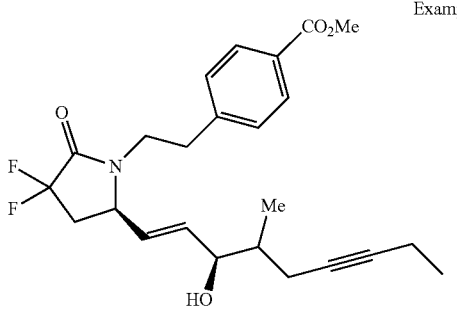

Methyl 4-(2-((5R)-3,3-difluoro-5-((E)-3-hydroxy-4-methylnon-1-en-6-yn-1-yl)-2-oxopyrrolidin-1-yl)ethyl)benzoate was prepared by the method described in Example 1, Steps A and B, except that (R)-methyl 4-(2-(3,3-difluoro-5-formyl-2-oxopyrrolidin-1-yl)ethyl)benzoate (13b) was used instead of (R)-methyl 7-(3,3-difluoro-5-formyl-2-oxopyrrolidin-1-yl) heptanoate (13a) and (±)-dimethyl (3-methyl-2-oxooct-5-yn-1-yl)phosphonate (15bb(i)/15bc(i)) was used instead of (±)-dimethyl (3-methyl-2-oxohept-5-yn-1-yl) phosphonate (15ab(i)/15ac(i)) in Step A.

Step C: From the stereoisomeric mixture comprising the four-diastereomer mixture methyl 4-(2-((5R)-3,3-difluoro-5-((E)-3-hydroxy-4-methylnon-1-en-6-yn-1-yl)-2-oxopyrrolidin-1-yl)ethyl)benzoate were separated the single isomers methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate (Example 12A) and methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate (Example 12B), and the diastereomeric mixture (at $C_{16}$) methyl 4-(2-((5R)-3,3-difluoro-5-((3R,E)-3-hydroxy-4-methylnon-1-en-6-yn-1-yl)-2-oxopyrrolidin-1-yl)ethyl)benzoate (Example 12C) by prep HPLC.

Agilent Semi-Prep instrument; ultraviolet detector at 205 nm; Luna Silica 5µ 250 mm×10 mm column; mobile phase of heptane-ethanol (98:2 v/v).

Example 12A (6.0 mg); a clear oil; HPLC retention time 78.9-83.9 minutes; $^1$H-NMR (CDCl$_3$) δ 8.0 (d, 2H), 7.3-7.2 (m, 2H), 5.7-5.6 (m, 1H), 5.5-5.4 (m, 1H), 4.2-4.1 (m, 1H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Example 12B (7.0 mg); a clear oil; HPLC retention time 72.7-77.6 minutes; $^1$H-NMR (CDCl$_3$) δ 8.0 (d, 2H), 7.3-7.2 (m, 2H), 5.7-5.6 (m, 1H), 5.5-5.4 (m, 1H), 4.3-4.2 (m, 1H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Example 12C (20.0 mg); a clear oil; HPLC retention time 59.6-68.8 minutes; $^1$H-NMR (CDCl$_3$) δ 8.0 (d, 2H), 7.3-7.2 (m, 2H), 5.7-5.6 (m, 1H), 5.5-5.4 (m, 1H), 4.3-4.2 (m, 0.5H), 4.2-4.1 (m, 0.5H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Step D1: Preparation of 4-(2-((R)-3,3-difluoro-5-((3S,4S,E)-3-hydroxy-4-methylnon-1-en-6-yn-1-yl)-2-oxopyrrolidin-1-yl)ethyl)benzoic Acid (Example 12D)

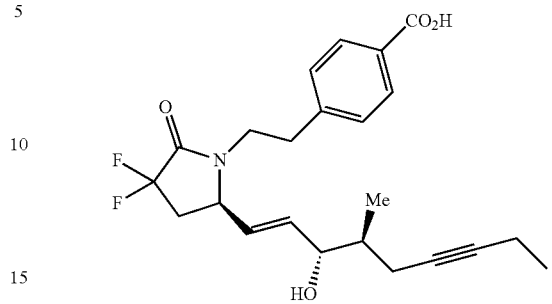

5.0 mg as a colorless oil; TLC R$_f$ 0.30 (solvent system: 96:4:1 v/v dichloromethane-methanol-acetic acid); $^1$H-NMR (CDCl$_3$) δ 8.0 (d, 2H), 7.4-7.3 (m, 2H), 5.9-5.8 (m, 1H), 5.5-5.4 (m, 1H), 4.2-4.0 (m, 2H), 3.9-3.8 (m, 1H), 3.4-3.3 (m, 1H), 3.1-3.0 (m, 1H), 3.0-2.9 (m, 1H), 2.8-2.7 (m, 1H), 2.3-2.2 (m, 2H), 2.2-2.1 (m, 2H), 2.1-2.0 (m, 1H), 1.8-1.7 (m, 1H) 1.2-1.1 (t, 3H), 1.0-0.9 (d, 3H); MS (ESI$^+$) m/z 442.1 (M+Na), (ESI$^-$) m/z 418.2.

Step D2: Preparation of 4-(2-((R)-3,3-difluoro-5-((3S,4R,E)-3-hydroxy-4-methylnon-1-en-6-yn-1-yl)-2-oxopyrrolidin-1-yl)ethyl)benzoic Acid (Example 12E)

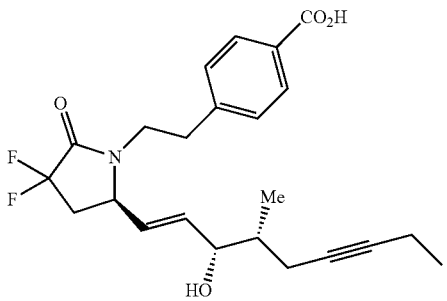 [SMILES: CCC#CC[C@@H](C)[C@H](O)/C=C/[C@H]1CC(F)(F)C(=O)N1CCc1ccc(C(=O)O)cc1]

4.8 mg as a colorless oil; TLC R$_f$ 0.30 (solvent system: 96:4:1 v/v dichloromethane-methanol-acetic acid); $^1$H-NMR (CDCl$_3$) δ 8.0 (d, 2H), 7.4-7.3 (m, 2H), 5.9-5.8 (m, 1H), 5.5-5.4 (m, 1H), 4.2-4.0 (m, 2H), 3.9-3.8 (m, 1H), 3.4-3.3 (m, 1H), 3.1-3.0 (m, 1H), 3.0-2.9 (m, 1H), 2.8-2.7 (m, 1H), 2.3-2.2 (m, 2H), 2.2-2.1 (m, 2H), 2.1-2.0 (m, 1H), 1.8-1.7 (m, 1H) 1.2-1.1 (t, 3H), 1.0-0.9 (d, 3H); MS (ESI$^+$) m/z 442.1 (M+Na), (ESI$^-$) m/z 418.2.

Step D3: Preparation of 4-(2-((5R)-3,3-difluoro-5-((3R,E)-3-hydroxy-4-methylnon-1-en-6-yn-1-yl)-2-oxopyrrolidin-1-yl)ethyl)benzoic Acid (Example 12F)

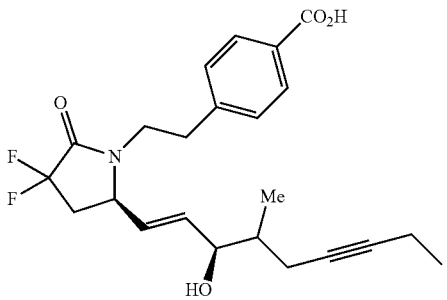 [SMILES: CCC#CCC(C)[C@@H](O)/C=C/[C@H]1CC(F)(F)C(=O)N1CCc1ccc(C(=O)O)cc1]

14.6 mg as a colorless oil; TLC $R_f$ 0.30 (solvent system: 96:4:1 v/v dichloromethane-methanol-acetic acid); $^1$H-NMR (CDCl$_3$) δ 8.0 (2H, d), 7.4-7.3 (2H, m), 5.9-5.8 (1H, m), 5.5-5.4 (1H, m), 4.2-4.0 (2H, m), 3.9-3.8 (1H, m), 3.4-3.3 (1H, m), 3.1-3.0 (1H, m), 3.0-2.9 (1H, m), 2.8-2.7 (1H, m), 2.3-2.2 (2H, m), 2.2-2.1 (2H, m), 2.1-2.0 (1H, m), 1.8-1.7 (1H, m) 1.2-1.1 (3H, t), 1.0-0.9 (3H, d); MS (ESI$^+$) m/z 442.1 (M+Na), (ESI$^-$) m/z 418.2.

Example 13D 4-(2-((R)-3,3-Difluoro-5-((3S,4S,E)-3-hydroxy-4-methyldec-1-en-6-yn-1-yl)-2-oxopyrrolidin-1-yl)ethyl)benzoic Acid

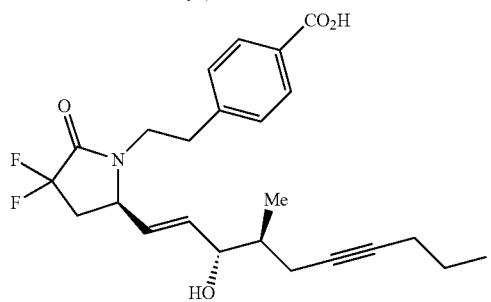

Example 14D 4-(2-((R)-3,3-Difluoro-5-((3S,4S,E)-3-hydroxy-4-methyl-7-phenyl hept-1-en-6-yn-1-yl)-2-oxopyrrolidin-1-yl)ethyl)benzoic Acid

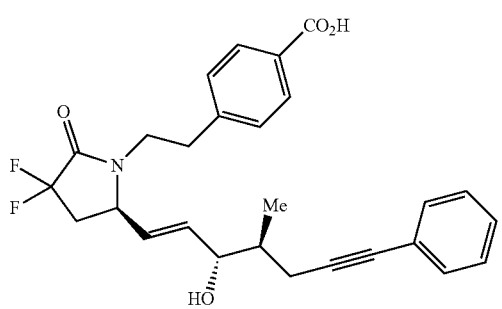 [SMILES: C[C@@H](CC#Cc1ccccc1)[C@H](O)/C=C/[C@H]1CC(F)(F)C(=O)N1CCc1ccc(C(=O)O)cc1]

Example 15D 4-(2-((R)-3,3-difluoro-5-((3S,4S,E)-3-hydroxy-4-methyloct-1-en-1-yl)-2-oxopyrrolidin-1-yl)ethyl)benzoic Acid

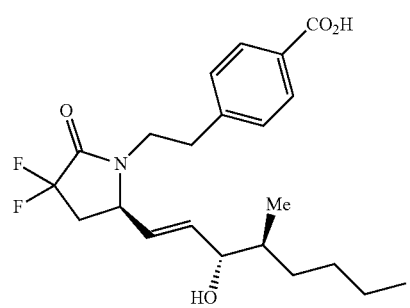 [SMILES: CCCC[C@H](C)[C@H](O)/C=C/[C@H]1CC(F)(F)C(=O)N1CCc1ccc(C(=O)O)cc1]

Example 16D 4-(2-((R)-3,3-Difluoro-5-((3S,4S,E)-3-hydroxy-4-methyl-7-phenylhept-1-en-1-yl)-2-oxopyrrolidin-1-yl)ethyl)benzoic Acid

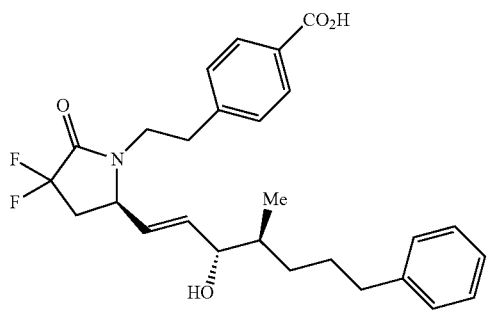 [SMILES: C[C@@H](CCCc1ccccc1)[C@H](O)/C=C/[C@H]1CC(F)(F)C(=O)N1CCc1ccc(C(=O)O)cc1]

Example 17C 4-(2-((R)-3,3-Difluoro-5-((S,E)-3-hydroxyoct-1-en-6-yn-1-yl)-2-oxopyrrolidin-1-yl)ethyl)benzoic Acid

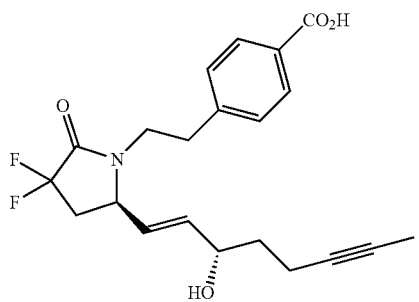 [SMILES: CC#CCC[C@H](O)/C=C/[C@H]1CC(F)(F)C(=O)N1CCc1ccc(C(=O)O)cc1]

Example 18C 4-(2-((R)-3,3-Difluoro-5-((S,E)-3-hydroxynon-1-en-6-yn-1-yl)-2-oxopyrrolidin-1-yl)ethyl)benzoic Acid

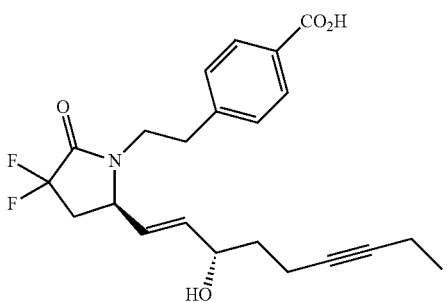 [SMILES: CCC#CCC[C@H](O)/C=C/[C@H]1CC(F)(F)C(=O)N1CCc1ccc(C(=O)O)cc1]

Example 19C 4-(2-((R)-3,3-Difluoro-5-((S,E)-3-hydroxydec-1-en-6-yn-1-yl)-2-oxopyrrolidin-1-yl)ethyl)benzoic Acid

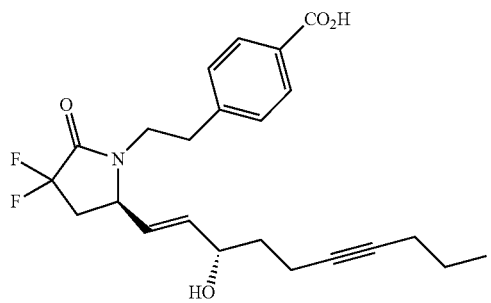 [SMILES: CCCC#CCC[C@H](O)/C=C/[C@H]1CC(F)(F)C(=O)N1CCc1ccc(C(=O)O)cc1]

Example 20C 4-(2-((R)-3,3-Difluoro-5-((S,E)-3-hydroxy-7-phenyl-hept-1-en-6-yn-1-yl)-2-oxopyrrolidin-1-yl)ethyl) benzoic Acid

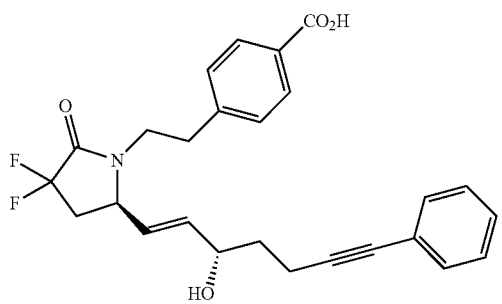 [SMILES: O=C(O)c1ccc(CCN2C(=O)C(F)(F)C[C@@H]2/C=C/[C@@H](O)CCC#Cc2ccccc2)cc1]

Examples 21A-21 D

Steps A, B, and C: Preparation of methyl 4-(2-((R)-3,3-difluoro-5-((S,E)-3-hydroxyoct-1-en-1-yl)-2-oxopyrrolidin-1-yl)ethyl)benzoate (Example 21A) and methyl 4-(2-((R)-3,3-difluoro-5-((R,E)-3-hydroxyoct-1-en-1-yl)-2-oxopyrrolidin-1-yl)ethyl)benzoate (Example 21B)

Example 21A

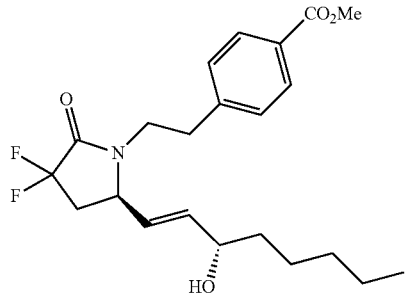 [SMILES: CCCCC[C@H](O)/C=C/[C@H]1CC(F)(F)C(=O)N1CCc1ccc(C(=O)O)cc1]

Example 21B

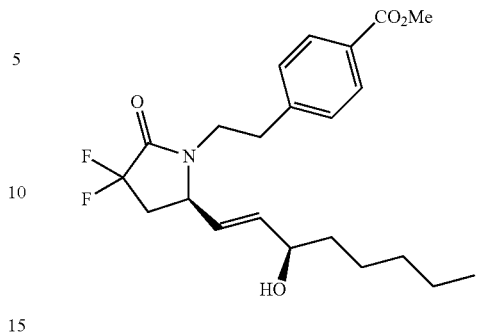

Methyl 4-(2-((R)-3,3-difluoro-5-((S,E)-3-hydroxyoct-1-en-1-yl)-2-oxopyrrolidin-1-yl)ethyl)benzoate was prepared by the method described in Example 9, Steps A and B, except that (R)-methyl 4-(2-(3,3-difluoro-5-formyl-2-oxopyrrolidin-1-yl)ethyl)benzoate (13b) was used instead of (R)-methyl 7-(3,3-difluoro-5-formyl-2-oxopyrrolidin-1-yl) heptanoate (13a) in Step A.

Step C: From the diastereomeric mixture methyl 4-(2-((5R)-3,3-difluoro-5-((E)-3-hydroxyoct-1-en-1-yl)-2-oxopyrrolidin-1-yl)ethyl)benzoate were separated the single isomers methyl 4-(2-((R)-3,3-difluoro-5-((S,E)-3-hydroxyoct-1-en-1-yl)-2-oxopyrrolidin-1-yl)ethyl)benzoate (Example 21A) and methyl 4-(2-((R)-3,3-difluoro-5-((R,E)-3-hydroxyoct-1-en-1-yl)-2-oxopyrrolidin-1-yl)ethyl)benzoate (Example 21B) by prep HPLC. The separations were performed on an Agilent Semi-Prep instrument equipped with an ultraviolet detector at 205 nm and using ultraviolet detector at 205 nm; Luna Silica 5µ 250×10 mm column eluting with a mobile phase of heptanes-ethanol (94:6 v/v).

Example 21A (12 mg); a clear oil; prep HPLC retention time 15.9-16.3 minutes; $^1$H-NMR (CDCl$_3$) δ 8.0 (d, 2H), 7.3-7.2 (m, 2H), 5.7-5.6 (m, 1H), 5.4-5.3 (m, 1H), 4.2-4.1 (m, 1H), 3.9 (s, 3H), 3.9-3.8 (m, 1H), 3.8-3.7 (m, 1H), 3.3-3.2 (m, 1H), 3.0-2.9 (m, 2H), 2.6-2.5 (m, 1H), 2.2-2.1 (m, 1H), 1.6 (br, 1H), 1.6-1.5 (m, 2H), 1.4-1.3 (m, 6H), 0.95-0.85 (m, 3H); MS (ESI$^+$) m/z 432.2 (M+Na).

Example 21B (24.0 mg); a clear oil; prep HPLC retention time 14.2-14.6 minutes; $^1$H-NMR (CDCl$_3$) δ 8.0 (d, 2H), 7.3-7.2 (m, 2H), 5.7-5.6 (m, 1H), 5.4-5.3 (m, 1H), 4.2-4.1 (m, 1H), 3.9 (s, 3H), 3.9-3.8 (m, 1H), 3.8-3.7 (m, 1H), 3.3-3.2 (m, 1H), 3.0-2.9 (m, 2H), 2.6-2.5 (m, 1H), 2.2-2.1 (m, 1H), 1.6 (br, 1H), 1.6-1.5 (m, 2H), 1.4-1.3 (m, 6H), 0.95-0.85 (m, 3H); MS (ESI$^+$) m/z 432.2 (M+Na).

Step D1: Preparation of 4-(2-((R)-3,3-difluoro-5-((S,E)-3-hydroxyoct-1-en-1-yl)-2-oxopyrrolidin-1-yl)ethyl)benzoic Acid (Example 21C)

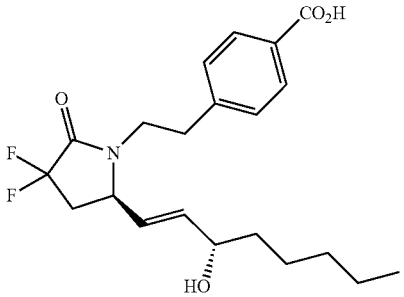

8.0 mg of a clear oil; TLC R$_f$ 0.35 (solvent system: 96:4:1 v/v dichloromethane-methanol-acetic acid); $^1$H-NMR (CDCl$_3$) δ 8.0 (d, 2H), 7.8 (d, 2H) 5.9-5.8 (m, 1H), 5.4-5.3 (m, 1H), 4.1-4.0 (m, 2H), 3.8-3.7 (m, 1H), 3.4-3.3 (m, 1H), 3.0-2.9 (m, 2H), 2.8-2.7 (m, 1H), 2.3-2.2 (m, 1H), 1.6-1.2 (m, 9H), 1.0-0.9 (m, 3H); MS (ESI$^-$) m/z 394 (M−1).

Step D2: Preparation of 4-(2-((R)-3,3-difluoro-5-((R,E)-3-hydroxyoct-1-en-1-yl)-2-oxopyrrolidin-1-yl)ethyl)benzoic Acid (Example 21D)

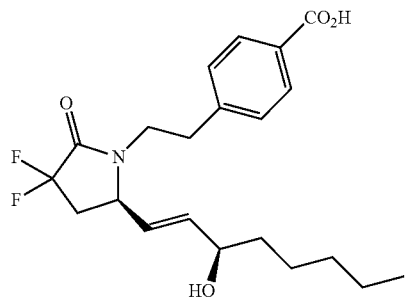 [SMILES: CCCCC[C@@H](O)/C=C/[C@H]1CC(F)(F)C(=O)N1CCc1ccc(C(=O)O)cc1]

16.6 mg of a clear oil; TLC R$_f$ 0.35 (solvent system: 96:4:1 v/v dichloromethane-methanol-acetic acid); $^1$H-NMR (CDCl$_3$) δ 8.0 (d, 2H), 7.8 (d, 2H) 5.9-5.8 (m, 1H), 5.4-5.3 (m, 1H), 4.1-4.0 (m, 2H), 3.8-3.7 (m, 1H), 3.4-3.3 (m, 1H), 3.0-2.9 (m, 2H), 2.8-2.7 (m, 1H), 2.3-2.2 (m, 1H), 1.6-1.2 (m, 9H), 1.0-0.9 (m, 3H); MS (ESI$^-$) m/z 394 (M−1).

Example 22C 4-(2-((R)-3,3-Difluoro-5-((S,E)-3-hydroxy-7-phenyl-hept-1-en-1-yl)-2-oxopyrrolidin-1-yl)ethyl)benzoic Acid

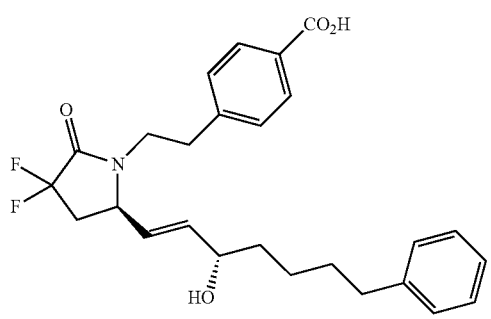 [SMILES: O=C(O)c1ccc(CCN2C(=O)C(F)(F)C[C@@H]2/C=C/[C@@H](O)CCCCc2ccccc2)cc1]

Example 23D 5-(3-((R)-3,3-Difluoro-5-((3S,4S,E)-3-hydroxy-4-methyloct-1-en-6-yn-1-yl)-2-oxopyrrolidin-1-yl)propyl)thiophene-2-carboxylic Acid

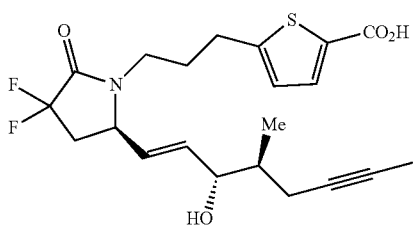 [SMILES: CC#CC[C@H](C)[C@H](O)/C=C/[C@H]1CC(F)(F)C(=O)N1CCCc1ccc(C(=O)O)s1]

Example 24A-24F

Step A, B, and C: Preparation of methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate (Example 24A), methyl 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylate (Example 24B), and methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate (Example 24C)

Example 24A

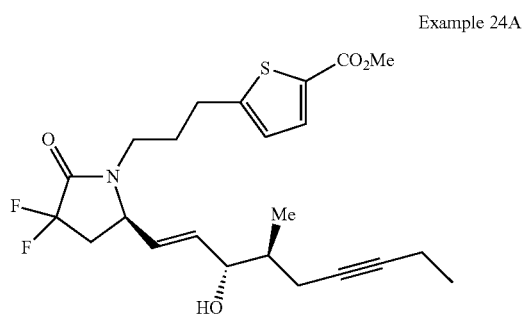

Example 24B

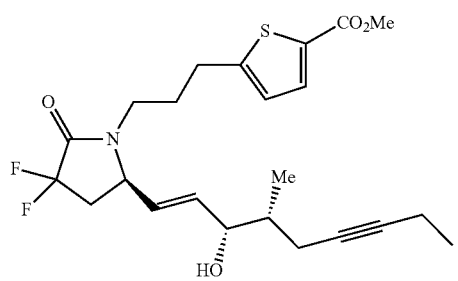

Example 24C

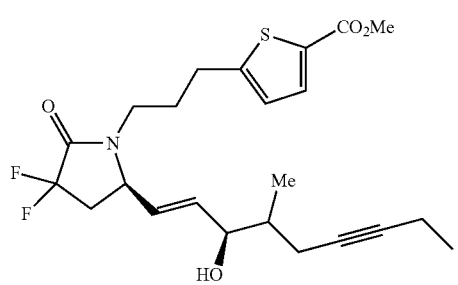

Methyl 5-(3-((5R)-3,3-difluoro-5-((E)-3-hydroxy-4-methylnon-1-en-6-yn-1-yl)-2-oxopyrrolidin-1-yl)propyl)thiophene-2-carboxylate was prepared by the method described in Examples 12, Steps A and B, except that (R)-methyl 5-(3-(3,3-difluoro-5-formyl-2-oxopyrrolidin-1-yl)propyl)thiophene-2-carboxylate (13f) was used instead of (R)-methyl 4-(2-(3,3-difluoro-5-formyl-2-oxopyrrolidin-1-yl)ethyl)benzoate (13b) in Step A.

Step C: From the stereoisomeric mixture comprising the four-diastereomer mixture methyl 5-(3-((5R)-3,3-difluoro-5-((E)-3-hydroxy-4-methylnon-1-en-6-yn-1-yl)-2-oxopyrrolidin-1-yl)propyl)thiophene-2-carboxylate were separated the single isomers methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate (Example 24A)

and methyl 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylate (Example 24B), and the diastereomeric mixture (at C16) methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate (Example 24C) by prep HPLC.

Agilent Semi-Prep instrument; ultraviolet detector at 205 nm; Luna Silica 5μ 250 mm×10 mm column; mobile phase of heptane-ethanol (98:2 v/v).

Example 24A (4.0 mg); a clear oil; HPLC retention time 78.9-83.9 minutes; $^1$H-NMR (CDCl$_3$) δ 7.6 (d, 1H), 6.8 (d, 1H), 5.9-5.8 (m, 1H), 5.6-5.5 (m, 1H), 4.2-4.1 (m, 2H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ–103.5 (d, 1F), –105.5 (d, 1F); MS (ESI$^+$) m/z 471.1 (M+Na).

Example 24B (5.0 mg); a clear oil; HPLC retention time 72.7-77.6 minutes; $^1$H-NMR (CDCl$_3$) δ 7.6 (d, 1H), 6.8 (d, 1H), 5.9-5.8 (m, 1H), 5.6-5.5 (m, 1H), 4.4-4.2 (m, 1H), 4.2-4.1 (m, 1H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ–103.5 (d, 1F), –105.5 (d, 1F); MS (ESI$^+$) m/z 471.1 (M+Na).

Example 24C (16.4 mg); a clear oil; HPLC retention time 59.6-68.8 minutes; $^1$H-NMR (CDCl$_3$) δ 7.6 (d, 1H), 6.8 (d, 1H), 5.9-5.8 (m, 1H), 5.6-5.5 (m, 1H), 4.4-4.2 (m, 0.5H), 4.2-4.1 (m, 1.5H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ–103.5 (d, 1F), –105.5 (d, 1F); MS (ESI$^+$) m/z 471.1 (M+Na).

Step D1: Preparation of 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylic Acid (Example 24D)

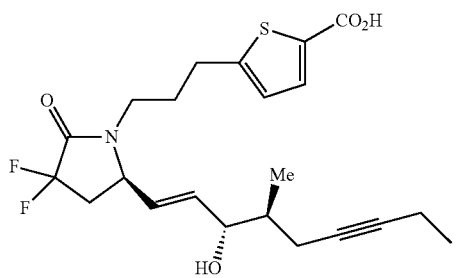 [SMILES: CCC#CC[C@H](C)[C@H](O)/C=C/[C@H]1CC(F)(F)C(=O)N1CCCc1ccc(C(=O)O)s1]

2.9 mg as a colorless oil; TLC R$_f$ 0.40 (solvent system: 95:5:1 v/v dichloromethane-methanol-acetic acid); MS (ESI$^+$) m/z 457.1 (M+Na).

Step D2: Preparation of 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylic Acid (Example 24E)

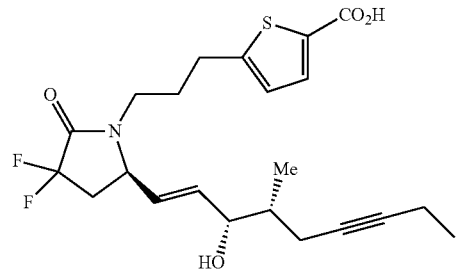 [SMILES: CCC#CC[C@@H](C)[C@H](O)/C=C/[C@H]1CC(F)(F)C(=O)N1CCCc1ccc(C(=O)O)s1]

Step D3: Preparation of 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylic Acid (Example 24F)

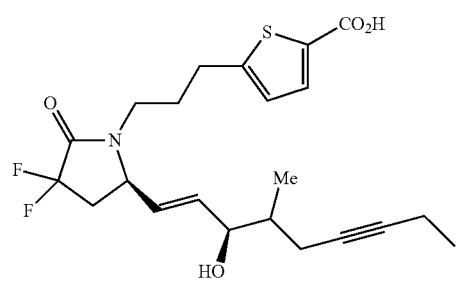 [SMILES: CCC#CCC(C)[C@@H](O)/C=C/[C@H]1CC(F)(F)C(=O)N1CCCc1ccc(C(=O)O)s1]

Example 25D 5-(3-((R)-3,3-Difluoro-5-((3S,4S,E)-3-hydroxy-4-methyldec-1-en-6-yn-1-yl)-2-oxopyrrolidin-1-yl)propyl)thiophene-2-carboxylic Acid

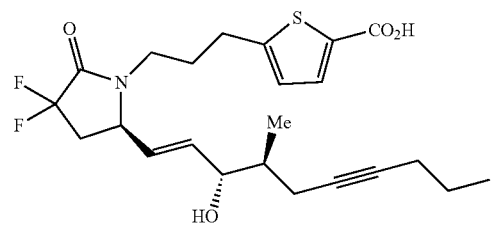 [SMILES: CCCC#CC[C@H](C)[C@H](O)/C=C/[C@H]1CC(F)(F)C(=O)N1CCCc1ccc(C(=O)O)s1]

Example 26D 5-(3-((R)-3,3-Difluoro-5-((3S,4S,E)-3-hydroxy-4-methyl-7-phenylhept-1-en-6-yn-1-yl)-2-oxopyrrolidin-1-yl)propyl)thiophene-2-carboxylic Acid

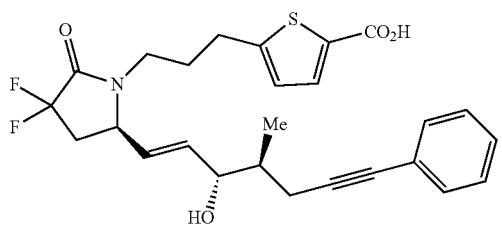 [SMILES: C[C@@H](CC#Cc1ccccc1)[C@H](O)/C=C/[C@H]1CC(F)(F)C(=O)N1CCCc1ccc(C(=O)O)s1]

Example 27D 5-(3-((R)-3,3-Difluoro-5-((3S,4S,E)-3-hydroxy-4-methyloct-1-en-1-yl)-2-oxopyrrolidin-1-yl)propyl)thiophene-2-carboxylic Acid

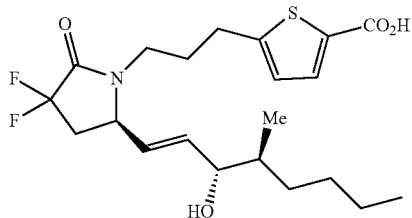 [SMILES: CCCC[C@H](C)[C@H](O)/C=C/[C@H]1CC(F)(F)C(=O)N1CCCc1ccc(C(=O)O)s1]

Examples 28A-28H

Steps A and B: Preparation of methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (28A) and methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (Example 28B)

Example 28A

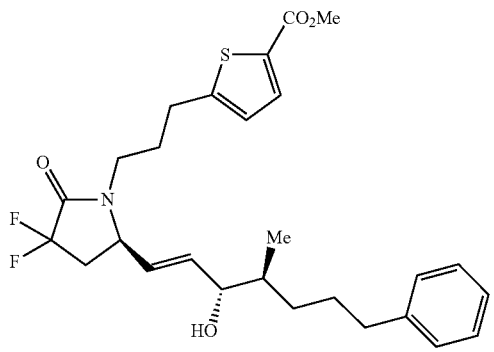

Example 28B

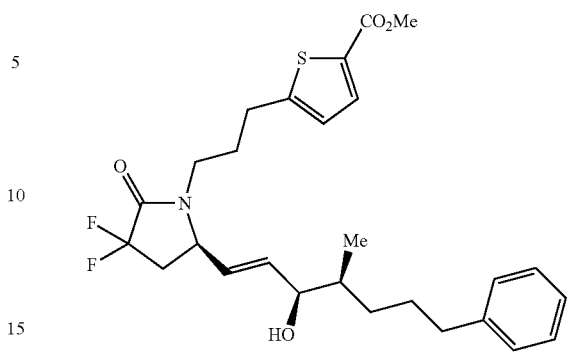

Methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate was prepared by the method described in Examples 24, Steps A and B, except that (S)-dimethyl (3-methyl-2-oxo-6-phenylhexyl)phosphonate (15mb(i)) was used in place of (±)-dimethyl (3-methyl-2-oxooct-5-yn-1-yl)phosphonate (15bb(i)/15bc(i)) in Step A.

Step C: From the stereoisomeric mixture comprising the two-diastereomer mixture methyl 5-(3-((5R)-3,3-difluoro-5-((4S,E)-3-hydroxy-4-methyl-7-phenylhept-1-en-1-yl)-2-oxopyrrolidin-1-yl)propyl)thiophene-2-carboxylate were separated the single isomers methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (28A) and methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (Example 28B) by prep HPLC.

Agilent Semi-Prep instrument; ultraviolet detector at 205 nm; Luna Silica 5μ 250 mm×10 mm column; mobile phase of heptane-ethanol (93:7 v/v).

Example 28A (3.6 mg); a clear oil; HPLC retention time 12.9-13.6 minutes; $^1$H-NMR (CDCl$_3$, 400 MHz) δ 7.6 (d, 1H), 7.3-7.2 (m, 2H), 7.2-7.1 (m, 3H), 6.8 (d, 1H), 5.8-5.7 (m, 1H), 5.5-5.4 (m, 1H), 4.1-4.0 (m, 2H), 3.85 (s, 3H), 3.7-3.5 (m, 1H), 3.1-3.0 (m, 1H), 2.9-2.8 (t, 2Ht), 2.7-2.5 (m, 3H), 2.3-2.1 (m, 1H), 2.0-1.8 (m, 2H), 1.8-1.5 (m, 5H), 1.5-1.4 (m, 1H), 1.3-1.2 (m, 1H), 1.2-1.1 (t, 1H), 0.85 (d, 3H); MS (ESI$^+$) m/z 528.2 (M+Na).

Example 28B (19.6 mg); a clear oil; HPLC retention time 12.0-12.9 minutes; $^1$H-NMR (CDCl$_3$, 400 MHz) δ 7.6 (d, 1H), 7.3-7.2 (m, 2H), 7.2-7.1 (m, 3H), 6.8 (d, 1H), 5.8-5.7 (m, 1H), 5.5-5.4 (m, 1H), 4.1-4.0 (m, 2H), 3.85 (s, 3H), 3.7-3.5 (m, 1H), 3.1-3.0 (m, 1H), 2.9-2.8 (t, 2H), 2.7-2.5 (m, 3H), 2.3-2.1 (m, 1H), 2.0-1.8 (m, 2H), 1.8-1.5 (m, 5H), 1.5-1.4 (m, 1H), 1.3-1.2 (m, 1H), 1.2-1.1 (t, 1H), 0.85 (d, 3H); MS (ESI$^+$) m/z 528.2 (M+Na).

Alternative preparations of Example 28A from methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate (Enone intermediate 22f-mb(i)).

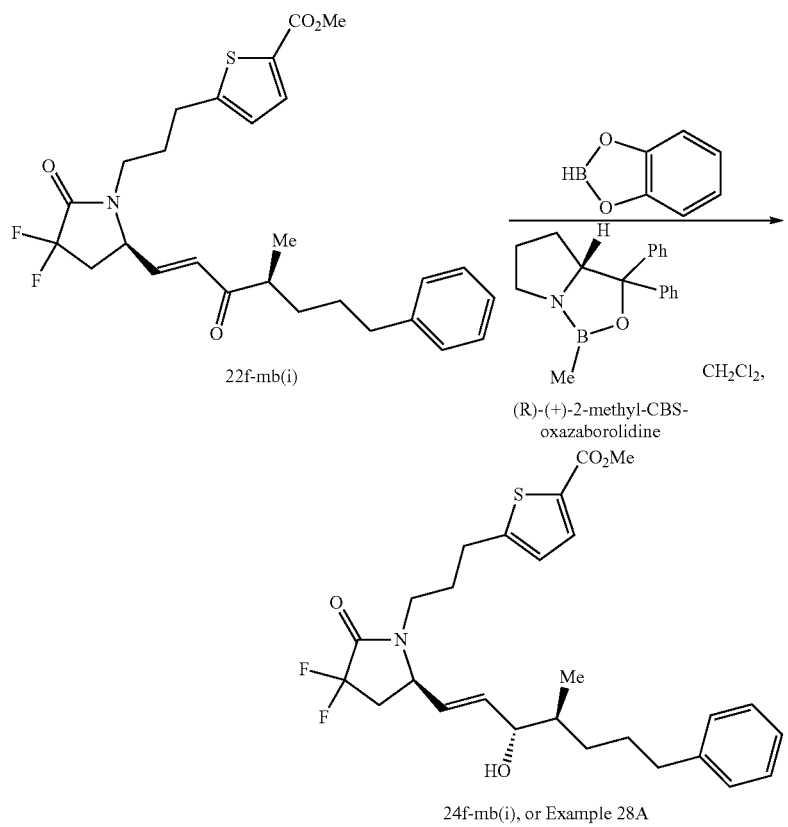

Enone 22f-mb(i) was prepared by reacting aldehyde 13f with □-keto phosphonate ester 15mb(i) using a Horner-Wadsworth-Emmons procedure similar to the protocol described in Step A for the preparation of Example 1A above.

Alternative Preparation 1:

To a stirring solution consisting of 22f-mb(i) (50 mg, 0.10 mmol) and R)-(+)-2-methyl-CBS-oxazaborolidine (0.12 mL, 0.12 mmol, 1 M in toluene) in dichloromethane (1 mL) was added a solution consisting of catecholborane (0.1 mL, 0.1 mmol, 1 M in THF) in dichloromethane (5 mL) over 15 minutes. The reaction was stirred for two hours. The reaction was quenched with 1 M HCl and extracted with ethyl acetate. The combined organic phase was sequentially washed with a 50% saturated aqueous solution of sodium chloride and a saturated aqueous solution of sodium chloride, dried over sodium sulfate, filtered, and concentrated to provide a residue comprising a diastereomeric mixture of Examples 28A and 28B, which was purified by silica gel chromatography. Elution with methanol-dichloromethane (1:250 v/v) afforded a purified diastereomeric mixture comprising Example 28A and Example 28B (23 mg) as a clear oil; TLC $R_f$ 0.50 (solvent system: 97:3 v/v dichloromethane:methanol).

Alternative Preparation 2:

A diastereomeric mixture comprising Example 28A and Example 28B, was prepared by the method as described above in Alternative preparation 1, except 4 molar equivalents of catecholborane (0.4 mL, 0.4 mmol, 1M in THF) were used instead of 1 molar equivalent to afford a second purified diastereomeric mixture comprising Example 28A and Example 28B (70 mg) as a clear oil; TLC $R_f$ 0.50 (solvent system: 3:97 v/v dichloromethane-methanol).

Alternative Preparation 3:

A diastereomeric mixture comprising Example 28A and Example 28B, was prepared by the method as described above in Alternative preparation 1, except on a larger scale. The reaction mixture comprising 22f-mb(i) (553 mg, 1.1 mmol), (R)-(+)-2-methyl-CBS-oxazaborolidine (1.32 mL, 1.32 mmol, 1M in toluene) and catecholborane (1.1 mL, 1.1 mmol, 1 M in THF) afforded a third purified diastereomeric mixture comprising Example 28A and Example 28B (226 mg) as a clear oil; TLC $R_f$ 0.50 (solvent system: 3:97 v/v dichloromethane-methanol).

Isolation of single diastereomer Example 28A by separation of a pooled mixture comprising the three purified diastereomeric mixtures generated from the three alternative Example 28A preparations above: The pooled mixture was injected onto the Agilent 1100 prep HPLC; stationary phase Luna 5m Silica 250×21.2 mm column; mobile phase 96:4 heptane-ethanol; Example 28A eluent collected at retention time 26-29 minutes and concentrated to afford the single diastereomer Example 28A (110 mg, 17%) as a white solid; TLC $R_f$ 0.50 (solvent system: 97:3 v/v dichloromethane: methanol); analytical HPLC, retention time 16.3 min, Agilent 1100 ultraviolet detector at 210 nm, stationary phase, Phenomenex Luna Silica, 5μ, 4.6×250 mm, mobile phase, 95:5 heptane-ethanol, flow rate 1 mL/min; $^1$H-NMR (CDCl$_3$) δ 7.6 (d, 1H), 7.3-7.2 (m, 2H), 7.2-7.1 (m, 3H), 6.8 (d, 1H), 5.75 (dd, 1H), 5.4 (dd, 1H), 4.1-4.0 (m, 2H), 3.82 (s, 3H), 3.6-3.5 (m, 1H), 3.0-2.9 (m, 1H), 2.80 (t, 2H), 2.6-2.5 (m, 3H), 2.2-2.1 (m, 1H), 2.1-2.0 (m, 1H), 1.9-1.8 (m, 2H), 1.7-1.4 (m, 4H), 1.2-1.1 (m, 1H), 0.84 (d, 3H); $^{19}$F-NMR (CDCl$_3$, 376 Hz) δ−103.6 (ddd, J=270, 15, 3 Hz, 1F), −105.6 (ddd, J=271, 17, 15 Hz, 1F).

Alternative Preparation 4:

To a solution consisting of 22f-mb(i) (10 mg, 0.02 mmol) and (R)-(+) 2-methyl-CBS-oxazaborolidine (0.040 mL, 0.040 mmol, 1 M in toluene) in dichloromethane (1 mL) was added catecholborane (0.060 mL, 0.060 mmol, 1M in THF) in dichloromethane (1 mL) over 15 minutes. The reaction mixture was stirred for two hours and was subsequently quenched with 1 M HCl and extracted with ethyl acetate. The crude product, as a clear oil, was analyzed by HPLC (Phenomenex Luna 5µ Silica (2) 4.6×250 mm column at 30° C.; mobile phase 95:5:0.1 hexanes-isopropanol-acetic acid): diastereomeric ratio Example 28A-Example 28B=64:36 by area; TLC $R_f$ 0.50 (solvent system: 3:97 v/v dichloromethane-methanol).

Step D1: Preparation of 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic Acid (Example 28C)

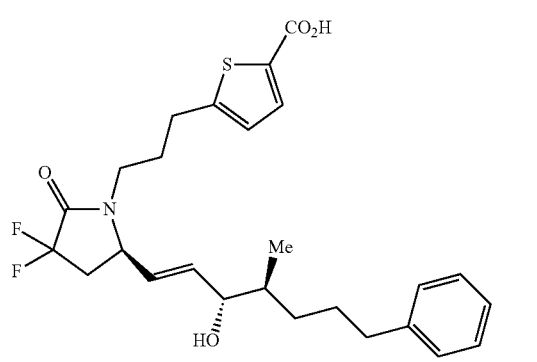

Example 28C

TLC $R_f$ 0.55 (solvent system: 96:4:1 v/v dichloromethane-methanol-acetic acid); MS (ESI⁻) m/z 490.2 (M−1).

Step D2: Preparation of 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylic Acid (Example 28D)

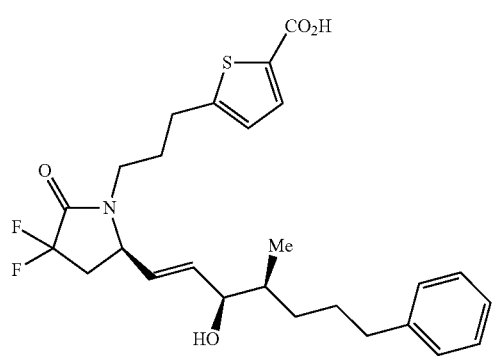

Example 28D

TLC $R_f$ 0.55 (solvent system: 96:4:1 v/v dichloromethane-methanol-acetic acid); MS (ESI⁻) m/z 490.2 (M−1).

Example 28E and 28F

Steps A, B, and C: Preparation of methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (Example 28E) and methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate (Example 28F)

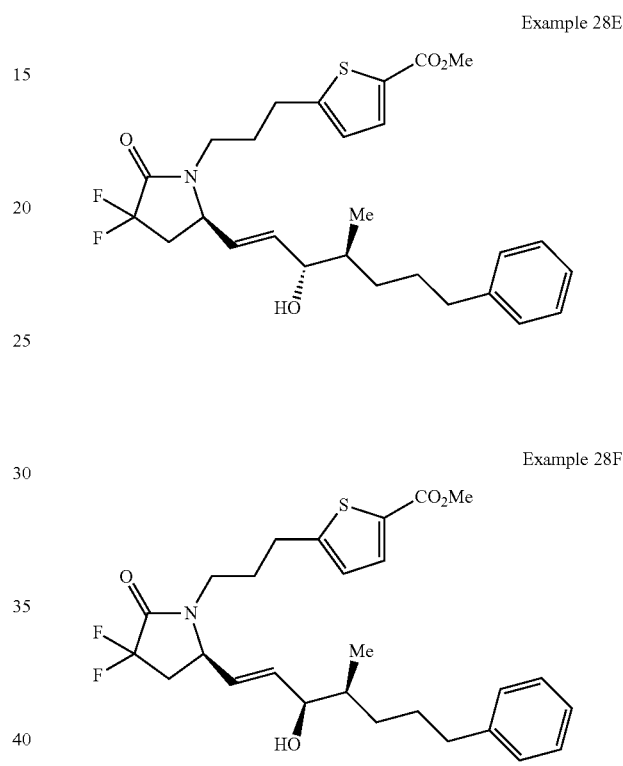

Methyl 5-(3-((5R)-3,3-difluoro-5-((4R,E)-3-hydroxy-4-methyl-7-phenylhept-1-en-1-yl)-2-oxopyrrolidin-1-yl)propyl)thiophene-2-carboxylate was prepared by the method described in Example 28, Steps A and B, except that (R)-dimethyl (3-methyl-2-oxo-6-phenylhexyl)phosphonate (15mc(i)) was used instead of (S)-dimethyl (3-methyl-2-oxo-6-phenylhexyl)phosphonate (15mb(i)) in Step A.

Step C: The pure diastereomers of Example 28E and Example 28F were isolated following separation by prep HPLC; Gilson Prep HPLC, Luna silica 5µ 21.2×250 mm, ultraviolet detector 210 nm, mobile phase 96:4:0.1 heptane-ethanol-acetic acid, 21.2 ml/min.

Example 28E: 175 mg as a clear oil; TLC $R_f$ 0.31 (solvent system: 35:65 v/v ethyl acetate-heptane); HPLC retention time 39 min; MS (ESI⁺) m/z 528 (M+Na)⁺; ¹H NMR (CD₃OD) δ 7.62 (d, J=3.66 Hz, 1H), 7.25-7.10 (m, 5H), 6.91 (d, J=3.92 Hz, 1H), 5.81 (dd, J=6.23, 15.38 Hz, 1H), 5.42 (dd, J=9.34, 15.20 Hz, 1H), 4.25 (dd, J=4.58, 7.87 Hz, 1H), 3.99-3.89 (m, 1H), 3.80 (s, 3H), 3.55-3.47 (m, 1H), 3.34 (s, 1H), 3.16-3.03 (m, 1H), 2.85 (dt, J=3.48, 7.42 Hz, 3H), 2.71-2.51 (m, 2H), 2.32-2.19 (m, 1H), 1.99-1.85 (m, 2H), 1.71-1.44 (m, 4H), 1.11 (s, 1H), 0.86 (d, J=6.96 Hz, 3H); ¹⁹F NMR (CD₃OD) δ −104.4 (ddd, 1F), −107.3 (ddd, 1F); $[α]^T_λ$=α/cl, $[α]^{21.9}_D$=−0.004/(0.01568 g/1.5 mL)(0.5)=−0.765° (c=1.045, CHCl₃). Example 28F: 580 mg as a clear oil; TLC $R_f$ 0.31 (solvent system: 35:65 v/v ethyl acetate-heptane); HPLC retention time 35 min; MS (ESI+) m/z 528 (M+Na)+; $^1$H NMR (CD$_3$OD) δ 7.63-7.61 (m, 1H), 7.25-7.10 (m, 5H), 6.92 (d, J=3.91 Hz, 1H,), 5.85 (dd, J=5.68, 15.20 Hz, 1H), 5.43 (dd, J=9.34, 15.20 Hz, 1H), 4.29-4.22 (m, 1H), 3.96 (dt, J=1.46, 5.49 Hz, 1H), 3.82-3.80 (m, 3H), 3.59-3.47 (m, 1H), 3.36-3.32 (m, 1H), 3.11 (dd, J=6.04, 7.87 Hz, 1H), 2.85 (t, J=7.51 Hz, 2H), 2.79-2.67 (m, 1H), 2.59 (t, J=7.51 Hz, 2H), 2.28-2.15 (m, 1H), 1.99-1.86 (m, 2H), 1.75-1.52 (m, 3H), 1.47 (td, J=5.17, 13.46 Hz, 1H), 1.17-1.07 (m, 1H), 0.85 (d, J=6.59 Hz, 3H); $^{19}$F NMR (CD$_3$OD) δ−104.5 (ddd, 1F), −107.2 (ddd, 1F).

Alternative preparation of Example 28E from methyl 5-(3-((R)-3,3-difluoro-5-((R,E)-4-methyl-3-oxo-7-phenyl-hept-1-en-1-yl)-2-oxopyrrolidin-1-yl)propyl)thiophene-2-carboxylate (Enone intermediate 22f-mc(i)).

Step D1: Preparation of 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylic Acid (Example 28G)

Example 28G

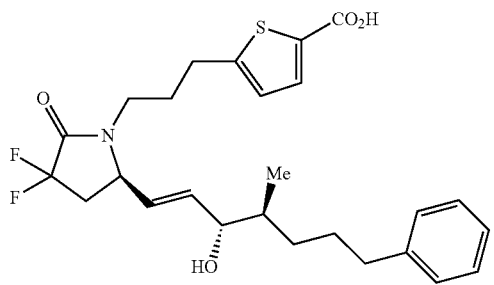

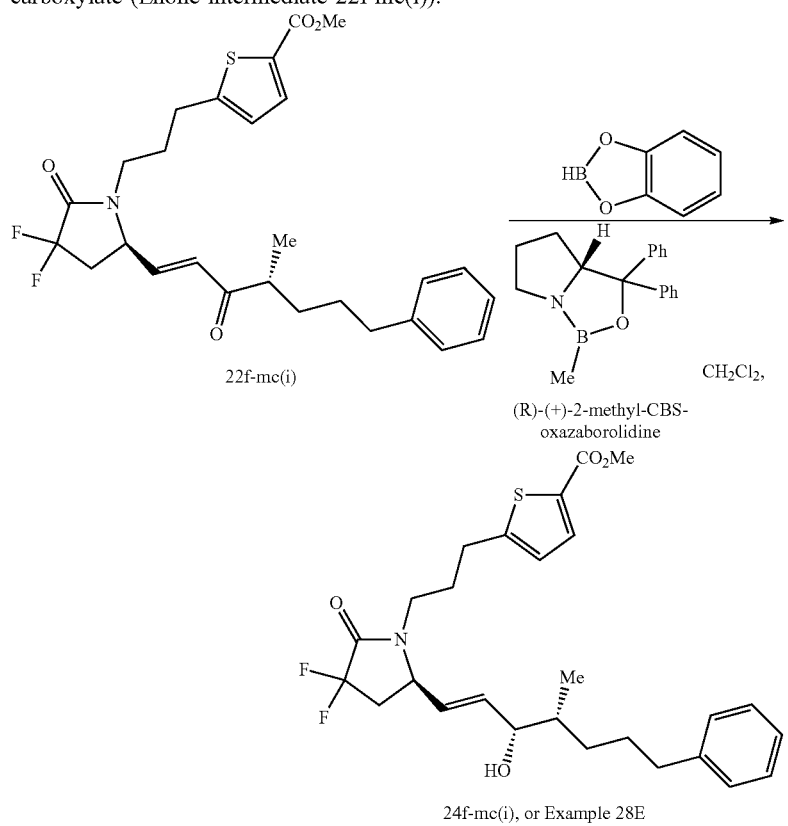

To a solution consisting of methyl 5-(3-((R)-3,3-difluoro-5-((R,E)-4-methyl-3-oxo-7-phenylhept-1-en-1-yl)-2-oxopyrrolidin-1-yl)propyl)thiophene-2-carboxylate (10 mg, 0.02 mmol) and (R)-(+) 2-methyl-CBS-oxazaborolidine (0.040 mL, 0.040 mmol, 1 M in toluene) in dichloromethane (1 mL) was added catecholborane (0.060 mL, 0.060 mmol, 1M in THF) in dichloromethane (1 mL) over 15 minutes. The reaction mixture was stirred for two hours and was subsequently quenched with 1 M HCl and extracted with ethyl acetate. The crude product, as a clear oil, was analyzed by HPLC (Phenomenex Luna 5μ Silica (2) 4.6×250 mm column at 30° C.; mobile phase 95:5:0.1 hexanes-isopropanol-acetic acid): diastereomeric ratio Example 28E-Example 28F=99:1 by area; TLC $R_f$ 0.50 (solvent system: 3:97 v/v dichloromethane-methanol).

Enone 22f-mc(i) was prepared by reacting aldehyde 13f with □-keto phosphonate ester 15mc(i) using a Horner-Wadsworth-Emmons procedure similar to the protocol described in Step A for the preparation of Example 1A above.

60 mg (44%) of the title compound as a colorless oil; TLC $R_f$ 0.45 (solvent system: 60:40:1 v/v/v ethyl acetate-heptane-acetic acid); MS (ESI−) m/z 490 (M−H)−; $^1$H NMR (CD$_3$OD) δ 7.58 (d, J=4.03 Hz, 1H), 7.25-7.10 (m, 5H), 6.89 (d, J=4.02 Hz, 1H), 5.81 (dd, J=6.23, 15.38 Hz, 1H), 5.42 (dd, J=9.34, 15.20 Hz, 1H), 4.30-4.21 (m, 1H), 3.93 (t, J=5.49 Hz, 1H), 3.62-3.42 (m, 1H), 3.15-3.04 (m, 1H), 2.89-2.68 (m, 4H), 2.65-2.51 (m, 2H), 2.32-2.14 (m, 1H), 2.01-1.85 (m, 2H), 1.71-1.44 (m, 4H), 1.19-1.05 (m, 1H), 0.92-0.83 (m, 3H); $^{19}$F NMR (CD$_3$OD) δ−104.3 (ddd, 1F), −107.2 (ddd, 1F); $[α]^T_λ=α/cl$ $[α]^{21.9}_D=-0.011/(0.0163$ g/1.5 mL)(0.5)=−2.03° (c=1.09, CHCl$_3$).

Step D2: Preparation of 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylic Acid (Example 28H)

Example 28H

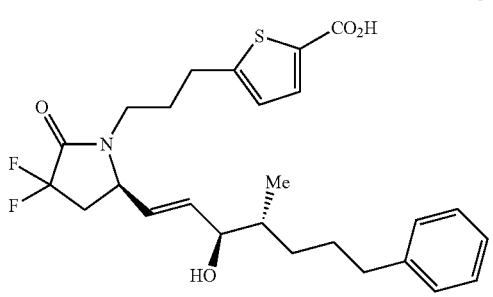

510 mg (94%) of the title compound as a white solid; TLC R_f 0.47 (solvent system: 50:50:1 v/v/v ethyl acetate-heptane-acetic acid); MP 133-134° C.; MS (ESI⁻) m/z 490 (M–H)⁻; ¹H-NMR (CD₃OD) δ 7.58 (d, J=3.66 Hz, 1H), 7.26-7.10 (m, 5H), 6.90 (d, J=3.86 Hz, 1H), 5.85 (dd, J=5.49, 15.38 Hz, 1H), 5.43 (dd, J=9.15, 15.38 Hz, 1H), 4.30-4.22 (m, 1H), 3.97 (dt, J=1.46, 5.49, Hz, 1H), 3.59-3.51 (m, 1H), 3.16-3.07 (m, 1H), 2.88-2.67 (m, 4H), 2.59 (t, J=7.51 Hz, 2H), 2.21 (dtd, 1H), 2.00-1.86 (m, 2H), 1.76-1.52 (m, 3H), 1.51-1.41 (m, 1H), 1.17-1.07 (m, 1H), 0.86 (d, J=6.59 Hz, 3H); ¹⁹F-NMR (CD₃OD) δ–104.5 (ddd, 1F), –107.2 (ddd, 1F); $[\alpha]^T_\lambda = \alpha/cl$, $[\alpha]^{21.9}_D = -0.140/(0.0194 \text{ g}/2.5 \text{ mL})(0.5) = -36.08°$ (c=0.776, CHCl₃).

Example 28C-H₂

Preparation of 5-(3-((S)-3,3-difluoro-5-((3R,4S)-3-hydroxy-4-methyl-7-phenylheptyl)-2-oxopyrrolidin-1-yl)propyl)thiophene-2-carboxylic Acid (Example 28C-H₂)

Example 28C-H₂

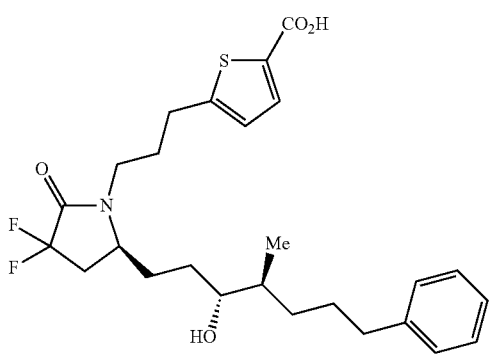

To a solution consisting of 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid (15.2 mg, 0.031 mmol) in ethanol (12 mL) and covered with an atmosphere of nitrogen was added palladium (12 mg, 10% on activated carbon). The nitrogen atmosphere was replaced with hydrogen and the reaction mixture was stirred vigorously for 5 hours at room temperature. The hydrogen was replaced with nitrogen and mixture was filtered through a small pad of celite which was washed with ethanol. The combined filtrate was concentrated under vacuum and the residue was purified by silica gel chromatography eluting with ethyl acetate-heptane-acetic acid (45:55:0.4 v/v/v) to give 9.5 mg (62%) of the title compound as a colorless oil; TLC R_f 0.29 (solvent system: 45:55:1 v/v/v ethyl acetate-heptane-acetic acid); MS (ESI⁻) m/z 492.2 (M–H)⁻; ¹H NMR (CD₃OD) δ 7.47 (d, J=3.66 Hz, 1H), 7.18-7.01 (m, 5H), 6.80 (d, J=3.30 Hz, 1H), 3.72-3.63 (m, 1H), 3.16-3.03 (m, 1H), 2.79 (t, J=7.32 Hz, 2H), 2.61-2.45 (m, 3H), 2.19-2.05 (m, 1H), 1.98-1.78 (m, 2H), 1.78-1.57 (m, 2H), 1.53-1.39 (m, 4H), 1.34-1.14 (m, 5H), 1.10-1.00 (m, 1H), 0.81-0.76 (m, 3H); ¹⁹F NMR (CD₃OD) δ–103.2 (ddd, 1F), –105.9 (ddd, 1F).

Example 29C 5-(3-((R)-3,3-Difluoro-5-((S,E)-3-hydroxyoct-1-en-6-yn-1-yl)-2-oxopyrrolidin-1-yl)propyl)thiophene-2-carboxylic Acid

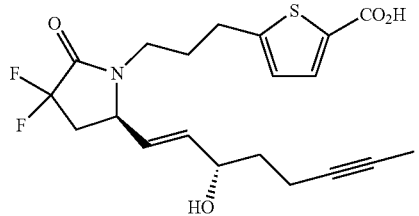 [SMILES: CC#CCC[C@H](O)/C=C/[C@H]1CC(F)(F)C(=O)N1CCCc1ccc(C(=O)O)s1]

Example 30C 5-(3-((R)-3,3-Difluoro-5-((S,E)-3-hydroxynon-1-en-6-yn-1-yl)-2-oxopyrrolidin-1-yl)propyl)thiophene-2-carboxylic Acid

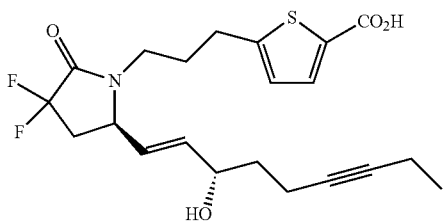 [SMILES: CCC#CCC[C@H](O)/C=C/[C@H]1CC(F)(F)C(=O)N1CCCc1ccc(C(=O)O)s1]

Example 31C 5-(3-((R)-3,3-Difluoro-5-((S,E)-3-hydroxydec-1-en-6-yn-1-yl)-2-oxopyrrolidin-1-yl)propyl)thiophene-2-carboxylic Acid

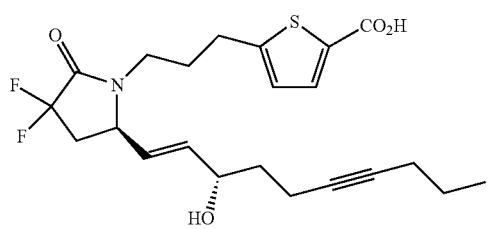 [SMILES: CCCC#CCC[C@H](O)/C=C/[C@H]1CC(F)(F)C(=O)N1CCCc1ccc(C(=O)O)s1]

Example 32C 5-(3-((R)-3,3-Difluoro-5-((S,E)-3-hydroxy-7-phenyl-hept-1-en-6-yn-1-yl)-2-oxopyrrolidin-1-yl)propyl)thiophene-2-carboxylic Acid

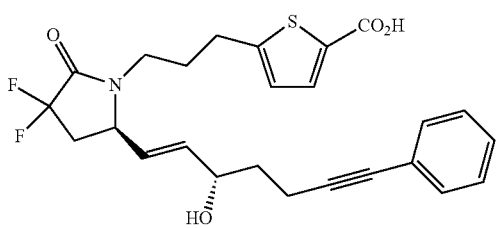 [SMILES: O=C(O)c1ccc(CCCN2C(=O)C(F)(F)C[C@@H]2/C=C/[C@@H](O)CCC#Cc2ccccc2)s1]

Examples 33A-33D

Steps A, B, and C: Preparation of methyl 5-(3-((R)-3,3-difluoro-5-((S,E)-3-hydroxyoct-1-en-1-yl)-2-oxopyrrolidin-1-yl)propyl)thiophene-2-carboxylate (Example 33A) and methyl 5-(3-((R)-3,3-difluoro-5-((R,E)-3-hydroxyoct-1-en-1-yl)-2-oxopyrrolidin-1-yl)propyl)thiophene-2-carboxylate (Example 33B)

Example 33A
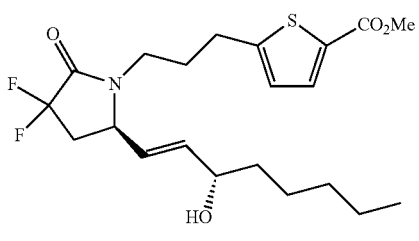

Example 33B
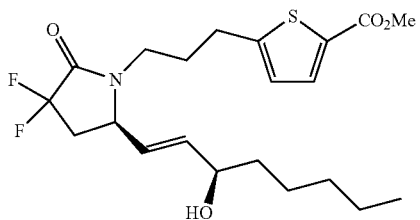

Methyl 5-(3-((5R)-3,3-difluoro-5-((E)-3-hydroxyoct-1-en-1-yl)-2-oxopyrrolidin-1-yl)propyl)thiophene-2-carboxylate was prepared by the method described in Example 9, Steps A and B, except that (R)-methyl 5-(3-(3,3-difluoro-5-formyl-2-oxopyrrolidin-1-yl)propyl)thiophene-2-carboxylate (13f) was used instead of (R)-methyl 7-(3,3-difluoro-5-formyl-2-oxopyrrolidin-1-yl) heptanoate (13a).

Step C: From the diastereomeric mixture methyl 5-(3-((5R)-3,3-difluoro-5-((E)-3-hydroxyoct-1-en-1-yl)-2-oxopyrrolidin-1-yl)propyl)thiophene-2-carboxylate were separated the single isomers methyl 5-(3-((R)-3,3-difluoro-5-((S,E)-3-hydroxyoct-1-en-1-yl)-2-oxopyrrolidin-1-yl)propyl)thiophene-2-carboxylate (Example 33A) and methyl 5-(3-((R)-3,3-difluoro-5-((R,E)-3-hydroxyoct-1-en-1-yl)-2-oxopyrrolidin-1-yl)propyl)thiophene-2-carboxylate (Example 33B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (94:6 v/v).

Example 33A (10.2 mg); a clear oil; prep HPLC retention time 15.9-16.3 minutes; $^1$H-NMR (CDCl$_3$) δ 7.6 (d, 1H), 6.8 (d, 1H), 5.9-5.7 (m, 1H), 5.5-5.4 (m, 1H), 4.2-4.1 (m, 1H), 4.1-4.0 (m, 1H), 3.9 (s, 3H), 3.7-3.6 (m, 1H), 3.2-3.0 (m, 1H), 2.8 (t, 2H), 2.8-2.6 (m, 1H), 2.3-2.1 (m, 1H), 2.0-1.8 (m, 2H), 1.8-1.7 (br, 1H), 1.6-1.5 (m, 2H), 1.4-1.2 (m, 6H), 0.9 (t, 3H); MS (ESI$^+$) m/z 452.0 (M+Na).

Example 33B (24.0 mg); a clear oil; prep HPLC retention time 14.2-14.6 minutes; $^1$H-NMR (CDCl$_3$) δ 7.6 (d, 1H), 6.8 (d, 1H), 5.9-5.7 (m, 1H), 5.5-5.4 (m, 1H), 4.2-4.1 (m, 1H), 4.1-4.0 (m, 1H), 3.9 (s, 3H), 3.7-3.6 (m, 1H), 3.2-3.0 (m, 1H), 2.8 (t, 2H), 2.8-2.6 (m, 1H), 2.3-2.1 (m, 1H), 2.0-1.8 (m, 2H), 1.8-1.7 (br, 1H), 1.6-1.5 (m, 2H), 1.4-1.2 (m, 6H), 0.9 (t, 3H); MS (ESI$^+$) m/z 452.0 (M+Na).

Step D1: Preparation of 5-(3-((R)-3,3-difluoro-5-((S,E)-3-hydroxyoct-1-en-1-yl)-2-oxopyrrolidin-1-yl)propyl)thiophene-2-carboxylic Acid (Example 33C)

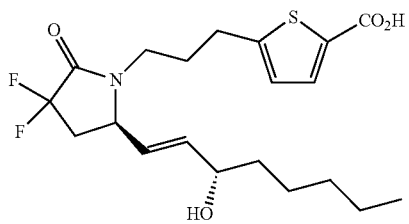 [SMILES: CCCCC[C@H](O)/C=C/[C@H]1CC(F)(F)C(=O)N1CCCc1ccc(C(=O)O)s1]

10.0 mg of a clear oil; TLC R$_f$ 0.40 (solvent system: 90:10:1 v/v dichloromethane-methanol-acetic acid); $^1$H-NMR (CDCl$_3$) δ 7.7 (d, 1H), 6.9 (d, 1H), 5.9-5.8 (m, 1H), 5.5-5.4 (m, 1H), 4.2-4.1 (m, 1H), 4.1-4.0 (m, 1H), 3.7-3.5 (m, 1H), 3.2-3.0 (m, 1H), 2.9 (t, 2H), 2.8-2.6 (m, 1H), 2.3-2.1 (m, 1H), 2.0-1.8 (m, 2H), 1.8-1.0 (m, 9H), 0.8 (t, 3H); MS (ESI$^+$) m/z 438.0 (M+Na) (ESI$^-$) m/z 414.2 (M−1).

Step D2: Preparation of 5-(3-((R)-3,3-difluoro-5-((R,E)-3-hydroxyoct-1-en-1-yl)-2-oxopyrrolidin-1-yl)propyl)thiophene-2-carboxylic Acid (Example 33D)

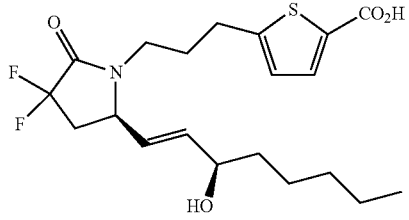 [SMILES: CCCCC[C@@H](O)/C=C/[C@H]1CC(F)(F)C(=O)N1CCCc1ccc(C(=O)O)s1]

10.0 mg of a clear oil; TLC R$_f$ 0.40 (solvent system: 90:10:1 v/v dichloromethane-methanol-acetic acid); $^1$H-NMR (CDCl$_3$) δ 7.7 (d, 1H), 6.9 (d, 1H), 5.9-5.8 (m, 1H), 5.5-5.4 (m, 1H), 4.2-4.1 (m, 1H), 4.1-4.0 (m, 1H), 3.7-3.5 (m, 1H), 3.2-3.0 (m, 1H), 2.9 (t, 2H), 2.8-2.6 (m, 1H), 2.3-2.1 (m, 1H), 2.0-1.8 (m, 2H), 1.8-1.0 (m, 9H), 0.8 (t, 3H); MS (ESI+) m/z 438.0 (M+Na) (ESI−) m/z 414.2 (M−1).

Example 34C 5-(3-((R)-3,3-Difluoro-5-((S,E)-3-hydroxy-7-phenyl-hept-1-en-1-yl)-2-oxopyrrolidin-1-yl)propyl)thiophene-2-carboxylic Acid

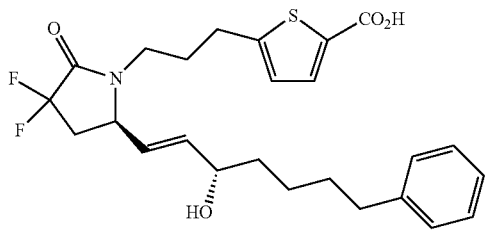 [SMILES: O=C(O)c1ccc(CCCN2C(=O)C(F)(F)C[C@@H]2/C=C/[C@@H](O)CCCCc2ccccc2)s1]

Examples 35A-35D

Steps A, B, and C: Preparation of methyl 5-(3-((R)-3,3-difluoro-5-((3R,4S,E)-3-hydroxy-4-phenylpent-1-en-1-yl)-2-oxopyrrolidin-1-yl)propyl)thiophene-2-carboxylate (Example 35A) and methyl 5-(3-((R)-3,3-difluoro-5-((3S,4S,E)-3-hydroxy-4-phenylpent-1-en-1-yl)-2-oxopyrrolidin-1-yl)propyl)thiophene-2-carboxylate (Example 35B)

Methyl 5-(3-((R)-3,3-difluoro-5-((4S,E)-3-hydroxy-4-phenylpent-1-en-1-yl)-2-oxopyrrolidin-1-yl)propyl)thiophene-2-carboxylate was prepared by the method described in Example 28, Steps A and B, except that (S)-dimethyl (2-oxo-3-phenylbutyl)phosphonate (15jb) was used instead of (S)-dimethyl (3-methyl-2-oxo-6-phenylhexyl)phosphonate (15mb(i)) in Step A.

Methyl 5-(3-((R)-3,3-difluoro-5-((4S,E)-3-hydroxy-4-phenylpent-1-en-1-yl)-2-oxopyrrolidin-1-yl)propyl)thiophene-2-carboxylate was prepared by the method described in Example 28, Steps A and B, except that (S)-dimethyl (2-oxo-3-phenylbutyl)phosphonate (15jb) was used instead of (S)-dimethyl (3-methyl-2-oxo-6-phenylhexyl)phosphonate (15mb(i)) in Step A.

The pure diastereomers of Example 35A and Example 35B were isolated following separation by prep HPLC.

Agilent Semi Prep, Chiralpak IA 250×10 mm, ultraviolet detector at 210 nm; mobile phase 90:10 heptane-ethanol, flowrate 21.2 mL/min, Example 35A (peak 2): 4 mg; colorless oil; HPLC retention time 21 min; TLC $R_f$ 0.23 (solvent system: 35:65 v/v ethyl acetate-heptane).

Example 35B (peak 1): 9 mg; colorless oil; HPLC retention time 16 min; TLC $R_f$ 0.23 (solvent system: 35:65 v/v ethyl acetate-heptane).

Step D1: Preparation of 5-(3-((R)-3,3-difluoro-5-((3R,4S,E)-3-hydroxy-4-phenylpent-1-en-1-yl)-2-oxopyrrolidin-1-yl)propyl)thiophene-2-carboxylic Acid (Example 35C)

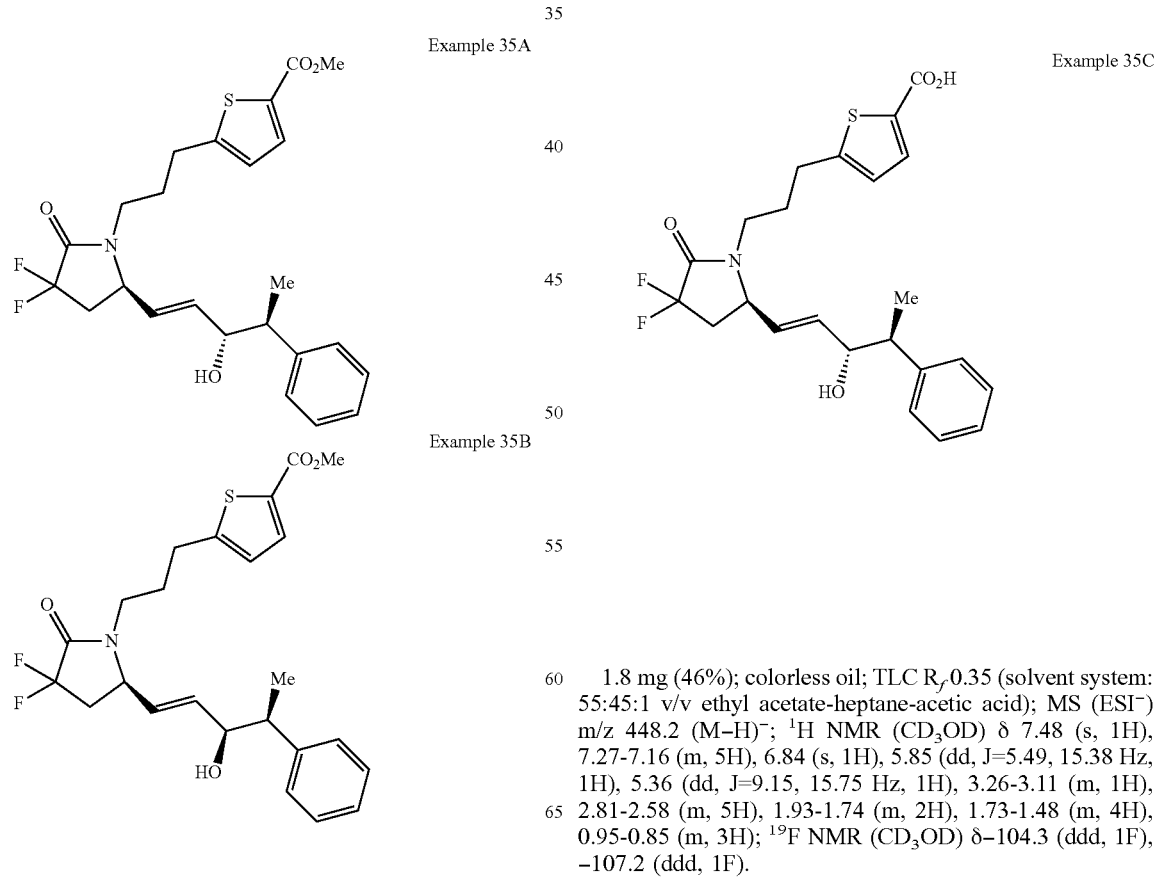

1.8 mg (46%); colorless oil; TLC $R_f$ 0.35 (solvent system: 55:45:1 v/v ethyl acetate-heptane-acetic acid); MS (ESI−) m/z 448.2 (M−H)−; $^1$H NMR (CD$_3$OD) δ 7.48 (s, 1H), 7.27-7.16 (m, 5H), 6.84 (s, 1H), 5.85 (dd, J=5.49, 15.38 Hz, 1H), 5.36 (dd, J=9.15, 15.75 Hz, 1H), 3.26-3.11 (m, 1H), 2.81-2.58 (m, 5H), 1.93-1.74 (m, 2H), 1.73-1.48 (m, 4H), 0.95-0.85 (m, 3H); $^{19}$F NMR (CD$_3$OD) δ−104.3 (ddd, 1F), −107.2 (ddd, 1F).

Step D2: Preparation of 5-(3-((R)-3,3-difluoro-5-((3S,4S,E)-3-hydroxy-4-phenylpent-1-en-1-yl)-2-oxopyrrolidin-1-yl)propyl)thiophene-2-carboxylic Acid (Example 35D)

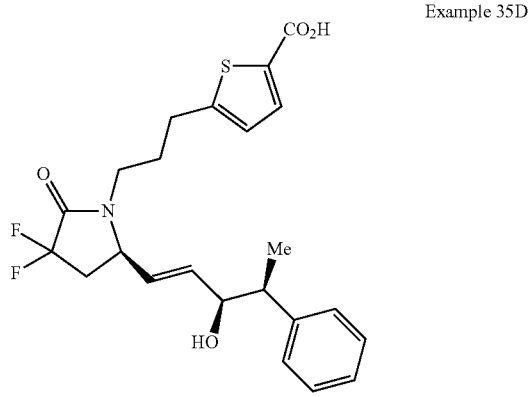 [SMILES: C[C@@H](c1ccccc1)[C@@H](O)/C=C/[C@H]1CC(F)(F)C(=O)N1CCCc1ccc(C(=O)O)s1]

Example 35D 8.7 mg (100% not pure product); colorless oil; TLC $R_f$ 0.35 (solvent system: 55:45:1 v/v ethyl acetate-heptane-acetic acid); MS (ESI⁻) m/z 448.2 (M−H)⁻.

Examples 36A-36D

Steps A, B, and C: Preparation of methyl 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylate (Example 36A) and methyl 5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylate (Example 36B)

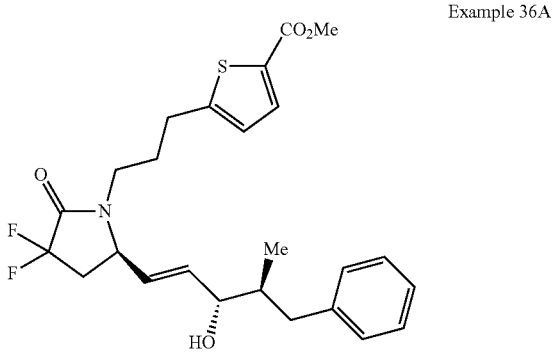 [SMILES: C[C@@H](Cc1ccccc1)[C@H](O)/C=C/[C@H]1CC(F)(F)C(=O)N1CCCc1ccc(C(=O)O)s1]

Example 36A

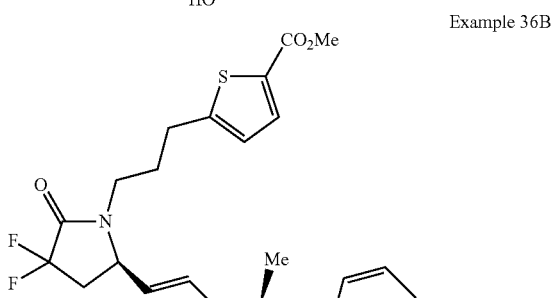

Example 36B

Methyl 5-(3-((5R)-3,3-difluoro-5-((4S,E)-3-hydroxy-4-methyl-5-phenylpent-1-en-1-yl)-2-oxopyrrolidin-1-yl)propyl)thiophene-2-carboxylate was prepared by the method described in Example 28, Steps A and B, except that (S)-dimethyl (3-methyl-2-oxo-4-phenylbutyl)phosphonate (15kb(i)) was used instead of (S)-dimethyl (3-methyl-2-oxo-6-phenylhexyl)phosphonate (15mb(i)) in Step A.

Step C: The pure diastereomers of Example 36A and Example 36B were isolated following separation by prep HPLC; Gilson Prep instrument; ultraviolet detector at 210 nm; Luna silica 5μ 21.2×250 mm column; mobile phase of heptane-ethanol (96:4 v/v), 21.2 mL/min.

Example 36A (39 mg); a clear oil; HPLC retention time 36 min; TLC $R_f$ 0.18 (solvent system: 35:65 v/v ethyl acetate-heptane); MS (ESI⁺) m/z 500 (M+Na)⁺; ¹H-NMR (CD₃OD) δ 7.59 (d, J=4.03 H, z1H), 7.27-7.22 (m, 2H), 7.19-7.10 (m, 3H), 6.91 (d, J=3.90 Hz, 1H), 5.90 (dd, J=6.41, 15.20 Hz, 1H), 5.49 (dd, J=9.34, 15.20 Hz, 1H), 4.30 (tt, J=4.17, 8.28 Hz, 1H), 3.96-3.91 (m, 1H), 3.80 (s, 3H), 3.63-3.54 (m, 1H), 3.13 (td, J=6.50, 13.37 Hz, 1H), 2.94-2.71 (m, 5H), 2.36-2.23 (m, 2H), 2.05-1.82 (m, 3H), 0.76 (d, J=6.96 Hz, 3H); ¹⁹F NMR (CD₃OD) δ−104.4 (ddd, 1F), −107.2 (ddd, 1F).

Example 36B (120 mg); a colorless oil; HPLC retention time 34 min; $R_f$ 0.23 (solvent system: 35:65 v/v ethyl acetate-heptane); MS (ESI⁺) m/z 500 (M+Na)⁺; ¹H-NMR (CD₃OD) δ 7.60 (d, J=4.03 Hz, 1H), 7.30-7.20 (m, 2H), 7.18-7.13 (m, 3H), 6.91 (d, J=3.50 Hz, 1H), 5.91 (dd, J=4.94, 15.20 Hz, 1H), 5.54-5.46 (m, 1H), 4.33-4.26 (m, 1H), 4.05-4.00 (m, 1H), 3.81 (s, 3H), 3.63-3.54 (m, 1H), 3.21-3.11 (m, 1H), 2.91-2.70 (m, 5H), 2.36-2.21 (m, 2H), 2.05-1.81 (m, 3H), 0.79 (d, J=6.59 Hz, 3H); ¹⁹F NMR (CD₃OD) δ−104.5 (ddd, 1F), −107.2 (ddd, 1F).

Step D1: Preparation of 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylic Acid (Example 36C)

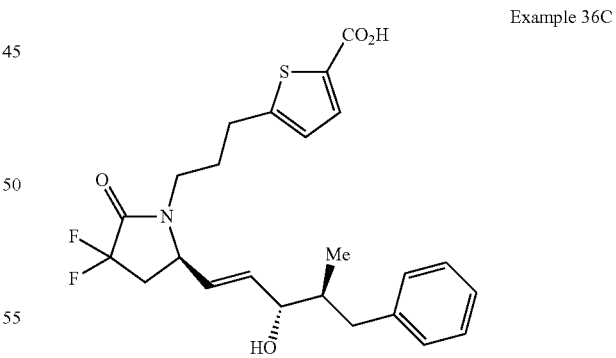

Example 36C 30 mg (97%), colorless oil; TLC $R_f$ 0.23 (solvent system: 50:50:1 v/v/v ethyl acetate-heptane-acetic acid; MS (ESI⁻) m/z 462.1 (M−H)⁻; ¹H NMR (CD₃OD) δ 7.56 (d, J=3.66 Hz, 1H), 7.27-7.22 (m, 2H), 7.17-7.12 (m, 3H), 6.89 (d, J=4.12, 8.33 Hz, 1H), 5.91 (dd, J=6.23, 15.38 Hz, 1H), 5.49 (dd, J=9.34, 15.20 Hz, 1H), 4.30 (tt, J=4.12, 8.33 Hz, 1H), 3.95 (dt, J=1.10, 6.04 Hz, 1H), 3.63-3.55 (m, 1H), 3.19-3.09 (m, 1H), 2.94-2.61 (m, 5H), 2.36-2.23 (m, 2H), 2.06-1.82 (m, 3H), 0.77 (d, J=6.59 Hz, 3H); ¹⁹F NMR (CD₃OD) δ−104.3

(ddd, 1F), −107.2 (ddd, 1F); [α]$^T_λ$=α/cl, [α]$^{21.9}_D$=0.025/ (0.01501 g/2 mL)(0.5)=+6.66 (c=0.75, CHCl$_3$).

Step D2: Preparation of 5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylic Acid (Example 36D)

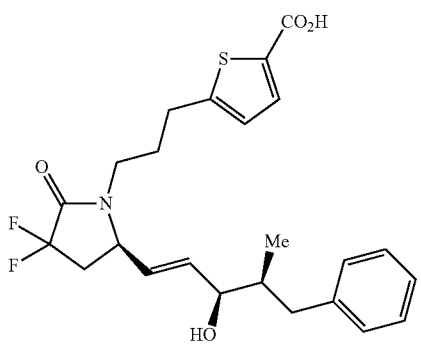

Example 36D 68 mg, colorless oil; TLC R$_f$ 0.256 (solvent system: 50:50:1 v/v/v ethyl acetate-heptane-acetic acid; MS (ESI⁻) m/z 462.1 (M−H)⁻; ¹H NMR (CD$_3$OD) δ 7.57 (d, J=3.66 1H, Hz), 7.30-7.20 (m, 2H), 7.18-7.12 (m, 3H), 6.89 (d, J=3.91 Hz, 1H), 5.91 (dd, J=4.94, 15.20 Hz, 1H), 5.50 (dd, J=9.34, 15.20 Hz, 1H), 4.33-4.27 (m, 1H), 4.05-4.01 (m, 1H), 3.64-3.55 (m, 1H), 3.27-3.12 (m, 1H), 2.91-2.69 (m, 5H), 2.37-2.15 (m, 2H), 2.05-1.81 (m, 3H), 0.80 (d, J=6.59 Hz, 3H); ¹⁹F NMR (CD$_3$OD) δ−104.4 (ddd, 1F), −107.2 (ddd, 1F); [α]$^T_λ$=α/cl, [α]$^{21.9}_D$=−0.142/(0.01838 g/1.5 mL) (0.5)=−23.17 (c=1.22, CHCl$_3$).

Examples 37A-37D

Steps A, B, and C: Preparation of methyl 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylate (Example 37A) and methyl 5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylate (Example 37B)

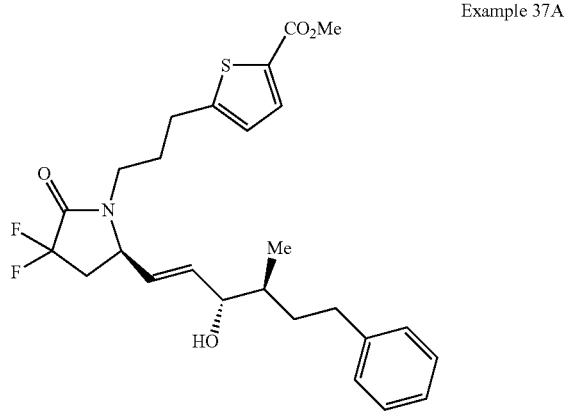 [SMILES: C[C@@H](CCc1ccccc1)[C@H](O)/C=C/[C@H]1CC(F)(F)C(=O)N1CCCc1ccc(C(=O)O)s1]

Example 37A

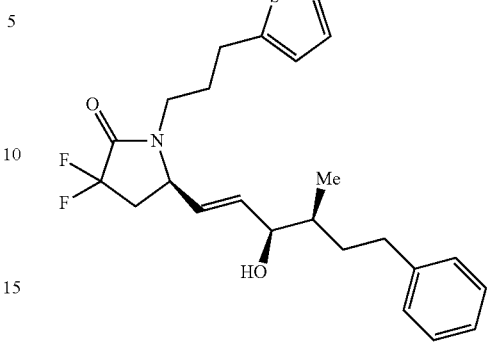

Example 37B

Methyl 5-(3-((R)-3,3-difluoro-5-((4S,E)-3-hydroxy-4-methyl-6-phenylhex-1-en-1-yl)-2-oxopyrrolidin-1-yl)propyl)thiophene-2-carboxylate was prepared by the method described in Example 28, Steps A and B, except that (S)-dimethyl (3-methyl-2-oxo-5-phenylpentyl)phosphonate (151b(i)) was used instead of (S)-dimethyl (3-methyl-2-oxo-6-phenylhexyl)phosphonate (15mb(i)) in Step A.

Step C: The pure diastereomers of Example 37A and Example 37B were isolated following separation by prep HPLC; Gilson Prep instrument; ultraviolet detector at 210 nm; Luna silica 5μ 21.2×250 mm column; mobile phase of heptane-ethanol (96:4 v/v), 21.2 mL/min.

Example 37A (35 mg): as a colorless oil; HPLC retention time 19 min; TLC R$_f$ 0.18 (solvent system: 35:65 v/v ethyl acetate-heptane); MS (ESI⁺) m/z 514.2 (M+Na)⁺; ¹H NMR (CD$_3$OD) δ 7.61 (d, J=3.83 Hz, 1H), 7.25-7.21 (m, 2H), 7.17-7.10 (m, 3H), 6.89 (d, J=3.83 Hz, 1H), 5.82 (dd, J=6.59, 15.38 Hz, 1H), 5.45 (dd, J=9.34, 15.20 Hz, 1H), 4.95-4.87 (m, 1H), 4.27 (tt, J=4.21, 8.24 Hz, 1H), 3.95 (t, J=6.23 Hz, 1H), 3.82 (s, 3H), 3.58-3.41 (m, 1H), 3.13-3.04 (m, 1H), 2.90-2.67 (m, 5H), 2.52 (ddd, J=6.59, 9.98, 13.82 Hz, 1H), 2.34-2.24 (m, 1H), 2.00-1.86 (m, 2H), 1.79-1.70 (m, 1H), 1.64-1.56 (m, 1H), 1.40-1.23 (m, 1H), 0.91 (d, J=6.59 Hz, 3H); ¹⁹F NMR (CD$_3$OD) δ−104.4 (ddd, 1F), −107.1 (ddd, 1F).

Example 37B (164 mg): colorless oil; HPLC retention time 16 min; TLC R$_f$ 0.22 (solvent system: 35:65 v/v ethyl acetate-heptane); MS (ESI⁺) m/z 514.2 (M+Na)⁺; ¹H NMR (CD$_3$OD) δ 7.61 (d, J=3.66 Hz, 1H), 7.25-7.10 (m, 5H), 6.88 (d, J=3.97 Hz, 1H), 5.89 (dd, J=4.94, 15.20 Hz, 1H), 5.47 (dd, J=9.34, 15.20 Hz, 1H), 4.32-4.25 (m, 1H), 4.08-4.01 (m, 1H), 3.83-3.82 (m, 3H), 3.59-3.47 (m, 1H), 3.12 (dddd, J=1.46, 5.77, 7.87, 13.82 Hz, 1H), 2.87-2.65 (m, 5H), 2.61-2.52 (m, 1H), 2.25 (dtd, 1H), 2.00-1.75 (m, 3H), 1.59 (dtt, 1H), 1.43-1.32 (m, 1H), 0.95-0.90 (m, 3H); ¹⁹F NMR (CD$_3$OD) δ−104.6 (ddd, 1F), −107.1 (ddd, 1F).

Step D1: Preparation of 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylic Acid (Example 37C)

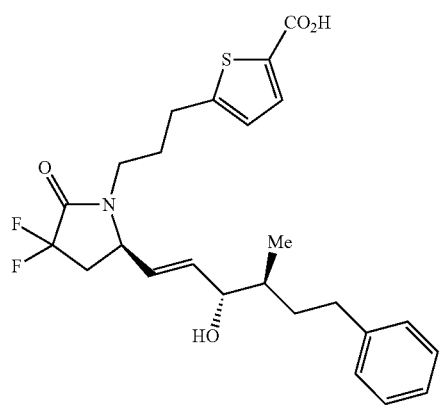

Example 37C 21 mg (81%), colorless oil; TLC $R_f$ 0.24 (solvent system: 50:50:1 v/v/v ethyl acetate-heptane-acetic acid); MS (ESI⁻) m/z 477.56 (M−H)⁻; ¹H NMR (CD₃OD) δ 7.57 (d, J=3.66 Hz, 1H), 7.25-7.10 (m, 5H), 6.86 (d, J=3.88 Hz, 1H), 5.88-5.80 (m, 1H), 5.44 (dd, J=9.15, 15.38 Hz, 1H), 4.27 (tt, J=4.21, 8.42 Hz, 1H), 3.98-3.93 (m, 1H), 3.59-3.46 (m, 1H), 3.13-3.04 (m, 1H), 2.90-2.67 (m, 5H), 2.53 (ddd, J=6.59, 9.80, 13.64 Hz, 1H), 2.34-2.21 (m, 1H), 2.03-1.84 (m, 2H), 1.80-1.71 (m, 1H), 1.65-1.55 (m, 1H), 1.42-1.28 (m, 1H), 0.92 (d, J=6.59 Hz, 3H); ¹⁹F NMR (CD₃OD) δ−104.5 (ddd, 1F), −107.2 (ddd, 1F); $[\alpha]^T_\lambda=\alpha/cl$, $[\alpha]^{21.9}_D=-0.049/(0.0158 \text{ g}/1.5 \text{ mL})(0.5)=-9.30$ (c=1.05, CHCl₃).

Step D2: Preparation of 5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylic Acid (Example 37D)

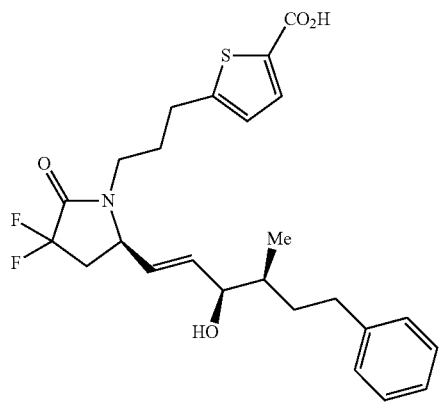

Example 37D 64 mg (43%); colorless oil; TLC $R_f$ 0.24 (solvent system: 50:50:1 v/v/v ethyl acetate-heptane-acetic acid); MS (ESI⁻) m/z 477.56 (M−H)⁻; ¹H NMR (CD₃OD) δ 7.58 (d, J=3.66 Hz, 1H), 7.26-7.10 (m, 5H), 6.87 (d, J=3.66 Hz, 1H), 5.89 (dd, J=5.13, 15.38 Hz, 1H), 5.48 (dd, J=9.34, 15.20 Hz, 1H), 4.29 (tt, J=0.35, 8.28 Hz, 1H), 4.05 (t, J=4.03 Hz, 1H), 3.60-3.52 (m, 1H), 3.17-3.07 (m, 1H), 2.87-2.65 (m, 5H), 2.57 (ddd, J=6.41, 9.89, 13.73 Hz, 1H), 2.32-2.19 (m, 1H), 2.02-1.75 (m, 3H), 1.64-1.55 (m, 1H), 1.44-1.32 (m, 1H), 0.97-0.88 (m, 3H); ¹⁹F NMR (CD₃OD) δ−104.4 (ddd, 1F), −107.1 (ddd, 1F); $[\alpha]^T_\lambda=\alpha/cl$, $[\alpha]^{21.9}_D=-0.170/(0.01556 \text{ g}/1.5 \text{ mL})(0.5)=-32.755$ (c=1.04, CHCl₃).

Examples 38A-38D

Steps A, B, and C: Preparation of methyl 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylate (Example 38A) and methyl 5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylate (Example 38B)

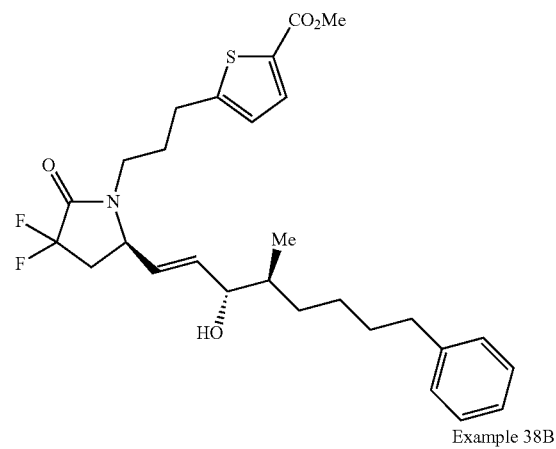

Example 38A

Example 38B

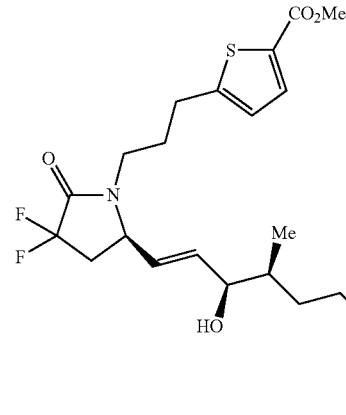

Methyl 5-(3-((5R)-3,3-difluoro-5-((4S,E)-3-hydroxy-4-methyl-8-phenyloct-1-en-1-yl)-2-oxopyrrolidin-1-yl)propyl)thiophene-2-carboxylate was prepared by the method described in Example 28, Steps A and B, except that (S)-dimethyl (3-methyl-2-oxo-7-phenylheptyl)phosphonate (15nb(i)) was used instead of (S)-dimethyl (3-methyl-2-oxo-6-phenylhexyl)phosphonate (15mb(i)) in Step A.

Step C: The pure diastereomers of Example 38A and Example 38B were isolated following separation by prep HPLC.

Agilent 1100 Prep instrument; ultraviolet detector at 210 nm; Luna silica 511 21.2×250 mm column; mobile phase of heptane-ethanol (96:4 v/v), 21.2 mL/min.

Example 38A (61 mg); a clear oil; HPLC retention time 29 min; $R_f$ 0.22 (solvent system: 35:65 v/v ethyl acetate-heptane); MS (ESI$^+$) m/z 542.2 (M+Na)$^+$; $^1$H NMR (CD$_3$OD) δ 7.61 (d, J=3.66 Hz, 1H), 7.26-7.19 (m, 2H), 7.17-7.10 (m, 3H), 6.91 (d, J=3.66 Hz, 1H), 5.82 (dd, J=6.59, 15.38 Hz, 1H), 5.42 (dd, J=9.15, 15.38 1H, Hz), 4.30-4.24 (m, 1H), 3.90 (t, J=6.04 Hz, 1H), 3.82 (s, 3H), 3.59-3.47 (m, 1H), 3.16-3.02 (m, 1H), 2.93-2.73 (m, 3H), 2.65-2.53 (m, 2H), 2.34-2.20 (m, 1H), 2.02-1.87 (m, 2H), 1.62-1.36 (m, 5H), 1.35-1.20 (m, 2H), 1.16-1.04 (m, 1H), 0.81 (d, J=6.59 Hz3H); $^{19}$F NMR (CD$_3$OD) δ−104.4 (ddd, 1F), −107.2 (ddd, 1F).

Example 38B (222 mg); a colorless oil; HPLC retention time 34 min; $R_f$ 0.26 (solvent system: 35:65 v/v ethyl acetate-heptane); MS (ESI$^+$) m/z 542.2 (M+Na)$^+$; $^1$H NMR (CD$_3$OD) δ 7.62 (d, J=4.03 Hz, 1H), 7.26-7.18 (m, 2H), 7.16-7.09 (m, 3H), 6.91 (d, J=3.94 Hz, 1H), 5.88 (dd, J=5.13, 15.38 Hz, 1H), 5.46 (dd, J=9.34, 15.56 Hz, 1H), 4.32-4.25 (m, 1H), 4.01-3.96 (m, 1H), 3.82 (s, 3H), 3.61-3.53 (m, 1H), 3.17-3.09 (m, 1H), 2.90-2.68 (m, 3H), 2.58 (t, J=7.69 Hz, 2H), 2.32-2.18 (m, 1H), 2.02-1.88 (m, 2H), 1.64-1.47 (m, 3H), 1.40-1.24 (m, 4H), 1.11-0.99 (m, 1H), 0.84 (d, J=6.96 Hz, 3H); $^{19}$F NMR (CD$_3$OD) δ−104.5 (ddd, 1F), −107.2 (ddd, 1F).

Step D1: Preparation of 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylic Acid (Example 38C)

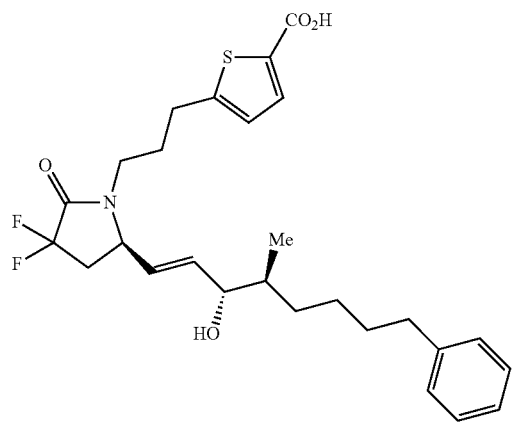

Example 38C 28 mg, colorless oil; TLC $R_f$ 0.21 (solvent system: 50:50:1 v/v/v ethyl acetate-heptane-acetic acid; MS (ESI$^-$) m/z 504.1 (M−H)$^-$; $^1$H NMR (CD$_3$OD) δ 7.58 (d, J=3.66 Hz, 1H), 7.27-7.09 (m, 5H), 6.89 (d, J=3.99 Hz, 1H), 5.84 (dd, J=6.59, 15.01 Hz, 1H), 5.43 (dd, J=9.15, 15.38 Hz, 1H), 4.32-4.25 (m, 1H), 3.92 (t, J=6.07 Hz, 1H), 3.61-3.45 (m, 1H), 3.17-3.02 (m, 1H), 2.94-2.70 (m, 4H), 2.60 (dt, J=3.84, 7.60 Hz, 2H), 2.35-2.21 (m, 1H), 2.05-1.88 (m, 2H), 1.63-1.37 (m, 5H), 1.34-1.22 (m, 1H), 1.17-1.04 (m, 1H), 0.83 (d, J=6.59 Hz, 3H); $^{19}$F NMR (CD$_3$OD) δ−100.5 (ddd, 1F), −103.2 (ddd, 1F); $[α]^T_λ$=α/cl, $[α]^{21.9}_D$=−0.032/(0.01617 g/1.5 mL)(0.5)=−5.937 (c=1.08, CHCl$_3$).

Step D2: Preparation of 5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylic Acid (Example 38D)

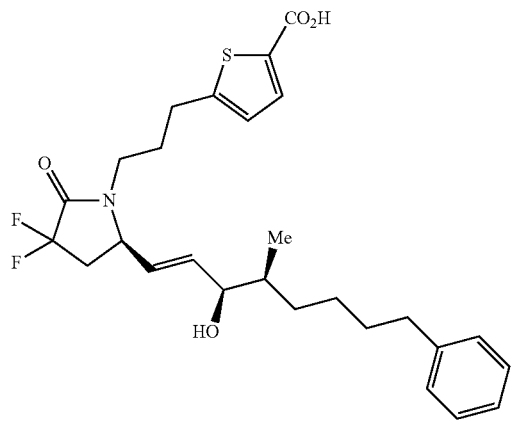

Example 38D 170 mg (88%), colorless oil; TLC $R_f$ 0.19 (solvent system: 50:50:1 v/v/v ethyl acetate-heptane-acetic acid; MS (ESI$^-$) m/z 504.1 (M−H)$^-$; $^1$H NMR (CD$_3$OD) δ 7.58 (d, J=3.66 Hz, 1H), 7.26-7.18 (m, 2H), 7.16-7.09 (m, 3H), 6.89 (d, J=3.66 Hz, 1H), 5.89 (dd, J=5.13, 15.38 Hz, 1H), 5.46 (dd, J=8.79, 15.38 Hz, 1H), 4.29 (tt, J=4.26, 8.38 Hz, 1H), 3.99 (dt, J=1.46, 4.76 Hz, 1H), 3.62-3.51 (m, 1H), 3.18-3.09 (m, 1H), 2.92-2.67 (m, 4H), 2.58 (t, J=7.69 Hz, 2H), 2.25 (dtd, 1H), 2.03-1.88 (m, 2H), 1.54-1.26 (m, 6H), 1.12-0.89 (m, 1H), 0.84 (d, J=6.96 Hz, 3H); $^{19}$F NMR (CD$_3$OD) δ−104.4 (ddd, 1F), −107.2 (ddd, 1F); $[α]^T_λ$=α/cl, $[α]^{21.9}_D$=−0.134/(0.017 g/2 mL)(0.5)=−31.53 (c=0.85, CHCl$_3$).

Example 39A-39D

Steps A, B, and C: Preparation of methyl 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylate (Example 39A) and methyl 5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylate (Example 39B)

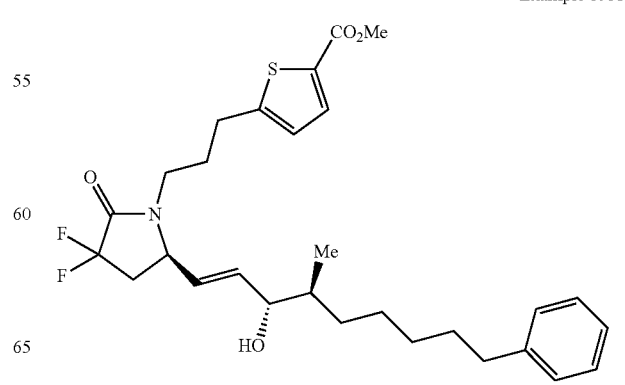

Example 39A

Example 39B

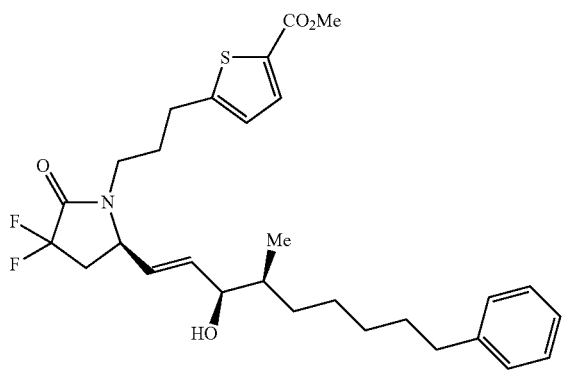

Methyl 5-(3-((R)-3,3-difluoro-5-((4S,E)-3-hydroxy-4-methyl-9-phenylnon-1-en-1-yl)-2-oxopyrrolidin-1-yl)propyl)thiophene-2-carboxylate was prepared by the method described in Example 28, Steps A and B, except that (S)-dimethyl (3-methyl-2-oxo-8-phenyloctyl)phosphonate (15ob(i)) was used instead of (S)-dimethyl (3-methyl-2-oxo-6-phenylhexyl)phosphonate (15mb(i)) in Step A.

Step C: The pure diastereomers of Example 39A and Example 39B were isolated following separation by prep HPLC.

Gilson Prep instrument; ultraviolet detector at 210 nm; Luna silica 5μ 21.2×250 mm column; mobile phase of heptane-ethanol (96:4 v/v), 21.2 mL/min.

Example 39A: 46 mg; colorless oil; HPLC retention time 22.5 min; TLC $R_f$ 0.24 (solvent system: 35:65 v/v ethyl acetate-heptane); MS (ESI+) m/z 556.2 (M+Na)+; $^1$H NMR (CD$_3$OD) δ 7.62 (d, J=3.66 Hz, 1H), 7.25-7.19 (m, 2H), 7.16-7.10 (m, 3H), 6.90 (d, J=3.86 Hz, 1H), 5.82 (dd, J=6.59, 15.38 Hz, 1H), 5.44 (dd, J=9.15, 15.38 Hz, 1H), 4.30-4.24 (m, 1H), 3.93-3.89 (m, 1H), 3.82 (s, 3H), 3.58-3.47 (m, 1H), 3.13-3.05 (m, 1H), 2.91-2.73 (m, 3H), 2.58 (t, J=7.51 Hz, 2H), 2.27 (dtd, 1H), 2.01-1.87 (m, 2H), 1.64-1.51 (m, 3H), 1.44-1.21 (m, 6H), 1.03 (q, J=9.03 Hz, 1H), 0.82 (d, J=6.96 Hz, 3H); $^{19}$F NMR (CD$_3$OD) δ –104.4 (ddd, 1F), –107.2 (ddd, 1F).

Example 39B: 211 mg; colorless oil; HPLC retention time 19 min; TLC $R_f$ 0.27 (solvent system: 35:65 v/v ethyl acetate-heptane); MS (ESI+) m/z 556.2 (M+Na)+.

Step D1: Preparation of 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylic Acid (Example 39C)

Example 39C

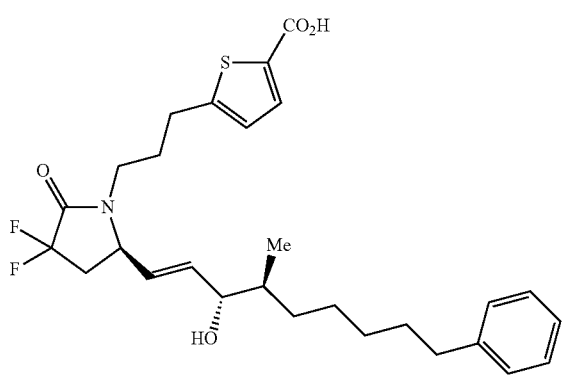

3 mg (8%); colorless oil; TLC $R_f$ 0.13 (solvent system: 50:50:1 v/v/v ethyl acetate-heptane-acetic acid; MS (ESI−) m/z 518.2 (M−H)−; $^1$H NMR (CD$_3$OD) δ 7.51 (d, J=3.66 Hz, 1H), 7.28-7.18 (m, 2H), 7.17-7.08 (m, 3H), 6.84 (d, J=3.66 Hz, 1H), 5.83 (dd, J=6.59, 15.38 Hz, 1H), 5.44 (dd, J=9.15, 15.38 Hz, 1H), 4.27 (tt, J=4.17, 8.47 Hz, 1H), 3.91 (t, J=6.04 Hz, 1H), 3.57-3.43 (m, 1H), 3.17-2.99 (m, 1H), 2.89-2.71 (m, 3H), 2.65-2.51 (m, 2H), 2.29-2.19 (m, 1H), 2.03-1.88 (m, 2H), 1.36-1.20 (m, 9H), 1.12-1.01 (m, 1H), 0.89-0.82 (m, 3H); $^{19}$F NMR (CD$_3$OD) δ –104.4 (ddd, 1F), –107.2 (ddd, 1F).

Step D2: Preparation of 5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylic Acid (Example 39D)

Example 39D

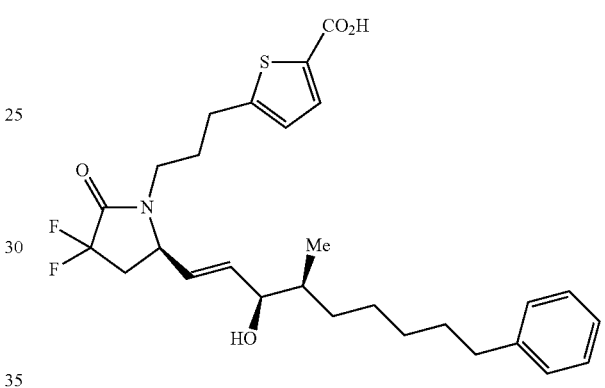

90 mg (46%); colorless oil; TLC $R_f$ 0.2 (solvent system: 50:50:1 v/v/v ethyl acetate-heptane-acetic acid; MS (ESI−) m/z 518.2 (M−H)−; $[\alpha]T_\lambda=\alpha/cl$, $[\alpha]^{21.9}_D=-0.177/(0.026$ g/2 mL)(0.5)=−27.23° (c=1.3, CHCl$_3$).

Example 92

Radioligand Binding Assay for the Evaluation of the Affinity of Compounds for the Agonist Site of the Human Prostanoid EP$_4$ Receptor in Transfected HEK-293 Cells Assay Volume and Format:

200 μl in 96-well plate

Cell membrane homogenates (20 μg protein) are incubated for 120 min at 22° C. with 0.5 nM [$^3$H]PGE$_2$ in the absence or presence of the test compound in a buffer containing 10 mM MES/KOH (pH 6.0), 10 mM MgCl$_2$ and 1 mM EDTA.

Nonspecific binding is determined in the presence of 10 μNA PGE$_2$.

Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The standard reference compound is PGE$_2$, which is tested in each experiment at several concentrations to obtain a competition curve from which its IC$_{50}$ is calculated.

Example 93

Functional Cellular Assays (STEP Plate Format)

Both SEAP activity assay and cAMP level assay for $EP_2$ or $EP_4$ agonist were performed on $EP_2/EP_4$ STEP (Surface Transfection and Expression Protocol) plates (from Originus®) which are coated with both rat $EP_2$ or $EP_4$ receptor and secreted alkaline phosphatase (SEAP) reporter constructs. Cells grown on the STEP complex will express $EP_2$ or $EP_4$ at the cell surface. Binding of agonists to $EP_2$ or $EP_4$ initiates a signal transduction cascade results in a transient increase in cAMP and an increase in expression of SEAP which is secreted into the cell culture media. cAMP levels were then measured with an ELISA assay and SEAP activity was measured with a luminescence-based alkaline phosphatase substrate.

Procedure of SEAP Activity Assay for $EP_2/EP_4$ Agonist

1. Seed cells on an $EP_2$ or $EP_4$ STEP plate at a density of 40,000-80,000 cells/well in 200 µl of reduced serum medium containing 0.5% FBS. Place the plate in a 37° C. incubator with 5% $CO_2$ and incubate overnight.
2. After 16-18 hours of incubation, aspirate the culture media from each well.
3. Add 200 µl of culture medium containing different concentration of test compounds to the assigned wells. For each test compound, at least 8 concentrations starting at highest 10 µM and lowest 0.01 pM were tested. In addition each concentration had triplicates. A $PGE_2$ curve (concentrations from lowest to highest, 0 pM, 0.384 pM, 1.92 pM, 9.6 pM, 48 pM, 240 pM, 1200 pM, and 6000 pM) was always run in parallel with test compounds.
4. After 6-8 hours of stimulation with test compounds and $PGE_2$, 10 µl of culture media from each well was transferred to a corresponding well of a 96-well solid black plate. Cover the plate with the lid.
5. Inactivate the endogenous alkaline phosphatase by heating the samples at 65° C. for 30 minutes.
6. Add 50 µl of luminescence-based alkaline phosphatase substrate (Michigan Diagnostics, LLC, Cat # SAP450101) to each well.
7. Measure the SEAP activity by reading the luminescent signal from each well.
8. The data was analyzed and the $EC_{50}$ for $PGE_2$ and each test compound was calculated using GraphPad Prism 5.

Procedure of cAMP Assay for $EP_2/EP_4$ Agonist

1. Seed cells on an $EP_2$ or $EP_4$ STEP plate at a density of 40,000-80,000 cells/well in 200 µL of reduced serum medium containing 0.5% FBS. Place the plate in a 37° C. incubator with 5% $CO_2$ and incubate overnight.
2. After 16-18 hours of incubation, aspirate the culture media from each well.
3. Add 200 µl of culture medium containing 500 µM IBMX (an inhibitor of cAMP phosphodiesterase) and different concentration of test compounds to the assigned wells. For each test compound, at least 8 concentrations starting at highest 10 µM and lowest 0.01 pM were tested. In addition each concentration had triplicates. A $PGE_2$ curve (concentrations from lowest to highest, 0 pM, 0.384 pM, 1.92 pM, 9.6 pM, 48 pM, 240 pM, 1200 pM, and 6000 pM) was always run in parallel with test compounds.
4. Incubate the cells in a cell culture incubator for 30 minutes.
5. Centrifuge the plate at 1,000×rpm for 10 minutes.
6. Aspirate the supernatant.
7. Add 100 µL of EIA assay buffer to each well and put the plate with the lid in a −80° C. freezer. Freeze the sample in the −80° C. for at least one hour.
8. Take the plate out from the −80° C. freezer and leave it at room temperature to thaw completely.
9. Centrifuge the plate at 1,000×rpm for 10 minutes.
10. Pick up 50 µl of supernatant from each well for cAMP level measurement, using an ELISA assay kit from Cayman chemical, Item #581001.
11. The data was analyzed and the $EC_{50}$ for $PGE_2$ and each test compound was calculated using GraphPad Prism 5.

Specificity of $EP_2/EP_4$ Agonist on the Receptors

Compounds demonstrating potency in SEAP or cAMP functional assays were confirmed for receptor agonist specificity by incubation of the cells with the compound together with an $EP_2$ specific antagonist AH-6809 or an $EP_4$ specific antagonist L-161,982. Compounds that showed agonist activity for either $EP_2$ or $EP_4$ are specific if the stimulation effect was diminished when incubated together with their receptor specific antagonist.

TABLE 1

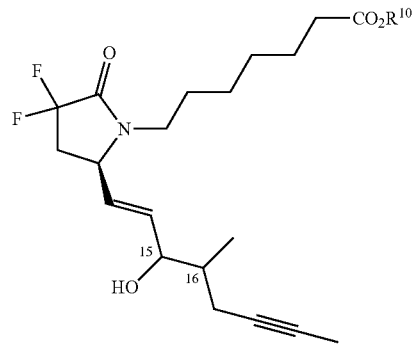

| | Absolute Configuration | | | hEP$_4$ receptor binding | | STEP cell functional assay EC$_{50}$s (nM) | | |
|---|---|---|---|---|---|---|---|---|
| Example No. | C-15 | C-16 | $R^{10}$ | IC$_{50}$ (nM) | K$_i$ (nM) | cAMP/EP$_4$ | SEAP/EP$_4$ | SEAP/EP$_2$ |
| PGE$_2$ | | | | 0.38 ± 0.07 (N = 10) | 0.14 ± 0.02 (N = 10) | 0.48 ± 0.36 (N = 22) | 0.05 ± 0.03 (N = 38) | 59 ± 17 (N = 15) |
| PGE$_1$ | | | | | | 0.22 ± 0.04 (N = 5) | | 16.5 |

TABLE 1-continued

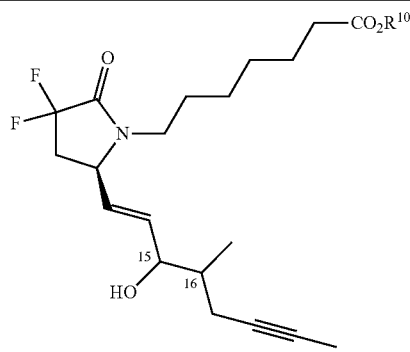

| Example No. | Absolute Configuration | | $R^{10}$ | hEP$_4$ receptor binding | | STEP cell functional assay EC$_{50}$s (nM) | | |
| --- | --- | --- | --- | --- | --- | --- | --- | --- |
| | C-15 | C-16 | | IC$_{50}$ (nM) | K$_i$ (nM) | cAMP/EP$_4$ | SEAP/EP$_4$ | SEAP/EP$_2$ |
| 1A | α | β | Me | | | | | |
| 1B | α | α | Me | | | | | |
| 1C | β | α/β | Me | | | | | |
| 1D | β | β | Me | | | | | |
| 1E | β | α | Me | | | | | |
| 1F | α | β | H | 1.2 | 0.44 | 0.15 | 0.059 | |
| 1G | α | α | H | | | | | |
| 1H | β | β | H | | | | | |
| 1I | β | α | H | | | | | |

α = ⫽ or ⫽  β = ╱ or ╱

TABLE 2

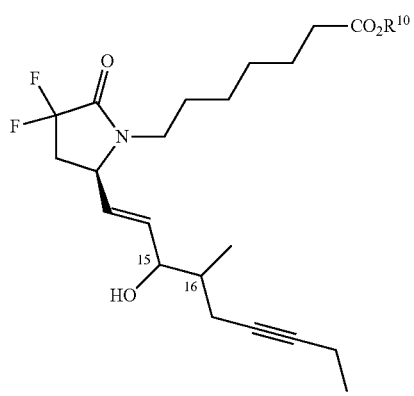

| Example No. | Absolute Configuration | | $R^{10}$ | hEP$_4$ receptor binding | | STEP cell functional assay EC$_{50}$s (nM) | | |
| --- | --- | --- | --- | --- | --- | --- | --- | --- |
| | C-15 | C-16 | | IC$_{50}$ (nM) | K$_i$ (nM) | cAMP/EP$_4$ | SEAP/EP$_4$ | SEAP/EP$_2$ |
| 2A | α | β | Me | | | | | |
| 2B | β | β | Me | | | | | |
| 2C | α | β | H | 1.3 | 0.49 | 0.24 ± 0.08 (N = 11) | 0.038 ± 0.037 (N = 4) | >1,000 |
| 2D | β | β | H | | | | | |

α = ⫽ or ⫽  β = ╱ or ╱

TABLE 3

|  | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/EP$_4$ | SEAP/EP$_4$ | SEAP/EP$_2$ |
| 3A | α | β | Me | | | | | |
| 3B | α | α | Me | | | | | |
| 3C | β | α/β | Me | | | | | |
| 3D | β | β | Me | | | | | |
| 3E | β | α | Me | | | | | |
| 3F | α | β | H | | | | | |
| 3G | α | α | H | | | | | |
| 3H | β | β | H | | | | | |
| 3I | β | α | H | | | | | |

α = ⫽ or ⫽   β = ╱ or ╱

TABLE 4

|  | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/EP$_4$ | SEAP/EP$_4$ | SEAP/EP$_2$ |
| 4A | α | β | Me | | | | | |
| 4B | α | α | Me | | | | | |
| 4C | β | α/β | Me | | | | | |
| 4D | β | β | Me | | | | | |
| 4E | β | α | Me | | | | | |
| 4F | α | β | H | | | | | |
| 4G | α | α | H | | | | | |
| 4H | β | β | H | | | | | |
| 4I | β | α | H | | | | | |

α = ⫽ or ⫽   β = ╱ or ╱

TABLE 5

|  | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/EP$_4$ | SEAP/EP$_4$ | SEAP/EP$_2$ |
| 5A | α | β | Me | | | | | |
| 5B | α | α | Me | | | | | |
| 5C | β | α/β | Me | | | | | |
| 5D | β | β | Me | | | | | |
| 5E | β | α | Me | | | | | |
| 5F | α | β | H | | | | | |
| 5G | α | α | H | | | | | |
| 5H | β | β | H | | | | | |
| 5I | β | α | H | | | | | |

α = ⟋ or ⟋   β = ⟋ or ⟋

TABLE 6

|  | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/EP$_4$ | SEAP/EP$_4$ | SEAP/EP$_2$ |
| 6A | α | β | Me | | | | | |
| 6B | α | α | Me | | | | | |
| 6C | β | α/β | Me | | | | | |
| 6D | α | β | H | 2.4 | 0.89 | 0.023 ± 0.019 (N = 9) | <0.001 | >1,000 |
| 6E | α | α | H | | | | | |
| 6F | β | α/β | H | | | | | |

α = ⟋ or ⟋   β = ⟋ or ⟋

TABLE 7

| | Absolute Configuration | | hEP$_4$ receptor binding | | STEP cell functional assay EC$_{50}$s (nM) | | |
|---|---|---|---|---|---|---|---|
| Example No. | C-15 | R$^{10}$ | IC$_{50}$ (nM) | K$_i$ (nM) | cAMP/EP$_4$ | SEAP/EP$_4$ | SEAP/EP$_2$ |
| 7A | α | Me | | | | | |
| 7B | β | Me | | | | | |
| 7C | α | H | | | | | |
| 7D | β | H | | | | | |

α = ⦀ or ⦀   β = / or /

TABLE 8

| | Absolute Configuration | | hEP$_4$ receptor binding | | STEP cell functional assay EC$_{50}$s (nM) | | |
|---|---|---|---|---|---|---|---|
| Example No. | C-15 | R$^{10}$ | IC$_{50}$ (nM) | K$_i$ (nM) | cAMP/EP$_4$ | SEAP/EP$_4$ | SEAP/EP$_2$ |
| 8A | α | Me | | | | | |
| 8B | β | Me | | | | | |
| 8C | α | H | | | | | |
| 8D | β | H | | | | | |

α = ⦀ or ⦀   β = / or /

TABLE 9

[Structure: difluoro-pyrrolidinone with CO₂R¹⁰ chain and hydroxy-alkenyl side chain, positions labeled 15 and 16]

| Example No. | Absolute Configuration C-15 | R¹⁰ | hEP₄ receptor binding | | STEP cell functional assay EC₅₀s (nM) | | |
|---|---|---|---|---|---|---|---|
| | | | IC₅₀ (nM) | $K_i$ (nM) | cAMP/EP₄ | SEAP/EP₄ | SEAP/EP₂ |
| 9A | α | Me | | | | | |
| 9B | β | Me | | | | | |
| 9C | α | H | 0.57 | 0.21 | 0.37 | 0.059 | 205 ± 124 (N = 2) |
| 9D | β | H | | | | | |

α = ⫽ or ⫽   β = ∕ or ∕

TABLE 10

[Structure: difluoro-pyrrolidinone with CO₂R¹⁰ chain and hydroxy-alkenyl side chain with phenyl group, positions labeled 15 and 16]

| Example No. | Absolute Configuration C-15 | R¹⁰ | hEP₄ receptor binding | | STEP cell functional assay EC₅₀s (nM) | | |
|---|---|---|---|---|---|---|---|
| | | | IC₅₀ (nM) | $K_i$ (nM) | cAMP/EP₄ | SEAP/EP₄ | SEAP/EP₂ |
| 10A | α | Me | | | | | |
| 10B | β | Me | | | | | |
| 10C | α | H | 4.9 | 1.8 | 1.10 | 0.010 | |
| 10D | β | H | | | | | |

α = ⫽ or ⫽   β = ∕ or ∕

TABLE 11

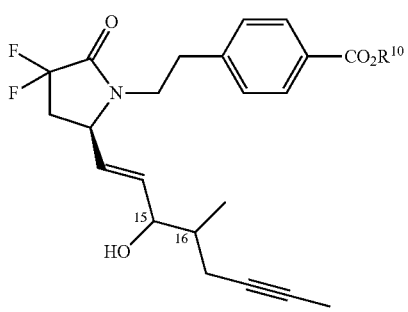

| | | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/ EP$_4$ | SEAP/ EP$_4$ | SEAP/ EP$_2$ |
| 11A | α | β | Me | | | | | |
| 11B | α | α | Me | | | | | |
| 11C | β | α/β | Me | | | | | |
| 11D | α | β | H | | | | | |
| 11E | α | α | H | | | | | |
| 11F | β | α/β | H | | | | | |

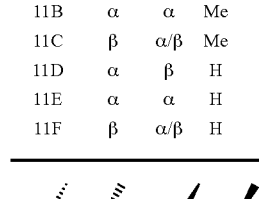

Absolute Configuration

TABLE 12

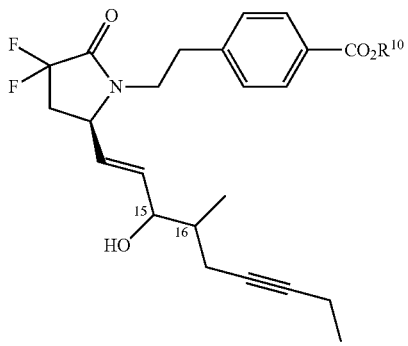

| | | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/ EP$_4$ | SEAP/ EP$_4$ | SEAP/ EP$_2$ |
| 12A | α | β | Me | | | | | |
| 12B | α | α | Me | | | | | |
| 12C | β | α/β | Me | | | | | |
| 12D | α | β | H | 0.32 | 0.12 | 0.047 | 0.035 | 1,630 |
| 12E | α | α | H | | | | | |
| 12F | β | α/β | H | | | | | |

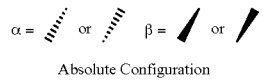

Absolute Configuration

TABLE 13

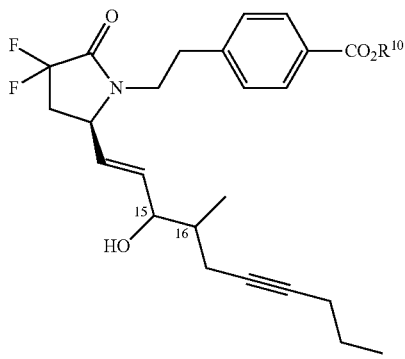

| | | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/ EP$_4$ | SEAP/ EP$_4$ | SEAP/ EP$_2$ |
| 13A | α | β | Me | | | | | |
| 13B | α | α | Me | | | | | |
| 13C | β | α/β | Me | | | | | |
| 13D | α | β | H | | | | | |
| 13E | α | α | H | | | | | |
| 13F | β | α/β | H | | | | | |

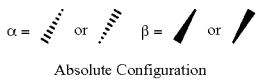

Absolute Configuration

TABLE 14

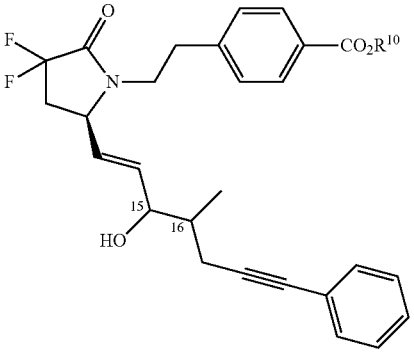

| | | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/ EP$_4$ | SEAP/ EP$_4$ | SEAP/ EP$_2$ |
| 14A | α | β | Me | | | | | |
| 14B | α | α | Me | | | | | |
| 14C | β | α/β | Me | | | | | |
| 14D | α | β | H | | | | | |
| 14E | α | α | H | | | | | |
| 14F | β | α/β | H | | | | | |

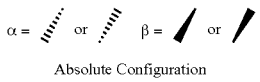

Absolute Configuration

TABLE 15

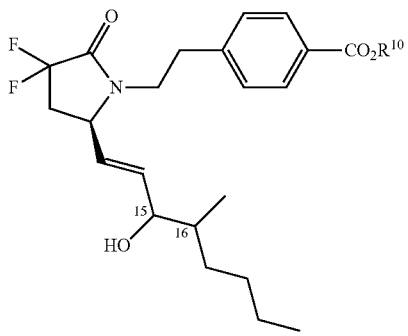

| Example No. | C-15 | C-16 | R[10] | hEP$_4$ receptor binding | | STEP cell functional assay EC$_{50}$s (nM) | | |
|---|---|---|---|---|---|---|---|---|
| | | | | IC$_{50}$ (nM) | K$_i$ (nM) | cAMP/ EP$_4$ | SEAP/ EP$_4$ | SEAP/ EP$_2$ |
| 15A | α | β | Me | | | | | |
| 15B | α | α | Me | | | | | |
| 15C | β | α/β | Me | | | | | |
| 15D | α | β | H | | | | | |
| 15E | α | α | H | | | | | |
| 15F | β | α/β | H | | | | | |

α = ⫶⫶⫶ or ⫶⫶⫶   β = ▰ or ▱

Absolute Configuration

TABLE 16

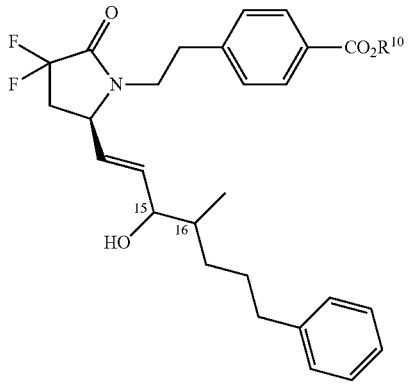

| Example No. | C-15 | C-16 | R[10] | hEP$_4$ receptor binding | | STEP cell functional assay EC$_{50}$s (nM) | | |
|---|---|---|---|---|---|---|---|---|
| | | | | IC$_{50}$ (nM) | K$_i$ (nM) | cAMP/ EP$_4$ | SEAP/ EP$_4$ | SEAP/ EP$_2$ |
| 16A | α | β | Me | | | | | |
| 16B | α | α | Me | | | | | |
| 16C | β | α/β | Me | | | | | |
| 16D | α | β | H | | | | | |
| 16E | α | α | H | | | | | |
| 16F | β | α/β | H | | | | | |

α = ⫶⫶⫶ or ⫶⫶⫶   β = ▰ or ▱

Absolute Configuration

TABLE 17

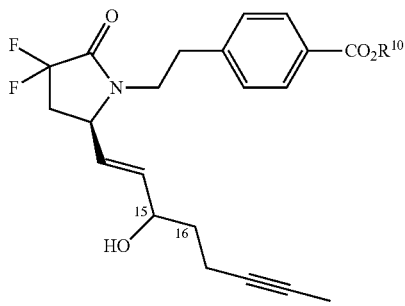

| Example No. | C-15 | R[10] | hEP$_4$ receptor binding | | STEP cell functional assay EC$_{50}$s (nM) | | |
|---|---|---|---|---|---|---|---|
| | | | IC$_{50}$ (nM) | K$_i$ (nM) | cAMP/ EP$_4$ | SEAP/ EP$_4$ | SEAP/ EP$_2$ |
| 17A | α | Me | | | | | |
| 17B | β | Me | | | | | |
| 17C | α | H | | | | | |
| 17D | β | H | | | | | |

α = ⫶⫶⫶ or ⫶⫶⫶   β = ▰ or ▱

Absolute Configuration

TABLE 18

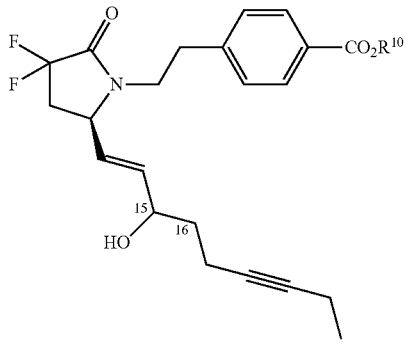

| Example No. | C-15 | R[10] | hEP$_4$ receptor binding | | STEP cell functional assay EC$_{50}$s (nM) | | |
|---|---|---|---|---|---|---|---|
| | | | IC$_{50}$ (nM) | K$_i$ (nM) | cAMP/ EP$_4$ | SEAP/ EP$_4$ | SEAP/ EP$_2$ |
| 18A | α | Me | | | | | |
| 18B | β | Me | | | | | |
| 18C | α | H | | | | | |
| 18D | β | H | | | | | |

α = ⫶⫶⫶ or ⫶⫶⫶   β = ▰ or ▱

Absolute Configuration

TABLE 19

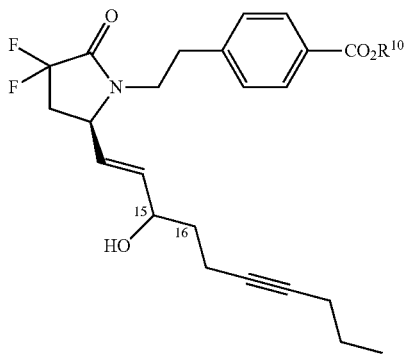

| Example No. | C-15 | R[10] | hEP4 receptor binding IC50 (nM) | Ki (nM) | STEP cell functional assay EC50s (nM) cAMP/EP4 | SEAP/EP4 | SEAP/EP2 |
|---|---|---|---|---|---|---|---|
| 19A | α | Me | | | | | |
| 19B | β | Me | | | | | |
| 19C | α | H | | | | | |
| 19D | β | H | | | | | |

α = ⦀ or ⦀    β = ◢ or ◢

Absolute Configuration

TABLE 20

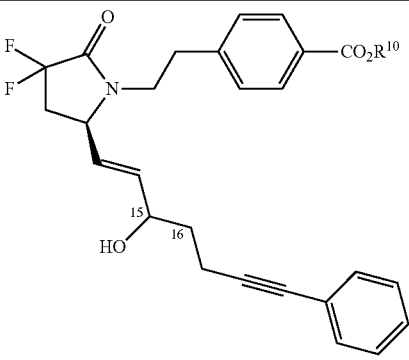

| Example No. | C-15 | R[10] | hEP4 receptor binding IC50 (nM) | Ki (nM) | STEP cell functional assay EC50s (nM) cAMP/EP4 | SEAP/EP4 | SEAP/EP2 |
|---|---|---|---|---|---|---|---|
| 20A | α | Me | | | | | |
| 20B | β | Me | | | | | |
| 20C | α | H | | | | | |
| 20D | β | H | | | | | |

α = ⦀ or ⦀    β = ◢ or ◢

Absolute Configuration

TABLE 21

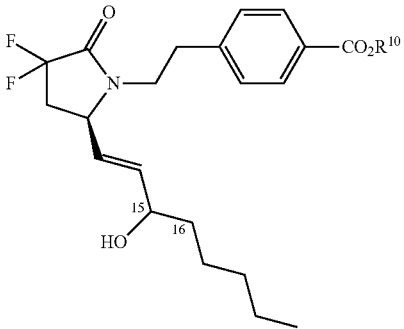

| Example No. | C-15 | R[10] | hEP4 receptor binding IC50 (nM) | Ki (nM) | STEP cell functional assay EC50s (nM) cAMP/EP4 | SEAP/EP4 | SEAP/EP2 |
|---|---|---|---|---|---|---|---|
| 21A | α | Me | | | | | |
| 21B | β | Me | | | | | |
| 21C | α | H | 0.22 | 0.082 | 0.61 | 0.075 | 1,960 |
| 21D | β | H | | | | | |

α = ⦀ or ⦀    β = ◢ or ◢

Absolute Configuration

TABLE 22

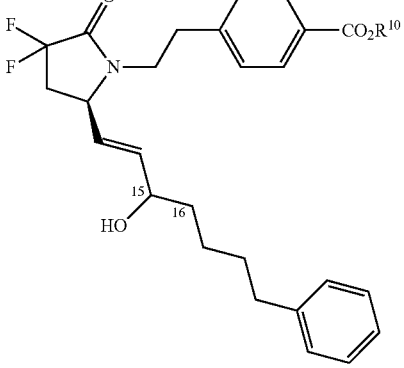

| Example No. | C-15 | R[10] | hEP4 receptor binding IC50 (nM) | Ki (nM) | STEP cell functional assay EC50s (nM) cAMP/EP4 | SEAP/EP4 | SEAP/EP2 |
|---|---|---|---|---|---|---|---|
| 22A | α | Me | | | | | |
| 22B | β | Me | | | | | |
| 22C | α | H | | | | | |
| 22D | β | H | | | | | |

α = ⦀ or ⦀    β = ◢ or ◢

Absolute Configuration

TABLE 23

| Example No. | C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 23A | α | β | Me | | | | | |
| 23B | α | α | Me | | | | | |
| 23C | β | α/β | Me | | | | | |
| 23D | α | β | H | | | | | |
| 23E | α | α | H | | | | | |
| 23F | β | α/β | H | | | | | |

α =  or   β =  or 

TABLE 24

| Example No. | C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 24A | α | β | Me | | | | | |
| 24B | α | α | Me | | | | | |
| 24C | β | α/β | Me | | | | | |
| 24D | α | β | H | 3.3 | 1.2 | 0.73 ± 0.31 (N = 6) | 0.11 | 763 |

TABLE 24-continued

| Example No. | C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 24E | α | α | H | | | | | |
| 24F | β | α/β | H | | | | | |

α =  or  β =  or

Absolute Configuration

TABLE 25

| Example No. | C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 25A | α | β | Me | | | | | |
| 25B | α | α | Me | | | | | |
| 25C | β | α/β | Me | | | | | |
| 25D | α | β | H | | | | | |
| 25E | α | α | H | | | | | |
| 25F | β | α/β | H | | | | | |

α =  or  β =  or

Absolute Configuration

TABLE 26

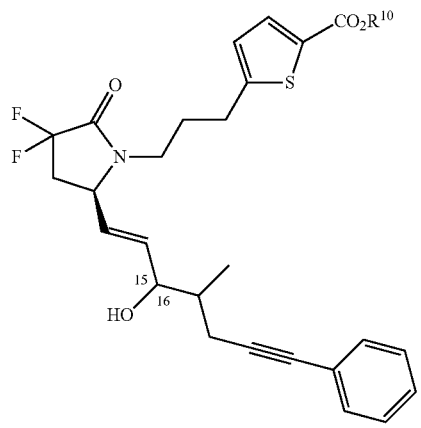

| Example No. | Absolute Configuration C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 26A | α | β | Me | | | | | |
| 26B | α | α | Me | | | | | |
| 26C | β | α/β | Me | | | | | |
| 26D | α | β | H | | | | | |
| 26E | α | α | H | | | | | |
| 26F | β | α/β | H | | | | | |

α = ⦀ or ⦀   β = ╱ or ╱

TABLE 27

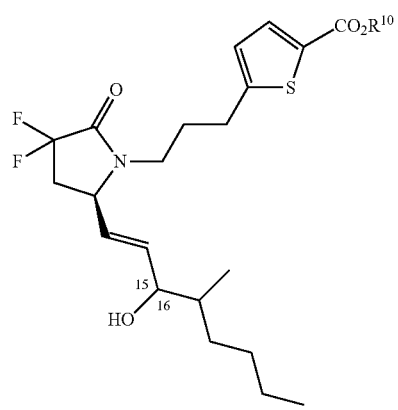

| Example No. | Absolute Configuration C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 27A | α | β | Me | | | | | |
| 27B | α | α | Me | | | | | |
| 27C | β | α/β | Me | | | | | |
| 27D | α | β | H | | | | | |
| 27E | α | α | H | | | | | |
| 27F | β | α/β | H | | | | | |

α = ⦀ or ⦀   β = ╱ or ╱

TABLE 28

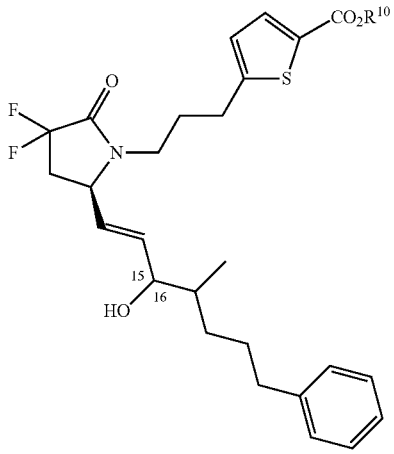

| Example No. | Absolute Configuration | | | hEP$_4$ receptor binding | | STEP cell functional assay EC$_{50}$s (nM) | | |
| --- | --- | --- | --- | --- | --- | --- | --- | --- |
| | C-15 | C-16 | R$^{10}$ | IC$_{50}$ (nM) | K$_i$ (nM) | cAMP/EP$_4$ | SEAP/EP$_4$ | SEAP/EP$_2$ |
| 28A | α | β | Me | | | | | |
| 28B | β | β | Me | | | | | |
| 28C | α | β | H | 0.74 | 0.28 | 0.010 ± 0.021 (N = 10) | | 148 ± 5 (N = 2) |
| 28D | β | β | H | | | 5.68 | | |
| 28E | α | α | Me | | | 50.8 | | |
| 28F | β | α | Me | | | >1,000 | | |
| 28G | α | α | H | | | 0.0162 | | 65 |
| 28H | β | α | H | | | 3.15 | | |

α = ⫽⫽⫽ or ⫽⫽⫽  β = ╱ or ╱

TABLE 28C-H$_2$

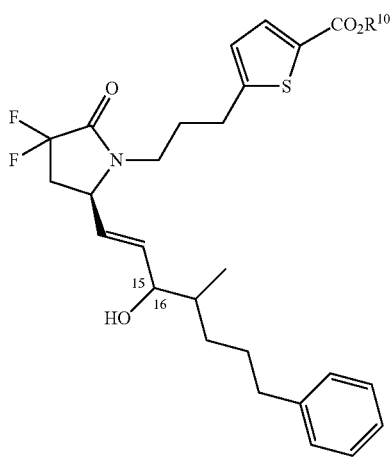

| Example No. | Absolute Configuration | | | hEP$_4$ receptor binding | | STEP cell functional assay EC$_{50}$s (nM) | | |
| --- | --- | --- | --- | --- | --- | --- | --- | --- |
| | C-15 | C-16 | R$^{10}$ | IC$_{50}$ (nM) | K$_i$ (nM) | cAMP/EP$_4$ | SEAP/EP$_4$ | cAMP/EP$_2$ |
| 28C-H$_2$ | α | β | H | | | 0.0029 ± 0.0008 (N = 2) | | 1,310 |

α = ⫽⫽⫽ or ⫽⫽⫽  β = ╱ or ╱

TABLE 29

| | Absolute Configuration | | hEP$_4$ receptor binding | | STEP cell functional assay EC$_{50}$s (nM) | | |
|---|---|---|---|---|---|---|---|
| Example No. | C-15 | R$^{10}$ | IC$_{50}$ (nM) | K$_i$ (nM) | cAMP/EP$_4$ | SEAP/EP$_4$ | SEAP/EP$_2$ |
| 29A | α | Me | | | | | |
| 29B | β | Me | | | | | |
| 29C | α | H | | | | | |
| 29D | β | H | | | | | |

α = or    β = or

TABLE 30

| | Absolute Configuration | | hEP$_4$ receptor binding | | STEP cell functional assay EC$_{50}$s (nM) | | |
|---|---|---|---|---|---|---|---|
| Example No. | C-15 | R$^{10}$ | IC$_{50}$ (nM) | K$_i$ (nM) | cAMP/EP$_4$ | SEAP/EP$_4$ | SEAP/EP$_2$ |
| 30A | α | Me | | | | | |
| 30B | β | Me | | | | | |
| 30C | α | H | | | | | |
| 30D | β | H | | | | | |

α = or    β = or

TABLE 31
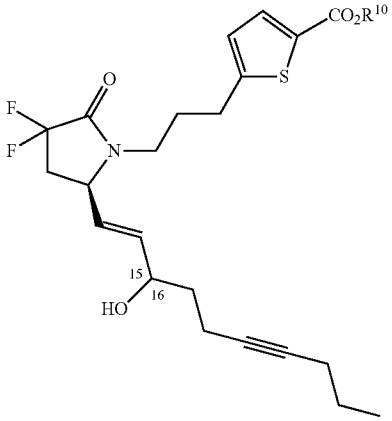
| Example No. | Absolute Configuration C-15 | R[10] | hEP4 receptor binding IC50 (nM) | K_i (nM) | STEP cell functional assay EC50s (nM) cAMP/EP4 | SEAP/EP4 | SEAP/EP2 |
|---|---|---|---|---|---|---|---|
| 31A | α | Me | | | | | |
| 31B | β | Me | | | | | |
| 31C | α | H | | | | | |
| 31D | β | H | | | | | |
α =  or    β =  or 
TABLE 32
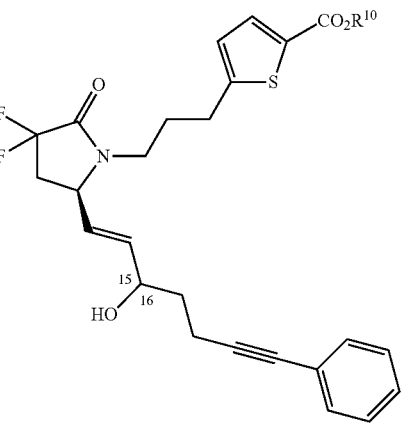
| Example No. | Absolute Configuration C-15 | R[10] | hEP4 receptor binding IC50 (nM) | K_i (nM) | STEP cell functional assay EC50s (nM) cAMP/EP4 | SEAP/EP4 | SEAP/EP2 |
|---|---|---|---|---|---|---|---|
| 32A | α | Me | | | | | |
| 32B | β | Me | | | | | |
| 32C | α | H | | | | | |
| 32D | β | H | | | | | |
α =  or    β =  or 

TABLE 33

|  | Absolute Configuration | | hEP$_4$ receptor binding | | STEP cell functional assay EC$_{50}$s (nM) | | |
|---|---|---|---|---|---|---|---|
| Example No. | C-15 | R$^{10}$ | IC$_{50}$ (nM) | K$_i$ (nM) | cAMP/EP$_4$ | SEAP/EP$_4$ | SEAP/EP$_2$ |
| 33A | α | Me | | | | | |
| 33B | β | Me | | | | | |
| 33C | α | H | 0.28 | 0.10 | 0.079 | 0.063 | 326 |
| 33D | β | H | | | | | |

α = ⟋⟋ or ⟋⟋  β = ╱ or ╱

TABLE 34

|  | Absolute Configuration | | hEP$_4$ receptor binding | | STEP cell functional assay EC$_{50}$s (nM) | |
|---|---|---|---|---|---|---|
| Example No. | C-15 | R$^{10}$ | IC$_{50}$ (nM) | K$_i$ (nM) | cAMP/EP$_4$ | SEAP/EP$_4$ |
| 34A | α | Me | | | | |
| 34B | β | Me | | | | |
| 34C | α | H | | | | |
| 34D | β | H | | | | |

α = ⟋⟋ or ⟋⟋  β = ╱ or ╱

TABLE 35

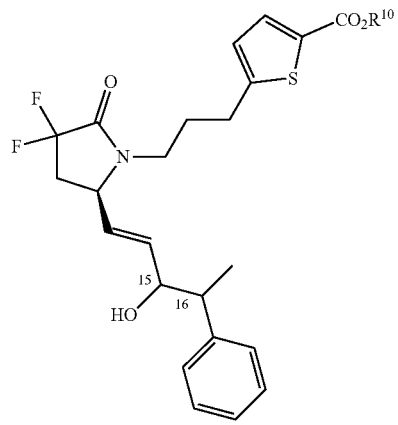

| Example No. | Absolute Configuration C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 35A | α | β | Me | | | | | |
| 35B | β | β | Me | | | | | |
| 35C | α | β | H | | | 62 | | |
| 35D | β | β | H | | | | | |

α = ⫽ or ⫽  β = ╱ or ╱

TABLE 36

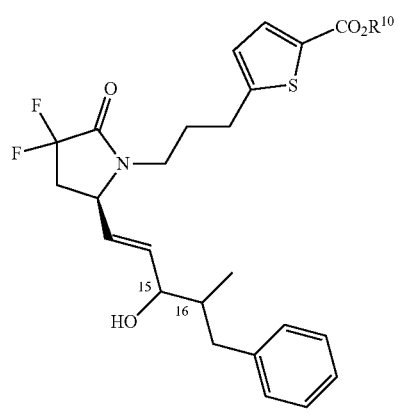

| Example No. | Absolute Configuration C-15 | C-16 | $R^{10}$ | hEP$_4$ receptor binding IC$_{50}$ (nM) | K$_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 36A | α | β | Me | | | 5.02 | | |
| 36B | β | β | Me | | | >1,000 | | |
| 36C | α | β | H | | | 0.038 | | 1,000 |
| 36D | β | β | H | | | | | |

α = ⫽ or ⫽  β = ╱ or ╱

TABLE 37

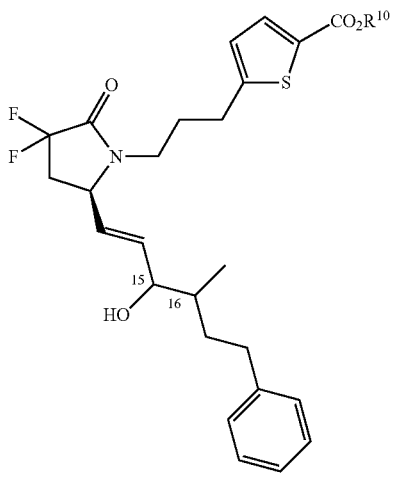

| Example No. | Absolute Configuration C-15 | C-16 | $R^{10}$ | hEP$_4$ receptor binding IC$_{50}$ (nM) | $K_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 37A | α | β | Me | | | 8.09 | | |
| 37B | β | β | Me | | | | | |
| 37C | α | β | H | | | 0.15 | | |
| 37D | β | β | H | | | 198 | | 743 |

α = ⦀ or ⦀  β = ╱ or ╱

TABLE 38

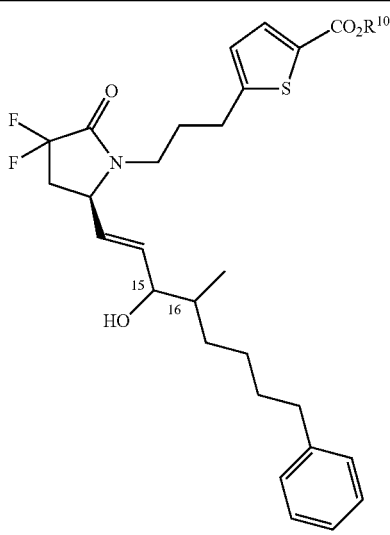

| Example No. | Absolute Configuration C-15 | C-16 | $R^{10}$ | hEP$_4$ receptor binding IC$_{50}$ (nM) | $K_i$ (nM) | STEP cell functional assay EC$_{50}$s (nM) cAMP/EP$_4$ | SEAP/EP$_4$ | SEAP/EP$_2$ |
|---|---|---|---|---|---|---|---|---|
| 38A | α | β | Me | | | >1,000 | | |
| 38B | β | β | Me | | | >1,000 | | |
| 38C | α | β | H | | | 0.00000014 | | 157 |
| 38D | β | β | H | | | 0.37 | | >10,000 |

α = ⦀ or ⦀  β = ╱ or ╱

TABLE 39

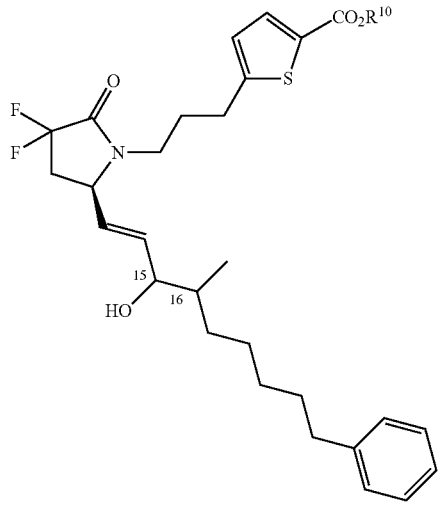

| | Absolute Configuration | | | hEP$_4$ receptor binding | | STEP cell functional assay EC$_{50}$s (nM) | | |
|---|---|---|---|---|---|---|---|---|
| Example No. | C-15 | C-16 | R$^{10}$ | IC$_{50}$ (nM) | K$_i$ (nM) | cAMP/EP$_4$ | SEAP/EP$_4$ | SEAP/EP$_2$ |
| 39A | α | β | Me | | | >1,000 | | |
| 39B | β | β | Me | | | >1,000 | | |
| 39C | α | β | H | | | 0.0000027 | | 1,020 |
| 39D | β | β | H | | | 0.059 | | 79,000 |

α = ⦀ or ⦀   β = ╱ or ╱

Example 94

Accelerated Healing of a Calvarial Bone Defect by Example 2C

The rat calvarial defect model is a widely used model through which the ability of a treatment agent to induce bone formation is assessed (Aghaloo et al., The effect of NELL1 and bone morphogenetic protein-2 on calvarial bone regeneration, J. Oral Maxillofac. Surg. 2010: 68:300-308; Mark et al., Repair of calvarial nonunions by osteogenin, a bone-inductive protein, Plast. Reconstr. Surg. 1990: 86:623-30).

Bone defects are created by removal of bone from the cranium of female Sprague Dawley rats by a bone trephine (cranial defect). Cranial defects are 2.6 mm in diameter and the cranium approximately 1 mm thick. A matrix of approximately 2 mm thickness is applied to the defect. Thus the dosing volume for each defect is calculated as $\pi*r^2*$matrix thickness=$3.14*1.3^2*2=10.61$ μl and rounded to 11 μl for purposes of dose calculation.

EXAMPLE 2C is delivered set inside calcium phosphate cement that, after loading with drug and setting, is ground to a fine powder and suspended in demineralized bone matrix at a ratio of 1:8 (weight/volume). EXAMPLE 2C is tested at seven doses with five rats in each group. These are 3, 10, 30, 100 and 300 μg/ml and 1 and 3 mg/ml. A negative control group treated with dosing matrix containing no drug (Vehicle) as well as a positive control group treated with 50 μg/ml recombinant human bone morphogenetic protein 2 (BMP-2) are also included in the study.

Calcium Phosphate cement powders may be combinations of α-tri-Calcium phosphate, β-tri-Calcium phosphate and hydroxyapatite; combinations of Dicalcium Phosphate and Tetracalcium Phosphate; or a commercially available calcium phosphate cement. Commercially available Human demineralized bone matrix, Puros Demineralized Bone Matrix Putty manufactured by RTI Biologics (Alachua, Fla.) using the Urist & Dowell method, is used in the studies described. Demineralized bone matrix can also be made by the method described by Urist & Dowell (Inductive Substratum for Osteogenesis in Pellets of Particulate Bone Matrix, Clin. Orthop. Relat. Res., 1968, 61, 61-78.)

Dosing solutions are made from a 5 mg/ml EXAMPLE 2C stock which is made by dissolving 1.5 mg of neat EXAMPLE 2C in 300 μl of 100% ethanol.

The dosing volume of a single defect is 11 μl. Thus for each group of five rats the total treatment volume is 55 μl. The ratio of calcium phosphate cement to volume is 1:8 thus for each group of five rats 6.8 mg of calcium phosphate cement was used.

The dosing solutions were made up by adding 5 mg/ml Example 2C dissolved in ethanol onto 6.8 mg of calcium phosphate cement using the volumes shown in the table below. The 10 μg/ml dose and the 3 μg/ml dose were not made directly from the 5 mg/ml stock but were made with 5.5 μl of a further 1:50 dilution of the stock and 3.3 μl of a 1:100 stock dilution respectively.

| | mg/defect =Dose * (11/1000) | mg/group =(mg/defect) *5 | μl of 5 mg/ml stock/group =(mg/group)/ (5/1000) |
|---|---|---|---|
| Vehicle | 0 | 0 | 0 |
| BMP-2 | 0 | 0 | 0 |
| 3 mg/ml | 0.033 | 0.165 | 33 |
| 1 mg/ml | 0.011 | 0.055 | 11 |
| 300 μg/ml | 0.0033 | 0.0165 | 3.3 |
| 100 μg/ml | 0.0011 | 0.0055 | 1.1 |

-continued

|  | mg/defect =Dose * (11/1000) | mg/group =(mg/defect) *5 | μl of 5 mg/ml stock/group =(mg/group)/ (5/1000) |
|---|---|---|---|
| 30 μg/ml | 0.00033 | 0.00165 | 0.33 |
| 10 μg/ml | 0.00011 | 0.00055 | 5.5 μl of 1:50 stock dilution in ethanol |
| 3 μg/ml | 0.000033 | 0.000165 | 3.3 μl of 1:100 stock dilution in ethanol |

After the ethanol has been vented off, the cement is wetted with a setting solution and mixed thoroughly for 1 minute as the cement begins to set. Calcium phosphate cement containing no Example 2C is also made up for the Vehicle and BMP-2 groups. The cement-drug mixture is allowed to set overnight at room temperature before being ground to a fine powder in a mortar and pestle.

Following grinding the cement is added to 55 μl of demineralized bone matrix (DBM) and thoroughly mixed using two spatulas. The cement-DBM mix is rolled into a single length of material of equal thickness and using a ruler as a guide cut into five equal length pieces. The dosing matrix is placed in a test subject within four hours of mixing the cement with the DBM.

Immediately after creation the bone defect is filled with dosing matrix containing either no drug, 50 μg/ml BMP-2 or a defined concentration of Example 2C. The operation area is closed and sutured and the animal allowed to recover. Eight weeks after the beginning of treatment each rat is anaesthetized with isoflurane and the defect area is imaged using a cone beam dental CT scanner (Vatech Pax-Duo3D).

The area measured each week is compared to that of the first week and the degree of repair calculated by the following formula:

(original area−current area)/original area*100

The mean repair for each group after eight weeks of treatment is shown in the FIG. 1.

The above description of the examples and embodiments of the invention is merely exemplary in nature and, thus, variations thereof are not to be regarded as a departure from the spirit and scope of the invention.

We claim:
1. A compound of formula (10)

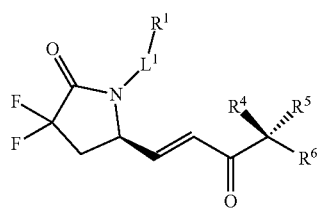

(10)

or salts thereof wherein:
$L^1$ is
  a) $C_3$-$C_7$alkylene, $C_3$-$C_7$alkenylene, or $C_3$-$C_7$alkynylene; or
  b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

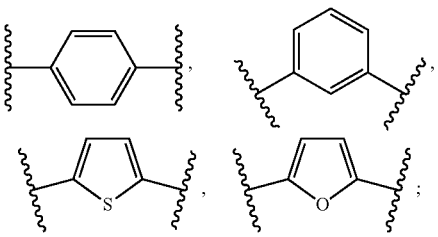

$R^1$ is a carboxylic acid or a protected carboxylic acid;
$R^{12}$, at each occurrence, is independently H or $C_1$-$C_4$alkyl;
$R^4$ and $R^5$ are each independently H or $C_1$-$C_4$ alkyl; or $R^4$ and $R^5$ together with the carbon to which they are attached form a $C_3$-$C_5$ cycloalkyl;
$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy;
$L^3$ is $C_1$-$C_6$alkylene, $C_2$-$C_6$alkenylene, $C_2$-$C_6$alkynylene; and
$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

2. The compound of claim 1, or salts thereof, wherein:
$L^1$ is n-hexylene, —$(CH_2)_3$-$G^2$-, —$CH_2$—C≡C-$G^2$-, or —$CH_2$—C(H)=C(H)-$G^2$-;
$G^2$ is

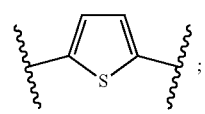 [SMILES: *c1ccc(*)s1]

$R^4$ and $R^5$ are each independently H or $C_1$-$C_4$ alkyl;
$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and
$R^7$ is phenyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

3. The compound of claim 2 wherein:
$L^1$ is —$(CH_2)_3$-$G^2$-;
$R^4$ is methyl;
$R^5$ is hydrogen;
$R^6$ is —$CH_2$—C≡C—$C_1$-$C_4$alkyl or $L^3$-$R^7$;
$L^3$ is $C_3$-$C_6$alkylene; and
$R^7$ is phenyl.

4. The compound of claim 2 wherein:
$L^1$ is —$(CH_2)_3$-$G^2$-;
$R^4$ is hydrogen;
$R^5$ is methyl;
$R^6$ is —$CH_2$—C≡C—$C_1$-$C_4$alkyl or $L^3$-$R^7$;
$L^3$ is $C_3$-$C_6$alkylene; and
$R^7$ is phenyl.

* * * * *